(12) United States Patent
Cywin et al.

(10) Patent No.: US 6,730,671 B2
(45) Date of Patent: May 4, 2004

(54) COMPOUNDS USEFUL AS REVERSIBLE INHIBITORS OF CATHESPIN S

(75) Inventors: Charles L. Cywin, Bethel, CT (US); Michel J. Emmanuel, Danbury, CT (US); Tina Morwick, New Milford, CT (US); Denice M. Spero, West Redding, CT (US); David S. Thomson, Ridgefield, CT (US); Yancey D. Ward, Sandy Hook, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 21 days.

(21) Appl. No.: 10/366,282

(22) Filed: Feb. 13, 2003

(65) Prior Publication Data

US 2003/0158406 A1 Aug. 21, 2003

Related U.S. Application Data

(62) Division of application No. 10/082,952, filed on Oct. 24, 2001, now Pat. No. 6,608,057, which is a continuation of application No. 09/434,106, filed on Nov. 5, 1999, now Pat. No. 6,395,897.

(51) Int. Cl.[7] .................... C07D 417/02; A61K 31/535; A61P 43/00

(52) U.S. Cl. ................... 514/232.8; 514/233.5; 514/233.8; 514/234.2; 514/234.5; 514/234.8; 514/235.2; 514/235.5; 514/233.2; 514/236.2; 514/236.5; 514/236.8; 514/317; 514/318; 514/319; 514/333; 514/336; 514/354; 514/355; 544/115; 544/116; 544/118; 544/126; 544/128; 544/135; 544/138; 544/139; 544/140; 544/141; 544/142; 544/143; 544/145; 544/146; 544/147; 544/152; 544/153; 546/192; 546/195; 546/197; 546/245

(58) Field of Search ................. 514/317, 318, 514/319, 336, 333, 355, 354, 233.5, 233.8, 233.2, 234.2, 234.5, 234.8, 235.2, 235.5, 236.2, 236.5, 236.8; 544/115, 116, 118, 126, 128, 135, 138, 145, 146, 147, 152, 153; 546/192, 195, 197, 245

(56) References Cited

U.S. PATENT DOCUMENTS

| | | | |
|---|---|---|---|
| 4,734,425 A | 3/1988 | Nakane et al. | |
| 4,749,715 A | 6/1988 | Hall | |
| 4,797,202 A | 1/1989 | Klimpel et al. | |
| 4,957,932 A | 9/1990 | Young et al. | |
| 4,962,117 A | 10/1990 | Young et al. | |
| 5,196,291 A | 3/1993 | Okada et al. | |
| 5,218,123 A | 6/1993 | Horwell et al. | |
| 5,250,732 A | 10/1993 | Kogan et al. | |
| 5,328,803 A | 7/1994 | Fujikura et al. | |
| 5,346,907 A | 9/1994 | Kerwin et al. | |
| 5,461,176 A | 10/1995 | Sun et al. | |
| 5,504,109 A | 4/1996 | Seitz et al. | |
| 5,514,778 A | 5/1996 | Hammond et al. | |
| 5,633,248 A | 5/1997 | Kato et al. | |
| 5,691,368 A | 11/1997 | Peet et al. | |
| 5,710,129 A | 1/1998 | Lynch et al. | |
| 5,744,451 A | 4/1998 | Allen et al. | |
| 5,756,528 A | 5/1998 | Anthony et al. | |
| 5,847,135 A | 12/1998 | Bemis et al. | |
| 5,872,122 A | 2/1999 | Bovy et al. | |
| 5,976,858 A | 11/1999 | Palmer et al. | |
| 6,395,897 B1 | 5/2002 | Cywin et al. | |

FOREIGN PATENT DOCUMENTS

| | | |
|---|---|---|
| DE | 3827727 A1 | 2/1990 |
| DE | 4343528 A1 | 12/1993 |
| DE | 4225487 A1 | 2/1994 |
| DE | 4303145 A1 | 8/1994 |
| DE | 4321897 A1 | 1/1995 |
| DE | 19609955 A1 | 9/1997 |
| DE | 19653647 A1 | 6/1998 |
| EP | 0 115 472 | 8/1984 |
| EP | 0294668 A2 | 12/1988 |
| EP | 030885 A2 | 3/1989 |
| EP | 0314060 A2 | 5/1989 |
| EP | 0318083 A2 | 5/1989 |
| EP | 0336356 A2 | 10/1989 |
| EP | 0374098 A2 | 6/1990 |
| EP | 0398072 A3 | 11/1990 |
| EP | 0483667 A2 | 5/1992 |
| EP | 0506008 A1 | 9/1992 |
| EP | 0529737 A1 | 3/1993 |
| EP | 0533244 A1 | 3/1993 |
| EP | 0542463 A1 | 5/1993 |
| EP | 0547699 A1 | 6/1993 |
| EP | 587110 A2 | 3/1994 |
| EP | 0 604 182 A2 | 6/1994 |
| EP | 0611756 A2 | 8/1994 |
| EP | 0611756 A3 | 8/1994 |

(List continued on next page.)

Primary Examiner—Joseph K. McKane
Assistant Examiner—Andrea D. Small
(74) Attorney, Agent, or Firm—Robert P. Raymond; Anthony P. Bottino; Timothy X. Witkowski

(57) ABSTRACT

Disclosed are cathepsin S reversible inhibitory compounds of the formulas (I),(Ia) and (II),(IIa) as defined herein. The compounds are useful for treating autoimmune diseases. Also disclosed are processes, for making such novel compounds.

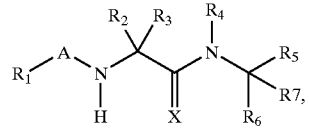

(I)/(Ia)

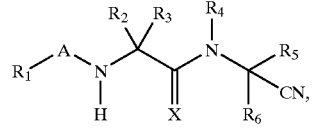

(II)/(IIa)

25 Claims, No Drawings

FOREIGN PATENT DOCUMENTS

| | | |
|---|---|---|
| EP | 0644198 A1 | 3/1995 |
| EP | 0649057 A2 | 4/1995 |
| EP | 0 652 229 A2 | 5/1995 |
| EP | 0672654 | 9/1995 |
| EP | 805147 A1 | 11/1997 |
| EP | 810206 A1 | 12/1997 |
| EP | 0 838 471 A1 | 4/1998 |
| EP | 844248 A2 | 5/1998 |
| EP | 844248 A3 | 5/1998 |
| EP | 846464 A3 | 6/1998 |
| EP | 846464 A2 | 6/1998 |
| EP | 897908 A1 | 2/1999 |
| FR | 2694006 A1 | 1/1994 |
| JP | 662788 | 8/1965 |
| JP | 43-10619 | 5/1968 |
| JP | 68010619 | 5/1968 |
| JP | 6358346 A2 | 3/1988 |
| JP | 63301868 | 12/1988 |
| JP | 63301868 A2 | 12/1988 |
| JP | 3002872 A2 | 1/1991 |
| JP | 6003787 A2 | 1/1994 |
| JP | 6051451 A2 | 2/1994 |
| JP | 6145173 A2 | 5/1994 |
| JP | 6293772 A2 | 10/1994 |
| JP | 6340643 A2 | 12/1994 |
| JP | 7-101959 A2 | 4/1995 |
| JP | 7285931 A2 | 10/1995 |
| JP | 8248579 A2 | 9/1996 |
| JP | 11100373 A2 | 4/1999 |
| WO | WO 8808717 A2 | 11/1988 |
| WO | WO 89/10920 A1 | 11/1989 |
| WO | WO 90/13561 A1 | 11/1990 |
| WO | WO 91/19733 A1 | 12/1991 |
| WO | WO 92/01675 A2 | 2/1992 |
| WO | WO 92/14465 A1 | 9/1992 |
| WO | WO 92/17453 | 10/1992 |
| WO | WO 92/21361 A1 | 12/1992 |
| WO | WO 92/22570 A1 | 12/1992 |
| WO | WO 93/05444 A1 | 3/1993 |
| WO | WO 93/12075 A1 | 6/1993 |
| WO | WO 93/14069 A1 | 7/1993 |
| WO | WO 94/00435 A1 | 1/1994 |
| WO | WO 94/06757 A1 | 3/1994 |
| WO | WO 94/07841 A1 | 4/1994 |
| WO | WO 94/21657 A1 | 9/1994 |
| WO | WO 94/22911 A2 | 10/1994 |
| WO | WO 94/25432 A1 | 10/1994 |
| WO | WO 95/01344 A1 | 1/1995 |
| WO | WO 95/06029 A1 | 3/1995 |
| WO | WO 95/09838 | 4/1995 |
| WO | WO 95/12611 A1 | 5/1995 |
| WO | WO 95/15749 | 6/1995 |
| WO | WO 95/23222 A1 | 8/1995 |
| WO | WO 95/24382 A1 | 9/1995 |
| WO | WO 95/29899 A1 | 11/1995 |
| WO | WO 95/33728 A1 | 12/1995 |
| WO | WO 95/35308 A1 | 12/1995 |
| WO | WO 96/07638 A1 | 3/1996 |
| WO | WO 96/10559 A1 | 4/1996 |
| WO | WO 96/12499 A1 | 5/1996 |
| WO | WO 96/13502 A1 | 5/1996 |
| WO | WO 96/16940 A1 | 6/1996 |
| WO | WO 96/20725 A2 | 7/1996 |
| WO | WO 96/20949 A1 | 7/1996 |
| WO | WO 96/22970 A1 | 8/1996 |
| WO | WO 96/26194 A1 | 8/1996 |
| WO | WO 96/30353 A1 | 10/1996 |
| WO | WO 96/33168 A1 | 10/1996 |
| WO | WO 96/33170 A1 | 10/1996 |
| WO | WO 96/33211 A1 | 10/1996 |
| WO | WO 96/37499 A1 | 11/1996 |
| WO | WO 96/39137 A1 | 12/1996 |
| WO | WO 96/39384 A1 | 12/1996 |
| WO | WO 96/40647 | 12/1996 |
| WO | WO 96/40737 A1 | 12/1996 |
| WO | WO 96/40741 A1 | 12/1996 |
| WO | WO 96/40742 A1 | 12/1996 |
| WO | WO 96/40744 A1 | 12/1996 |
| WO | WO 96/40751 A1 | 12/1996 |
| WO | WO 96/40752 A1 | 12/1996 |
| WO | WO 96/40753 A1 | 12/1996 |
| WO | WO 97/01275 A1 | 1/1997 |
| WO | WO 97/10219 A1 | 3/1997 |
| WO | WO 97/19908 A1 | 6/1997 |
| WO | WO 97/22618 A1 | 6/1997 |
| WO | WO 97/22619 A3 | 6/1997 |
| WO | WO 97/22621 A3 | 6/1997 |
| WO | WO 97/22621 A2 | 6/1997 |
| WO | WO 97/24343 A1 | 7/1997 |
| WO | WO 97/26246 A1 | 7/1997 |
| WO | WO 97/27200 A1 | 7/1997 |
| WO | WO 97/27220 A2 | 7/1997 |
| WO | WO 97/31016 A2 | 8/1997 |
| WO | WO 97/31016 A3 | 8/1997 |
| WO | WO 97/45016 A1 | 12/1997 |
| WO | WO 97/46518 A1 | 12/1997 |
| WO | WO 98/04278 A2 | 2/1998 |
| WO | WO 98/04518 A1 | 2/1998 |
| WO | WO 98/14450 A1 | 4/1998 |
| WO | WO 98/17679 A1 | 4/1998 |
| WO | WO 98/21199 A2 | 5/1998 |
| WO | WO 98/21199 A3 | 5/1998 |
| WO | WO 98/22433 A1 | 5/1998 |
| WO | WO 98/25617 A1 | 6/1998 |
| WO | WO 98/26654 A2 | 6/1998 |
| WO | WO 98/26654 A3 | 6/1998 |
| WO | WO 98/28269 A1 | 7/1998 |
| WO | WO 98/38177 A1 | 9/1998 |
| WO | WO 98/47863 A1 | 10/1998 |
| WO | WO 98/52558 A1 | 11/1998 |
| WO | WO 98/52559 A1 | 11/1998 |
| WO | WO 98/52941 A1 | 11/1998 |
| WO | WO 98/57937 A3 | 12/1998 |
| WO | WO 98/57937 A1 | 12/1998 |
| WO | WO 98/57951 A1 | 12/1998 |
| WO | WO 99/23063 A1 | 5/1999 |
| WO | WO 99/24460 A2 | 5/1999 |
| WO | WO 99/32106 A1 | 7/1999 |
| WO | WO 99/32455 A1 | 7/1999 |
| WO | WO 99/56765 A1 | 11/1999 |
| WO | WO 00/55125 | 9/2000 |
| WO | WO 00/55126 | 9/2000 |
| ZA | 950892 | 2/1995 |

US 6,730,671 B2

COMPOUNDS USEFUL AS REVERSIBLE INHIBITORS OF CATHESPIN S

CONTINUING APPLICATION DATA

This is a divisional application of U.S. application Ser. No. 10/082,952 filed Oct. 24, 2001 now U.S. Pat. No. 6,608,057 which is a continuation of application Ser. No. 09/434,106, filed Nov. 5, 1999, now U.S. Pat. No. 6,395,897.

TECHNICAL FIELD OF THE INVENTION

This invention relates to peptidyl cysteine protease inhibitors. The compounds are reversible inhibitors of the cysteine protease cathepsin S and are therefore useful in the treatment of autoimmune diseases. The invention also relates to processes for preparing such compounds and pharmaceutical compositions comprising them.

BACKGROUND OF THE INVENTION

Cathepsin S is a member of the papain family, within the papain superfamily of cysteine proteases. The papain family is the largest group of cysteine proteases and includes proteases such as cathepsins B, H, K, L, O and S. (A. J. Barrett et al., 1996, Perspectives in Drug Discovery and Design, 6,1). The cysteine proteases have important roles in human biology and diseases including atherosclerosis, emphysema, osteoporosis, chronic inflammation and immune disorders (H. A. Chapman et al., 1997, Ann. Rev. Physiol., 59, 63). Cathepsin S plays a key role in regulating antigen presentation and immunity (H. A. Chapman, 1998, Current Opinion in Immunology, 10, 93; R. J. Riese et al., 1998, J. Clin. Invest., 101, 2351; R. J. Riese et al., 1996, Immunity, 4, 357).

The specificity of the immune response relies on processing of foreign protein and presentation of antigenic peptide at the cell surface. Antigenic peptide is presented bound to MHC Class II, a heterodimeric glycoprotein expressed in certain antigen presenting cells of hematopoietic lineage, such as B cells, macrophages and dendritic cells. Presentation of antigen to effector cells, such as T-cells, is a fundamental step in recognition of non-self and thus initiation of the immune response. Recently MHC Class II heterodimers were shown to associate intracellularly with a third molecule designated invariant chain. Invariant chain facilitates Class II transport to the endosomal compartment and stabilizes the Class II protein prior to loading with antigen. Invariant chain interacts directly with Class II dieters in the antigen-binding groove and therefore must be proteolyzed and removed or antigen cannot be loaded or presented. Current research suggests that invariant chain is selectively proteolyzed by cathepsin S, which is compartmentalized with MHC Class II complexes within the cell. Cathepsin S degrades invariant chain to a small peptide, termed CLIP, which occupies the antigen—binding groove. CLIP is released from MHC Class II the interaction MHC Class II with HLA-DM, a MHC-like molecule thus freeing MHC Class II to associate with antigenic peptides. MHC Class II-antigen complexes are then transported to the cell surface for presentation to T-cells, and initiation of the immune response.

Cathepsin S, through proteolytic degradation of invariant chain to CLIP, provides a fundamental step in generation of an immune response. It follows that inhibition of antigen presentation via prevention of invariant chain degradation by cathepsin S could provide a mechanism for immunoregulation. Control of antigen-specific immune responses has long been desirable as a useful and safe therapy for autoimmune diseases. Such diseases include Crohn's disease and arthritis, as well as other T-cell-mediated immune responses (C. Janeway and P. Travers, 1996, Immunobiology, The Immune System in Health and Disease, Chapter 12). Furthermore, cathepsin S, which has broad pH specificity, has been implicated in a variety of other diseases involving extracellular proteolysis, such as Alzheimer's disease (U. Muller-Ladner et al., 1996, Perspectives in Drug Discovery and Design, 6, 87) and atherosclerosis (G. K. Sukhova et al., 1998, J. Clin. Invest., 102, 576).

Cysteine proteases are characterized by having a cysteine residue at the active site which serves as a nucleophile. The active site also contains a histidine residue. The imidazole ring on the histidine serves as a base to generate a thiolate anion on the active site cysteine, increasing its nucleophilicity. When a substrate is recognized by the protease, the amide bond to be cleaved is directed to the active site, where the thiolate attacks the carbonyl carbon forming an arylenzyme intermediate and cleaving the amide, liberating an amine. Subsequently, water cleaves the acyl-enzyme species regenerating the enzyme and liberating the other cleavage product of the substrate, a carboxylic acid.

A proposed mechanism of action of the cysteine protease inhibitors of this invention is that the inhibitors-contain a functionality that can react (reversibly or irreversibly) with the active site cysteine. The reactive functionality is attached to a peptide or peptide mimic that can be recognized and accommodated by the region of the protease surrounding the active site. The nature of both the reactive functionality and the remaining portion of the inhibitor determine the degree of selectivity and potency toward a particular protease.

Examples of reactive functionalities that have been described (D. Rasnick, 1996, Perspectives in Drug Discovery and Design, 6, 47) on cysteine protease inhibitors include peptidyl diazomethanes, epoxides, monofluoroalkanes and acyloxymethanes, which irreversibly alkylate the cysteine thiol. Other irreversible inhibitors include Michael acceptors such as peptidyl vinyl esters and other carboxylic acid derivatives (S. Liu et al., J. Med Chem., 1992, 35, 1067) and vinyl sulfones (J. T. Palmer et al., 1995, J. Mod Chem., 38, 3193)

Reactive functionalities that form reversible complexes with the active site cysteine include peptidyl aldehydes (R. P. Hanzlik et al., 1991, Biochim. Biophys. Acta.,1073, 33), which are non-selective, inhibiting both cysteine end serine proteases as well as other nucleophiles. Peptidyl nitriles (R. P. Hanzlik et al., 1990, Biochim. Biophys. Acta., 1035, 62) are less reactive than aldehydes and therefore more selective for the more nucleophilic cysteine proteases. Various reactive ketones have also been reported to be reversible inhibitors of cysteine proteases (D. Rasnick, 1996, ibid). In addition to reacting with the nucleophilic cysteine of the active site, reactive ketones may react with water, forming a hemiketal which may act as a transition state inhibitor.

Examples of cathepsin S inhibitors have been reported previously. J. T. Palmer (U.S. Pat. No. 5,776,718, 1998) described reversible peptidyl sulfones as inhibitors of cysteine proteases including cathepsin S. J. L. Klaus et al. (WO 9640737, 1996) described reversible inhibitors of cysteine proteases including cathepsin S, containing an ethylene diamine.

Additional peptidyl nitriles or peptidyl ketoheterocycles have been reported either as protease inhibitors or as having other utilities. For example, both nitriles and ketoheterocycles are described by B. A. Rowe et al. (U.S. Pat. No. 5,714,471, 1998) as protease inhibitors useful in the treatment of neurodegenerative diseases. Peptidyl nitriles are reported by B. Malcolm et al. (WO 9222570, 1992) as inhibitors of picornavirus protease. H. Saika et al. (WO 9512611, 1995) report peptidyl nitriles among compounds having endothelin receptor antagonist activity. B. J. Gour-Salin (Can. J. Chem., 1991, 69,1288) and T. C. Liang (Arch. Biochim. Biophys., 1987, 252, 626) described peptidyl nitriles as inhibitors of papain. D. W. Woolley et al. (J. Org. Chem, 1963, 28, 2012) described a peptidyl nitrile as a chemical intermediate.

Peptidyl ketoheterocycles having protease inhibiting or other activities have been reported, include inhibitors of serine proteases described by R. D. Tung et al. (WO 9817679, 1998). Inhibitors of Factor X, have been described by C. K. Marlowe et al. (WO 9640744,1996). Peptidyl ketoheterocycles useful in the treatment of thrombin related diseases have been described by M. Costanzo et al. (WO 9640742,1996).

A reversible inhibitor presents a more attractive therapy than irreversible inhibitors. Even compounds with high specificity for a particular protease can bind non-target enzymes. An irreversible compound could therefore permanently inactivate a non-target enzyme, increasing the likelihood of toxicity. Furthermore, any toxic effects resulting from inactivation of the target enzyme would be mitigated by reversible inhibitors, and could be easily remedied by modified or lower dosing. Finally, covalent modification of an enzyme by an irreversible inhibitor could potentially generate an antibody response by acting as a hapten.

In light of the above, there is a clear need for compounds which reversibly and selectively inhibit cathepsin S, such inhibitors would be useful in therapy for antigen-specific immune responses as well as for indications in which cathepsin S exacerbates disease through extracellular activity.

BRIEF DESCRIPTION OF THE INVENTION

The work cited above supports the principle that inhibition of cathepsin S and subsequent inhibition of antigen presentation will be beneficial in the treatment of various disease states. It is therefore an object of this invention to provide novel compounds that inhibit antigen presentation by virtue of reversible inhibition of the cysteine protease cathepsin S. It is a further object of the invention to provide methods for treating diseases and pathological conditions involving immune disorders such as rheumatoid arthritis. It is yet a further object of the invention to provide processes for preparation of the above-mentioned novel compounds.

DETAILED DESCRIPTION OF THE INVENTION

The invention provides novel compounds of the formula (I):

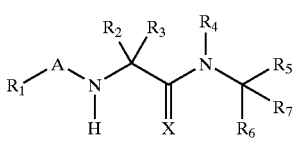

(I)

A is —C(Y)— or —SO$_2$—
Y is O, S or NR, wherein R$_4$ is selected from the group consisting of H, alkyl, aryl, alkoxy, aryloxy, alkylamino and arylamino;

R$_1$ is alkyl, cycloalkyl, aryl, heterocyclyl, heteroaryl or amino wherein R$_1$ is optionally substituted by one or more R$_b$;

R$_b$ is selected from the group consisting of alkyl, cycloalkyl, aryl, heterocyclyl, heteroaryl, alkoxy, aryloxy, alkoxycarbonyl, aryloxycarbonyl, alkanoyl, aroyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino, R$_b$ may be further optionally substituted by one or more R$_c$;

R$_c$ is selected from the group consisting of alkyl, cycloalkyl, aryl, heterocycle, heteroaryl, arylalkyl, alkoxy, aryloxy, arylalkoxy, alkanoyl, aroyl, amino wherein the nitrogen atom may be independently mono or di-substituted by alkyl, aryl, heterocyclyl or heteroaryl, halogen, hydroxy, oxo, carboxy, cyano, nitro, amidino and guanidino;

R$_2$ is H or alkyl;

R$_3$ is H, alkyl, cycloalkyl, aryl, heterocyclyl or heteroaryl, wherein R$_3$ is optionally substituted by one or more groups of the formula R$_d$;

R$_d$ is selected from the group consisting of alkyl, cycloalkyl, aryl, heterocyclyl, heteroaryl, alkoxy, aryloxy, arylalkoxy, alkoxycarbonyl, aryloxycarbonyl, alkanoyl, aroyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino, R$_d$ may be further optionally substituted by one or more R$_e$;

R$_e$ is selected from the group consisting of alkyl, cycloalkyl, aryl, arylalkyl, alkoxy, aryloxy, arylalkoxy, alkanoyl, aroyl, amino, halogen, hydroxy, oxo, carboxy, cyano, nitro, amidino and guanidino;

R$_4$ is H or alkyl;

R$_5$ is H, alkyl or cycloalkyl;

R$_6$ is H, alkyl, cycloalkyl, aryl, heterocyclyl or heteroaryl, wherein R$_6$ is optionally substituted by one or more groups of the formula R$_f$;

R$_f$ is selected from the group consisting of alkyl, cycloalkyl, aryl, heterocyclyl, heteroaryl, alkoxy, aryloxy, alkanoyl, aroyl, arylalkoxy, heteroarylalkoxy, alkoxycarbonyl, aryloxycarbonyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylthio wherein the sulfur atom may be oxidized to a sulfoxide or sulfone, arylthio wherein the sulfur atom may be oxidized to a sulfoxide or sulfone, arylalkylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino, $R_f$ may be further optionally substituted by one or more $R_g$;

$R_g$ is selected from the group consisting of alkyl, cycloalkyl, aryl optionally substituted by halogen, C1–5alkyl or C1–5alkoxy, heterocyclyl, heteroaryl, alkoxy, aryloxy, arylalkoxy, alkoxycarbonyl, aryloxycarbonyl, alkanoyloxy, aroyloxy, carbamoyl wherein the nitrogen atom may be independently mono or di-substituted by alkyl, aryl, heterocyclyl or heteroaryl; alkanoylamino, aroylamino, alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl or heteroaryl; alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl amino wherein the nitrogen atom may be independently mono or di-substituted by alkyl, aryl, heterocyclyl or heteroaryl; halogen, hydroxy, oxo, carboxy, cyano; nitro, amidino and guanidino;

or $R_5$ together with $R_6$ form a 3 to 6 membered carbocyclic ring, the carbocyclic ring being optionally substituted with one or more $R_h$;

$R_h$ is selected from the group consisting of alkyl, aryl, alkoxycarbonyl, aryloxycarbonyl, arylalkoxycarbonyl, carbamoyl wherein the nitrogen atom may be optionally mono or di-substituted with a group selected from alkyl, cycloalkyl, aryl, arylalkyl, heterocyclyl or heteroaryl; halogen, hydroxy, carboxy and cyano;

$R_7$ is $R_8$—C(Z)—;

wherein Z is O, S, or $NR_i$ wherein $R_i$ is selected from the group consisting of H, alkyl, aryl, alkoxy, aryloxy and hydroxy;

$R_8$ is a 5–8 membered monocyclic heteroaryl or 8–11 membered bicyclic heteroaryl ring system; each of the monocyclic or bicyclic ring systems having 1–4 of the same or different heteroatoms selected from the group consisting of N, O and S wherein any of the above $R_8$ can be optionally substituted by one or more $R_j$;

$R_j$ is selected from the group consisting of alkyl, cycloalkyl, aryl, heterocyclyl, heteroaryl, arylalkyl, alkoxy, aryloxy, alkanoyl, aroyl, arylalkoxy, alkoxycarbonyl, aryloxycarbonyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylthio wherein the sulfur atom may be oxidized to a sulfoxide or sulfone, arylthio wherein the sulfur atom may be oxidized to a sulfoxide or sulfone, arylalkylthio wherein the sulfur atom may be oxidized to a sulfoxide or sulfone, ureido wherein either nitrogen atom may be independently substituted by alkyl, aryl, heterocyclyl or heteroaryl; alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl; halogen, hydroxy, oxo, carboxy, cyano, nitro, amidino and guanidino, $R_j$ may be further optionally substituted by one or more $R_k$;

$R_k$ is selected from the group consisting of alkyl, cycloalkyl, aryl, heterocyclyl, heteroaryl, alkoxy, aryloxy, arylalkoxy, alkoxycarbonyl, aryloxycarbonyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, arylalkoxycarbonylamino, arylalkoxycarbonylaminoalkyl, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino;

X is O, S or N—OH;

and the pharmaceutically acceptable derivatives thereof;

with the proviso that when $R_6$ is alkyl the alkyl must be substituted with $R_f$ wherein $R_f$ is not hydroxy, sulfhydryl or halogen.

Preferred compounds of the formula (I) are those wherein:

$R_a$ is selected from the group consisting of H, alkyl and aryl;

$R_1$ is C1–8 alkyl, C3–7 cycloalkyl, aryl, heterocyclyl selected from the group consisting of pyrrolidinyl, piperidinyl, morpholinyl, thiomorpholinyl, pyranyl, thiopyranyl, piperazinyl and indolinyl; heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, or amino wherein $R_1$ is optionally substituted by one or more $R_b$;

$R_b$ is selected from the group consisting of C1–8 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkoxy, aryloxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperidinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, C1–8 alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperidinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_b$ may be further optionally substituted by one or more $R_c$;

$R_c$ is selected from the group consisting of C1–8 alkyl, C3–6 cycloalkyl, aryl, heterocyclyl selected from the group consisting of pyrrolidinyl, piperidinyl, morpholinyl, thiomorpholinyl, piperidinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkoxy, aryloxy, halogen, hydroxy, oxo, carboxy, cyano, nitro, amidino and guanidino;

$R_3$ is H, C1–8 alkyl, C3–7 cycloalkyl or aryl wherein $R_3$ is optionally substituted by one or more $R_d$;

$R_d$ is selected from the group consisting of C1–8 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkoxy, aryloxy, alkanoyl, amyl, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, . morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperidinyl and indolinyl or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, C1–8 alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_d$ may be further optionally substituted by one or more $R_e$;

$R_e$ is selected from the group consisting of C1–8 alkyl, C3–6 cycloalkyl, aryl, arylalkyl, C1–8 alkoxy, aryloxy, arylalkoxy, amyl, amino, halogen, hydroxy, oxo, carboxy, cyano, nitro, amidino and guanidino;

$R_5$ is H or alkyl;

$R_6$ is H, C1–8 alkyl, C3–7 cycloalkyl or aryl wherein $R_6$ is optionally substituted by one or more $R_f$;

$R_f$ is selected from the group consisting of C1–8 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of Amyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkoxy, aryloxy, arylC1–8alkoxy, heteroarylC1–8alkoxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, arylC1–8 alkylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, C1–8 alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_f$ may be further optionally substituted by one or more $R_g$;

$R_g$ is selected from the group consisting of C1–8 alkyl, C3–7 cycloalkyl, aryl optionally substituted by halogen, C1–3alkyl or C1–3alkoxy, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkoxy, aryloxy, arylC1–8alkoxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl or phenoxazinyl, alkoxycarbonylamino, aryloxycarbonylamino, C1–8 alkylcarbamoyloxy, arylcarbamoyloxy, alkylsulfonylamino, arylsulfonylamino, alkylaminosulfonyl and arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino;

$R_h$ is selected from the group consisting of C1–8 alkyl, aryl, C1–8 alkoxycarbonyl, aryloxycarbonyl, arylC1–8alkoxycarbonyl, carbamoyl wherein the nitrogen atom may be optionally mono or di-substituted with a group selected from C1–8 alkyl, C3–7 cycloalkyl, aryl, arylC1–8alkyl, heterocyclyl selected from the group consisting of pyrrolidinyl, piperdinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyrazinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, carboxy and cyano;

$R_8$ is a heteroaryl ring selected from the group consisting of furanyl, thienyl, pyrrolyl, oxazolyl, thiazolyl, imidazolyl, pyrazolyl, isoxazolyl, isothiazolyl, pyridyl, pyridazinyl, pyrimidinyl, pyrazinyl, triazinyl, indolizinyl, indolyl, isoindolyl, benzofuranyl, benzothienyl, indazolyl, benzimidazolyl, benzthiazolyl, benzoxazolyl, triazolyl, tetrazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl and phenazinyl, wherein any of the above $R_8$ can be optionally substituted by one or more $R_j$;

$R_j$ is selected from the group consisting of alkyl, cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, arylalkyl, alkoxy, aryloxy, arylalkoxy, alkoxycarbonyl, aryloxycarbonyl, alkanoyloxy, aroyloxy, carbamoyl wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkanoylamino, aroylamino, alkylthio wherein the sulfur atom may be oxidized to a sulfoxide or sulfone, arylthio wherein the sulfur atom may be oxidized to a sulfoxide or sulfone, arylalkylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinylor heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, C1–8 alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_j$ may be further optionally substituted by one or more $R_k$;

$R_k$ is selected from the group consisting of alkyl, cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkoxy, aryloxy, arylalkoxy, alkoxycarbonyl, aryloxycarbonyl, alkanoyloxy, aroyloxy, carbamoyl wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinylor heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkanoylamino, aroylamino, alkylthio wherein the sulfur atom maybe oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinylor heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, arylalkoxycarbonylamino, arylalkoxycarbonylaminoalkyl, C1–8 alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinylor heteroaryl selected from the group consisting of furanyl, thienyl, pyrrolyl, oxazolyl, thiazolyl, imidazolyl, isoxazolyl, isothiazolyl, oxadiazolyl, triazolyl, thiazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino;

X is O or S.

More preferred compounds of the formula (I) are those wherein:

Y is O or S;

$R_1$ is C1–5 alkyl, C3–7 cycloalkyl, phenyl, naphthyl, heterocyclyl selected from the group consisting of pyrrolidinyl, piperidinyl, morpholinyl, thiomorpholinyl, pyranyl, thiopyranyl, piperazinyl and indolinyl, heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl or amino wherein R1 is optionally substituted by one or more $R_b$;

$R_b$ is selected from the group consisting of C1–5 alkyl, C3–7 cycloalkyl, phenyl, naphthyl, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxy, aryloxy, C1–5 alkoxycarbonyl, aryloxycarbonyl, C1–5 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl; halogen, hydroxy, oxo, carboxy, cyano, nitro, amidino and guanidino, $R_b$ may be further optionally substituted by one or more $R_c$;

$R_c$ is selected from the group consisting of C1–5 alkyl, C3–6 cycloalkyl, aryl, heterocyclyl selected from the group consisting of piperidinyl, morpholinyl and piperazinyl; heteroaryl selected from the group consisting of furanyl, thienyl, pyrrolyl, oxazolyl, thiazolyl, imidazolyl, tetrazolyl and pyridinyl, C1–5 alkoxy, aryloxy, halogen, hydroxy, oxo, carboxy, cyano, nitro, amidino and guanidino;

$R_2$ is H or C1–3 alkyl;

$R_3$ is H, C1–5 alkyl, C3–7 cycloalkyl or aryl, wherein $R_3$ is optionally substituted by one or more $R_d$;

$R_d$ is selected from the group consisting of C1–5 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxy, aryloxy, C1–5alkanoyl, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinylor heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, heterocyclyl selected from the group consisting of pyrrolidinyl, piperidinyl, morpholinyl, thiomorpholinyl, piperazinyl and indolinyl or heteroaryl selected the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, halogen, hydroxy, oxo, carboxy, cyano, nitro, amidino and guanidino, $R_d$ may be further optionally substituted by one or more $R_e$;

$R_e$ is selected from the group consisting of C1–5 alkyl, C3–6 cycloalkyl, aryl, arylalkyl, C1–5 alkoxy, aryloxy, arylC1–5alkoxy, amyl, amino, halogen, hydroxy, oxo, carboxy, cyano, nitro, amidino and guanidino;

$R_4$ is H or C1–3 alkyl;

$R_5$ is H or C1–8 alkyl;

$R_6$ is H, C1–5 alkyl, C3–7 cycloalkyl or aryl wherein $R_6$ is optionally substituted by one or more $R_f$;

$R_f$ is selected from the group consisting of C1–5 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxy, aryloxy, arylC1–5alkoxy, heteroarylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, arylC1–5 alkylthio wherein the sulfur atom maybe oxidized to a sulfoxide or sulfone, ureido wherein either nitrogen atom may be independently substituted by C1–5alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxycarbonylamino, aryloxycarbonylamino, C–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, halogen, hydroxy, oxo, carboxy, cyano, nitro, amidino and guanidino, $R_f$ may be further optionally substituted by one or more $R_g$;

$R_g$ is selected from the group consisting of C1–5 alkyl, C3–7 cycloalkyl, aryl optionally substituted by halogen, methyl or methoxy; heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxy, aryloxy, arylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, halogen, hydroxy, oxo, carboxy, cyano, nitro, amidino and guanidino;

$R_h$ is selected from the group consisting of C1–5 alkyl, aryl, C1–5 alkoxycarbonyl, aryloxycarbonyl, arylC1–5alkoxycarbonyl, carbamoyl wherein the nitrogen atom may be optionally mono or di-substituted with a group selected from C1–5 alkyl, C3–7 cycloalkyl, aryl, arylC1–5alkyl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, halogen, hydroxy, carboxy and cyano;

$R_g$ is a heteroaryl ring selected from the group consisting of furanyl, thienyl, pyrrolyl, oxazolyl, thiazolyl, imidazolyl, pyrazolyl, isoxazolyl, isothiazolyl, pyridyl, pyridazinyl, pyrimidinyl, pyrazinyl, triazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl and phenazinyl, wherein any of the above $R_g$ can be optionally substituted by one or more $R_j$;

$R_j$ is selected from the group consisting of C1–8alkyl, C3–7cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl; arylC1–8alkyl, C1–8alkoxy, aryloxy, arylC1–8alkoxy, C1–8alkoxycarbonyl, aryloxycarbonyl, C1–8alkanoyloxy, aroyloxy, carbamoyl wherein the nitrogen atom may be independently mono or di-substituted by C1–8alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8alkanoylamino, aroylamino, C1–8alkylthio wherein the sulfur atom may be oxidized to a sulfoxide or sulfone, arylthio wherein the sulfur atom may be oxidized to a sulfoxide or sulfone, arylC1–8alkylthio wherein the sulfur atom may be oxidized to a sulfoxide or sulfone, ureido wherein either nitrogen atom may be independently substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, . benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, C1–8 alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazoyl, phenothiazinyl and phenoxazinyl, halogen, hydroxy, oxo, carboxy, cyano, nitro, amidino and guanidino, $R_j$ may be further optionally substituted by one or more $R_k$;

$R_k$ is selected from the group consisting of C1–8 alkyl, C3–7 cycloalkyl, aryl, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbaxolyl, phenothiazinyl and phenoxazinyl, C1–8 alkoxy, aryloxy, arylC1–8alkoxy, C1–8alkoxycarbonyl, aryloxycarbonyl, C1–8alkanoyloxy, aroyloxy, carbamoyl wherein the nitrogen atom may be independently mono or di-substituted by C1–8alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinoazolinyl, quinoxalinyl, carbazolyl, phenothiazinyl and phenoxazinyl, alkanoylamino, aroylamino, C1–8alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–8alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8alkoxycarbonylamino, aryloxycarbonylamino, arylC1–8alkoxycarbonylamino, arylalkoxycarbonylaminoC1–8-alkyl, C1–8 alkylcarbamoyloxy, arylcarbamoyloxy, C1–8-alkylsulfonylamino arylsulfonylamino, C1–8-alkylaminosulfonyl, arylaminosulfonyl, amino wherein the nitrogen atom may be independently mono or di-substituted by C1–8alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and quanidino.

Even more preferred compounds of the formula (I) are those wherein:

Y is O;

$R_1$ is C1–5 alkyl, C3–7 cycloalkyl, phenyl, naphthyl, heterocyclyl selected from the group consisting of piperidinyl, morpholinyl, thiomorpholinyl, piperazinyl, pyranyl and thiopyranyl, heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, or amino wherein $R_1$ is optionally substituted by one or more $R_b$;

$R_b$ is selected from the group consisting of C1–5 alkyl, C3–7 cycloalkyl, phenyl, naphthyl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl and isoquinolinyl; C1–5 alkoxy, aryloxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenyl, naphthyl, heterocyclyl selected from the group consisting of pyrrolidinyl, piperidinyl, morpholinyl, piperazinyl and indolinyl, or heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl and isoquinolinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl or aryl; C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, halogen, hydroxy, oxo, carboxy, cyano and nitro, $R_b$ may be further optionally substituted by one or more $R_c$;

$R_c$ is selected from the group consisting of C1–5 alkyl, C3–6 cycloalkyl, aryl, C1–5 alkoxy, aryloxy, halogen, hydroxy, oxo, carboxy, and cyano;

$R_2$ is H or methyl;

$R_3$ is H, C1–5 alkyl, C3–7 cycloalkyl or phenyl, wherein $R_3$ is optionally substituted by one or more $R_d$;

$R_d$ is selected from the group consisting of C1–3 alkyl, C3–6 cycloalkyl, phenyl, naphthyl, heterocyclyl selected from the group consisting of piperidinyl, morpholinyl and piperazinyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1–5 alkoxy, aryloxy, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, phenyl, naphthyl, heterocyclyl selected from the group consisting of piperidinyl, morpholinyl and piperazinyl or heteroaryl selected the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, halogen, hydroxy, oxo, carboxy and cyano, $R_4$ may be further optionally substituted by one or more $R_e$;

$R_e$ is selected from the group consisting of C1–5 alkyl, C3–6 cycloalkyl, aryl, arylC1–5alkyl, C1–5 alkoxy, aryloxy, arylC1–3alkoxy, aroyl, amino, halogen, hydroxy, oxo, carboxy and cyano;

$R_4$ is H or methyl;

$R_5$ is H or C1–5 alkyl;

$R_6$ is H, C1–5 alkyl, C3–7 cycloalkyl, phenyl or naphthyl wherein $R_6$ is optionally substituted by one or more $R_f$;

$R_f$ is selected from the group consisting of C1–5 alkyl, C3–7 cycloalkyl, phenyl, naphthyl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinozolinyl and quinoxalinyl, C1–5 alkoxy, aryloxy, arylC1–5alkoxy, pyridylC1–5alkoxy, thienylC1–5alkoxy, furanylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, arylC1–5 alkylthio wherein the sulfur atom may be oxidized to a sulfoxide or sulfone, ureido wherein either nitrogen atom may be independently substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, halogen, hydroxy, oxo, carboxy and cyano, $R_f$ may be further optionally substituted by one or more $R_g$;

$R_g$ is selected from the group consisting of C1–5 alkyl, C3–7 cycloalkyl, phenyl optionally substituted by halogen, methyl or methoxy; naphthyl optionally substituted by halogen, methyl or methoxy; heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuanyl, benzothienyl, benzimidazolyl, benzthiazolyl, benzoxazolyl, quinolinyl, isoquinolinyl, quinozaolinyl and quinoxalinyl, C1–5 alkoxy, aryloxy, arylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl, isoquinolinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, halogen, hydroxy, oxo, carboxy and cyano;

$R_h$ is selected from the group consisting of C1–5 alkyl, phenyl, naphthyl, C1–5 alkoxycarbonyl, aryloxycarbonyl, arylC1–3alkoxycarbonyl, carbamoyl wherein the nitrogen atom may be optionally mono or di-substituted with a group selected from C1–5 alkyl, C3–6 cycloalkyl, phenyl, naphthyl, arylC1–3alkyl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, halogen, hydroxy, carboxy and cyano;

Z is O or S;

$R_8$ is a heteroaryl ring selected from the group consisting of furanyl, thienyl, pyrrolyl, oxazolyl, thiazolyl, imidazolyl, pyrazolyl, isoxazolyl, isothiazolyl, pyridyl, pyridazinyl, pyrimidinyl, pyrazinyl, triazinyl, indolizinyl, indolyl, isoindolyl, benzofuranyl, benzothienyl, indazolyl, benzimidazolyl, benzthiazolyl, benzoxazolyl, purinyl, quinolinzinyl, quinolinyl, isoquinolinyl, cinnolinyl, phthalazinyl, quinozolinyl, quinoxalinyl, naphthyridinyl, pteridinyl, carbazolyl, acridinyl and phenazinyl, wherein any of the above $R_8$ can be optionally substituted by one or more groups of the formula $R_j$;

$R_j$ is selected from the group consisting of C1–5alkyl, C3–6cycloalkyl, phenyl, naphthyl, heterocyclyl selected from the group consisting of piperidinyl, morpholinyl and piperazinyl; heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl and isoquinolinyl, arylC1–5alkyl, C1–5alkoxy, aryloxy, arylC1–5alkoxy, C1–5alkoxycarbonyl, aryloxycarbonyl, C1–5alkanoyloxy, aroyloxy, carbamoyl wherein the nitrogen atom may be independently mono or di-substituted by C1–5alkyl, aryl, heterocyclyl selected from the group consisting of piperidinyl, morpholinyl and piperazinylor heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl and isoquinolinyl, C1–5alkanoylamino, aroylamino, C1–5alkylthio wherein the sulfur atom may be oxidized to a sulfoxide or sulfone, arylthio wherein the sulfur atom may be oxidized to a sulfoxide or sulfone, arylC1–5alkylthio wherein the sulfur atom may be oxidized to a sulfoxide or sulfone, ureido wherein either nitrogen atom may be independently substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl and isoquinolinyl, C1–5alkoxycarbonylamino, aryloxycarbonylamino C1–5 alkylcarbamoyloxy, arylcarbamoyloxy, C1–5alkylsulfonylamino, arylsulfonylamino, C1–5alkylaminosulfonyl, arylaminosulfonyl, amino wherein the nitrogen atom may be independently mono or di-substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, purinyl, quinolinyl and isoquinolinyl, halogen, hydroxy, oxo, carboxy, cyano, nitro, amidino and quanidino, Rj may be further optionally substituted by one or more $R_k$;

$R_k$ is selected from the group consisting of C1–3 alkyl, C3–6 cycloalkyl, phenyl, naphthyl, heterocyclyl selected from the group consisting of piperidinyl, morpholinyl and piperazinyl; heteroaryl selected from the group consisting of furanyl, thienyl, pyrrolyl, tetrazolyl and pyridinyl, C1–3 alkoxy, aryloxy, arylC1–3alkoxy, C1–3alkoxycarbonyl, aryloxycarbonyl, C1–3alkanoyloxy, aroyloxy, carbamoyl wherein the nitrogen atom may be independently mono or di-substituted by C1–3 alkyl, aryl, heterocyclyl selected from the group consisting of morpholinyl and piperazinyl or heteroaryl selected from the group consisting of furanyl, thienyl, pyrrolyl, oxazolyl, thiazolyl, imidazolyl, tetrazolyl, and pyridinyl, C1–3alkanoylamino, aroylamino, C1–3alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3alkyl, phenyl, naphthylor heteroaryl selected from the group consisting of furanyl, thienyl, pyrrolyl, oxazolyl, thiazolyl, imidazolyl, tetrazolyl and pyridinyl, C1–3alkoxycarbonylamino, aryloxycarbonylamino, arylC1–3alkoxycarbonylamino, benzyloxycarbonylaminoC1–5alkyl, C1–3alkylcarbamoyloxy, arylcarbamoyloxy, C1–3alkylsulfonylamino, arylsulfonylamino, C1–3alkylaminosulfonyl, arylaminosulfonyl, amino wherein the nitrogen atom may be independently mono or di-substituted by C1–3alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, tetrazolylpyridinyl, indolyl, benzofuranyl, benzothienyl, benzimidazolyl, benzthiazolyl, benzoxazolyl, quinolinyl and isoquinolinyl, halogen, hydroxy, oxo, carboxy, cyano and nitro;

and

X is O.

Yet even more preferred compounds of the formula (I) are those wherein:

$R_1$ is C1–5 alkyl, C3–6 cycloalkyl, phenyl, naphthyl, heterocyclyl selected from the group consisting of piperidinyl, morpholinyl, piperazinyl, pyranyl and thiopyranyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, or amino, wherein $R_1$ is optionally substituted by one or more $R_b$;

$R_b$ is selected from the group consisting of C1–3 alkyl, C3–6 cycloalkyl, phenyl, naphthyl, heterocyclyl selected from the group consisting of pyrrolidinyl, piperidinyl, morpholinyl and piperazinyl, heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl and isoquinolinyl, C1–3 alkoxy, phenoxy, C1–3 alkoxycarbonyl, aryloxycarbonyl, C1–5 alkanoyloxy, aroyloxy, carbamoyl wherein the nitrogen atom may be independently mono or di-substituted by C1–5 alkyl, phenylor heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5alkyl, phenyl or naphthyl; C1–5 alkoxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, halogen, hydroxy, oxo, carboxy and cyano, $R_b$ may be further optionally substituted by one or more $R_c$;

$R_c$ is selected from the group consisting of C1–3 alkyl, C5–6 cycloalkyl, aryl, C1–3 alkoxy, phenoxy, halogen, hydroxy, oxo, carboxy and cyano;

$R_2$ is H;

$R_3$ is C1–5 alkyl, C3–6 cycloalkyl or phenyl, wherein $R_3$ is optionally substituted by one or more $R_d$;

$R_d$ is selected from the group consisting of C1–3 alkyl, C3–6 cycloalkyl, phenyl, naphthyl, heterocyclyl selected from the group consisting of piperidinyl, morpholinyl and piperazinyl; heteroaryl selected from the group consisting of furanyl, thienyl, thiazolyl, imidazolyl, pyridinyl, indolyl, quinolinyl and isoquinolinyl, C1–5 alkoxy, phenoxy, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, C1–5 alkanoylamino, aroylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl or heteroaryl selected the group consisting of furanyl, thienyl, pyrrolyl, oxazolyl, thiazolyl, imidazolyl, pyridinyl and indolyl, C1–5 alkoxycarbonylamino, C1–5 alkylcarbamoyloxy, arylcarbamoyloxy, C1–5 alkylsulfonylamino, arylsulfonylamino, amino wherein the nitrogen atom may be independently mono or di-substituted by C1–3 alkyl, phenyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, halogen, hydroxy, oxo, carboxy and cyano, $R_d$ may be further optionally substituted by one or more $R_e$;

$R_e$ is selected from the group consisting of C1–5 alkyl, C5–6 cycloalkyl, phenyl, naphthyl, arylC1–3alkyl, C1–5 alkoxy, phenoxy, arylC1–3alkoxy, aroyl, amino, halogen, hydroxy, oxo, carboxy and cyano; wherein the configuration at the stereocenter defined by $R_2$ and $R_3$ and the carbon they are attached to is L;

$R_4$ is H;

$R_5$ is H or C1–3 alkyl;

$R_6$ is H, C1–5 alkyl, C3–6 cycloalkyl or phenyl, wherein $R_6$ is optionally substituted by one or more $R_f$;

$R_f$ is selected from the group consisting of C1–3 alkyl, C3–6 cycloalkyl, phenyl, naphthyl, heterocyclyl selected from the group consisting of pyrrolidinyl, piperidinyl, morpholinyl and piperazinyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1–5 alkoxy, aryloxy, arylC1–3alkoxy, pyridylC1–5alkoxy, thienylC1–5alkoxy, furanylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenylor heteroaryl selected from the group consisting of furanyl, thienyl, pyrrolyl, oxazolyl, thiazolyl, imidazolyl, pyridinyl and indolyl, C1–5 alkanoylamino, aroylamino, C1–3 alkylthio wherein the sulfur atom may be oxidized to a sulfoxide or sulfone, arylthio wherein the sulfur atom may be oxidized to a sulfoxide or sulfone, arylC1–3alkylthio wherein the sulfur atom may be oxidized to a sulfoxide or sulfone, ureido wherein either nitrogen atom may be independently substituted by C1–5 alkyl or phenyl; C1–5 alkoxycarbonylamino, C1–5 alkylsulfonylamino, arylsulfonylamino, amino wherein the nitrogen atom may be independently mono or di-substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, halogen, hydroxy, oxo, carboxy and cyano, Rf may be further optionally substituted by one or more $R_g$;

$R_g$ is selected from the group consisting of C1–3 alkyl, C5–6 cycloalkyl, phenyl optionally substituted by halogen, methyl or methoxy; heterocyclyl selected from the group consisting of pyrrolidinyl, piperidinyl, morpholinyl and piperazinyl; heteroaryl selected from the group consisting of furanyl, thienyl, pyrrolyl, oxazolyl, thiazolyl, imidazolyl, pyridinyl, pyrimidinyl, pyrazinyl and indolyl, C1–5 alkoxy, aryloxy, arylC1–3alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl or aryl; C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl or aryl; C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl or aryl; halogen, hydroxy, oxo, carboxy and cyano;

$R_h$ is selected from the group consisting of C1–5 alkyl, phenyl, C1–5 alkoxycarbonyl, aryloxycarbonyl, arylC1–3alkoxycarbonyl, carbamoyl wherein the nitrogen atom may be optionally mono or di-substituted with C1–5 alkyl, C3–6 cycloalkyl, phenyl, naphthyl, arylC1–3alkyl, halogen, hydroxy, carboxy and cyano; wherein Z is O;

$R_g$ is a heteroaryl ring selected from the group consisting of oxazolyl, thiazolyl, imidazolyl, pyrazolyl, isoxazolyl, isothiazolyl, pyridyl, pyridazinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, wherein any of the above $R_g$ can be optionally substituted by one or more $R_j$;

Rj is selected from the group consisting of C1–3 alkyl, C5–6 cycloalkyl, phenyl, naphthyl, morpholinyl, piperazinyl, furanyl, thienyl, pyrrolyl, tetrazolyl, pyridinyl, indolyl, benzofuranyl, benzothienyl, benzimidazolyl, benzthiazolyl, benzoxazolyl, arylC1–3alkyl, C1–3alkoxy, aryloxy, arylC1–3alkoxy, C1–3alkoxycarbonyl, aryloxycarbonyl, C1–3alkanoyloxy, aroyloxy, carbamoyl wherein the nitrogen atom may be independently mono or di-substituted by C1–3alkyl, phenyl, naphthyl, piperidinyl, furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl or isoquinolinyl; C1–3alkanoylamino, aroylamino, C1–3alkylthio wherein the sulfur atom may be oxidized to a sulfoxide or sulfone, arylthio wherein the sulfur atom may be oxidized to a sulfoxide or sulfone, arylC1–3alkylthio wherein the sulfur atom may be oxidized to a sulfoxide or sulfone, ureido wherein either nitrogen atom may be independently substituted by C1–3 alkyl, phenyl, naphthyl, piperidinyl, morpholinyl, thiazolyl, imidazolyl, tetrazolyl, pyridinyl, indolyl, benzofuranyl, benzothienyl, benzimidazolyl, benzthiazolyl, benzoxazolyl, quinolinyl or isoquinolinyl; C1–3 alkoxycarbonylamino, aryloxycarbonylamino, C1–3 alkylcarbamoyloxy, arylcarbamoyloxy, C1–3alkylsulfonylamino, arylsulfonylamino, C1–3alkylaminosulfonyl, arylaminosulfonyl, amino wherein the nitrogen atom may be independently mono or di-substituted by C1–3 alkyl, phenyl, naphthyl, piperidinyl, furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl or isoquinolinyl; halogen, hydroxy, oxo, carboxy, cyano and nitro, $R_j$ may be further optionally substituted by one or more $R_k$;

$R_k$ is selected from the group consisting of methyl, C5–6 cycloalkyl, phenyl, morpholinyl, furanyl, thienyl, pyrrolyl, tetrazolyl, pyridinyl, methoxy, phenoxy, benzyloxy, methoxycarbonyl, acetyloxy, benzoyloxy, carbamoyl wherein the nitrogen atom may be independently mono or di-substituted by C1–3 alkyl, phenyl, furanyl, thienyl, pyrrolyl, oxazolyl, thiazolyl, imidazolyl or pyridinyl; acetylamino, benzoylamino, methylthio wherein the sulfur atom may be oxidized to a sulfoxide or sulfone, ureido wherein either nitrogen atom may be independently substituted by methyl, phenyl, furanyl, thienyl, pyrrolyl, oxazolyl, thiazolyl, imidazolyl or pyridinyl; arylC1–3alkoxycarbonylamino, benzyloxycarbonylaminoC1–5alkyl, amino wherein the nitrogen atom may be independently mono or di-substituted by C1–3alkyl, phenyl, naphthyl, furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl or isoquinolinyl, halogen, hydroxy, oxo, carboxy, cyano and nitro.

Still yet even more preferred compounds of the formula (I) are those wherein:

$R_1$ is C1–3 alkyl, C5–6 cycloalkyl, phenyl, naphthyl, heterocyclyl selected from the group consisting of piperidinyl, morpholinyl, piperazinyl, pyranyl and thiopyranyl; heteroaryl selected from the group consisting of furanyl, thienyl, pyrrolyl, oxazolyl, thiazolyl, imidazolyl, pyridinyl and indolyl, or amino, wherein $R_1$ is optionally substituted by one or more $R_b$;

$R_b$ is selected from the group consisting of C1–3 alkyl, C5–6 cycloalkyl, phenyl, heterocyclyl selected from the group consisting of piperidinyl, morpholinyl and piperazinyl; heteroaryl selected from the group consisting of furanyl, thienyl, pyrrolyl, imidazolyl, tetrazolyl, pyridinyl, indolyl, benzofuranyl, benzothienyl, benzimidazolyl, benzthiazolyl, benzoxazolyl, quinolinyl and isoquinolinyl, C1–3 alkoxy, C1–3 alkoxycarbonyl, aryloxycarbonyl, C1–5 alkanoyloxy, aroyloxy, carbamoyl wherein the nitrogen atom may be independently mono or di-substituted by C1–3 alklyl, phenylor heteroaryl selected from the group consisting of pyrrolyl, imidazolyl, pyridinyl, indolyl, benzofuranyl, benzothienyl, benzimidazolyl and benzthiazolyl; C1–5 alkanoylamino, aroylamino, C1–3 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl or phenyl; C1–5 alkylsulfonylamino, arylsulfonylamino, amino wherein the nitrogen atom may be independently mono or di-substituted by C1–3alkyl, phenyl, heterocyclyl selected from the group consisting of piperidinyl, morpholinyl and piperazinylor heteroaryl selected from the group consisting of pyrrolyl, imidazolyl, pyridinyl, indolyl, benzofuranyl, benzothienyl, benzimidazolyl, benzthiazolyl, benzoxazolyl, quinolinyl and isoquinolinyl; halogen, hydroxy, oxo, carboxy and cyano, $R_b$ may be further optionally substituted by one or more $R_c$;

$R_c$ is selected from the group consisting of C1–3 alkyl, C5–6 cycloalkyl, C1–3 alkoxy, halogen and hydroxy;

$R_3$ is C1–5 alkyl, C5–6 cycloalkyl or phenyl wherein $R_3$ is optionally substituted by one or more $R_d$;

$R_d$ is selected from the group consisting of C1–3 alkyl, C3–6 cycloalkyl, phenyl, naphthyl, 4-piperidinyl, 4-morpholinyl, piperazinyl, furanyl, thienyl, thiazolyl, imidazolyl, pyridinyl, indolyl, C1–5 alkoxy, phenoxy, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl or phenyl; C1–5 alkanoylamino, C1–3 alkylthio wherein the sulfur atom may be oxidized to a sulfoxide or sulfone, ureido wherein either the nitrogen atom may be independently substituted by C1–3 alkyl or phenyl; C1–5 alkoxycarbonylamino, C1–5 alkylsulfonylammino, arylsulfonylamino, amino wherein the nitrogen atom may be independently mono or di-substituted by C1–3 alkyl or phenyl; halogen, hydroxy, oxo, carboxy and cyano, $R_d$ may be further optionally substituted by one or more $R_e$;

$R_e$ is selected from the group consisting of C1–5 alkyl, C5–6 cycloalkyl, phenyl, benzyl, C1–5 alkoxy, phenoxy, benzyloxy, aroyl, halogen, hydroxy, oxo, carboxy and cyano;

$R_6$ is H, C1–5 alkyl or phenyl wherein $R_6$ is optionally substituted by one or more $R_f$;

$R_f$ is selected from the group consisting of C1–3 alkyl, C3–6 cycloalkyl, phenyl, naphthyl, furanyl, thienyl, thiazolyl, imidazolyl, pyridinyl, indolyl, C1–3 alkoxy, benzyloxy, pyridyl, C1–3alkoxy, thienylC1–3alkoxy, furanylC1–3alkoxy, C1–3 alkoxycarbonyl, phenoxyoxycarbonyl, C1–5 alkanoyloxy, aroyloxy, carbamoyl wherein the nitrogen atom may be independently mono or di-substituted by C1–3 alkyl or phenyl; C1–5 alkanoylamino, aroylamino, methylthio wherein the sulfur atom may be oxidized to a sulfoxide or sulfone, benzylthio wherein the sulfur atom may be oxidized to a sulfoxide or sulfone, ureido wherein either nitrogen atom may be independently substituted by C1–5 alkyl or phenyl; C1–3 alkoxycarbonylamino, amino wherein the nitrogen atom may be independently mono or di-substituted by C1–5 alkyl or phenyl; halogen, hydroxy, oxo, carboxy and cyano, $R_f$ may be further optionally substituted by one or more $R_g$;

$R_g$ is selected from the group consisting of C1–3 alkyl, phenyl optionally substituted by halogen, methyl or methoxy; heterocyclyl selected from the group consisting of piperidinyl, morpholinyl and piperazinyl; heteroaryl selected from the group consisting of furanyl, thienyl, pyrrolyl and pyridinyl, C1–3 alkoxy, aryloxy, benzyloxy, C1–5 alkoxycarbonyl, C1–5 alkanoyloxy, aroyloxy, carbamoyl wherein the nitrogen atom may be independently mono or di-substituted by C1–5 alkyl or phenyl; C1–5 alkanoylamino, aroylamino, C1–5 alkylthio wherein the sulfur atom may be oxidized to a sulfoxide or sulfone, ureido wherein either nitrogen atom may be independently substituted by C1–5 alkyl or phenyl; C1–5 alkoxycarbonylamino, C1–5 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–3 alkyl or phenyl; halogen, hydroxy, oxo, carboxy and cyano;

$R_h$ is selected from the group consisting of C1–3 alkyl, phenyl, C1–3 alkoxycarbonyl, phenoxyoxycarbonyl, benzyloxy, carbamoyl wherein the nitrogen atom may be optionally mono or di-substituted with C1–5 alkyl, phenyl, benzyl, halogen, hydroxy, carboxy and cyano;

$R_8$ is a heteroaryl ring selected from the group consisting of oxazolyl, thiazolyl, imidazolyl, pyridyl, indolyl, benzofuranyl, benzothienyl, benzimidazolyl, benzthiazolyl, benzoxazolyl, quinolinyl and isoquinolinyl, wherein any of the above $R_8$ can be optionally substituted by one or more $R_j$;

$R_j$ is selected from the group consisting of C1–3 alkyl, C5–6 cycloalkyl, phenyl, naphthyl, morpholinyl, piperazinyl, furanyl, thienyl, pyrrolyl, tetrazolyl, pyridinyl, benzyl, C1–3alkoxy, phenoxy, benzyloxy, C1–3alkoxycarbonyl, acetyloxy, benzoyloxy, carbamoyl wherein the nitrogen atom may be independently mono or di-substituted by methyl, phenyl, furanyl, thienyl, pyrrolyl, oxazolyl, thiazolyl, imidazolyl or pyridinyl; acetylamino, benzoylamino, methylthio wherein the sulfur atom may be oxidized to a sulfoxide or sulfone, benzylthio wherein the sulfur atom may be oxidized to a sulfoxide or sulfone, ureido wherein either nitrogen atom may be independently substituted by methyl, phenyl, thiazolyl, imidazolyl or pyridinyl; C1–3 alkoxycarbonylamino, C1–3 alkylcarbamoyloxy, arylcarbamoyloxy, C1–3alkylsulfonylamino, arylsulfonylamino, amino wherein the nitrogen atom may be independently mono or di-substituted by methyl, phenyl, furanyl, thienyl, pyrrolyl, oxazolyl, thiazolyl, imidazolyl or pyridinyl; halogen, hydroxy, carboxy, cyano and nitro, $R_j$ may be further optionally substituted by one or more $R_k$;

$R_k$ is selected from the group consisting of methyl, C5–6 cycloalkyl, phenyl, furanyl, thienyl, pyrrolyl, pyridinyl, methoxy, phenoxy, benzyloxy, methoxycarbonyl, acetyloxy, benzoyloxy, carbamoyl wherein the nitrogen atom may be independently mono or di-substituted by methyl, phenyl, furanyl or thienyl; acetylamino, benzoylamino, methylthio wherein the sulfur atom may be oxidized to a sulfoxide or sulfone, ureido wherein either nitrogen atom may be independently substituted by methyl, phenyl, furanyl, thienyl, pyrrolyl, oxazolyl and thiazolyl, benzyloxycarbonylamino, benzyloxycarbonylaminoC1–5alkyl, amino wherein the nitrogen atom may be independently mono or di-substituted by C1–3alkyl, phenyl, furanyl, thienyl, pyrrolyl, oxazolyl, thiazolyl, imidazolyl and pyridinyl, halogen, hydroxy, carboxy, cyano and nitro.

Even much more preferred compounds of the formula (I) are those wherein:

$R_1$ is C5–6 cycloalkyl, phenyl, naphthyl, piperidinyl, morpholinyl, piperazinyl, furanyl, thienyl, pyrrolyl, pyranyl, thiopyranyl or amino wherein $R_1$ is optionally substituted by one or more $R_b$;

$R_b$ is selected from the group consisting of C1–3 alkyl, C5–6 cycloalkyl, phenyl, furanyl, thienyl, pyrrolyl, imidazolyl, indolyl, benzofuranyl, benzothienyl, benzimidazolyl, benzthiazolyl, benzoxazolyl, C1–3 alkoxy, C1–3 alkoxycarbonyl, carbamoyl wherein the nitrogen atom may be independently mono or di-substituted by C1–3 alkyl or phenyl; C1–5 alkanoylamino, aroylamino, ureido wherein either nitrogen atom may be independently substituted by C1–3alkyl or phenyl; C1–5 alkylsulfonylamino, arylsulfonylamino, amino wherein the nitrogen atom may be independently mono or di-substituted by C1–3alkyl or phenyl; halogen, hydroxy, oxo, carboxy and cyano, $R_b$ may be further optionally substituted by one or more $R_c$;

$R_c$ is selected from the group consisting of C1–3 alkyl, C1–3 alkoxy, halogen and hydroxy;

$R_d$ is selected from the group consisting of C1–3 alkyl, C3–6 cycloalkyl, phenyl, naphthyl, 4-piperidinyl, furanyl, thienyl, thiazolyl, imidazolyl, pyridinyl, indolyl, C1–3alkoxy, C1–5alkoxycarbonyl, C1–5alkanoyloxy, benzoyloxy, carbamoyl wherein the nitrogen atom may be independently mono or di-substituted by C1–3alkyl or phenyl; C1–5alkanoylamino, C1–3 alkylthio wherein the sulfur atom may be oxidized to a sulfoxide or sulfone, C1–3alkoxycarbonylamino, C1–3alkylsulfonylamino, amino wherein the nitrogen atom may be independently mono or di-substituted by C1–3 alkyl or phenyl, halogen, hydroxy, oxo, carboxy and cyano, $R_d$ may be further optionally substituted by one or more $R_e$;

$R_e$ is selected from the group consisting of C1–3 alkyl, phenyl, benzyl, C1–3 alkoxy, phenoxy, benzyloxy, benzoyl, halogen, hydroxy, oxo, carboxy and cyano;

$R_5$ is H or methyl;

$R_6$ is C1–5 alkyl or phenyl, wherein $R_6$ is optionally substituted by one or more groups of the formula $R_f$, $R_f$ is selected from the group consisting of methyl, C3–6 cycloalkyl, phenyl, naphthyl, furanyl, thienyl, thiazolyl, imidazolyl, pyridinyl, indolyl, C1–3 alkoxy, benzyloxy, C1–5 alkanoylamino, aroylamino, methylthio wherein the sulfur atom may be oxidized to a sulfoxide or sulfone, benzylthio wherein the sulfur atom may be oxidized to a sulfoxide or sulfone, C1–3 alkoxycarbonylamino, amino wherein the nitrogen atom may be independently mono or di-substituted by C1–5 alkyl or phenyl; halogen, hydroxy, oxo, carboxy and cyano, $R_f$ may be further optionally substituted by one or more $R_g$;

$R_g$ is selected from the group consisting of C1–3 alkyl, phenyl optionally substituted by halogen or methyl; C1–3 alkoxy, aryloxy, benzyloxy, C1–3 alkoxycarbonyl, carbamoyl wherein the nitrogen atom may be independently mono or di-substituted by C1–3 alkyl or phenyl; C1–5 alkanoylamino, aroylamino, amino wherein the nitrogen atom may be independently mono or di-substituted by C1–3 alkyl or phenyl; halogen, hydroxy, oxo, carboxy and cyano;

$R_h$ is selected from the group consisting of C1–3 alkyl, phenyl, C1–3 alkoxycarbonyl, benzyloxy and carboxy;

$R_8$ is a heteroaryl ring selected from the group consisting of oxazolyl, thiazolyl, imidazolyl, pyridyl, benzimidazolyl, benzthiazolyl and benzoxazolyl, wherein any of the above $R_8$ can be optionally substituted by one or more $R_j$;

$R_j$ is selected from the group consisting of methyl, cyclohexyl, phenyl, furanyl, thienyl, benzyl, methoxy, phenoxy, benzyloxy, methoxycarbonyl, acetyloxy, benzoyloxy, carbamoyl wherein the nitrogen atom may be independently mono or di-substituted by methyl, phenyl, furanyl or thienyl; acetylamino, benzoylamino, ureido wherein either nitrogen atom may be independently substituted by methyl or phenyl; methoxycarbonylamino, C1–3 alkylsulfonylamino, arylsulfonylamino, amino wherein the nitrogen atom may be independently mono or di-substituted by methyl, phenyl, furanyl or thienyl; halogen, hydroxy, carboxy and cyano, $R_j$ may be further optionally substituted by one or more $R_k$;

$R_k$ is selected from the group consisting of methyl, phenyl, furanyl, thienyl, methoxy, phenoxy, benzyloxy, methoxycarbonyl, acetyloxy, benzoyloxy, carbamoyl wherein the nitrogen atom may be independently mono or di-substituted by methyl or phenyl; acetylamino, benzoylamino, ureido wherein either nitrogen atom may be independently substituted by methyl or phenyl; benzyloxycarbonylamino, benzyloxycarbonylaminoC1–3alkyl, amino wherein the nitrogen atom may be independently mono or di-substituted by C1–3alkyl, phenyl, furanyl or thienyl; halogen, hydroxy, carboxy, cyano and nitro.

Yet even more preferred compounds of the formula (I) are those wherein:

A is —C(O)— or —SO$_2$—;

$R_1$ is cyclohexyl, phenyl, naphthyl, piperidinyl, morpholinyl, piperazinyl, pyranyl, thiopyranyl or amino, wherein R1 is optionally substituted by one or more $R_b$;

$R_b$ is selected from the group consisting of C1–3 alkyl, C5–6 cycloalkyl, phenyl, furanyl, thienyl, pyrrolyl, imidazolyl, indolyl, benzofuranyl, benzothienyl, benzimidazolyl, benzthiazolyl, benzoxazolyl, C1–3 alkoxy, C1–3 alkoxycarbonyl, carbamoyl wherein the nitrogen atom may be independently mono or di-substituted by C1–3 alkyl or phenyl; C1–5 alkanoylamino, aroylamino, C1–5 alkylsulfonylamino, arylsulfonylamino, amino wherein the nitrogen atom may be independently mono or di-substituted by C1–3 alkyl; halogen, hydroxy, oxo, carboxy and cyano, $R_b$ may be further optionally substituted by one or more $R_c$;

$R_c$ is selected from the group consisting of C1–3 alkoxy, halogen and hydroxy;

$R_3$ is C1–5 alkyl or C5–6 cycloalkyl, wherein $R_3$ is optionally substituted by one or more $R_d$;

$R_d$ is selected from the group consisting of methyl, C3–6 cycloalkyl, phenyl, thienyl, imidazolyl, pyridinyl, indolyl, C1–4 alkoxy, C1–5 alkanoylamino, methylthio wherein the sulfur atom may be oxidized to a sulfoxide or sulfone, halogen, hydroxy, oxo, carboxy and cyano, $R_d$ may be further optionally substituted by one or more $R_e$;

$R_e$ is selected from the group consisting of methyl, phenyl, benzyl, methoxy, phenoxy, benzyloxy, benzoyl, halogen and hydroxy;

$R_f$ is selected from the group consisting of C3–6 cycloalkyl, phenyl, naphthyl, thienyl, imidazolyl, pyridinyl, indolyl, methoxy, benzyloxy, C1–3 alkanoylamino, methylthio wherein the sulfur atom may be oxidized to a sulfoxide or sulfone, benzylthio wherein the sulfur atom may be oxidized to a sulfoxide or sulfone, methoxycarbonylamino, amino wherein the nitrogen atom may be independently mono or di-substituted by C1–3 alkyl; halogen, hydroxy, carboxy and cyano, $R_f$ may be further optionally substituted by one or more $R_g$;

$R_g$ is selected from the group consisting of methyl, phenyl optionally substituted by halogen or methyl; methoxy, phenoxy, benzyloxy, methoxycarbonyl, amino wherein the nitrogen atom may be independently mono or di-substituted by C1–3 alkyl or phenyl; halogen, hydroxy and carboxy;

$R_8$ is a heteroaryl ring selected from the group consisting of oxazolyl, thiazolyl, imidazolyl, pyridyl, benzthiazolyl and benzoxazolyl, wherein any of the above $R_8$ can be optionally substituted by one or more $R_j$;

$R_j$ is selected from the group consisting of methyl, phenyl, furanyl, thienyl, benzyl, methoxy, methoxycarbonyl, acetyloxy, benzoyloxy, carbamoyl wherein the nitrogen atom may be independently mono or di-substituted by methyl or phenyl; acetylamino, benzoylamino, ureido wherein either nitrogen atom may be independently substituted by methyl or phenyl; methoxycarbonylamino, amino wherein the nitrogen atom may be independently mono or di-substituted by methyl or phenyl; halogen, hydroxy, carboxy and cyano, $R_j$ may be further optionally substituted by one or more $R_k$;

$R_k$ is selected from the group consisting of methyl, phenyl, methoxy, phenoxy, benzyloxy, methoxycarbonyl, carbamoyl wherein the nitrogen atom may be independently mono or di-substituted by methyl or phenyl; ureido wherein either nitrogen atom may be independently substituted by methyl or phenyl; benzyloxycarbonylamino, enzyloxycarbonylaminoC1–5alkyl, amino wherein the nitrogen atom may be independently mono or di-substituted by C1–3alkyl, phenyl, furanyl or thienyl; halogen, hydroxy, carboxy, cyano and nitro.

Penultimately preferred compounds of the formula (I) are those wherein:

$R_1$ is cyclohexyl, phenyl, naphthyl, piperidinyl, morpholinyl, piperazinyl, pyranyl or thiopyranyl, wherein $R_1$ is optionally substituted by one or more $R_b$;

$R_b$ is selected from the group consisting of, pyrrolyl, imidazolyl, indolyl, benzimidazolyl, methoxy, methoxycarbonyl, amino wherein the nitrogen atom may be independently mono or di-substituted by C1–3 alkyl; halogen, hydroxy and carboxy, $R_b$ may be further optionally substituted by one or more $R_c$;

$R_c$ is selected from the group consisting of methoxy, halogen and hydroxy;

$R_d$ is selected from the group consisting of methyl, C3–6 cycloalkyl, phenyl, C1–4 alkoxy, C1–3 alanoylamino, methylthio wherein the sulfur atom may be oxidized to a sulfoxide or sulfone, halogen, hydroxy, oxo, carboxy and cyano, $R_d$ may be further optionally substituted by one or more $R_e$;

$R_e$ is selected from the group consisting of methyl, phenyl, methoxy, halogen and hydroxy;

$R_5$ is H;

$R_f$ is selected from the group consisting of C5–6 cycloalkyl, phenyl, naphthyl, thienyl, indolyl, methoxy, methylthio wherein the sulfur atom may be oxidized to a sulfoxide or sulfone, methoxycarbonylamino, halogen, hydroxy, carboxy and cyano, $R_f$ may be further optionally substituted by one or more $R_g$;

$R_g$ is selected from the group consisting of methyl, phenyl optionally substituted by halogen; methoxy, phenoxy, benzyloxy, methoxycarbonyl, halogen, hydroxy and carboxy;

$R_8$ is a heteroaryl ring selected from the group consisting of oxazolyl, pyridyl, benzthiazolyl and benzoxazolyl, wherein any of the above $R_8$ can be optionally substituted by one or more $R_j$;

$R_j$ is selected from the group consisting of methyl, phenyl, benzyl, methoxy, methoxycarbonyl, acetyloxy, benzoyloxy, carbamoyl wherein the nitrogen atom may be independently mono or di-substituted by methyl or phenyl; methoxycarbonylamino, halogen, hydroxy and carboxy, $R_j$ may be further optionally substituted by one or more $R_k$;

$R_k$ is selected from the group consisting of methyl, phenyl, methoxy, methoxycarbonyl, carbamoyl wherein the nitrogen atom may be independently mono or di-substituted by methyl or phenyl; benzyloxycarbonylamino, amino wherein the nitrogen atom may be independently mono or di-substituted by methyl or phenyl; halogen, hydroxy and carboxy.

Ultimately preferred compounds of the formula(I) are those wherein:

$R_1$ is phenyl or 4-morpholinyl, wherein $R_1$ is optionally substituted by one or more $R_b$;

$R_b$ is selected from the group consisting of benzimidazolyl, methoxy and dimethylamino, $R_b$ may be further optionally substituted by a halogen atom;

$R_3$ is C1–5 alkyl wherein $R_3$ is optionally substituted by one or more $R_d$;

$R_d$ is selected from the group consisting of C3–6 cycloalkyl and phenyl, $R_d$ may be further optionally substituted by one or more $R_e$;

$R_e$ is selected from the group consisting of methyl and halogen;

$R_6$ is C1–5 alkyl optionally substituted by one or more $R_f$;

$R_f$ is selected from the group consisting of C5–6 cycloalkyl, phenyl, methylthio wherein the sulfur atom may be oxidized to a sulfoxide or sulfone, and halogen, $R_f$ may be further optionally substituted by one or more $R_g$;

$R_g$ is selected from the group consisting of methyl, methoxy, methoxycarbonyl, halogen and hydroxy;

$R_8$ is a heteroaryl ring selected from the group consisting of oxazolyl, pyridyl, benzthiazolyl and benzoxazolyl, wherein any of the above $R_8$ can be optionally substituted by one or more $R_j$;

$R_j$ is selected from the group consisting of phenyl, methoxycarbonyl, carbamoyl wherein the nitrogen atom may be independently mono or disubstituted by methyl or phenyl; methoxycarbonylamino and halogen, $R_j$ may be further optionally substituted by one or more $R_k$;

$R_k$ is selected from the group consisting of phenyl, methoxycarbonyl, carbamoyl, benzyloxycarbonylamino and halogen.

In another embodiment of the invention there are provided novel compounds of the formula (Ia):

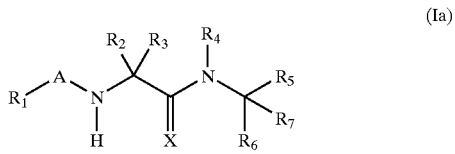

(Ia)

wherein:

A is —C(Y)— or —SO$_2$—

Y is O, S or NR$_a$ where R$_a$ is selected from the group consisting of H, alkyl, aryl, alkoxy, aryloxy, alkylamino and arylamino;

$R_1$ is alkyl, cycloalkyl, aryl, heterocyclyl, heteroaryl or amino wherein $R_1$ is optionally substituted by one or more $R_b$;

$R_b$ is selected from the group consisting of alkyl, cycloalkyl, aryl, heterocyclyl, heteroaryl, alkoxy, aryloxy, alkoxycarbonyl, aryloxycarbonyl, alkanoyl, aroyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino, $R_b$ may be further optionally substituted by one or more $R_c$;

$R_c$ is selected from the group consisting of alkyl, cycloalkyl, aryl, heterocycle, heteroaryl, arylalkyl, alkoxy, aryloxy, arylalkoxy, alkanoyl, aroyl, amino wherein the nitrogen atom may be independently mono or di-substituted by alkyl, aryl, heterocyclyl or heteroaryl, halogen, hydroxy, oxo, carboxy, cyano, nitro, amidino and guanidino;

$R_2$ is H or alkyl;

$R_3$ is H, alkyl, cycloalkyl, aryl, heterocyclyl or heteroaryl, wherein $R_3$ is optionally substituted by one or more groups of the formula $R_d$;

$R_d$ is selected from the group consisting of alkyl, cycloalkyl, aryl, heterocyclyl, heteroaryl, alkoxy, aryloxy, arylalkoxy, alkoxycarbonyl, aryloxycarbonyl, alkanoyl, aroyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsufonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino, $R_d$ may be further optionally substituted by one or more $R_e$;

$R_e$ is selected from the group consisting of alkyl, cycloalkyl, aryl, arylalkyl, alkoxy, aryloxy, arylalkoxy, alkanoyl, aroyl, amino, halogen, hydroxy, oxo, carboxy, cyano, nitro, amidino and guanidino;

$R_4$ is H or alkyl;

$R_5$ is H, alkyl or cycloalkyl;

$R_6$ is H, alkyl, cycloalkyl, aryl, heterocyclyl or heteroaryl, wherein $R_6$ is optionally substituted by one or more groups of the formula $R_f$;

$R_f$ is selected from the group consisting of alkyl, cycloalkyl, aryl, heterocyclyl, heteroaryl, alkoxy, aryloxy, alkanoyl, aroyl, arylalkoxy, heteroarylalkoxy, alkoxycarbonyl, aryloxycarbonyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylthio wherein the sulfur atom may be oxidized to a sulfoxide or sulfone, arylthio wherein the sulfur atom may be oxidized to a sulfoxide or sulfone, arylalkylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino, $R_f$ may be further optionally substituted by one or more $R_g$;

$R_g$ is selected from the group consisting of alkyl, cycloalkyl, aryl optionally substituted by halogen, C1–5alkyl or C1–5alkoxy, heterocyclyl, heteroaryl, alkoxy, aryloxy, arylkoxy, alkoxycarbonyl, aryloxycarbonyl, alkanoyloxy, aroyloxy, carbamoyl wherein the nitrogen atom may be independently mono or di-substituted by alkyl, aryl, heterocyclyl or heteroaryl; alkanoylamino, aroylamino, alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl or heteroaryl; alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl; halogen, hydroxy, oxo, carboxy, cyano, nitro, amidino and guanidino;

or $R_5$ together with $R_6$ membered carbocyclic ring, the ring being optionally substituted with one or more $R_h$;

$R_h$ is selected from the group consisting of alkyl, aryl, alkoxycarbonyl, aryloxycarbonyl, arylalkoxycarbonyl, carbamoyl wherein the nitrogen atom may be optionally mono or di-substituted with a group selected from alkyl, cycloalkyl, aryl, arylalkyl, heterocyclyl or heteroaryl; halogen, hydroxy, carboxy and cyano;

$R_7$ is $R_8$—C(Z)—;

wherein Z is O, S, or $NR_i$ wherein $R_i$ is selected from the group consisting of H, alkyl, aryl, alkoxy, aryloxy and hydroxy;

$R_8$ is a 5–8 membered monocyclic heteroaryl or 8–11 member bicyclic heteroaryl ring system, each of the monocyclic or bicyclic ring systems having 1–4 of the same or different heteroatoms selected from the group consisting of N, O and S wherein any of the above $R_8$ can be optionally substituted by one or more $R_j$;

$R_j$ is selected from the group consisting of alkyl, cycloalkyl, aryl, heterocyclyl, heteroaryl, arylalkyl, alkoxy, aryloxy, alkanoyl, aroyl, arylalkoxy, alkoxycarbonyl, aryloxycarbonyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylthio wherein the sulfur atom may be oxidized to a sulfoxide or sulfone, arylthio wherein the sulfur atom may be oxidized to a sulfoxide or sulfone, arylalkylthio wherein the sulfur atom may be oxidized to a sulfoxide or sulfone, ureido wherein either nitrogen atom may be independently substituted by alkyl, aryl, heterocyclyl or heteroaryl; alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl; halogen, hydroxy, oxo, carboxy, cyano, nitro, amidino and guanidino, $R_j$ may be further optionally substituted by one or more $R_k$;

$R_k$ is selected from the group consisting of alkyl, cycloalkyl, aryl, heterocyclyl, heteroaryl, alkoxy, aryloxy, arylalkoxy, alkoxycarbonyl, aryloxycarbonyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, arylalkoxycarbonylamino, arylalkoxycarbonylaminoalkyl, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl aryl, heterocyclyl or heteroaryl, halogen, hydroxy, oxo, carboxy, cyano, nitro, amidino and guanidino, wherein $R_k$ may be further optionally substituted by $R_l$;

$R_l$ is selected from the group consisting of alkyl, cycloalkyl, aryl, and benzyl;

X is O, S or N—OH;

and the pharmaceutically acceptable derivatives thereof;

with the following provisos:

when $R_6$ is alkyl the alkyl must be substituted with $R_f$ wherein $R_f$ is not hydroxy, sulfhydryl or halogen; and when $R_l$ is C1 alkyl then $R_b$ cannot be carbamoyl, alkanoylamino, aroylamino, ureido, alkoxycarbonylamino, aryloxycarbonylamino, alkylsulfonylamino, arylsulfonylamino, amino, amidino or guanidino wherein each said $R_b$ is linked to said $R_l$ via the nitrogen atom thereof.

Preferred compounds of the formula (Ia) are those wherein:

$R_a$ is selected from the group consisting of H, alkyl and aryl;

$R_l$ is C1–8 alkyl, C3–7 cycloalkyl, aryl, heterocyclyl selected from the group consisting of pyrrolidinyl, piperidinyl, morpholinyl, thiomorpholinyl, pyranyl, thiopyranyl, piperazinyl and indolinyl; heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, or amino wherein R1 is optionally substituted by one or more $R_b$;

$R_b$ is selected from the group consisting of C1–8 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkoxy, aryloxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, C1–8 alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyol, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_b$ may be further optionally substituted by one or more $R_c$;

$R_c$ is selected from the group consisting of C1–8 alkyl, C3–6 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkoxy, aryloxy, halogen, hydroxy, oxo, carboxy, cyano, nitro, amidino and guanidino;

$R_3$ is H, C1–8 alkyl, C3–7 cycloalkyl or aryl wherein $R_3$ is optionally substituted by one or more $R_d$;

$R_d$ is selected from the group consisting of C1–8 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkoxy, aryloxy, alkanoyl, aroyl, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, C1–8 alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_d$ may be further optionally substituted by one or more $R_e$;

$R_e$ is selected from the group consisting of C1–8 alkyl, C3–6 cycloalkyl, aryl, arylalkyl, C1–8 alkoxy, aryloxy, arylalkoxy, aroyl, amino, halogen, hydroxy, oxo, carboxy, cyano, nitro, amidino and guanidino;

$R_5$ is H or alkyl;

$R_6$ is H, C1–8 alkyl, C3–7 cycloalkyl or aryl wherein $R_6$ is optionally substituted by one or more $R_f$;

$R_f$ is selected from the group consisting of C1–8 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkoxy, aryloxy, arylC1–8alkoxy, heteroarylC1–8alkoxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrroidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, arylC1–8 alkylthio wherein the sulfur atom may be oxidized to a sulfoxide or sulfone, ureido wherein either nitrogen atom may be independently substituted by alkyl, aryl, heterocyclyl selected from the group consisting of pyrrolindinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, C1–8 alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_f$ may be further optionally substituted by one or more $R_g$;

$R_g$ is selected from the group consisting of C1–8 alkyl, C3–7 cycloalkyl, aryl optionally substituted by halogen, C1–3 alkyl or C1–3 alkoxy; heterocyclyl selected from the group consisting of pyrrolindinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkoxy, aryloxy, arylC1–8alkoxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolindyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl or phenoxazinyl, alkoxycarbonylamino, aryloxycarbonylamino, C1–8 alkylcarbamoyloxy, arylcarbamoyloxy, alkylsulfonylamino, arylsulfonylamino, alkylaminosulfonyl and arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino;

$R_h$ is selected from the group consisting of C1–8 alkyl, aryl, C1–8 alkoxycarbonyl, aryloxycarbonyl, arylC1–8alkoxycarbonyl, carbamoyl wherein the nitrogen atom may be optionally mono or di-substituted with a group selected from C1–8 alkyl, C3–7 cycloalkyl, aryl, arylC1–8alkyl, heterocyclyl selected from the group consisting of pyrrolindinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, carboxy and cyano;

$R_8$ is heteroaryl ring selected from the group consisting of furanyl, thienyl, pyrrolyl, oxazolyl, thiazolyl, imidazolyl, pyrazolyl, isoxazolyl, isothiazolyl, pyridyl, pyridazinyl, pyrimidinyl, pyrazinyl, triazinyl, indolizinyl, indolyl, isoindolyl, benzofuranyl, benzothienyl, indazolyl, benzimidazolyl, benzthiazolyl, benzoxazolyl, tetrazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl and phenazinyl, wherein any of the above $R_8$ can be optionally substituted by one or more $R_j$;

$R_j$ is selected from the group consisting of alkyl, cycloalkyl, aryl, heterocyclyl selected from the group consisting of pyrrolindinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, arylalkyl, alkoxy, aryloxy, arylalkoxy, alkoxycarbonyl, aryloxycarbonyl, alkanoyloxy, aroyloxy, carbamoyl wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkanoylamino, aroylamino, alkylthio wherein the sulfur atom may be oxidised to a sulfoxide or sulfone, arylthio wherein the sulfur atom may be oxidized to a sulfoxide or sulfone, arylalkylthio wherein the sulfur atom may be oxidised to a sulfoxide or sulfone, ureido wherein either nitrogen atom may be independently substituted by alkyl, aryl, heterocyclyl selected from the group consisting of pyrrolindinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, C1–8 alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_j$ may be further optionally substituted by one or more $R_k$;

$R_k$ is selected from the group consisting of alkyl, cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkoxy, aryloxy, arylalkoxy, alkoxycarbonyl, aryloxycarbonyl, alkanoyloxy, aroyloxy, carbamoyl wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl, heteroaryl selected from furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkanoylamino, aroylamino, alkylthio wherein the sulfur atom may be oxidised to a sulfoxide or sulfone, arylthio wherein the sulfur atom may be oxidised to a sulfoxide or sulfone, ureido wherein either nitrogen atom may be independently substituted by alkyl, aryl, heterocyclyl selected from the group consisting of pyrrolidinyl, piperidinyl, morpholinyl, thiomorphoinyl, piperazinyl and indolinyl, heteroaryl selected from furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, arylalkoxycarbonylamino, arylalkoxycarbonylaminoalkyl, C1–8 alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-susbstituted by alkyl, aryl, heterocyclyl selected from pyrrolindinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyrindinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinazolinyl, quinoxalinyl, carbazolyl, phenothiazinyl and phenoxazinyl, halogen, hydroxy, oxo, carboxy, cyano, nitro, amidino and guanidino, wherein $R_k$ may be further optionally substituted by $R_l$;

$R_l$ is selected from the group consisting of C1–3 alkyl, C3–7 cycloalkyl, phenyl and benzyl; and X is O or S.

More preferred compounds of the formula (Ia) are those wherein:

Y is O or S;

$R_l$ is C1–5 alkyl, C3–7 cycloalkyl, phenyl, naphthyl, heterocyclyl selected from the group consisting of pyrrolidinyl, piperidinyl, morpholinyl, thiomorpholinyl, pyranyl, thiopyranyl, piperazinyl and indolinyl, heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl or amino wherein $R_l$ is optionally substituted by one or more $R_b$;

$R_b$ is selected from the group consisting of C1–5 alkyl, C3–7 cycloalkyl, phenyl, naphthyl, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxy, aryloxy, C1–5 alkoxycarbonyl, aryloxycarbonyl, C1–5 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, halogen, hydroxy, oxo, carboxy, cyano, nitro, amidino and guanidino, $R_b$ may be further optionally substituted by one or more $R_c$;

$R_c$ is selected from the group consisting of C1–5 alkyl, C3–6 cycloalkyl, aryl, heterocyclyl selected from the group consisting of piperidinyl, morpholinyl and piperazinyl; heteroaryl selected from the group consisting of furnayl, thienyl, pyrrolyl, oxazolyl, thiazolyl, imidazolyl, tetrazolyl and pyridinyl, C1–5 alkoxy, aryloxy, halogen, hydroxy, oxo, carboxy, cyano, nitro, amidino and guanidino;

$R_2$ is H or C1–3 alkyl;

$R_3$ is H, C1–5 alkyl, C3–7 cycloalkyl or aryl, wherein $R_3$ is optionally substituted by one or more $R_d$;

$R_d$ is selected from the group consisting of C1–5 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthizolyl, benzoxazolyl, quinolinyl, isoquinolinyl, quinazolinyl and quinoxalinyl, C1–5 alkoxy, aryloxy, C1–5 alkanoyl, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinylor heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, heterocyclyl selected from the group consisting of pyrrolindinyl, piperidinyl, morpholinyl, thiomorpholinyl, piperazinyl and indolinyl or heteroaryl selected the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, halogen, hydroxy, oxo, carboxy, cyano, nitro, amidino and guanidino, $R_d$ may be further optionally substituted by one or more $R_e$;

$R_e$ is selected from the group consisting of C1–5 alkyl, C3–6 cycloalkyl, aryl, arylalkyl, C1–5 alkoxy, aryloxy, arylC1–5alkoxy, aroyl, amino, halogen, hydroxy, oxo, carboxy, cyano, nitro, amidino and guanidino;

$R_4$ is H or C1–3 alkyl;

$R_5$ is H or C1–8 alkyl;

$R_6$ is H, C1–5 alkyl, C3–7 cycloalkyl or aryl wherein $R_6$ is optionally substituted by one or more $R_f$;

$R_f$ is selected from the group consisting of C1–5 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxy, aryloxy, arylC1–5alkoxy, heteroarylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of pyrrolindinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, arylC1–5 alkylthio wherein the sulfur atom may be oxidized to a sulfoxide or sulfone, ureido wherein either nitrogen atom may be independently substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, halogen, hydroxy, oxo, carboxy, cyano, nitro, amidino and guanidino, $R_f$ may be further optionally substituted by one or more $R_g$.

$R_g$ is selected from the group consisting of C1–5 alkyl, C3–7 cycloalkyl, aryl optionally substituted by halogen, methyl or methoxy; heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxy, aryloxy, arylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolindinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, halogen, hydroxy, oxo, carboxy, cyano, nitro amidino and guanidino;

$R_h$ is selected from the group consisting of C1–5 alkyl, aryl C1–5 alkoxycarbonyl, aryloxycarbonyl, arylC1–5alkoxycarbonyl, carbamoyl wherein the nitrogen atom may be optionally mono or di-substituted with a group selected from C1–5 alkyl, C3–7 cycloalkyl, aryl, arylC1–5alkyl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, halogen, hydroxy, carboxy and cyano;

$R_i$ is alkoxy, aryloxy or hydroxy;

$R_8$ is a heteroaryl ring selected from the group consisting of furanyl, thienyl, pyrrolyl, oxazolyl, thiazolyl, imidazolyl, pyrazolyl, isoxazolyl, isothiazolyl, pyridyl, pyridazinyl, pyrimidinyl, pyrazinyl, triazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl and phenazinyl, wherein any of the above $R_8$ can be optionally substituted by one or more $R_j$;

$R_j$ is selected from the group consisting of C1–8alkyl, C3–7cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl; arylC1–8alkyl, C1–8alkoxy, aryloxy, arylC1–8alkoxy, C1–8alkoxycarbonyl, aryloxycarbonyl, C1–8alkanoyloxy, aroyloxy, carbamoyl wherein the nitrogen atom may be independently mono or di-substituted by C1–8alkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8alkanoylamino, aroylamino, C1–8alkylthio wherein the sulfur atom may be oxidised to a sulfoxide or sulfone, arylthio wherein the sulfur atom may be oxidised to a sulfoxide or sulfone, arylC1–8alkylthio wherein the sulfur atom may be oxidised to a sulfoxide or sulfone, ureido wherein either nitrogen atom may be independently substituted by C1–8 alkyl, aryl, heterocyclyl selected from the group consisting of pyrrolindinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl quinoxalinyl, carbazolyl, phenothiazinyl and phenoxazinyl, alkoxycarbonylamino, aryloxycarbonylamino, C1–8 alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_j$ may be further optionally substituted by one or more $R_k$;

$R_k$ is selected from the group consisting of C1–8 alkyl, C3–7 cycloalkyl, aryl, heterocyclyl selected from pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkoxy, aryloxy, arylC1–8alkoxy, C1–8alkoxycarbonyl, aryloxycarbonyl, C1–8alkanoyloxy, aroyloxy, carbamoyl wherein the nitrogen atom may be independently mono or di-susbstituted by C1–8alkyl, aryl, heterocyclyl selected from pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkanoylamino, aroylamino, C1–8alkylthio wherein the sulfur atom may be oxidised to a sulfoxide or sulfone, arylthio wherein the sulfur atom may be oxidised to a sulfoxide or sulfone, ureido wherein either nitrogen atom may be independently substituted by C1–8alkyl, aryl, heterocyclyl selected from the group consisting of pyrrolindinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8alkoxycarbonylamino, aryloxycarbonylamino, arylC1–8alkoxycarbonylamino, arylalkoxycarbonylaminoC1–8alkyl, C1–8alkylcarbamoyloxy, arylcarbamoyloxy, C1–8alkylsulfonylamino, arylsulfonylamino, C1–8alkylaminosulfonyl, arylaminosulfonyl, amino wherein the nitrogen atom may be independently mono or di-substituted by C1–8alkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl halogen, hydroxy, oxo, carboxy, cyano, nitro, amidino and guanidino, wherein $R_k$ may be further optionally substituted by $R_l$.

Even more preferred compounds of the formula (Ia) are those wherein:

Y is O;

$R_l$ is C1–5 alkyl, C3–7 cycloalkyl, phenyl, naphthyl, heterocyclyl selected from the group consisting of piperidinyl, morpholinyl, thiomorpholinyl, piperazinyl, pyranyl and thiopyranyl, heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, or amino wherein $R_l$ is optionally substituted by one or more $R_b$;

$R_b$ is selected from the group consisting of C1–5 alkyl, C3–7 cycloalkyl, phenyl, naphthyl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl and isoquinolinyl; C1–5 alkoxy, aryloxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenyl, naphthyl, heterocyclyl selected from the group consisting of pyrrolidinyl, piperidinyl, morpholinyl, piperazinyl and indolinyl, or heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl and isoquinolinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl or aryl; C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino, wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, halogen, hydroxy, oxo, carboxy, cyano and nitro, $R_b$ may be further optionally substituted by one or more $R_c$;

$R_c$ is selected from the group consisting of C1–5 alkyl, C3–6 cycloalkyl aryl, C1–5 alkoxy, aryloxy, halogen, hydroxy, oxo, carboxy, and cyano;

$R_2$ is H or methyl;

$R_3$ is H, C1–5 alkyl, C3–7 cycloalkyl or phenyl, wherein $R_3$ is optionally substituted by one or more $R_d$;

$R_d$ is selected from the group consisting of C1–3 alkyl, C3–6 cycloalkyl, phenyl, naphthyl, heterocyclyl selected from the group consisting of piperidinyl, morpholinyl and piperazinyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1–5 alkoxy, aryloxy, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, phenyl, naphthyl, heterocyclyl selected from the group consisting of piperidinyl, morpholinyl and piperazinyl or heteroaryl selected the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, halogen, hydroxy, oxo, carboxy and cyano, $R_d$ may be further optionally substituted by one or more $R_e$;

$R_e$ is selected from the group consisting of C1–5 alkyl, C3–6 cycloalkyl, aryl, arylC1–5alkyl, C1–5 alkoxy, aryloxy, arylC1–3alkoxy, aroyl, amino, halogen, hydroxy, oxo, carboxy and cyano;

$R_4$ is H or methyl;

$R_5$ is H or C1–5 alkyl;

$R_6$ is H, C1–5 alkyl, C3–7 cycloalkyl, phenyl or naphthyl wherein $R_6$ is optionally substituted by one or more $R_f$.

$R_f$ is selected from the group consisting of C1–5 alkyl, C3–7 cycloalkyl, phenyl, naphthyl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxy, aryloxy, arylC1–5alkoxy, pyridylC1–5alkoxy, thienylC1–5alkoxy, furanylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, arylC1–5 alkylthio wherein the sulfur atom may be oxidized to a sulfoxide or sulfone, ureido wherein neither nitrogen atom may be independently substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl benzothienyl, benzimidazolyl, benzthiazolyl, benzoxazolyl, quinolinyl and isoquinolinyl, halogen, hydroxy, oxo, carboxy and cyano, Rf may be further optionally substituted by one or more $R_g$;

$R_g$ is selected from the group consisting of C1–5 alkyl, C3–7 cycloalkyl, phenyl optionally substituted by halogen, methyl or methoxy; naphthyl optionally substituted by halogen, methyl or methoxy; heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1-5 alkoxy, aryloxy, arylC1-5alkoxy, C1-5 alkoxycarbonyl, aryloxycarbonyl, C1-5 alkanoyloxy, aroyloxy, carbamoyl wherein the nitrogen atom may be independently mono or di-substituted by C1-5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1-5 alkanoylamino, aroylamino, C1-5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1-5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl, isoquinolinyl, C1-5 alkoxycarbonylamino, aryloxcarbonylamino, C1-5 alkylcarbamoyloxy, arylcarbamoyloxy, C1-5 alkylsulfonylamino, arylsulfonylamino, C1-5 alkylaminosulfonyl, arylaminosulfonyl, amino wherein the nitrogen atom may be independently mono or di-substituted by C1-5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, halogen, hydroxy, oxo, carboxy and cyano;

$R_h$ is selected from the group consisting of C1-5 alkyl, phenyl, naphthyl, C1-5 alkoxycarbonyl, aryloxycarbonyl, arylC1-3alkoxycarbonyl, carbamoyl wherein the nitrogen atom may be optionally mono or di-substituted with a group selected from C1-5 alkyl, C3-6 cycloalkyl, phenyl, naphthyl, arylC1-3-alkyl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, halogen, hydroxy, carboxy and cyano;

Z is O or S;

$R_g$ is a heteroaryl ring selected from the group consisting of furanyl, thienyl, pyrrolyl, oxazolyl, thiazolyl, imidazolyl, pyrazolyl, isoxazolyl, isothiazolyl, pyridyl, pyridazinyl, pyrimidinyl, pyrazinyl, triazinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl and phenazinyl, wherein any of the above $R_g$ can be optionally substituted by one or more groups of the formula $R_j$;

$R_j$ is selected from the group consisting of C1-5alkyl, C3-6cycloalkyl, phenyl, naphthyl, heterocyclyl selected from the group consisting of pyrrolidinyl, piperidinyl, morpholinyl and piperazinyl; heteroaryl selected from the group consisting of furanyl, thienyl, pyrrolyl, oxazolyl, thiazolyl, imidazolyl, tetrazolyl, pyridinyl, pyridazinyl, pyrimidinyl, pyrazinyl, indolyl, benzofuranyl, benzothienyl, benzimidazolyl, benzthiazolyl, benzoxazolyl, quinolinyl and isoquinolinyl, arylC1-5alkyl, C1-5alkoxy, aryloxy, arylC1-5alkoxy, C1-5alkoxycarbonyl, aryloxycarbonyl, C1-5alkanoyloxy, aroyloxy, carbamoyl wherein the nitrogen atom may be independently mono or di-substituted by C1-5alkyl, aryl, heterocyclyl selected from the group consisting of piperidinyl, morpholinyland piperazinyl, heteroaryl selected from furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl and isoquinolinyl, C1-5-alkanoylamino, aroylamino, C1-5alkylthio wherein the sulfur atom may be oxidised to a sulfoxide or sulfone, arylthio wherein the sulfur atom may be oxidised to a sulfoxide or sulfone, arylC1-5alkylthio wherein the sulfur atom may be oxidised to a sulfoxide or sulfone, ureido wherein either nitrogen atom may be independently substituted by C1-5 alkyl, aryl, heterocyclyl selected from the group consisting of piperidinyl, morpholinyl and piperazinyl; heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl and isoquinolinyl, C1-5alkoxycarbonylamino, aryloxycarbonylamino, C1-5 alkylcarbamoyloxy, arylcarbamoyloxy, C1-5alkylsulfonylamino, arylsulfonylamino, C1-5alkylaminosulfonyl, arylaminosulfonyl, amino wherein the nitrogen atom may be independently mono or di-susbstituted by C1-5 alkyl, aryl, heterocyclyl selected from the group consisting of piperidinyl, morpholinyland piperazinyl; heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, purinyl, quinolinyl and isoquinolinyl, halogen, hydroxy, oxo, carboxy, cyano, nitro, amidino and guanidino, wherein $R_j$ may be further optionally substituted by one or more $R_k$;

$R_k$ is selected from the group consisting of C1-3 alkyl, C3-6 cycloalkyl, phenyl, naphthyl, heterocyclyl selected from the group consisting of pyrrolidinyl, piperidinyl, morpholinyl and piperazinyl; heteroaryl selected from the group consisting of furanyl, thienyl, pyrrolyl, tetrazolyl, pyridinyl, pyridazinyl, pyrimidinyl, pyrazinyl, C1-3 alkoxy, aryloxy, arylC1-3-alkoxy, C1-3alkoxycarbonyl, aryloxycarbonyl, C1-3alkanoyloxy, aroyloxy, carbamoyl wherein the nitrogen atom may be independently mono or di-susbstituted by C1-3 alkyl, aryl, heterocyclyl selected from the group consisting of morpholinyland piperazinyl; heteroaryl selected from the group consisting of furanyl, thienyl, pyrrolyl, oxazolyl, thiazolyl, imidazolyl, tetrazolyl, and pyridinyl, C1-3alkanoylamino, aroylamino, C1-3-alkylthio wherein the sulfur atom may be oxidised to a sulfoxide or sulfone, arylthio wherein the sulfur atom may be oxidised to a sulfoxide or sulfone, ureido wherein either nitrogen atom may be independently substituted by C1-3alkyl, phenyl, naphthyl, heteroaryl selected from the group consisting of furanyl, thienyl, pyrrolyl, oxazolyl, thiazolyl, imidazolyl, tetrazolyl and pyridinyl, C1-3alkoxycarbonylamino, aryloxycarbonylamino, arylC1-3-alkoxycarbonylamino, benzyloxycarbonylaminoC1-5alkyl, C1-3 alkylcarbamoyloxy, arylcarbamoyloxy, C1-3alkylsulfonylamino, arylsulfonylamino, C1-3alkylaminosulfonyl, arylaminosulfonyl, amino wherein the nitrogen atom may be independently mono or di-substituted by C1-3alkyl, aryl, heterocyclyl selected from the group consisting of pyrrolidinyl, piperidinyl, morpholinyl and piperazinyl; heteroaryl selected from the group consisting of furanyl, thienyl, pyrrolyl, oxazolyl, thiazolyl, imidazolyl, tetrazolyl, pyridinyl, pyridazinyl, pyrimidinyl, pyrazinyl, indolyl, benzofuranyl, benzothienyl, benzimidazolyl, benzthiazolyl, benzoxazolyl, quinolinyl and isoquinolinyl, halogen, hydroxy, oxo, carboxy, cyano and nitro, wherein $R_k$ may be further optionally substituted by $R_j$;

$R_1$ is selected from the group consisting of C1-5 alkyl, C3-7 cycloalkyl and phenyl.

Yet even more preferred compounds of the formula (Ia) are those wherein:

$R_1$ is C1-5 alkyl, C3-6 cycloalkyl, phenyl, naphthyl, heterocyclyl selected from the group consisting of piperidinyl, morpholinyl, piperazinyl, pyranyl and thiopyranyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, or amino, wherein $R_1$ is optionally substituted by one or more $R_b$;

$R_b$ is selected from the group consisting of C1-3 alkyl, C3-6 cycloalkyl, phenyl, naphthyl, heterocyclyl selected from the group consisting of pyrrolidinyl, piperidinyl, morpholinyl and piperazinyl, heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl and isoquinolinyl, C1-3 alkoxy, phenoxy, C1-3 alkoxycarbonyl, aryloxycarbonyl, C1-5 alkanoyloxy, aroyloxy, carbamoyl wherein the nitrogen atom may be independently mono or di-substituted by C1-5 alkyl, phenyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1-5 alkanoylamino, aroylamino, C1-5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1-5alkyl, phenyl or naphthyl; C1-5 alkoxycarbonylamino, C1-5 alkylcarbamoyloxy, arylcarbamoyloxy, C1-5 alkylsulfonylamino, arylsulfonylamino, C1-5 alkylaminosulfonyl, arylaminosulfonyl, amino wherein the nitrogen atom may be independently mono or di-substituted by C1-5alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, halogen, hydroxy, oxo, carboxy and cyano, $R_b$ may be further optionally substituted by one or more $R_c$;

$R_c$ is selected from the group consisting of C1-3 alkyl, C5-6 cycloalkyl, aryl, C1-3 alkoxy, phenoxy, halogen, hydroxy, oxo, carboxy and cyano;

$R_2$ is H;

$R_3$ is C1-5 alkyl, C3-6 cycloalkyl or phenyl, wherein $R_3$ is operationally substituted by one or more $R_d$;

$R_d$ is selected from the group consisting of C1-3 alkyl, C3-6 cycloalkyl, phenyl, naphthyl, heterocyclyl selected from the group consisting of piperidinyl, morpholinyl and piperazinyl; heteroaryl selected from the group consisting of furanyl, thienyl, thiazolyl, imidazolyl, pyridinyl, indolyl, quinolinyl andisoquinolinyl, C1-5 alkoxy, phenoxy, aroyl, C1-5 alkoxycarbonyl, aryloxycarbonyl, C1-5 alkanoyloxy, aroyloxy, carbamoyl wherein the nitrogen atom may be independently mono or di-substituted by C1-5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, C1-5 alkanoylamino, aroylamino, C1-3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1-3 alkyl, phenyl or heteroaryl selected the group consisting of furanyl, thienyl, pyrrolyl, oxazolyl, thiazolyl, imidazolyl, pyridinyl and indolyl, C1-5 alkoxycarbonylamino, C1-5 alkylcarbamoyloxy, arylcarbamoyloxy, C1-5 alkylsulfonylamino, arylsulfonylamino, amino wherein the nitrogen atom may be independently mono or di-substituted by C1-3 alkyl, phenyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, halogen, hydroxy, oxo, carboxy and cyano, $R_d$ may be further optionally substituted by one or more $R_e$;

$R_e$ is selected from the group consisting of C1-5 alkyl, C5-6 cycloalkyl, phenyl, naphthyl, arylC1-3alkyl, C1-5 alkoxy, phenoxy, arylC1-3 alkoxy, aroyl, amino, halogen, hydroxy, oxo, carboxy and cyano;

wherein the configuration at the stereocenter defined by $R_2$ and $R_3$ and the carbon they are attached to is L;

$R_4$ is H;

$R_5$ is H or C1-3 alkyl;

$R_6$ is H, C1-5 alkyl, C3-6 cycloalkyl or phenyl, wherein $R_6$ is optionally substituted by one or more $R_f$;

$R_f$ is selected from the group consisting of C1-3 alkyl, C3-6 cycloalkyl, phenyl, naphthyl, heterocyclyl selected from the group consisting of pyrrolidinyl, piperidinyl, morpholinyl and piperazinyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1-5 alkoxy, aryloxy, arylC1-3alkoxy, pyridylC1-5-alkoxy, thienylC1-5-alkoxy, furanylC1-5alkoxy, C1-5 alkoxycarbonyl, aryloxycarbonyl, C1-5 alkanoyloxy, aroyloxy, carbamoyl wherein the nitrogen atom may be independently mono or di-substituted by C1-5 alkyl, phenyl or heteroaryl selected from the group consisting of furanyl, thienyl, pyrrolyl, oxazolyl, thiazolyl, imidazolyl, pyridinyl, and indolyl, C1-5 alkanoylamino, aroylamino, C1-3 alkylthio wherein the sulfur atom may be oxidized to a sulfoxide or sulfone, arylthio wherein the sulfur atom may be oxidized to a sulfoxide or sulfone, arylC1-3alkylthio wherein the sulfur atom may be oxidized to a sulfoxide or sulfone, ureido wherein either nitrogen atom may be independently substituted by C1-5 alkyl or phenyl; C1-5 alkoxycarbonylamino, C1-5 alkylsulfonylamino, arylsulfonylamino, amino wherein the nitrogen atom may be independently mono or di-substituted by C1-5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, halogen, hydroxy, oxo, carboxy and cyano, Rf may be further optionally substituted by one or more $R_g$;

$R_g$ is selected from the group consisting of C1-3 alkyl, C5-6 cycloalkyl, phenyl optionally substituted by halogen, methyl or methoxy; heterocyclyl selected from the group consisting of pyrrolidinyl, piperidinyl, morpholinyl and piperazinyl; heteroaryl selected from the group consisting of furanyl, thienyl, pyrrolyl, oxazolyl, thiazolyl, imidazolyl, pyridinyl, pyrimidinyl, pyrazinyl and indolyl, C1-5 alkoxy, aryloxy, arylC1-3alkoxy, C1-5 alkoxycarbonyl, aryloxycarbonyl, C1-5 alkanoyloxy, aroyloxy, carbamoyl wherein the nitrogen atom may be independently mono or di-substituted by C1-5 alkyl or aryl; C1-5 alkanoylamino, aroylamino, C1-5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1-5 alkyl or aryl; C1-5 alkoxycarbonylamino, aryloxycarbonylamino, C1-5 alkylcarbamoyloxy, arylcarbamoyloxy, C1-5 alkylsulfonylamino, arylsulfonylamino, C1-5 alkylaminosulfonyl, arylaminosulfonyl, amino wherein the nitrogen atom may be independently mono or di-substituted by C1-5 alkyl or aryl; halogen, hydroxy, oxo, carboxy and cyano;

$R_h$ is selected from the group consisting of C1-5 alkyl, phenyl, C1-5 alkoxycarbonyl, aryloxycarbonyl, arylC1-3alkoxycarbonyl, carbamoyl wherein the nitrogen atom may be optionally mono or di-substituted with C1-5 alkyl, C3-6 cycloalkyl, phenyl, naphthyl, arylC1-3alkyl, halogen, hydroxy, carboxy and cyano; wherein Z is O;

$R_8$ is a heteroaryl ring selected from the group consisting of oxazolyl, thiazolyl, imidazolyl, pyrazolyl, isoxazolyl, isothiazolyl, pyridyl, pyridazinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, wherein any of the above $R_8$ can be optionally substituted by one or more $R_j$;

$R_j$ is selected from the group consisting of C1-5 alkyl, C5-6 cycloalkyl, phenyl, naphthyl, pyrrolidinyl, piperidinyl, morpholinyl, piperazinyl, furanyl, thienyl, pyrrolyl, tetrazolyl, pyridinyl, pyridazinyl, pyrimidinyl, pyrazinyl, indolyl, benzofuranyl, benzothienyl, benzimidazolyl, benzthiazolyl, benzoxazolyl, arylC1-3alkyl, C1-3alkoxy, aryloxy, arylC1-3alkoxy, C1-3alkoxycarbonyl, aryloxycarbonyl, C1-3alkanoyloxy, aroyloxy, carbamoyl wherein the nitrogen atom may be independently mono or di-substituted by C1-3alkyl, phenyl, naphthyl, piperidinyl, furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl and isoquinolinyl; C1-3alkanoylamino, aroylamino, C1-3alkylthio wherein the sulfur atom may be oxidised to a sulfoxide or sulfone, arylthio wherein the sulfur atom may be oxidised to a sulfoxide or sulfone, arylC1-3alkylthio wherein the sulfur atom may be oxidised to a sulfoxide or sulfone, ureido wherein either nitrogen atom may be independently substituted by C1-3 alkyl, phenyl, naphthyl, piperidinyl, morpholinyl, thiazolyl, imidazolyl, tetrazolyl, pyridinyl, indolyl, benzofuranyl, benzothienyl, benzimidazolyl, benzthiazolyl, benzoxazolyl, quinolinyl and isoquinolinyl; C1-3 alkoxycarbonylamino, aryloxycarbonylamino, C1-3 alkylcarbamoyloxy, arylcarbamoyloxy, C1-3alkylsulfonylamino, arylsulfonylamino, C1-3alkylaminosulfonyl, arylaminosulfonyl, amino wherein the nitrogen atom may be independently mono or di-susbstituted by C1-3 alkyl, phenyl, naphthyl, piperidinyl, furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyland isoquinolinyl; halogen, hydroxy, oxo, carboxy, cyano and nitro, $R_j$ may be further optionally substituted by one or more $R_k$;

$R_k$ is selected from the group consisting of methyl, C5-6 cycloalkyl, phenyl, pyrrolidinyl, piperidinyl, morpholinyl, piperazinyl, furanyl, thienyl, pyrrolyl, tetrazolyl, pyridinyl, pyrimidinyl, C1-3 alkoxy, phenoxy, benzyloxy, methoxycarbonyl, acetyloxy, benzoyloxy, carbamoyl wherein the nitrogen atom may be independently mono or di-substituted by C1-3 alkyl, phenyl, furanyl, thienyl, pyrrolyl, oxazolyl, thiazolyl, imidazolyl or pyridinyl; acetylamino, benzoylamino, methylthio wherein the sulfur atom may be oxidised to a sulfoxide or sulfone, ureido wherein either nitrogen atom may be independently substituted by methyl, phenyl, furanyl, thienyl, pyrrolyl, oxazolyl, thiazolyl, imidazolyl or pyridinyl; arylC1-3alkoxycarbonylamino, benzyloxycarbonylaminoC1-5alkyl, methylcarbamoyloxy, amino wherein the nitrogen atom may be independently mono or di-susbstituted by C1-3alkyl, phenyl, naphthyl, pyrrolidinyl, piperidinyl, furanyl, thienyl, pyrrolyl, oxazolyl, thiazolyl, imidazolyl, pyridinyl, pyrimidinyl, indolyl, benzofuranyl, benzothienyl, benzimidazolyl, benzthiazolyl, benzoxazolyl, quinolinyl or isoquinolinyl, halogen, hydroxy, oxo, carboxy, cyano and nitro, wherein $R_k$ may be further optionally substituted by $R_l$;

R$_l$ is selected from the group consisting of C1-3 alkyl, C3-6 cycloalkyl and phenyl.

Still yet even more preferred compounds of the formula (Ia) are those wherein:

R$_l$ is C1-3 alkyl, C5-6 cycloalkyl, phenyl, naphthyl, heterocyclyl selected from the group consisting of piperidinyl, morpholinyl, piperazinyl, pyranyl and thiopyranyl; heteroaryl selected from the group consisting of furanyl, thienyl, pyrrolyl, oxazolyl, thiazolyl, imidazolyl, pyridinyl, and indolyl, or amino, wherein R$_l$ is optionally substituted by one or more R$_b$;

R$_b$ is selected from the group consisting of C1-3 alkyl, C5-6 cycloalkyl, phenyl, heterocyclyl selected from the group consisting of piperidinyl, morpholinyl and piperazinyl; heteroaryl selected from the group consisting of furanyl, thienyl, pyrrolyl, imidazolyl, tetrazolyl, pyridinyl, indolyl, benzofuranyl, benzothienyl, benzimidazolyl, benzthiazolyl, benzoxazolyl, quinolinyl and isoquinolinyl, C1-3 alkoxy, C1-3 alkoxycarbonyl, aryloxycarbonyl, C1-5 alkanoyloxy, aroyloxy, carbamoyl wherein the nitrogen atom may be independently mono or di-substituted by C1-3 alkyl, phenylor heteroaryl selected from the group consisting of pyrrolyl, imidazolyl, pyridinyl, indolyl, benzofuranyl, benzothienyl, benzimidazolyl and benzthiazolyl; C1-5 alkanoylamino, aroylamino, C1-3 arylthio wherein the sulfur atom may be oxidized to a sulfoxide or sulfone, ureido wherein either nitrogen atom may be independently substituted by C1-3alkyl or phenyl; C1-5 alkylsulfonylamino, arylsulfonylamino, amino wherein the nitrogen atom may be independently mono or di-substituted by C1-3alkyl, phenyl, heterocyclyl selected from the group consisting of piperidinyl, morpholinyl and piperazinylor heteroaryl selected from the group consisting of pyrrolyl, imidazolyl, pyridinyl, indolyl, benzofuranyl, benzothienyl, benzimidazolyl, benzthiazolyl, benzoxazolyl, quinolinyl and isoquinolinyl; halogen, hydroxy, oxo, carboxy and cyano R$_b$ may be further optionally substituted by one or more R$_c$;

R$_c$ is selected from the group consisting of C1-3 alkyl, C5-6 cycloalkyl, C1-3 alkoxy, halogen and hydroxy;

R$_3$ is C1-5 alkyl, C5-6 cycloalkyl or phenyl wherein R$_3$ is optionally substituted by one or more R$_d$;

R$_d$ is selected from the group consisting of C1-3 alkyl, C3-6 cycloalkyl, phenyl, naphthyl, 4-piperidinyl, 4-morpholinyl, piperazinyl, furanyl, thienyl, thiazolyl, imidazolyl, pyridinyl, indolyl, C1-5 alkoxy, phenoxy, aroyl, C1-5 alkoxycarbonyl, aryloxycarbonyl, C1-5 alkanoyloxy, aryloxy, carbamoyl wherein the nitrogen atom may be independently mono or di-substituted by C1-5 alkyl or phenyl; C1-5 alkanoylamino, C1-3 alkylthio wherein the sulfur atom may be oxidized to a sulfoxide or sulfone, ureido wherein either nitrogen atom may be independently substituted by C1-3 alkyl or phenyl; C1-5 alkoxycarbonylamino, C1-5 alkylsulfonylamino, arylsulfonylamino, amino wherein the nitrogen atom may be independently mono or di-substituted by C1-3 alkyl or phenyl; halogen, hydroxy, oxo, carboxy and cyano, R$_d$ may be further optionally substituted by one or more R$_e$;

R$_e$ is selected from the group consisting of C1-5 alkyl, C5-6 cycloalkyl, phenyl, benzyl, C1-5 alkoxy, phenoxy, benzyloxy, aroyl, halogen, hydroxy, oxo, carboxy and cyano;

R$_6$ is H, C1-5 alkyl or phenyl wherein R$_f$,

R$_f$ is selected from the group consisting of C1-3 alkyl, C3-6 cycloalkyl, phenyl, naphthyl, furanyl, thienyl, thiazolyl, imidazolyl, pyridinyl, indolyl, C1-3 alkoxy, benzyloxy, pyridyl, C1-3 alkoxy, thienylC1-3-alkoxy, furanylC1-3alkoxy, C1-3 alkoxycarbonyl, phenoxyoxycarbonyl, C1-5 alkanoyloxy, aroyloxy, carbamoyl wherein the nitrogen atom may be independently mono or di-substituted by C1-3 alkyl or phenyl; C1-5 alkanoylamino, aroylamino, methylthio wherein the sulfur atom may be oxidized to a sulfoxide or sulfone, benzylthio wherein the sulfur atom may be oxidized to a sulfoxide or sulfone, ureido wherein either nitrogen atom may be independently substituted by C1-5 alkyl or phenyl; C1-3 alkoxycarbonylamino, amino wherein the nitrogen atom may be independently mono or di-substituted by C1-5 alkyl or phenyl; halogen, hydroxy, oxo, carboxy and cyano, R$_f$ may be further optionally substituted by one or more R$_g$;

R$_g$ is selected from the group consisting of C1-3 alkyl, phenyl optionally substituted by halogen, methyl or methoxy; heterocyclyl selected from the group consisting of piperidinyl, morpholinyl and piperazinyl; heteroaryl selected from the group consisting of furanyl, thienyl, pyrrolyl and pyridinyl, C1-3 alkoxy, aryloxy, benzyloxy, C1-5 alkoxycarbonyl, C1-5 alkanoyloxy, aroyloxy, carbamoyl wherein the nitrogen atom may be independently mono or di-substituted by C1-5 alkyl or phenyl; C1-5 alkanoylamino, aroylamino, C1-5 alkylthio wherein the sulfur atom may be oxidized to a sulfoxide or sulfone, ureido wherein either nitrogen atom may be independently substituted by C1-5 alkyl or phenyl; C1-5 alkoxycarbonylamino, C1-5 alkylcarbamoyloxy, arylcarbamoyloxy, C1-3 alkylsulfonylamino, arylsulfonylamino, C1-3 alkylaminosulfonyl, arylaminosulfonyl, amino wherein the nitrogen atom may be independently mono or di-substituted by C1-3 alkyl or phenyl; halogen hydroxy, oxo, carboxy and cyano;

R$_h$ is selected from the group consisting of C1-3 alkyl, phenyl, C1-3 alkoxycarbonyl, phenoxyoxycarbonyl, benzyloxy, carbamoyl wherein the nitrogen atom may be optionally mono or di-substituted with C1-5 alkyl, phenyl, benzyl, halogen, hydroxy, carboxy and cyano;

R$_8$ is a heteroaryl ring selected from the group consisting of oxazolyl, thiazolyl, imidazolyl, pyrazolyl, pyridyl, indolyl, benzofuranyl, benzothienyl, benzimidazolyl, benzthiazolyl, benzoxazolyl, quinolinyland isoquinolinyl, wherein any of the above R8 can be optionally substituted by one or more R$_j$;

R$_j$ is selected from the group consisting of C1-5 alkyl, C5-6 cycloalkyl, phenyl, naphthyl, pyrrolidinyl, piperidinyl, morpholinyl, piperazinyl, furanyl, thienyl, pyrrolyl, tetrazolyl, pyridinyl, pyrimidinyl, benzyl, C1-3alkoxy, phenoxy, benzyloxy, C1-3alkoxycarbonyl, acetyloxy, benzoyloxy, carbamoyl wherein the nitrogen atom may be independantly mono or di-substituted by methyl, phenyl, furanyl, thienyl, pyrrolyl, oxazolyl, thiazolyl, imidazolyl and pyridinyl; acetylamino, benzoylamino, methylthio wherein the sulfur atom may be oxidised to a sulfoxide or sulfone, benzylthio wherein the sulfur atom may be oxidised to a sulfoxide or sulfone, ureido wherein either nitrogen atom may be independently substituted by methyl, phenyl, thiazolyl, imidazolyl and pyridinyl; C1-3 alkoxycarbonylamino, C1-3 alkylcarbamoyloxy, arylcarbamoyloxy, C1-3alkylsulfonylamino, arylsulfonylamino, amino wherein the nitrogen atom may be independently mono or di-susbstituted by methyl, phenyl, furanyl, thienyl, pyrrolyl, oxazolyl, thiazolyl, imidazolyl and pyridinyl; halogen, hydroxy, carboxy, cyano and nitro, $R_j$ may be further optionally substituted by one or more $R_k$;

$R_k$ is selected from the group consisting of methyl, C5-6 cycloalkyl, phenyl, pyrrolidinyl, piperidinyl, morpholinyl, piperazinyl, furanyl, thienyl, pyrrolyl, pyridinyl, C1-3 alkoxy, phenoxy, benzyloxy, methoxycarbonyl, acetyloxy, benzoyloxy, carbamoyl wherein the nitrogen atom may be independantly mono or di-substituted by methyl, phenyl, furanyl, thienyl; acetylamino, benzoylamino, methylthio wherein the sulfur atom may be oxidised to a sulfoxide or sulfone, ureido wherein either nitrogen atom may be independently substituted by methyl, phenyl, furanyl, thienyl, pyrrolyl, oxazolyl and thiazolyl, benzyloxycarbonylamino, benzyloxycarbonylaminoC1-5alkyl, amino wherein the nitrogen atom may be independently mono or di-substituted by C1-3alkyl, phenyl, furanyl, thienyl, pyrrolyl, oxazolyl, thiazolyl, imidazolyl and pyridinyl, halogen, hydroxy, carboxy, cyano and nitro, wherein $R_k$ may be further optionally substituted by $R_l$;

$R_l$ is selected from the group consisting of C1-3 alkyl, C3-6 cycloalkyl and phenyl.

Even much more preferred compounds of the formula (Ia) are those wherein:

$R_1$ is C5-6 cycloalkyl, phenyl, naphthyl, piperidinyl, morpholinyl, piperazinyl, furanyl, thienyl, pyrrolyl, pyranyl, thiopyranyl or amino wherein $R_1$ is optionally substituted by one or more $R_b$;

$R_b$ is selected from the group consisting of C1-3 alkyl, C5-6 cycloalkyl, phenyl, furanyl, thienyl, pyrrolyl, imidazolyl, indolyl, benzofuranyl, benzothienyl, benzimidazolyl, benzthiazolyl, benzoxazolyl, C1-3 alkoxy, C1-3 alkoxycarbonyl, carbamoyl wherein the nitrogen atom may be independently mono or di-substituted by C1-3 alkyl or phenyl; C1-5 alkanoylamino, aroylamino, ureido wherein either nitrogen atom may be independently substituted by C1-3alkyl or phenyl; C1-5 alkylsulfonylamino, arylsulfonylamino, amino wherein the nitrogen atom may be independently mono or di-substituted by C1-3alkyl or phenyl; halogen, hydroxy, oxo, carboxy and cyano, $R_b$ may be further optionally substituted by one or more $R_c$;

$R_c$ is selected from the group consisting of C1-3 alkyl, C1-3 alkoxy, halogen and hydroxy;

$R_d$ is selected from the group consisting of C1-3 alkyl, C3-6 cycloalkyl, phenyl, naphthyl, 4-piperidinyl, furanyl, thienyl, thiazolyl, imidazolyl, pyridinyl, indolyl, C1-3alkoxy, C1-5alkoxycarbonyl, C1-5-alkanoyloxy, benzoyloxy, carbamoyl wherein the nitrogen atom may be independently mono or di-substituted by C1-3alkyl or phenyl; C1-5-alkanoylamino, C1-3 alkylthio wherein the sulfur atom may be oxidized to a sulfoxide or sulfone, C1-3alkoxycarbonylamino, C1-3alkylsulfonylamino, amino wherein the nitrogen atom may be independently mono or di-substituted by C1-3 alkyl or phenyl, halogen, hydroxy, oxo, carboxy and cyano, $R_4$ may be further optionally substituted by one or more $R_e$;

$R_e$ is selected from the group consisting of C1-3 alkyl, phenyl, benzyl, C1-3 alkoxy, phenoxy, benzyloxy, benzoyl, halogen, hydroxy, oxo, carboxy and cyano;

$R_5$ is H or methyl;

$R_6$ is C1-3 alkyl or phenyl, wherein $R_6$ is optionally substituted by one or more groups of the formula $R_f$;

$R_f$ is selected from the group consisting of methyl, C3-6 cycloalkyl, phenyl, naphthyl, furanyl, thienyl, thiazolyl, imidazolyl, pyridinyl, indolyl, C1-3 alkoxy, benzyloxy, C1-5 alkanoylamino, aroylamino, methylthio wherein the sulfur atom may be oxidized to a sulfoxide or sulfone, benzylthio wherein the sulfur atom may be oxidized to a sulfoxide or sulfone, C1-3 alkoxycarbonylamino, amino wherein the nitrogen atom may be independently mono or di-substituted by C1-5 alkyl or phenyl; halogen, hydroxy, oxo, carboxy and cyano, $R_f$ may be further optionally substituted by one or more $R_g$;

$R_g$ is selected from the group consisting of C1-3 alkyl, phenyl optionally substituted by halogen or methyl; C1-3 alkoxy, aryloxy, benzyloxy, C1-3 alkoxycarbonyl, carbamoyl wherein the nitrogen atom may be independently mono or di-substituted by C1-3 alkyl or phenyl; C1-5 alkanoylamino, aroylamino, amino wherein the nitrogen atom may be independently mono or di-substituted by C1-3 alkyl or phenyl; halogen hydroxy, oxo, carboxy and cyano;

$R_h$ is selected from the group consisting of C1-3 alkyl, phenyl, C1-3 alkoxycarbonyl, benzyloxy and carboxy;

$R_8$ is a heteroaryl ring selected from the group consisting of oxazolyl, thiazolyl, imidazolyl, pyrazolyl, pyridyl, benzimidazolyl, benzthiazolyland benzoxazolyl, wherein any of the above $R_8$ can be optionally substituted by one or more $R_j$;

$R_j$ is selected from the group consisting of C1-5 alkyl, cyclohexyl, phenyl, piperidinyl, furanyl, thienyl, pyridinyl, benzyl, methoxy, phenoxy, benzyloxy, methoxycarbonyl, acetyloxy, benzoyloxy, carbamoyl wherein the nitrogen atom may be independantly mono or di-substituted by methyl, phenyl, furanyl, thienyl; acetylamino, benzoylamino, ureido wherein either nitrogen atom may be independently substituted by methyl or phenyl; methoxycarbonylamino, C1-3 alkylsulfonylamino, arylsulfonylamino, amino wherein the nitrogen atom may be independently mono or di-susbstituted by methyl, phenyl, furanyl, or thienyl; halogen, hydroxy, carboxy and cyano, $R_j$ may be further optionally substituted by one or more $R_k$;

$R_k$ is selected from the group consisting of methyl, C5-6 cycloalkyl, phenyl, piperidinyl, piperazinyl, furanyl, thienyl, C1-3 alkoxy, phenoxy, benzyloxy, methoxycarbonyl, acetyloxy, benzoyloxy, carbamoyl wherein the nitrogen atom may be independantly mono or di-susbstituted by methyl or phenyl; acetylamino, benzoylamino, ureido wherein either nitrogen atom may be independently substituted by methyl or phenyl; benzyloxycarbonylamino, benzyloxycarbonylamino C1-5alkyl, amino wherein the nitrogen atom may be independently mono or di-susbstituted by C1-3 alkyl, phenyl, furanyl, or thienyl; halogen, hydroxy, carboxy, cyano and nitro, wherein $R_k$ may be further optionally substituted by $R_l$;

$R_l$ is selected from the group consisting of methyl, C3-6 cycloalkyl and phenyl.

Yet even more preferred compounds of the formula (Ia) are those wherein:

A is —C(O)— or —SO$_2$—;

$R_1$ is cyclohexyl, phenyl, naphthyl, piperidinyl, morpholinyl, pipierazinyl, pyranyl, thiopyranyl or amino, wherein R1 is optionally substituted by one or more $R_b$;

$R_b$ is selected from the group consisting of C1-3 alkyl, C5-6 cycloalkyl, phenyl, furanyl, thienyl, pyrrolyl, imidazolyl, indolyl, benzofuranyl, benzothienyl, benzimidazolyl, benzthiazolyl, benzoxazolyl, C1-3 alkoxy, C1-3 alkoxycarbonyl, carbamoyl wherein the nitrogen atom may be independently mono or di-substituted by C1-3 alkyl or phenyl; C1-5 alkanoylamino, aroylamino, C1-5 alkylsulfonylamino, arylsulfonylamino, amino wherein the nitrogen atom may be independently mono or di-substituted by C1-3 alkyl; halogen, hydroxy, oxo, carboxy and cyano, $R_b$ may be further optionally substituted by one or more $R_c$;

$R_c$ is selected from the group consisting of C1-3 alkoxy, halogen and hydroxy;

$R_3$ is C1-5 alkyl or C5-6 cycloalkyl, wherein $R_3$ is optionally substituted by one or more $R_d$;

$R_d$ is selected from the group consisting of methyl, C3-6 cycloalkyl, phenyl, thienyl, imidazolyl, pyridinyl, indolyl, C1-4 alkoxy, C1-5 alkanoylamino, methylthio wherein the sulfur atom may be oxidized to a sulfoxide or sulfone, halogen, hydroxy, oxo, carboxy and cyano, $R_d$ may be further optionally substituted by one or more $R_e$;

$R_e$ is selected from the group consisting of methyl, phenyl, benzyl, methoxy, phenoxy, benzyloxy, benzoyl, halogen and hydroxy;

$R_f$ is selected from the group consisting of C3-6 cycloalkyl, phenyl, naphthyl, thienyl, imidazolyl, pyridinyl, indolyl, methoxy, benzyloxy, C1-3 alkanoylamino, methylthio wherein the sulfur atom may be oxidized to a sulfoxide or sulfone, benzylthio wherein the sulfur atom may be oxidized to a sulfoxide or sulfone, methoxycarbonylamino, amino wherein the nitrogen atom may be independently mono or di-substituted by C1-3 alkyl; halogen, hydroxy, carboxy and cyano, $R_f$ may be further optionally substituted by one or more $R_g$;

$R_g$ is selected from the group consisting of methyl, phenyl optionally substituted by halogen or methyl; methoxy, phenoxy, benzoyloxy, methoxycarbonyl, amino wherein the nitrogen atom may be independently mono or di-substituted by C1-3 alkyl or phenyl; halogen, hydroxy and carboxy;

$R_8$ is a heteroaryl ring selected from the group consisting of oxazolyl, thiazolyl, imidazolyl, pyridyl, benzthiazolyl and benzoxazolyl, wherein any of the above $R_8$ can be optionally substituted by one or more $R_j$;

$R_j$ is selected from the group consisting of C1-5 alkyl, phenyl, furanyl, thienyl, piperidinyl, pyridinyl, benzyl, methoxy, methoxycarbonyl, acetyloxy, benzoyloxy, carbamoyl wherein the nitrogen atom may be independantly mono or di-susbstituted by methyl or phenyl; acetylamino, benzoylamino, ureido wherein either nitrogen atom may be independently substituted by methyl or phenyl; methoxycarbonylamino, amino wherein the nitrogen atom may be independently mono or di-substituted by methyl, phenyl; halogen, hydroxy, carboxy and cyano, $R_j$ may be further optionally substituted by one or more $R_k$; and $R_k$ is selected from the group consisting of methyl, C5-6 cycloalkyl, phenyl, piperidinyl, methoxy, phenoxy, benzyloxy, methoxycarbonyl, carbamoyl wherein the nitrogen atom may be independantly mono or di-susbstituted by methyl or phenyl; ureido wherein either nitrogen atom may be independently substituted by methyl or phenyl; benzyloxycarbonylamino, benzyloxycarbonylaminoC1-5alkyl, amino wherein the nitrogen atom may be independently mono or di-substituted by C1-3alkyl, phenyl, furanyl and thienyl; halogen, hydroxy, carboxy, cyano and nitro, wherein $R_k$ may be further optionally substituted by $R_l$;

$R_l$ is selected from the group consisting of methyl and phenyl.

Penultimately preferred compounds of the formula (Ia) are those wherein:

$R_1$ is cyclohexyl, phenyl, naphthyl, piperidinyl, morpholinyl, piperazinyl, pyranyl or thiopyranyl, wherein $R_1$ is optionally substituted by one or more $R_b$;

$R_b$ is selected from the group consisting of, pyrrolyl, imidazolyl, indolyl, benzimidazolyl, methoxy, methoxycarbonyl, amino wherein the nitrogen atom may be independently mono or di-substituted by C1-3 alkyl; halogen, hydroxy and carboxy, $R_b$ may be further optionally substituted by one or more $R_c$;

$R_c$ is selected from the group consisting of methoxy, halogen and hydroxy;

$R_d$ is selected from the group consisting of methyl, C3-6 cycloalkyl, phenyl, C1-4 alkoxy, C1-3 alkanoylamino, methythio wherein the sulfur atom may be oxidized to a sulfoxide or sulfone, halogen, hydroxy, oxo, carboxy and cyano, $R_d$ may be further optionally substituted by one or more $R_e$;

$R_e$ is selected from the group consisting of methyl, phenyl, methoxy, halogen and hydroxy;

$R_5$ is H;

$R_f$ is selected from the group consisting of C5-6 cycloalkyl, phenyl, naphthyl, thienyl, indolyl, methoxy, methylthio wherein the sulfur atom may be oxidized to a sulfoxide or sulfone, methoxycarbonylamino, halogen, hydroxy, carboxy and cyano, $R_f$ may be further optionally substituted by one or more $R_g$;

$R_g$ is selected from the group consisting of methyl, phenyl optionally substituted by halogen; methoxy, phenoxy, benzyloxy, methoxycarbonyl, halogen, hydroxy and carboxy;

$R_8$ is a heteroaryl ring selected from the group consisting of oxazolyl, thiazolyl, pyridyl, benzthiazolyl and benzoxazolyl, wherein any of the above $R_8$ can be optionally substituted by one or more $R_j$;

$R_j$ is selected from the group consisting of C1-5 alkyl, phenyl, piperidinyl, pyridinyl, benzyl, methoxy, methoxycarbonyl, acetyloxy, benzoyloxy, carbamoyl wherein the nitrogen atom may be independantly mono or di-susbstituted by methyl or phenyl; methoxycarbonylamino, halogen, hydroxy and carboxy, $R_j$ may be further optionally substituted by one or more $R_k$;

$R_k$ is selected from the group consisting of methyl, C5-6 cycloalkyl, phenyl, piperidinyl, methoxy, methoxycarbonyl, carbamoyl wherein the nitrogen atom may be independently mono or di-susbstituted by methyl or phenyl; benzyloxycarbonylamino, amino wherein the nitrogen atom may be independently mono or di-susbstituted by methyl or phenyl; halogen, hydroxy and carboxy.

Ultimately preferred compounds of the formula (Ia) are those wherein:

$R_1$ is phenyl or 4-morpholinyl, wherein $R_1$ is optionally substituted by one or more $R_b$;

$R_b$ is selected from the group consisting of benzimidazolyl, methoxy and dimethylamino, $R_b$ may be further optionally substituted by a halogen atom;

$R_3$ is C1-5 alkyl wherein $R_3$ is optionally substituted by one or more $R_d$;
  $R_d$ is selected from the group consisting of C3-6 cycloalkyl and phenyl, $R_d$ may be further optionally substituted by one or more $R_e$;
    $R_e$ is selected from the group consisting of methyl and halogen;
$R_6$ is C1-5 alkyl optionally substituted by one or more $R_f$;
  $R_f$ is selected from the group consisting of C5-6 cycloalkyl, phenyl, methylthio wherein the sulfur atom may be oxidized to a sulfoxide or sulfone, and halogen, $R_f$ may be further optionally substituted by one or more $R_g$;
    $R_g$ is selected from the group consisting of methyl, methoxy, methoxycarbonyl, halogen and hydroxy;
$R_8$ is a heteroaryl ring selected from the group consisting of oxazolyl, pyridyl, benzthiazolyl and benzoxazolyl, wherein any of the above $R_8$ can be optionally substituted by one or more $R_j$;
  $R_j$ is selected from the group consisting of C1-5 alkyl, phenyl, pyridinyl, piperidinyl, methoxycarbonyl, carbamoyl wherein the nitrogen atom may be independantly mono or disubstituted by methyl or phenyl; methoxycarbonylamino and halogen, $R_j$ may be further optionally substituted by one or more $R_k$;
    $R_k$ is selected from the group consisting of methyl, C5-6 cycloalkyl, phenyl, methoxycarbonyl, carbamoyl, benzyloxycarbonylamino and halogen.

The invention also provides novel compounds of the formula (II):

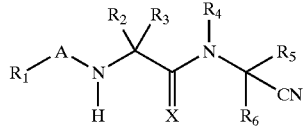

(II)

wherein
A is —C(Y)— or —SO$_2$—
  Y is O, S or NR$_a$ wherein R$_a$ is selected from the group consisting of H, alkyl, aryl, alkoxy, aryloxy, alkylamino and arylamino;
$R_1$ is alkyl, cycloalkyl, aryl, heterocyclyl, heteroaryl or amino wherein $R_1$ is optionally substituted by one or more $R_b$;
  $R_b$ is selected from the group consisting of alkyl, cycloalkyl, aryl, heterocyclyl, heteroaryl, alkoxy, aryloxy, alkanoyl, aroyl, alkoxycarbonyl, aryloxycarbonyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino; $R_b$ may be further optionally substituted by one or more $R_c$;
    $R_c$ is selected from the group consisting of alkyl, cycloalkyl, aryl, heterocyclyl, heteroaryl, arylalkyl, alkoxy, aryloxy, arylalkoxy, alkanoyl, aroyl, amino wherein the nitrogen atom may be independently mono or di-substituted by alkyl, aryl, heterocyclyl or heteroaryl, halogen, hydrogen, oxo, carboxy, cyano, nitro, amidino and guanidino;
$R_2$ is H or alkyl;
$R_3$ is H, alkyl, cycloalkyl, aryl, heterocyclyl or heteroaryl, wherein $R_3$ is optionally substituted by one or more $R_d$;
  $R_d$ is selected from the group consisting of alkyl, cycloalkyl, aryl, heterocyclyl, heteroaryl, alkoxy, aryloxy, arylalkoxy, alkoxycarbonyl, aryloxycarbonyl, alkanoyl, aroyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino, $R_d$ may be further optionally substituted by one or more $R_e$;
    $R_e$ is selected from the group consisting of alkyl, cycloalkyl, aryl, arylalkyl, alkoxy, aryloxy, arylalkoxy, alkanoyl, aroyl, amino, halogen, hydroxy, oxo, carboxy, cyano, nitro, amidino and guanidino;
$R_4$ is H or alkyl;
$R_5$ is H or alkyl;
$R_6$ is H, alkyl, cycloalkyl, aryl, heterocyclyl, aryl, heteroaryl or cyano, wherein $R_6$ is optionally substituted by one or more $R_f$;
  $R_f$ is selected from the group consisting of alkyl, cycloalkyl, aryl, heterocyclyl, heteroaryl, alkoxy, aryloxy, aryloxy, arylalkoxy, alkanoyl, aroyl, alkoxycarbonyl, aryloxycarbonyl, alkanoyloxy, aroyloxy, heteroarylalkoxy, carbamoyl wherein the nitrogen atom may be independently mono or di-substituted by alkyl, aryl, heterocyclyl or heteroaryl, alkanoylamino, aroylamino, alkylcarbamoyl, arylcarbamoyl, alkylthio wherein the sulfur atom may be oxidized to a sulfoxide or sulfone, arylthio wherein the sulfur atom may be oxidized to a sulfoxide or sulfone, arylalkylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino, $R_f$ may be further optionally substituted by one or more $R_g$;
    $R_g$ is selected from the group consisting of alkyl, cycloalkyl, aryl optionally substituted by one or more groups selected from halogen, methyl or methoxy, heterocyclyl, heteroaryl, alkoxy, aryloxy, arylalkoxy, alkoxycarbonyl, aryloxycarbonyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylcarbamoyl, arylcarbamoyl, alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino;

or $R_5$ together with $R_6$ form a 3 to 6 membered carbocyclic ring, the carbocyclic ring being optionally substituted with one or more $R_h$;

$R_h$ is selected from the group consisting of alkyl, aryl, alkoxycarbonyl, aryloxycarbonyl, arylalkoxycarbonyl, carbamoyl wherein the nitrogen atom may be optionally mono or di-substituted with a group selected from alkyl, cycloalkyl, aryl, arylalkyl, heterocyclyl, heteroaryl, halogen, hydroxy, carboxy and cyano;

X is O, S or N—OH;

with the proviso that when Y is O and $R_6$ is arylalkyl or heteroarylalkyl when $R_1$ cannot be alkyl, cycloalkyl, aryl, heteroaryl, cycloalkyl-alkyl, aryl-alkyl or aryl-cycloalkyl, Preferred compounds of the formula (II) are those wherein:

Y is O, S or $NR_a$ wherein $R_a$ is H, alkyl or aryl;

$R_1$ is C1-8alkyl, C3-7cycloalkyl, aryl, heterocyclyl selected from the group consisting of pyrrolidinyl, piperidinyl, morpholinyl, thiomorpholinyl, piperazinyl, indolinyl, pyranyl and thiopyranyl, heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl, phenoxazinyl, and amino wherein R1 is optionally substituted by one or more $R_b$;

$R_b$ is selected from the group consisting of C1-8 alkyl, C3-7 cycloalkyl, aryl, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl or phenoxazinyl, C1-8 alkoxy, aryloxy, C1-8 alkoxycarbonyl, aryloxycarbonyl, C1-8 alkanoyloxy, aroyloxy, carbamoyl wherein the nitrogen atom may be independently mono or di-substituted by C1-8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1-8 alkanoylamino, aroylamino, C1-8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl or phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, pyrazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino, guanidino; $R_b$ may be further optionally substituted by one or more $R_c$;

$R_c$ is selected from the group consisting of C1–8 alkyl, C3–6 cycloalkyl, aryl, C1–8 alkoxy, aryloxy, halogen, hydroxy, oxo, carboxy, cyano, nitro, amidino and guanidino;

$R_3$ is H, C1–8 alkyl, C3–7 cycloalkyl, aryl wherein $R_3$ is optionally substituted by one or more $R_d$;

$R_d$ is selected from the group consisting of C1–8 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, alkanoyl, aroyl, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino, guanidino, $R_d$ may be further optionally substituted by one or more $R_e$;

$R_e$ is selected from the group consisting of C1–8 alkyl, C3–6 cycloalkyl, aryl, arylalkyl, C1–8 alkoxy, aryloxy, arylalkoxy, aroyl, amino, halogen, hydroxy, oxo, carboxy, cyano, nitro, amidino and guanidino;

$R_6$ is H, C1–8 alkyl, C3–7 cycloalkyl, aryl or cyano, wherein $R_6$ is optionally substituted by one or more $R_f$;

$R_f$ is selected from the group consisting of C1–8 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, arylC1–8alkoxy, heteroarylC1–8alkoxy, C1–8alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, arylC1–8 alkylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_f$ may be further optionally substituted by one or more $R_g$;

$R_g$ is selected from the group consisting of C1–8 alkyl, C3–7 cycloalkyl, aryl optionally substituted by one or more groups selected from halogen, methyl or methoxy, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, arylC1–8alkoxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino, and guanidino;

$R_h$ is selected from the group consisting of C1–8 alkyl, aryl, C1–8 alkoxycarbonyl, aryloxycarbonyl, arylC1–8alkoxycarbonyl, carbamoyl wherein the nitrogen atom may be optionally mono or di-substituted with a group selected from C1–8 alkyl, C3–7 cycloalkyl, aryl, arylC1–8alkyl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, carboxy, and cyano; and X is O or S.

More preferred compounds of the formula (II) are those wherein:

Y is O or S;

$R_1$ is C1–5 alkyl, C3–7 cycloalkyl, phenyl, naphthyl, heterocyclyl selected from the group consisting of pyrrolidinyl, piperidinyl, morpholinyl, thiomorpholinyl, piperazinyl, indolinyl, pyranyl and thiopyranyl, heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl or amino; wherein R1 is optionally substituted by one or more $R_b$;

$R_b$ is selected from the group consisting of C1–5 alkyl, C3–7 cycloalkyl, phenyl, naphthyl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, C1–5 alkoxycarbonyl, aryloxycarbonyl, C1–5 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazolyl, indolyl, benzofuranyl, benzothienyl, benzimidazolyl, benzthiazolyl, quinolinyl, isoquinolinyl, quinazolinyl and quinoxalinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazolyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino and guanidino, $R_b$ may be further optionally substituted by one or more $R_c$;

$R_c$ is selected from the group consisting of C1–5 alkyl, C3–6 cycloalkyl, aryl, C1–5 alkoxy, aryloxy, halogen, hydroxy, oxo, carboxy, cyano, nitro, amidino and guanidino;

$R_2$ is H or C1–3 alkyl;

$R_3$ is H, C1–5 alkyl, C3–7 cycloalkyl, aryl wherein $R_3$ is optionally substituted by one or more $R_d$;

$R_d$ is selected from the group consisting of C1–5 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, C1–5 alkanoyl, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazolyl, indolyl, benzofuranyl, benzothienyl, benzimidazolyl, benzthiazolyl, quinolinyl, isoquinolinyl, quinazolinyl and quinoxalinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino and guanidino, $R_d$ may be further optionally substituted by one or more $R_e$;

$R_e$ is selected from the group consisting of C1–5 alkyl, C3–6 cycloalkyl, aryl, arylalkyl, C1–5 alkoxy, aryloxy, arylC1–5alkoxy, aroyl, amino, halogen, hydroxy, oxo, carboxy, cyano, nitro, amidino and guanidino;

$R_4$ is H or C1–3 alkyl $R_5$ is H or C1–8 alkyl $R_6$ is H, C1–5 alkyl, C3–7 cycloalkyl, aryl or cyano, wherein $R_6$ is optionally substituted by one or more $R_f$;

$R_f$ is selected from the group consisting of C1–5 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, arylC1–5 alkanoyloxy, aroyloxy, carbamoyl wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, arylC1–5 alkylthio wherein the sulfur atom may be oxidized to a sulfoxide or sulfone, ureido wherein either nitrogen atom may be independently substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino and guanidino, $R_f$ may be further optionally substituted by one or more $R_g$;

$R_g$ is selected from the group consisting of C1–5 alkyl, C3–7 cycloalkyl, aryl optionally substituted by one or more groups selected from halogen, methyl or methoxy, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, arylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino and guanidino;

$R_h$ is selected from the group consisting of C1–5 alkyl, aryl, C1–5 alkoxycarbonyl, aryloxycarbonyl, arylC1–5alkoxycarbonyl, carbamoyl wherein the nitrogen atom may be optionally mono or di-substituted with a group selected from C1–5 alkyl, C3–7 cycloalkyl, aryl, arylC1–5alkyl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, carboxy and cyano.

Even more preferred compounds of the formula (II) are those wherein:

Y is O;

$R_1$ is C1–5 alkyl, C3–7 cycloalkyl, phenyl, naphthyl, heterocyclyl selected from the group consisting of piperidinyl, morpholinyl, thiomorpholinyl, piperazinyl, pyranyl and thiopyranyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl; or amino wherein $R_1$ is optionally substituted by one or more $R_b$;

$R_b$ is selected from the group consisting of C1–5 alkyl, C3–7 cycloalkyl, phenyl, naphthyl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, quinolinyl and isoquinolinyl, C1–5 alkoxy, aryloxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenyl, naphthyl, heterocyclyl selected from the group consisting of pyrrolidinyl, piperidinyl, morpholinyl, piperazinyl and indolinyl, or heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl or aryl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, oxo, carboxy, cyano and nitro, $R_b$ may be further optionally substituted by one or more $R_c$;

$R_c$ is selected from the group consisting of C1–5 alkyl, C3–6 cycloalkyl, aryl, C1–5 alkoxy, aryloxy, halogen, hydroxy, oxo, carboxy and cyano;

$R_2$ is H or methyl;

$R_3$ is H, C1–5 alkyl, C3–7 cycloalkyl or phenyl wherein $R_3$ is optionally substituted by one or more $R_d$;

$R_d$ is selected from the group consisting of C1–3 alkyl, C3–6 cycloalkyl, phenyl, naphthyl, heterocyclyl selected from the group consisting of piperidinyl, morpholinyl and piperazinyl, heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxy, aryloxy, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, oxo, carboxy and cyano, $R_d$ may be further optionally substituted by one or more $R_e$;

$R_e$ is selected from the group consisting of C1–5 alkyl, C3–6 cycloalkyl, aryl, arylC1–5alkyl, C1–5 alkoxy, aryloxy, arylC1–3alkoxy, aroyl, amino, halogen, hydroxy, oxo, carboxy and cyano;

$R_4$ is H or methyl;

$R_5$ is H or C1–5 alkyl;

$R_6$ is H, C1–5 alkyl; C3–7 cycloalkyl, phenyl, naphthyl or cyano, wherein $R_6$ is optionally substituted by one or more $R_f$;

$R_f$ is selected from the group consisting of C1–5 alkyl, C3–7 cycloalkyl, phenyl, naphthyl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, arylC1–5alkoxy, heteroarylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, arylC1–5 alkylthio wherein the sulfur atom may be oxidized to a sulfoxide or sulfone, ureido wherein either nitrogen atom may be independently substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, oxo, carboxy and cyano, $R_f$ may be further optionally substituted by one or more $R_g$;

$R_g$ is selected from the group consisting of C1–5 alkyl, C3–7 cycloalkyl, phenyl optionally substituted by one or more groups selected from halogen, methyl or methoxy, naphthyl optionally substituted by one or more groups selected from halogen, methyl or methoxy, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, arylC1–5alkoxy, C1–5alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, oxo, carboxy and cyano;

$R_h$ is selected from the group consisting of C1–5 alkyl, phenyl, naphthyl, C1–5 alkoxycarbonyl, aryloxycarbonyl, arylC1–3alkoxycarbonyl, carbamoyl wherein the nitrogen atom may be optionally mono or di-substituted with a group selected from C1–5 alkyl, C3–6 cycloalkyl, phenyl, naphthyl, arylC1–3alkyl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, carboxy and cyano; and X is O.

Yet even more preferred compounds of the formula (II) are those wherein:

Y is O;

$R_1$ is C1–5 alkyl, C3–6 cycloalkyl, phenyl, naphthyl, heterocyclyl selected from the group consisting of piperidinyl, morpholinyl, piperazinyl, pyranyl and thiopyranyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl or amino, wherein R1 is optionally substituted by one or more $R_b$;

$R_b$ is selected from the group consisting of C1–3 alkyl, C3–6 cycloalkyl, phenyl, naphthyl, heterocyclyl selected from the group consisting of pyrrolidinyl, piperidinyl, morpholinyl and piperazinyl, heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, quinolinyl and isoquinolinyl, C1–3 alkoxy, phenoxy, C1–3 alkoxycarbonyl, aryloxycarbonyl, C1–5 alkanoyloxy, aroyloxy, carbamoyl wherein the nitrogen atom may be independently mono or di-substituted by C1–5 alkyl, phenylor heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5alkyl, phenyl or naphthyl; C1–5 alkoxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, oxo, carboxy and cyano, $R_b$ may be further optionally substituted by one or more $R_c$;

$R_c$ is selected from the group consisting of C1–3 alkyl, C5–6 cycloalkyl, aryl, C1–3 alkoxy, phenoxy, halogen, hydroxy, oxo, carboxy and cyano;

$R_2$ is H;

$R_3$ is C1–5 alkyl, C3–6 cycloalkyl or phenyl, wherein $R_3$ is optionally substituted by one or more $R_d$;

$R_d$ is selected from the group consisting of C1–3 alkyl, C3–6 cycloalkyl, phenyl, naphthyl, heterocyclyl selected from the group consisting of piperidinyl, morpholinyl and piperazinyl; heteroaryl selected from the group consisting of furanyl, thienyl, thiazolyl, imidazolyl, pyridinyl, indolyl, quinolinyl and isoquinolinyl, C1–5 alkoxy, phenoxy, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, C1–5 alkanoylamino, aroylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl or heterocyclyl selected the group consisting of furanyl, thienyl, pyrrolyl, oxazolyl, thiazolyl, imidazolyl, pyridinyl and indolyl, C1–5 alkoxycarbonylamino, C1–5 alkylcarbamoyloxy, arylcarbamoyloxy, C1–5 alkylsulfonylamino, arylsulfonylamino, amino wherein the nitrogen atom may be independently mono or di-substituted by C1–3 alkyl, phenyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, halogen, hydroxy, oxo, carboxy and cyano, $R_d$ may be further optionally substituted by one or more $R_e$;

$R_e$ is selected from the group consisting of C1–5 alkyl, C5–6 cycloalkyl, phenyl, naphthyl, arylC1–3alkyl, C1–5 alkoxy, phenoxy, arylC1–3alkoxy, aroyl, amino, halogen, hydroxy, oxo, carboxy and cyano;

$R_4$ is H;

$R_6$ is H, C1–5 alkyl, C3–6 cycloalkyl, phenyl or cyano, wherein $R_6$ is optionally substituted by one or more $R_f$;

$R_f$ is selected from the group consisting of C1–3 alkyl, C3–6 cycloalkyl, phenyl, naphthyl, heterocyclyl selected from the group consisting of pyrrolidinyl, piperidinyl, morpholinyl and piperazinyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxy, aryloxy, arylC1–3alkoxy, heteroarylC1–3alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenyl or heteroaryl selected from the group consisting of furanyl, thienyl, pyrrolyl, oxazolyl, thiazolyl, imidazolyl, pyridinyl and indolyl, C1–5 alkanoylamino, aroylamino, C1–3 alkylthio wherein the sulfur atom may be oxidized to a sulfoxide or sulfone, arylthio wherein the sulfur atom may be oxidized to a sulfoxide or sulfone, arylC1–3alkylthio wherein the sulfur atom may be oxidized to a sulfoxide or sulfone, ureido wherein either nitrogen atom may be independently substituted by C1–5 alkyl or phenyl, C1–5 alkoxycarbonylamino, C1–5 alkylsulfonylamino, arylsulfonylamino, amino wherein the nitrogen atom may be independently mono or di-substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, halogen, hydroxy, oxo, carboxy and cyano, Rf may be further optionally substituted by one or more $R_g$;

$R_g$ is selected from the group consisting of C1–3 alkyl, C5–6 cycloalkyl, phenyl optionally substituted by one or more groups selected from halogen or methyl, heterocyclyl selected from the group consisting of pyrrolidinyl, piperidinyl, morpholinyl and piperazinyl, heteroaryl selected from the group consisting of furanyl, thienyl, pyrrolyl, oxazolyl, thiazolyl, imidazolyl, pyridinyl, pyrimidinyl, pyrazinyl and indolyl, C1–5 alkoxy, aryloxy, arylC1–3alkoxy, C1–5alkoxycarbonyl, aryloxycarbonyl, C1–5 alkanoyloxy, aroyloxy, carbamoyl wherein the nitrogen atom may be independently mono or di-substituted by C1–5 alkyl or aryl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl or aryl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl or aryl, halogen, hydroxy, oxo, carboxy and cyano;

$R_h$ is selected from the group consisting of C1–5 alkyl, phenyl, C1–5 alkoxycarbonyl, aryloxycarbonyl, arylC1–3alkoxycarbonyl, carbamoyl wherein the nitrogen atom may be optionally mono or di-substituted with C1–5 alkyl, C3–6 cycloalkyl, phenyl, naphthyl or arylC1–3alkyl; halogen, hydroxy, carboxy and cyano.

Still yet even more preferred compounds of the formula (II) are those wherein:

$R_1$ is C1–3 alkyl, C5–6 cycloalkyl, phenyl, naphthyl, heterocyclyl selected from the group consisting of piperidinyl, morpholinyl, piperazinyl, pyranyl and thiopyranyl; heteroaryl selected from the group consisting of furanyl, thienyl, pyrrolyl, oxazolyl, thiazolyl, imidazolyl, pyridinyl and indolyl or amino, wherein $R_1$ is optionally substituted by one or more $R_b$;

$R_b$ is selected from the group consisting of C1–3 alkyl, C5–6 cycloalkyl, phenyl, heterocyclyl selected from the group consisting of piperidinyl, morpholinyl and piperazinyl; heteroaryl selected from the group consisting of furanyl, thienyl, pyrrolyl, imidazolyl, tetrazolyl, pyridinyl, indolyl, benzofuranyl, benzothienyl, benzimidazolyl, benzthiazolyl, quinolinyl and isoquinolinyl, C1–3 alkoxy, C1–3 alkoxycarbonyl, aryloxycarbonyl, C1–5 alkanoyloxy, aroyloxy, carbamoyl wherein the nitrogen atom may be independently mono or di-substituted by C1–3 alkyl, phenyl or heteroaryl selected from the group consisting of pyrrolyl, imidazolyl, pyridinyl and indolyl, benzofuranyl, benzothienyl, benzimidazolyl and benzthiazolyl C1–5 alkanoylamino, aroylamino, C1–3 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3alkyl or phenyl, C1–5 alkylsulfonylamino, arylsulfonylamino, amino wherein the nitrogen atom may be independently mono or di-substituted by C1–3alkyl, phenyl, heterocyclyl selected from the group consisting of piperidinyl, morpholinyl and piperazinyl or heteroaryl selected from the group consisting of pyrrolyl, imidazolyl, pyridinyl, indolyl, benzofuranyl, benzothienyl, benzimidazolyl, benzthiazolyl, quinolinyl and isoquinolinyl, halogen, hydroxy, oxo, carboxy and cyano, $R_b$ may be further optionally substituted by one or more $R_c$;

$R_c$ is selected from the group consisting of C1–3 alkyl, C5–6 cycloalkyl, C1–3 alkoxy, halogen and hydroxy;

$R_3$ is C1–5 alkyl, C5–6 cycloalkyl or phenyl wherein $R_3$ is optionally substituted by one or more $R_d$;

$R_d$ is selected from the group consisting of C1–3 alkyl, C3–6 cycloalkyl, phenyl, naphthyl, 4-piperidinyl, 4-morpholinyl, piperazinyl, furanyl, thienyl, thiazolyl, imidazolyl, pyridinyl, indolyl, C1–5 alkoxy, phenoxy, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl or phenyl, C1–5 alkanoylamino, C1–3 alkylthio wherein the sulfur atom may be oxidized to a sulfoxide or sulfone, ureido wherein either nitrogen atom may be independently substituted by C1–3 alkyl or phenyl, C1–5 alkoxycarbonylamino, C1–5 alkylsulfonylamino, arylsulfonylamino, amino wherein the nitrogen atom may be independently mono or di-substituted by C1–3 alkyl or phenyl, halogen, hydroxy, oxo, carboxy and cyano, $R_d$ may be further optionally substituted by one or more $R_e$;

$R_e$ is selected from the group consisting of C1–5 alkyl, C5–6 cycloalkyl, phenyl, benzyl, C1–5 alkoxy, phenoxy, benzyloxy, aroyl, halogen, hydroxy, oxo, carboxy and cyano;

$R_5$ is H or C1–3alkyl;

$R_6$ is H, C1–5 alkyl, phenyl or cyano, wherein $R_6$ is optionally substituted by one or more $R_f$;

$R_f$ is selected from the group consisting of C1–3 alkyl, C3–6 cycloalkyl, phenyl, naphthyl, furanyl, thienyl, thiazolyl, imidazolyl, pyridinyl, indolyl, C1–3 alkoxy, benzyloxy, pyridylC1–3alkoxy, thienylC1–3alkoxy, furanylC1–3alkoxy, C1–3 alkoxycarbonyl, phenoxyoxycarbonyl, C1–5 alkanoyloxy, aroyloxy, carbamoyl wherein the nitrogen atom may be independently mono or di-substituted by C1–3 alkyl or phenyl, C1–5 alkanoylamino, aroylamino, methylthio wherein the sulfur atom may be oxidized to a sulfoxide or sulfone, benzylthio wherein the sulfur atom may be oxidized to a sulfoxide or sulfone, ureido wherein either nitrogen atom may be independently substituted by C1–5 alkyl or phenyl, C1–3 alkoxycarbonylamino, amino wherein the nitrogen atom may be independently mono or di-substituted by C1–5 alkyl or phenyl, halogen, hydroxy, oxo, carboxy and cyano, $R_f$ may be further optionally substituted by one or more $R_g$;

$R_g$ is selected from the group consisting of C1–3 alkyl, phenyl optionally substituted by one or more groups selected from the group consisting of halogen and methyl, heterocyclyl selected from the group consisting of piperidinyl, morpholinyl and piperazinyl; heteroaryl selected from the group consisting of furanyl, thienyl, pyrrolyl and pyridinyl, C1–3 alkoxy, aryloxy, benzyloxy, C1–5 alkoxycarbonyl, C1–5 alkanoyloxy, aroyloxy, carbamoyl wherein the nitrogen atom may be independently mono or di-substituted by C1–5 alkyl or phenyl, C1–5 alkanoylamino, aroylamino, C1–5 alkylthio wherein the sulfur atom may be oxidized to a sulfoxide or sulfone, ureido wherein either nitrogen atom may be independently substituted by C1–5 alkyl or phenyl, C1–5 alkoxycarbonylamino, C1–5 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–3 alkyl or phenyl, halogen, hydroxy, oxo, carboxy and cyano;

$R_h$ is selected from the group consisting of C1–3 alkyl, phenyl, C1–3 alkoxycarbonyl, phenoxyoxycarbonyl, benzyloxy, carbamoyl wherein the nitrogen atom may be optionally mono or di-substituted with a group selected from the group consisting of C1–5 alkyl, phenyl and benzyl, halogen, hydroxy, carboxy and cyano.

Even more preferred compounds of the formula (II) are those wherein:

$R_1$ is C5–6 cycloalkyl, phenyl, naphthyl, piperidinyl, morpholinyl, piperazinyl, pyranyl, thiopyranyl, furanyl, thienyl, pyrrolyl or amino, wherein $R_1$ is optionally substituted by one or more $R_b$;

$R_b$ is selected from the group consisting of C1–3 alkyl, C5–6 cycloalkyl, phenyl, furanyl, thienyl, pyrrolyl, imidazolyl, indolyl, benzofuranyl, benzothienyl, benzimidazolyl, benzthiazolyl, C1–3 alkoxy, C1–3 alkoxycarbonyl, carbamoyl wherein the nitrogen atom may be independently mono or di-substituted by C1–3 alkyl or phenyl; C1–5 alkanoylamino, aroylamino, ureido wherein either nitrogen atom may be independently substituted by C1–3alkyl or phenyl; C1–5 alkylsulfonylamino, arylsulfonylamino, amino wherein the nitrogen atom may be independently mono or di-substituted by C1–3alkyl or phenyl, halogen, hydroxy, oxo, carboxy and cyano, $R_b$ may be further optionally substituted by one or more $R_c$;

$R_c$ is selected from the group consisting of C1–3alkyl, C1–3alkoxy, halogen and hydroxy;

$R_3$ is C1–5 alkyl, C5–6 cycloalkyl or phenyl, wherein $R_3$ is optionally substituted by one or more groups of the formula $R_d$;

$R_d$ is selected from the group consisting of C1–3 alkyl, C3–6 cycloalkyl, phenyl, naphthyl, 4-piperidinyl, furanyl, thienyl, thiazolyl, imidazolyl, pyridinyl, indolyl, C1–3 alkoxy, C1–5 alkoxycarbonyl, C1–5 alkanoyloxy, benzoyloxy, carbamoyl wherein the nitrogen atom may be independently mono or di-substituted by C1–3 alkyl or phenyl, C1–5 alkanoylamino, C1–3 alkylthio wherein the sulfur atom may be oxidized to a sulfoxide or sulfone, C1–3 alkoxycarbonylamino, C1–3 alkylsulfonylamino, amino wherein the nitrogen atom may be independently mono or di-substituted by C1–3 alkyl or phenyl, halogen, hydroxy, oxo, carboxy and cyano, $R_d$ may be further optionally substituted by one or more $R_e$;

$R_e$ is selected from the group consisting of C1–3 alkyl, phenyl, benzyl, C1–3 alkoxy, phenoxy, benzyloxy, benzoyl, halogen, hydroxy, oxo, carboxy and cyano;

wherein the configuration at the stereocenter defined by $R_2$ and $R_3$ and the carbon they are attached to is defined as L;

$R_5$ is H or methyl;

$R_6$ is C1–5 alkyl, phenyl or cyano wherein $R_6$ is optionally substituted by one or more groups of the formula $R_f$;

$R_f$ is selected from the group consisting of methyl, C3–6 cycloalkyl, phenyl, naphthyl, furanyl, thienyl, thiazolyl, imidazolyl, pyridinyl, indolyl, C1–3 alkoxy, benzyloxy, pyridylC1–3alkoxy, thienylC1–3alkoxy, furanylC1–3alkoxy, C1–5 alkanoylamino, aroylamino, methylthio wherein the sulfur atom may be oxidized to a sulfoxide or sulfone, benzylthio wherein the sulfur atom may be oxidized to a sulfoxide or sulfone, C1–3 alkoxycarbonylamino, amino wherein the nitrogen atom may be independently mono or di-substituted by C1–5 alkyl or phenyl, halogen, hydroxy, oxo, carboxy and cyano, $R_f$ may be further optionally substituted by one or more $R_g$;

$R_g$ is selected from the group consisting of C1–3 alkyl, phenyl optionally substituted by one or more groups selected from halogen or methyl, C1–3 alkoxy, aryloxy, benzyloxy, C1–3 alkoxycarbonyl, carbamoyl wherein the nitrogen atom may be independently mono or di-substituted by C1–3 alkyl or phenyl, C1–5 alkanoylamino, aroylamino, amino wherein the nitrogen atom may be independently mono or di-substituted by C1–3 alkyl or phenyl, halogen, hydroxy, oxo, carboxy and cyano;

$R_h$ is selected from the group consisting of C1–3 alkyl, phenyl, C1–3 alkoxycarbonyl, benzyloxy and carboxy.

Much more preferred compounds of formula (II) are those wherein:

$R_1$ is cyclohexyl, phenyl, naphthyl, piperidinyl, morpholinyl, piperazinyl, pyranyl, thiopyranyl or amino wherein $R_1$ is optionally substituted by one or more $R_b$;

$R_b$ is selected from the group consisting of C1–3 alkyl, C5–6 cycloalkyl, phenyl, furanyl, thienyl, pyrrolyl, imidazolyl, indolyl, benzofuranyl, benzothienyl, benzimidazolyl, benzthiazolyl, C1–3 alkoxy, C1–3 alkoxycarbonyl, carbamoyl wherein the nitrogen atom may be independently mono or di-substituted by C1–3 alkyl or phenyl, C1–5 alkanoylamino, aroylamino, C1–5 alkylsulfonylamino, arylsulfonylamino, amino wherein the nitrogen atom may be independently mono or di-substituted by C1–3 alkyl, halogen, hydroxy, oxo, carboxy and cyano, $R_b$ may be further optionally substituted by one or more $R_c$;

$R_c$ is selected from the group consisting of C1–3 alkoxy, halogen and hydroxy, $R_3$ is C1–5 alkyl or C5–6 cycloalkyl wherein $R_3$ is optionally substituted by one or more $R_d$;

$R_d$ is selected from the group consisting of methyl, C3–6 cycloalkyl, phenyl, naphthyl, thienyl, imidazolyl, pyridinyl, indolyl, C1–4 alkoxy, C1–5 alkanoylamino, methylthio wherein the sulfur atom may be oxidized to a sulfoxide or sulfone, halogen, hydroxy, oxo, carboxy and cyano, $R_d$ may be further optionally substituted by one or more $R_e$;

$R_e$ is selected from the group consisting of methyl, phenyl, benzyl, methoxy, phenoxy, benzyloxy, benzoyl, halogen and hydroxy;

$R_6$ is C1–5 alkyl or phenyl, wherein $R_6$ is optionally substituted by one or more $R_f$;

$R_f$ is selected from the group consisting of C3–6 cycloalkyl, phenyl, naphthyl, thienyl, imidazolyl, pyridinyl, indolyl, methoxy, benzyloxy, C1–3 alkanoylamino, methylthio wherein the sulfur atom may be oxidized to a sulfoxide or sulfone, benzylthio wherein the sulfur atom may be oxidized to a sulfoxide or sulfone, methoxycarbonylamino, amino wherein the nitrogen atom may be independently mono or di-substituted by C1–3 alkyl, halogen, hydroxy, carboxy and cyano, $R_f$ may be further optionally substituted by one or more $R_g$;

$R_g$ is selected from the group consisting of methyl, phenyl optionally substituted by one or more groups selected from halogen or methyl, methoxy, phenoxy, benzyloxy, methoxycarbonyl, amino wherein the nitrogen atom may be independently mono or di-substituted by C1–3 alkyl or phenyl, halogen, hydroxy and carboxy;

$R_h$ is selected from the group consisting of vinyl, phenyl, methoxycarbonyl, benzyloxycarbonyl and carboxy;

Penultimately preferred compounds of the formula (II) are those wherein:

$R_1$ is cyclohexyl, phenyl, naphthyl, piperidinyl, morpholinyl, piperazinyl, pyranyl or thiopyranyl, wherein $R_1$ is optionally substituted by one or more $R_b$;

$R_b$ is selected from the group consisting of pyrrolyl, imidazolyl, indolyl, benzimidazolyl, methoxy, methoxycarbonyl, amino wherein the nitrogen atom may be independently mono or di-substituted by C1–3 alkyl, halogen, hydroxy and carboxy, $R_b$ may be further optionally substituted by one or more $R_c$;

$R_c$ is selected from the group consisting of methoxy, halogen and hydroxy;

$R_d$ is selected from the group consisting of methyl, C3–6 cycloalkyl, phenyl, naphthyl, C1–4 alkoxy, C1–3 alkanoylamino, methylthio wherein the sulfur atom may be oxidized to a sulfoxide or sulfone, halogen, hydroxy, oxo, carboxy and cyano, $R_d$ may be further optionally substituted by one or more $R_e$;

$R_e$ is selected from the group consisting of methyl, phenyl, methoxy, halogen and hydroxy;

$R_5$ is H;

$R_f$ is selected from the group consisting of C5–6 cycloalkyl, phenyl, naphthyl, thienyl, indolyl, methoxy, benzyloxy, methylthio wherein the sulfur atom may be oxidized to a sulfoxide or sulfone, benzylthio wherein the sulfur atom may be oxidized to a sulfoxide or sulfone, methoxycarbonylamino, halogen, hydroxy, carboxy and cyano, $R_f$ may be further optionally substituted by one or more $R_g$;

$R_g$ is selected from the group consisting of methyl, phenyl optionally substituted by halogen, methoxy, phenoxy, benzyloxy, methoxycarbonyl, halogen, hydroxy and carboxy;

$R_h$ is vinyl or phenyl.

Ultimately preferred compounds of formula (II) are those wherein:

$R_1$ is phenyl, naphthyl or 4-morpholinyl wherein $R_1$ is optionally substituted by one or more $R_b$;

$R_b$ is selected from the group consisting of benzimidazolyl, methoxy and dimethylamino $R_b$ may be further optionally substituted by $R_c$ wherein $R_c$ is a halogen atom;

$R_3$ is C1–5 alkyl wherein $R_3$ is optionally substituted by one or more $R_d$;

$R_d$ is selected from the group consisting of C3–6 cycloalkyl, phenyl or naphthyl, $R_d$ may be further optionally substituted by one or more $R_e$;

$R_e$ is selected from the group consisting of methyl and halogen, $R_f$ is selected from the group consisting of C5–6 cycloalkyl, phenyl, naphthyl, indolyl, benzyloxy, methylthio wherein the sulfur atom may be oxidized to a sulfoxide or sulfone, benzylthio wherein the sulfur atom may be oxidized to a sulfoxide or sulfone, halogen and carboxy, $R_f$ may be further optionally substituted by one or more $R_g$;

$R_g$ is selected from the group consisting of methyl, methoxy, methoxycarbonyl, halogen and hydroxy.

In another embodiment of the invention, there are provided compounds of the formula (IIa):

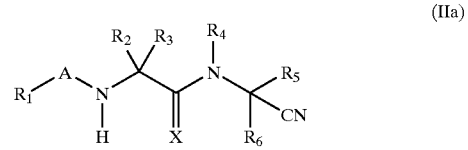

(IIa)

wherein:

A is —C(Y)— or —SO$_2$—

Y is O, S or NR$_a$ wherein R$_a$ is selected from the group consisting of H, alkyl aryl, alkoxy, aryloxy, alkylamino and arylamino;

$R_1$ is alkyl, cycloalkyl, aryl, heterocyclyl, heteroaryl or amino wherein $R_1$ is optionally substituted by one or more $R_b$;

$R_b$ is selected from the group consisting of alkyl, cycloalkyl, aryl, heterocyclyl, heteroaryl, alkoxy, aryloxy, alkanoyl, aroyl, alkoxycarbonyl, aryloxycarbonyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino; $R_b$ may be further optionally substituted by one or more $R_c$;

$R_c$ is selected from the group consisting of alkyl, cycloalkyl, aryl, heterocyclyl, heteroaryl, arylalkyl, alkoxy, aryloxy, arylalkoxy, alkanoyl, aroyl, amino wherein the nitrogen atom may be independently mono or di-substituted by alkyl, aryl, heterocyclyl or heteroaryl, halogen, hydroxy, oxo, carboxy, cyano, nitro, amidino and guanidino;

$R_2$ is H or alkyl;

$R_3$ is H, C2–8alkyl, cycloalkyl, aryl, heterocyclyl or heteroaryl, wherein $R_3$ is optionally substituted by one or more $R_d$;

$R_d$ is selected from the group consisting of alkyl, cycloalkyl, aryl, heterocyclyl, heteroaryl, alkoxy, aryloxy, arylalkoxy, alkoxycarbonyl, aryloxycarbonyl, alkanoyl, aroyl, alkanoyloxy, aroyloxy, carbamoyl wherein the nitrogen atom may be independently mono or di-substituted by alkyl, aryl, heterocyclyl or heteroaryl, alkanoylamino, aroylamino, alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino, $R_d$ may be further optionally substituted by one or more $R_e$;

$R_e$ is selected from the group consisting of alkyl, cycloalkyl, aryl, arylalkyl, alkoxy, aryloxy, arylalkoxy, alkanoyl, aroyl, amino, halogen, hydroxy, oxo, carboxy, cyano, nitro, amidino and guanidino;

$R_4$ is H or alkyl;

$R_5$ is H or alkyl;

$R_6$ is H, alkyl, cycloalkyl, aryl, heterocyclyl, aryl, heteroaryl or cyano, wherein $R_6$ is optionally substituted by one or more $R_f$;

$R_f$ is selected from the group consisting of alkyl, cycloalkyl, aryl, heterocyclyl, heteroaryl, alkoxy, aryloxy, arylalkoxy, alkanoyl, aroyl, alkoxycarbonyl, aryloxycarbonyl, alkanoyloxy, aroyloxy, heteroarylalkoxy, carbamoyl wherein the nitrogen atom may be independently mono or di-substituted by alkyl, aryl, heterocyclyl or heteroaryl, alkanoylamino, aroylamino, alkylcarbamoyl, arylcarbamoyl, alkylthio wherein the sulfur atom may be oxidized to a sulfoxide or sulfone, arylthio wherein the sulfur atom may be oxidized to a sulfoxide or sulfone, arylalkylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen, hydroxy, oxo, carboxy, cyano, nitro, amidino and guanidino, $R_f$ may be further optionally substituted by one or more $R_g$;

$R_g$ is selected from the group consisting of alkyl, cycloalkyl, aryl optionally substituted by one or more groups selected from halogen, methyl or methoxy, heterocyclyl, heteroaryl, alkoxy, aryloxy, arylalkoxy, alkoxycarbonyl, aryloxycarbonyl, alkanoyloxy, aroyloxy, carbamoyl wherein the nitrogen atom may be indpendently mono or di-substituted by alkyl, aryl, heterocyclyl or heteroaryl, alkanoylamino, aroylamino, alkylcarbamoyl, arylcarbamoyl, alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl or heteroaryl, halogen hydroxy, oxo, carboxy, cyano, nitro, amidino and guanidino;

or $R_5$ and $R_6$ together with the carbon they are attached form a carbocyclic ring of 3 to 6 carbon atoms, the carbocyclic ring being optionally substituted with one or more $R_h$;

$R_h$ is selected from the group consisting of alkyl, aryl, alkoxycarbonyl, aryloxycarbonyl, arylalkoxycarbonyl, carbamoyl wherein the nitrogen atom may be optionally mono or di-substituted with a group selected from alkyl, cycloalkyl, aryl, arylalkyl, heterocyclyl, heteroaryl, halogen, hydroxy, carboxy and cyano;

X is O, S or N—OH;

and the pharmaceutically acceptable salts, esters or tautomers thereof;

with the following provisos:

when Y is O and $R_6$ is arylalkyl or heteroarylalkyl then $R_1$ cannot be alkyl, cycloalkyl, aryl, heteroaryl, cycloalkylalkyl, aryl-alkyl or aryl-cycloalkyl;

when $R_5$ is H then $R_6$ cannot be H; and when $R_1$ is C1 alkyl then $R_b$ cannot be carbamoyl, alkanoylamino, aroylamino, ureido, alkoxycarbonylamino, aryloxycarbonylamino, alkylsulfonylamino, arylsulfonylamino, amino, amidino or guanidino wherein each said $R_b$ is linked to said $R_1$ via the nitrogen atom thereof.

Preferred compounds of the formula (IIa) are those wherein:

Y is O, S or $NR_a$ wherein $R_a$ is H, alkyl or aryl;

$R_1$ is C1–8alkyl, C3–7cycloalkyl, aryl, heterocyclyl selected from the group consisting of pyrrolidinyl, piperidinyl, morpholinyl, thiomorpholinyl, piperazinyl, indolinyl, pyranyl and thiopyranyl, heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl, phenoxazinyl, and amino wherein R1 is optionally substituted by one or more $R_b$;

$R_b$ is selected from the group consisting of C1–8 alkyl, C3–7 cycloalkyl, aryl, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinly, pyrimidinyl, pyrazinly, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl or phenoxazinyl, C1–8 alkoxy, aryloxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, qunioxalinyl, carbazolyl, phenothiazinyl and phenoxazinyl, C1–8 alkanoylamino, aroylamino, C1–8 alkythio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinly, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl or phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl, or heteroaryl selected from the group conssisting of furanyl, thienyl, pyrrolyl, oxazolyl, thiazolyl, imidazolyl, pyrazolyl, isoxazolyl, pyrazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino, guanidino; $R_b$ may be further optionally substituted by one or more $R_c$;

$R_c$ is selected from the group consisting of C1–8 alkyl, C3–6 cycloalkyl, aryl, C1–8 alkoxy, aryloxy, halogen, hydroxy, oxo, carboxy, cyano, nitro, amidino and guanidino;

$R_3$ is H, C2–8 alkyl, C3–7 cycloalkyl, aryl wherein $R_3$ is optionally substituted by one or more $R_d$;

$R_d$ is selected from the group consisting of C1–8 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, alkanoyl, aroyl, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, arylamino, C1–8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, carbazolyl, phenothiazinyl and phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridiazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen hydroxy, oxo, carboxy, cyano, nitro, amidino, quanidino, $R_d$ may be further optionally substituted by one or more $R_e$;

$R_e$ is selected from the group consisting of C1–8 alkyl, C3–6 cycloalkyl, aryl, arylalkyl, C1–8 alkoxy, aryloxy, arylalkoxy, aroyl, amino, halogen, hydroxy, oxo, carboxy, cyano, nitro, amidino and guanidino;

$R_6$ is H, C1–8 alkyl, C3∝7 cycloalkyl, aryl or cyano, wherein $R_6$ is optionally substituted by one or more $R_f$;

$R_f$ is selected from the group consisting of C1–8 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkoxy, aryloxy, arylC1–8alkoxy, heteroarylC1–8alkoxy, C1–8 alkoxycarbonyl, aryloxycarbonyl, C1–8 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, arylamino, C1–8 alkylthio wherein the sulfur atom may be oxidized to a sulfoxide or sulfone, arylthio wherein the sulfur atom may be oxidized to a sulfoxide or sulfone, arylC1–8 alkylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, halogen, hydroxy, oxox, carboxy, cyano, nitro, amidino and guanidino, $R_f$ may be further optionally substituted by one or more $R_g$;

$R_g$ is selected from the group consisting of C1–8 alkyl, C3–7 cycloalkyl, aryl optionally substituted by one or more groups selected from halogen, methyl or methoxy, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxyazinyl, C1–8 alkoxy, aryloxy, arylC1–8alkoxy, C1–8 alkoxycarbonyl, aryloxycarbonyl, C1–8 alkanoyloxy, aroyloxy, carbamoyl wherein the nitrogen atom may be independently mono di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, alkylcarbamoyloxy, arylcarbamoyloxy, alkylsulfonylamino, arylsulfonylamino, alklaminosulfonyl, arylaminosulfonyl, amino wherein the nitrogen atom may be independent mono or di-substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quinolinyl, isoqunilinyl, quinazolinyl, qunioxalinyl, carbazolyl, phenothiazinyl and phenoxazinyl, halogen, hydroxy, oxo, carboxy, cyano, nitro, amidino, and guanidino;

or $R_5$ and $R_6$ together with the carbon they are attached form a carbocyclic ring of 3 to 6 carbon atoms, the carbocyclic ring being optionally substituted with one or more $R_h$;

$R_h$ is selected from the group consisting of C1–8 alkyl, aryl, C1–8 alkoxycarbonyl, aryloxycarbonyl, arylC1–8alkoxycarbonyl, carbamoyl wherein the nitrogen atom may be optionally mono or di-substituted with a group selected from C1–8 alkyl, C3–7 cycloalkyl, aryl, arylC1–8alkyl, heterocyclyl selected from the group consisting of pyrrolidniyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, purinyl, quniolinyl, isoquinolinyl, quniazolyl, quinoxalinyl, carbazolyl, phenothiazinyl and phenoxazinyl, halogen hydroxy, carboxy, and cyano; and X is O or S.

More preferred compounds of the formula (IIa) are those wherein:

Y is O or S;

$R_1$ is C1–5 alkyl, C3–7 cycloalkyl, phenyl, naphthyl, heterocyclyl selected from the group consisting of pyrrolidinyl, piperidinyl, morpholinyl, thiomorpholinyl, piperazinyl, indolinyl, pyranyl and thiopyranyl, heteroaryl selected from the group consisting of furanyl, thienyl, pyrrolyl, oxazolyl, thiazolyl, imidazolyl, triazolyl, tetrazolyl, pyridinyl, pyrimidinyl, pyranzinyl, indolyl, benzofuranyl, benzothienyl, benzimidazolyl, benzthiazolyl, quniolinyl, isoquinolinyl, quinazolinyl and qunioxalinyl or amino; wherein R1 is optionally substituted by one or more $R_b$;

$R_b$ is selected from the group consisting of C1–5 alkyl, C3–7 cycloalkyl, phenyl, napthyl, heterocyclyl selected from the group consisting of pyrrolidinyl, piperidinyl, morpholinyl, thiomorpholinyl, piperazinyl and indolinyl;, heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, C1–5 alkoxycarbonyl, aryloxycarbonyl, C1–5 alkanoyloxy, aroyloxy, carbamoyl wherein the nitrogen atom may be independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyridazinyl, indolyl, benzofuranyl, benzothienyl, benzimidazolyl, benzthiazolyl, quinolinyl, isoquinolinyl, quinazolinyl and quinoxalinyl, C1–5 alkanoylamino, aroylamino, C1–5 alkythio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino and guanidino, $R_b$ may be further optionally substituted by one or more $R_c$;

$R_c$ is selected from the group consisting of C1–5 alkyl, C3–6 cycloalkyl, aryl, C1–5 alkoxy, aryloxy, halogen, hydroxy, oxo, carboxy, cyano, nitro, amidino and guanidino;

$R_2$ is H or C1–3 alkyl;

$R_3$ is H, C2–5 alkyl, C3–7 cycloalkyl, aryl wherein $R_3$ is optionally substituted by one or more $R_d$;

$R_d$ is selected from the group consisting of C1–5 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, C1–5 alkanoyl, aroyl, C1 . 5 alkoxycarbonyl, aryloxycarbonyl, C1–5 alkanoyloxy, aroyloxy, cabamoyl wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and qunioxalinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, heterocyclyl selected from the group consisting of pyrrolidinyl, piperidinyl, morpholinyl, thiomorpholinyl, piperazinyl and indolinyl, or heteroaryl selected the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino, guanidino, $R_d$ may be further optionally substituted by one or more $R_e$;

$R_e$ is selected from the group consisting of C1–5 alkyl, C3–6 cycloalkyl, aryl, arylalkyl, C1–5 alkxoy, aryloxy, arylC1–5 alkoxy, aroyl, amino, halogen, hydroxy, oxo, carboxy, cyano, nitro, amidino and guanidino;

R₄ is H or C1–3 alkyl

R₅ is H or C1–8 alkyl

R₆ is H, C1–5 alkyl, C3–7 cycloalkyl, aryl or cyano, wherein R₆ is optionally substituted by one or more $R_f$;

$R_f$ is selected from the group consisting of C1–5 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, purinyl, quinolinyl, isoquinolinyl, quinazolinyl, quinoxalinyl, C1–8 alkoxy, aryloxy, arylC1–5alkoxy, heteroarylC1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and qunioxalinyl, C1–5 alkanoylamino, aroylamino, C1–5 alkythio wherein the sulfur atom may be oxidized to a sulfoxide or sulfone, arylthio wherein the sulfur atom may be oxidized to a sulfoxide or sulfone, arylC1–5 alkylthio wherein the sulfur atom may be oxidized to a sulfoxide or sulfone, ureido wherein either nitrogen atom may be independently substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1"5 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino and guanidino, $R_f$ may be further optionally substituted by one or more $R_g$;

$R_g$ is selected from the group consisting of C1–5 alkyl, C3–7 cycloalkyl, aryl, opitonally substituted by one or more groups selected from halogen, methyl or methoxy, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, triazolyl, tetrazolyl, pyridinyl, pyrimidinyl, pyridazinyl, indolyl, benzofuranyl, benzothienyl, benzimidazolyl, benzthiazolyl, quinolinyl, isoquinolinyl, quinazolinyl and quinoxalinyl, C1–5 alkoxy, aryloxy, arylC3–5alkoxy, C1–5 alkoxycarbonyl, aryloxycarbonyl, C1–5 alkanoyloxy, aroyloxy, carbamoyl wherein the nitrogen atom may be independely mono or di-substituted by C1–8 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkanoylamino, aroylamino, C1–5 alkythio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5 alkoxycarbonylamino, aryloxycarbonylamino, C1–5 arylcarbamoyloxy, arylcarbamoyloxy, C1–5 alkylsulfonylamino arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, halogen, hydroxy, oxo, carboxy, cyano, nitro, amidino and guanidino;

or R₅ and R₆ together with the carbon they are attached form a carbocyclic ring of 3 to 6 carbon atoms, the carbocyclic ring being optionally substituted with one or more $R_h$;

$R_h$ is selected from the group consisting of C1–5 alkyl, aryl, C1–5 alkoxycarbonyl, aryloxycarbonyl, arylC1–5alkoxycarbonyl, carbamoyl wherein the nitrogen atom may be optionally mono or di-substituted with a group selected from C1–5 alkyl, C3–7 cycloalkyl, aryl, arylC1–5alkyl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquniolinyl, quinazolinyl and quinazolinyl and quinoxalinyl, halogen, hydroxy, carboxy and cyano.

Even more preferred compounds of the formula (IIa) are those wherein:

$Y$ is O;

$R_1$ is C1–5 alkyl, C3–7 cycloalkyl, phenyl, naphthyl, heterocyclyl selected from the group consisting of piperidinyl, morpholinyl, thiomorpholinyl, piperazinyl, pyranyl and thiopyranyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl; or amino wherein $R_1$ is optionally substituted by one or more $R_b$;

$R_f$ is selected from the group consisting of C1–5 alkyl, C3–7 cycloalkyl, phenyl, naphthyl, heterocyclyl selected from the group consisting of pyrrolidinyl, piperidinyl morpholinyl, thiomorpholinyl, piperazinyl and indolinyl; heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, quinolinyl and isoquinolinyl, C1–5 alkoxy, aryloxy, C1–5alkoxycarbonyl, aryloxycarbonyl, C1–5 alkanoyloxy, aroloxy, carbamoyl wherein the nitrogen atom may be independently mono or di-substituted by C1–5 alkyl, aryl, phenyl, naphthyl, heterocyclyl selected from the group consisting of pyrrolidinyl, piperidinyl, morpholinyl, piperazinyl and indolinyl, or heteroaryl selected from the group consisting of furanyl, thienyl, pyrrolyl, oxazolyl, thiazolyl, imidazolyl, triazolyl, pyridinyl, indolyl, benzofuranyl, benzothienyl, benzimidazolyl, benzthiazolyl, quinolinyl, isoquinolinyl, C1–5 alkanoylamino, aroylamino, C1–5 alkythio wherein the sulfur atom may be oxidized to a sulfoxide or sulfone, arylthio wherein the sulfur atom may be oxidized to a sulfoxide or sulfone, ureido wherein either nitrogen atom may be independently substituted by alkyl or aryl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, oxo, carboxy, cyano and nitro, $R_b$ may be further optionally substituted by one or more $R_c$;

$R_c$ is selected from the group consisting of C1–5 alkyl, C3–6 cycloalkyl, aryl, C1–5 alkoxy, aryloxy, halogen, hyrdoxy, oxo, carboxy and cyano;

$R_2$ is H or methyl; $R_3$ is H, C2–5 alkyl, C3–7 cycloalkyl or phenyl wherein $R_3$ is optionally substituted by one or more $R_d$;

$R_d$ is selected from the group consisting of C1–3 alkyl, C3–6 cycloalkyl, phenyl, naphthyl, heterocyclyl selected from the group consisting piperidinyl, morpholinyl and piperazinyl, heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxy, aryloxy, aroyl, C1–5alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkythio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen hydroxy, oxo, carboxy and cyano, $R_d$ may be further optionally substituted by one or more $R_e$;

$R_e$ is selected from the group consisting of C1–5 alkyl, C3–6 cycloalkyl, aryl, arylC1–5alkyl, C1–5 alkoxy, aryloxy, arylC1–3alkoxy, aroyl, amino, halogen, hydroxy, oxo, carboxy and cyano;

$R_4$ is H or methyl;

$R_5$ is H or C1–5 alkyl;

$R_6$ is H, C1–5 alkyl, C3–7 cycloalkyl, phenyl, naphthyl or cyano, wherein $R_6$ is optionally substituted by one or more $R_f$;

$R_f$ is selected from the group consisting of C1–5 alkyl, C3–7 cycloalkyl, phenyl, naphthyl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl and quinoxalinyl, C1–5alkoxy, aryloxy, arylC1–5alkoxy heteroaryl, C1–5alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, heterocyclyl selected from the group consisting of piperidinyl, morpholinyl, piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkythio wherein the sulfur atom may be oxidized to a sulfoxide or sulfone, arylthio wherein the sulfur atom may be oxidized to a sulfoxide or sulfone, arylC1–5 alkylthio wherein the sulfur atom may be oxidized to a sulfoxide or sulfone, ureido wherein either nitrogen atom may be independently substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be indpendently mono or di-substituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, oxo, carboxy and cyano, $R_f$ may be further optionally substituted by one or more $R_g$;

$R_g$ is selected from the group consisting of C1–5 alkyl, C3–7 cycloalkyl, phenyl optionally substituted by one or more groups selected from halogen, methyl or methoxy, naphthyl optionally substituted by one or more groups selected from halogen, methyl or methoxy, heterocyclyl selected from the group consisting of pyrrolidinyl, piperazinyl morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzothienyl, quinolinyl, isoquinolinyl, quinoazolinyl and quinoxalinyl, C1–5 alkoxy, arylC1–5alkoxy, C1–5 alkoxycarbonyl, arylloxycarbonyl, C1–5 k alkanoylamino, aroyloxy, carbamoyl wherein the nitrogen atom may be independently mono or di-substituted by C1–5 alkyl, aryl, heterocyclyl selected from the group consisting of piperidinyl, morholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkanoylamino, aroylamino, C1–5 alkythio wherein the sulfur atom may be sulfoxide or sulfone, arylthio wherein the sulfur atom may be oxidized to a sulfoxide or sulfone, ureido wherein either nitrogen atom may be independently substituted by C–5 alkyl, aryl, heterocyclyl selected from the group consisting of piperidinyl, morholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazoly, imidazoly, pyridinyl, indolyl, benzofuranyl, benzothienyl, benzimidazolyl, benzthiazolyl, quniolinyl and isoquinolinyl, halogen, hydroxy, oxo, carboxy, cyano; or $R_5$ and $R_6$ together with the carbon they are attached form a carbocyclic ring of 3 to 6 carbon atoms, the carbocyclic ring being optionally substituted with one or more $R_h$;

$R_h$ is selected from the group consisting of C1–5 alkyl, phenyl, naphthyl, C1–5 alkoxycarbonyl, aryloxycarbonyl, arylC1–3alkoxycarbonyl, carbamoyl wherein the nitrogen atom may be optionally mono or di-substituted with a group selected from C1–5 alkyl, C3–6 cycloalkyl, phenyl naphthyl, arylC1–3alkyl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, halogen, hydroxy, carboxy and cyano; and X is O.

Yet even more preferred compounds of the formula (IIa) are those wherein:

Y is O;

$R_l$ is C1–5 alkyl, C3–6 cycloalkyl, phenyl, naphthyl, heterocyclyl selected from the group consisting of piperidinyl, morpholinyl, piperazinyl, pyranyl and thiopyranyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl, isoquinolinyl, or amino, wherein R1 is optionally substituted by one or more $R_b$;

$R_b$ is selected from the group consisting of C1–3 alkyl, C3–6 cycloalkyl, phenyl, naphthyl, heterocyclyl selected from the group consisting of pyrrolidinyl, piperazinyl morpholinyl, and piperazinyl, heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, quinolinyl and isoquinolinyl, C1–3alkoxy, phenoxy, C1–3 alkoxycarbonyl, aryloxycarbonyl, C1–5 alkanoyloxy, aroyloxy, carbamoyl wherein the nitrogen atom may be independently mono or di-substituted by C1–5 alkyl, phenylor heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzothienyl, quinolinyl and isoquinolinyl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5alkyl, phenyl or naphthyl; C1–5 alkoxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5alkyl, phenyl, naphthyl, heterocyclyl selected from the group consisting of piperidinyl, morholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl halogen, hydroxy, oxo, carboxy and cyano, $R_b$ may be further optionally substituted by one or more $R_c$;

$R_c$ is selected from the group consisting of C1–3 alkyl, C5–6 cycloalkyl, aryl, C1–3 alkoxy, phenoxy, halogen, hydroxy, oxo, carboxy and cyano;

$R_2$ is H;

$R_3$ is C2–5 alkyl, C3–6 cycloalkyl or phenyl, wherein $R_3$ is optionally substituted by one or more $R_d$;

$R_d$ is selected from group consisting of C1–3 alkyl, C3–6 cycloalkyl, phenyl, naphthyl, heterocyclyl selected from the group consisting of piperidinyl, morpholinyl and piperazinyl; heteroaryl selected from the group consisting of furanyl, thienyl, thiazolyl, imidazolyl, pyridinyl, indolyl, quinolinyl and isoquinolinyl, C1–5alkoxy, phenoxy, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, C1–5 alkanoylamino aroylamino, C1–3 alkythio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3alkyl, phenyl or heterocyclyl selected the group consisting of furanyl, thienyl, pyrrolyl, oxazolyl, thiazolyl, imidazolyl, pyridinyl, and indolyl, C1–5 alkoxycarbonylamino, C1–5 alkylcarbamoyloxy, arylcarbamoyloxy, C1–5 alkylsulfonylamino, arylsulfonylamino, amino wherein the nitrogen atom may be independently mono or di-substituted by C1–3 alkyl, phenyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, halogen, hydroxy, oxo, carboxy and cyano, $R_d$ may be further optionally substituted by one or more $R_e$;

$R_e$ is selected from the group consisting of C1–5 alkyl, C5–6 cycloalkyl, phenyl, naphthyl, arylC1–3alkyl, C1–5 alkoxy, phenoxy, arylC1–3alkoxy, aroyl, amino, halogen, hydroxy, oxo, carboxy and cyano;

$R_4$ is H;

$R_6$ is H, C1–5 alkyl, C3–6 cycloalkyl, phenyl or cyano, wherein $R_6$ is optionally substituted by one or more $R_f$;

$R_f$ is selected from the group consisting of C1–3 alkyl, C3–6 cycloalkyl, phenyl, naphthyl, heterocyclyl selected from the group consisting of pyrrolidinyl, piperazinyl morpholinyl and piperazinyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, quinolinyl and isoquinolinyl, C1–5alkoxy, aryloxy, arylC1–3alkoxy, heteroarylC1–3alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl, phenylor heterocyclyl selected from the group consisting of furanyl, thienyl, pyrrolyl, oxazolyl, thiazolyl, imidazolyl, pyridinyl and indolyl, C1–5 alkanolamino, aroylamino, C1–3 alkylthio wherein the sulfur atom may be oxidized to a sulfoxide or sulfone, arylthio wherein the sulfur atom may be oxidized to a sulfoxide or sulfone, arylC1–3alkylthio wherein the sulfur atom may be oxidized to a sulfoxide or sulfone, ureido wherein either nitrogen atom may be independently substituted by C1–5alkyl or phenyl, C1–5 alkoxycarbonylamino, C1–5 alkylsulfonylamino, arylsulfonylamino, amino wherein the nitrogen atom may be independently mono di-substituted by C1–5alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, halogen, hydroxy, oxo, carboxy, cyano, Rf may be further optionally substituted by one or more $R_g$;

$R_g$ is selected from the group consisting of C14 3 alkyl, C5–6 cycloalkyl, phenyl optionally substituted by one or more groups selected from halogen or methyl, heterocyclyl selected from the group consisting of pyrrolidinyl, piperidinyl, morpholinyl and piperazinyl, heteroaryl selected from the group consisting of furanyl, thienyl, pyrrolyl, oxazolyl, thiazolyl, imidazolyl, pyridinyl, pyrimidinyl, pyrazinyl and indolyl, C–5 alkoxy, aryloxy, arylC1–3alkoxy, C1–5 alkoxycarbonyl, aryloxycarbonyl, C1–5 alkanoyloxy, aroyloxy, carbamoyl wherein the nitrogen atom may be independently mono or di-substituted by C1–5 alkyl or aryl, C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl or aryl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl or aryl, halogen, hydroxy, oxo, carboxy and cyano;

or $R_5$ and $R_6$ together with the carbon they are attached form a carbocyclic ring of 3 to 6 carbon atoms, the carbocyclic ring being optionally substituted with one or more $R_h$;

$R_h$ is selected from the group consisting of C1–5 alkyl, phenyl, C1–5 alkoxycarbonyl, aryloxycarbonyl, arylC1–3alkoxycarbonyl, carbamoyl wherein the nitrogen atom may be optionally mono or di-substituted with C1–5 alkyl, C3–6 cycloalkyl, phenyl, naphthyl or arylC1–3alkyl; halogen, hydroxy, carboxy and cyano.

Still yet even more preferred compounds of the formula (IIa) are those wherein:

$R_1$ is C1-3 alkyl, C5-6 cycloalkyl, phenyl, naphthyl, heterocyclyl selected from the group consisting of piperidinyl, morpholinyl, piperazinyl, pyranyl and thiopyranyl; heteroaryl selected from the group consisting of furanyl, thienyl, pyrrolyl, oxazolyl, thiazolyl, imidazolyl, pyridinyl and indolyl or amino, wherein $R_1$ is optionally substituted by one or more $R_b$;

$R_b$ is selected from the group consisting of C1-3 alkyl, C5-6 cycloalkyl, phenyl, heterocyclyl selected from the group consisting of piperidinyl, morpholinyl and piperazinyl; heteroaryl selected from the group consisting of furanyl, thienyl, pyrrolyl, imidazolyl, tetrazolyl, pyridinyl, indolyl, benzofuranyl, benzothienyl, benzimidazolyl, benzthiazolyl, quinolinyl and isoquinolinyl, C1-3 alkoxy, C1-3 alkoxycarbonyl, aryloxycarbonyl, C1-5 alkanoyloxy, aroyloxy, carbamoyl wherein the nitrogen atom may be independently mono or di-substituted by C1-3 alkyl, phenyl or heteroaryl selected from the group consisting of pyrrolyl, imidazolyl, pyridinyl, indolyl, benzofuranyl, benzothienyl, benzimidazolyl and benzthiazolyl C1-5 alkanoylamino, aroylamino, C1-3 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1-3 alkyl or phenyl, C1-5 alkylsulfonylamino, arylsulfonylamino, amino wherein the nitrogen atom may be independently mono or di-substituted by C1-3 alkyl, phenyl, heterocyclyl selected from the group consisting of piperidinyl, morpholinyl and piperazinyl or heteroaryl selected from the group consisting of pyrrolyl, imidazolyl, pyridinyl, indolyl, benzofuranyl, benzothienyl, benzimidazolyl, benzthiazolyl, quinolinyl and isoquinolinyl; halogen, hydroxy, oxo, carboxy and cyano, $R_b$ may be further optionally substituted by one or more $R_c$;

$R_c$ is selected from the group consisting of C1-3 alkyl, C5-6 cycloalkyl, C1-3 alkoxy, halogen and hydroxy;

$R_3$ is C2-5 alkyl, C5-6 cycloalkyl or phenyl wherein $R_3$ is optionally substituted by one or more $R_d$;

$R_d$ is selected from the group consisting of C1-3 alkyl, C3-6 cycloalkyl, phenyl, naphthyl, 4-piperidinyl, 4-morpholinyl, piperazinyl, furanyl, thienyl, thiazolyl, imidazolyl, pyridinyl, indolyl, C1-5 alkoxy, phenoxy, aroyl, C1-5 alkoxycarbonyl, aryloxycarbonyl, C1-5 alkanoyloxy, aroyloxy, carbamoyl wherein the nitrogen atom may be independently mono or di-substituted by C1-5 alkyl or phenyl, C1-5 alkanoylamino, C1-3 alkylthio wherein the sulfur atom may be oxidized to a sulfoxide or sulfone, ureido wherein either nitrogen atom may be independently substituted by C1-3 alkyl or phenyl, C1-5 alkoxycarbonylamino, C1-5 alkylsulfonylamino, arylsulfonylamino, amino wherein the nitrogen atom may be independently mono or di-substituted by C1-3 alkyl or phenyl, halogen, hydroxy, oxo, carboxy and cyano, $R_d$ may be further optionally substituted by one or more $R_e$;

$R_e$ is selected from the group consisting of C1-5 alkyl, C5-6 cycloalkyl, phenyl, benzyl, C1-5 alkoxy, phenoxy, benzyloxy, aroyl, halogen, hydroxy, oxo, carboxy and cyano;

$R_5$ is H or C1-3 alkyl;

$R_6$ is H, C1-5 alkyl, phenyl or cyano, wherein $R_6$ is optionally substituted by one or more $R_f$;

$R_f$ is selected from the group consisting of C1-3 alkyl, C3-6 cycloalkyl, phenyl, naphthyl, furanyl, thienyl, thiazolyl, imidazolyl, pyridinyl, indolyl, C1-3 alkoxy, benzyloxy, pyridyl C1-3 alkoxy, thienyl C1-3 alkoxy, furanyl C1-3 alkoxy, C1-3 alkoxycarbonyl, phenoxyoxycarbonyl, C1-5 alkanoyloxy, aroyloxy, carbamoyl wherein the nitrogen atom may be independently mono or di-substituted by C1-3 alkyl or phenyl, C1-5 alkanoylamino, aroylamino, methylthio wherein the sulfur atom may be oxidized to a sulfoxide or sulfone, benzylthio wherein the sulfur atom may be oxidized to a sulfoxide or sulfone, ureido wherein either nitrogen atom may be independently substituted by C1-5 alkyl or phenyl, C1-3 alkoxycarbonylamino, amino wherein the nitrogen atom may be independently mono or di-substituted by C1-5 alkyl or phenyl, halogen, hydroxy, oxo, carboxy and cyano, $R_f$ may be further optionally substituted by one or more $R_g$;

$R_g$ is selected from the group consisting of C1-3 alkyl, phenyl optionally substituted by one or more groups selected from the group consisting of halogen and methyl, heterocyclyl selected from the group consisting of piperidinyl, morpholinyl and piperazinyl; heteroaryl selected from the group consisting of furanyl, thienyl, pyrrolyl and pyridinyl, C1-3 alkoxy, aryloxy, benzyloxy, C1-5 alkoxycarbonyl, C1-5 alkanoyloxy, aroyloxy, carbamoyl wherein the nitrogen atom may be independently mono or di-substituted by C1-5 alkyl or phenyl, C1-5 alkanoylamino, aroylamino, C1-5 alkylthio wherein the sulfur atom may be oxidized to a sulfoxide or sulfone, ureido wherein either nitrogen atom may be independently substituted by C1-5 alkyl or phenyl, C1-5 alkoxycarbonylamino, C1-5 alkylcarbamoyloxy, arylcarbamoyloxy, C1-3 alkylsulfonylamino, arylsulfonylamino, C1-3 alkylaminosulfonyl, arylaminosulfonyl, amino wherein the nitrogen atom may be independently mono or di-substituted by C1-3 alkyl or phenyl, halogen, hydroxy, oxo, carboxy and cyano;

or $R_5$ and $R_6$ together with the carbon they are attached form a carbocyclic ring of 3 to 5 carbon atoms, the carbocyclic ring being optionally substituted with one or more $R_h$;

$R_h$ is selected from the group consisting of C1-3 alkyl, phenyl, C1-3 alkoxycarbonyl, phenoxyoxycarbonyl, benzyloxy, carbamoyl wherein the nitrogen atom may be optionally mono or di-substituted with a group selected from the group consisting of C1-5 alkyl, phenyl and benzyl, halogen, hydroxy, carboxy and cyano.

Even more preferred compounds of the formula (IIa) are those wherein:

$R_1$ is C5-6 cycloalkyl, phenyl, naphthyl, piperidinyl, morpholinyl, piperazinyl, pyranyl, thiopyranyl, furanyl, thienyl, pyrrolyl or amino, wherein $R_1$ is optionally substituted by one or more $R_b$;

$R_b$ is selected from the group consisting of C1-3 alkyl, C5-6 cycloalkyl, phenyl, furanyl, thienyl, pyrrolyl, imidazolyl, indolyl, benzofuranyl, benzothienyl, benzimidazolyl, benzthiazolyl, C1-3 alkoxy, C1-3 alkoxycarbonyl, carbamoyl wherein the nitrogen atom may be independently mono or di-substituted by C1-3 alkyl or phenyl; C1-5 alkanoylamino, aroylamino, ureido wherein either nitrogen atom may be independently substituted by C1-3 alkyl or phenyl; C1-5 alkylsulfonylamino, arylsulfonylamino, amino wherein the nitrogen atom may be independently mono or di-substituted by C1-3 alkyl or phenyl, halogen, hydroxy, oxo, carboxy and cyano, $R_b$ may be further optionally substituted by one or more $R_c$;

$R_c$ is selected from the group consisting of C1-3 alkyl, C1-3 alkoxy, halogen and hydroxy;

$R_3$ is C2-5 alkyl, C5-6 cycloalkyl or phenyl, wherein $R_3$ is optionally substituted by one or more groups of the formula $R_d$;

$R_d$ is selected from the group consisting of C1-3 alkyl, C3-6 cycloalkyl, phenyl, naphthyl, 4-piperidinyl, furanyl, thienyl, thiazolyl, imidazolyl, pyridinyl, indolyl, C1-3 alkoxy, C1-5 alkoxycarbonyl, C1-5 alkanoyloxy, benzoyloxy, carbamoyl wherein the nitrogen atom may be independently mono or di-substituted by C1-3 alkyl or phenyl, C1-5 alkanoylamino, C1-3 alkylthio wherein the sulfur atom may be oxidized to a sulfoxide or sulfone, C1-3 alkoxycarbonylamino, C1-3 alkylsulfonylamino, amino wherein the nitrogen atom may be independently mono or di-substituted by C1-3 alkyl or phenyl, halogen, hydroxy, oxo, carboxy and cyano, $R_d$ may be further optionally substituted by one or more $R_e$;

$R_e$ is selected from the group consisting of C1-3 alkyl, phenyl, benzyl, C1-3 alkoxy, phenoxy, benzyloxy, benzoyl, halogen, hydroxy, oxo, carboxy and cyano;

wherein the configuration at the stereocenter defined by $R_2$ and $R_3$ and the carbon they are attached to is defined as L;

$R_5$ is H or methyl;

$R_6$ is C1-5 alkyl, phenyl or cyano wherein $R_6$ is optionally substituted by one or more groups of the formula $R_f$;

$R_f$ is selected from the group consisting of methyl, C3-6 cycloalkyl, phenyl, naphthyl, furanyl, thienyl, thiazolyl, imidazolyl, pyridinyl, indolyl, C1-3 alkoxy, benzyloxy, pyridyl C1-3 alkoxy, thienyl C1-3 alkoxy, furanyl C1-3 alkoxy, C1-5 alkanoylamino, aroylamino, methylthio wherein the sulfur atom may be oxidized to a sulfoxide or sulfone, benzylthio wherein the sulfur atom may be oxidized to a sulfoxide or sulfone, C1-3 alkoxycarbonylamino, amino wherein the nitrogen atom may be independently mono or di-substituted by C1-5 alkyl or phenyl, halogen, hydroxy, oxo, carboxy and cyano, $R_f$ may be further optionally substituted by one or more $R_g$;

$R_g$ is selected from the group consisting of C1-3 alkyl, phenyl optionally substituted by one or more groups selected from halogen or methyl, C1-3 alkoxy, aryloxy, benzyloxy, C1-3 alkoxycarbonyl, carbamoyl wherein the nitrogen atom may be independently mono or di-substituted by C1-3 alkyl or phenyl, C1-5 alkanoylamino, aroylamino, amino wherein the nitrogen atom may be independently mono or di-substituted by C1-3 alkyl or phenyl, halogen, hydroxy, oxo, carboxy and cyano;

or $R_5$ and $R_6$ together with the carbon they are attached form a carbocyclic ring of 3 to 5 carbon atoms, the carbocyclic ring being optionally substituted with one or more $R_h$;

$R_h$ is selected from the group consisting of C1-3 alkyl, phenyl, C1-3 alkoxycarbonyl, benzyloxy and carboxy.

Much more preferred compounds of formula (IIa) are those wherein:

$R_1$ is cyclohexyl, phenyl, naphthyl, piperidinyl, morpholinyl, piperazinyl, pyranyl, thiopyranyl or amino wherein $R_1$ is optionally substituted by one or more $R_b$;

$R_b$ is selected from the group consisting of C1-3 alkyl, C5-6 cycloalkyl, phenyl, furanyl, thienyl, pyrrolyl, imidazolyl, indolyl, benzofuranyl, benzothienyl, benzimidazolyl, benzthiazolyl, C1-3 alkoxy, C1-3 alkoxycarbonyl, carbamoyl wherein the nitrogen atom may be independently mono or di-substituted by C1-3 alkyl or phenyl, C1-5 alkanoylamino, aroylamino, C1-5 alkylsulfonylamino, arylsulfonylamino, amino wherein the nitrogen atom may be independently mono or di-substituted by C1-3 alkyl, halogen, hydroxy, oxo, carboxy and cyano, $R_b$ may be further optionally substituted by one or more $R_c$;

$R_c$ is selected from the group consisting of C1-3 alkoxy, halogen and hydroxy, $R_3$ is C2-5 alkyl or C5-6 cycloalkyl wherein $R_3$ is optionally substituted by one or more $R_d$;

$R_d$ is selected from the group consisting of methyl, C3-6 cycloalkyl, phenyl, naphthyl, thienyl, imidazolyl, pyridinyl, indolyl, C1-4 alkoxy, C1-5 alkanoylamino, methylthio wherein the sulfur atom may be oxidized to a sulfoxide or sulfone, halogen, hydroxy, oxo, carboxy and cyano, $R_d$ may be further optionally substituted by one or more $R_e$;

$R_e$ is selected from the group consisting of methyl, phenyl, benzyl, methoxy, phenoxy, benzyloxy, benzoyl, halogen and hydroxy;

$R_6$ is C1-5 alkyl or phenyl, wherein $R_6$ is optionally substituted by one or more $R_f$;

$R_f$ is selected from the group consisting of C3-6 cycloalkyl, phenyl, naphthyl, thienyl, imidazolyl, pyridinyl, indolyl, methoxy, benzyloxy, C1-3 alkanoylamino, methylthio wherein the sulfur atom may be oxidized to a sulfoxide or sulfone, benzylthio wherein the sulfur atom may be oxidized to a sulfoxide or sulfone, methoxycarbonylamino, amino wherein the nitrogen atom may be independently mono or di-substituted by C1-3 alkyl, halogen, hydroxy, carboxy and cyano, $R_f$ may be further optionally substituted by one or more $R_g$;

$R_g$ is selected from the group consisting of methyl, phenyl optionally substituted by one or more groups selected from halogen or methyl, methoxy, phenoxy, benzyloxy, methoxycarbonyl, amino wherein the nitrogen atom may be independently mono or di-substituted by C1-3 alkyl or phenyl, halogen, hydroxy and carboxy;

or $R_5$ and $R_6$ together with the carbon they are attached form a carbocyclic ring of 3 to 5 carbon atoms, the carbocyclic ring being optionally substituted with one or more $R_h$;

$R_h$ is selected from the group consisting of vinyl, phenyl, methoxycarbonyl, benzyloxycarbonyl and carboxy;

Penultimately preferred compounds of the formula (IIa) are those wherein:

$R_1$ is cyclohexyl, phenyl, naphthyl, piperidinyl, morpholinyl, piperazinyl, pyranyl or thiopyranyl, wherein $R_1$ is optionally substituted by one or more $R_b$;

$R_b$ is selected from the group consisting of pyrrolyl, imidazolyl, indolyl, benzimidazolyl, methoxy, methoxycarbonyl, amino wherein the nitrogen atom may be independently mono or di-substituted by C1-3 alkyl, halogen, hydroxy and carboxy, $R_b$ may be further optionally substituted by one or more $R_c$;

$R_c$ is selected from the group consisting of methoxy, halogen and hydroxy;

$R_d$ is selected from the group consisting of methyl, C3-6 cycloalkyl, phenyl, naphthyl, C1-4 alkoxy, C1-3 alkanoylamino, methylthio wherein the sulfur atom may be oxidized to a sulfoxide or sulfone, halogen, hydroxy, oxo, carboxy and cyano, $R_d$ may be further optionally substituted by one or more $R_e$;

$R_e$ is selected from the group consisting of methyl, phenyl, methoxy, halogen and hydroxy;

$R_5$ is H;

$R_f$ is selected from the group consisting of C5-6 cycloalkyl, phenyl, naphthyl, thienyl, indolyl, methoxy, benzyloxy, methylthio wherein the sulfur atom may be oxidized to a sulfoxide or sulfone, benzylthio wherein the sulfur atom may be oxidized to a sulfoxide or sulfone, methoxycarbonylamino, halogen, hydroxy, carboxy and cyano, $R_f$ may be further optionally substituted by one or more $R_g$;

$R_g$ is selected from the group consisting of methyl, phenyl optionally substituted by halogen, methoxy, phenoxy, benzyloxy, methoxycarbonyl, halogen, hydroxy and carboxy;

or R₅ and R₆ together with the carbon they are attached form a carbocyclic ring of 3 carbon atoms, the carbocyclic ring being optionally substituted with one or more $R_h$;

$R_h$ is vinyl or phenyl.

Ultimately preferred compounds of formula (IIa) are those wherein:

$R_1$ is phenyl, naphthyl or 4-morpholinyl wherein $R_1$ is optionally substituted by one or more $R_b$;

$R_b$ is selected from the group consisting of benzimidazolyl, methoxy and dimethylamino $R_b$ may be further optionally substituted by $R_c$ wherein $R_c$ is a halogen atom;

$R_3$ is C2-5 alkyl wherein $R_3$ is optionally substituted by one or more $R_d$;

$R_d$ is selected from the group consisting of C3-6 cycloalkyl, phenyl or naphthyl, $R_d$ may be further optionally substituted by one or more $R_e$;

$R_e$ is selected from the group consisting of methyl and halogen, $R_f$ is selected from the group consisting of C5-6 cycloalkyl, phenyl, naphthyl, indolyl, benzyloxy, methylthio wherein the sulfur atom may be oxidized to a sulfoxide or sulfone, benzylthio wherein the sulfur atom may be oxidized to a sulfoxide or sulfone, halogen and carboxy, $R_f$ may be further optionally substituted by one or more $R_g$;

$R_g$ is selected from the group consisting of methyl, methoxy, methoxycarbonyl, halogen and hydroxy and $R_5$ and $R_6$ together with the carbon they are attached form a carbocyclic ring of 3 carbon atoms, the carbocyclic ring being optionally substituted with one or more $R_h$.

The following are representative compounds according to the invention:

N-(4-morpholylinecarbonyl)-L-leucine (1S-cyano-3-phenylpropyl)amide;
N-(4-morpholinecarbonyl)-L-Homophenylalanine(1S-cyano-3-phenylpropyl)amide;
N-(5-dimethylaminonaphth-1-ylsulfonyl)-L-leucine (1S-cyano-3-phenylpropyl)amide;
N-(4-morpholinecarbonyl)-L-leucine-(1S-cyano-3-phenylpropyl)-N-methylamide;
N-(4-Morpholinecarbonyl)-L-leucine-[1R,S(benzthiazol-2-ylcarbonyl)-3-phenylpropyl]amide;
N-[(4-Morpholinecarbonyl]-L-leucine-[1R,S-(thiazol-2-ylcarbonyl)-3-phenylpropyl]amide;
N-(4-Morpholinecarbonyl)-L-leucine-[1R,S-[(1-(3-N-Benzyl)imidazol-2-ylcarbonyl]-3-phenylpropyl]amide;
N-(4-Morpholinecarbonyl)-L-leucine-[1R,S-(2-imidazolylcarbonyl)-3-phenylpropyl]amide;
N-(4-morpholinecarbonyl)-L-leucine (cyanomethyl)amide;
N-(4-Morpholinecarbonyl)-L-leucine [1S-cyano-5-((benzyloxycarbonyl)-amino)-pentyl]amide;
N-(4-morpholinecarbonyl)-L-leucine (1R-cyano-3-phenylpropyl)amide;
N-(4-Morpholinecarbonyl]-L-leucine-(1S-cyano-5-aminopentyl)amide;
N-(4-morpholinecarbonyl]-L-phenylalanine-(1S-cyano-3-phenylpropyl)amide;
N-(4-morpholinecarbonyl)-L-(p-ethoxy)phenylalanine-(1S-cyano-3-phenylpropyl)amide;
N-(4-Morpholinecarbonyl)-L-leucine-[1S-cyano-4-(benzyloxycarbonylamino)-butyl]amide;
N-(4-Morpholinecarbonyl)-L-leucine-[1-(benzthiazol-2-ylcarbonyl)-5-[(benzyloxycarbonyl)amino]-pentyl]amide;
N-(1-naphthylsulfonyl)-L-leucine (1S-cyano-3-phenylpropyl)amide;
N-(4-morpholinecarbonyl)-L-(4-methyl)leucine (1S-cyano-3-phenylpropyl)amide;
N-(4-morpholinecarbonyl)-L-leucine (1R-cyano-2-benzyloxyethyl)amide;
N-(methanesulfonyl)-D-(O-benzyl)serine (1S-cyano-3-phenylpropyl)amide;
N-(5-dimethylaminonaphth-1-ylsulfonyl)-D-leucine (1R-cyano-3-phenylpropyl)amide;
N-(4-morpholinecarbonyl)-L-(4-methyl)leucine (1R-cyano-2-benzyloxyethyl)amide;
N-((4-dimethylaminophenyl)sulfonyl)-L-leucine (1S-cyano-3-(phenylpropyl))amide;
N-(t-Butoxycarbonyl)-L-leucine [1-(Benzothiazo-2-ylcarbonyl)-3-phenylpropyl]amide;
N-(5-dimethylaminonaphth-1-ylsulfonyl)-L-leucine [1-(Benzothiazol-2-ylcarbonyl)-3-phenylpropyl]amide;
N-(4-methoxy-phenylsulfonyl)-L-leucine [1-(Benzothiazol-2-ylcarbonyl)-3-phenylpropyl]amide;
N-(4-Morpholinecarbonyl)-L-leucine-[1R,S(benzoxazol-2-ylcarbonyl)-3-phenylpropyl]amide;
N-(4-morpholinecarbonyl)-L-leucine (1R-cyano-2R-benzyloxypropyl)amide;
N-(4-Morpholinecarbonyl)-L-leucine-[1R,S-[(4-phenylthiazol-2-yl)-carbonyl]-3-phenylpropyl]amide;
N-(4-morpholinecarbonyl)-D-leucine (1S-cyano-3-phenylpropyl)amide;
N-(4-morpholinecarbonyl)-L-leucine [[1-[(6-phenylcarbamoyl)benzothiazol-2-ylcarbonyl]-3-phenylpropyl]]amide;
N-(methylsulfonyl)-L-leucine [1-(Benzothiazol-2-ylcarbonyl)-3-phenylpropyl]amide;
N-(4-morpholinecarbonyl)-L-(p-phenyl)phenylalanine (1S-cyano-3-phenylpropyl)amide;
N-(4-Morpholinecarbonyl)-L-leucine-[1R,S-[(5-phenylthiazol-2-yl)-carbonyl]-3-phenylpropyl]amide;
N-(4-morpholinecarbonyl)-L-leucine (1R-cyano-2-(benzylsulfanyl)ethyl)amide;
N-(4-morpholinecarbonyl)-L-leucine (1R-cyano-2-(2-chlorophenyl)methyloxyethyl)amide;
N-(4-morpholinecarbonyl)-L-phenylglycine (1S-cyano-3-phenylpropyl)amide;
N-(4-morpholinecarbonyl)-L-leucine [1-(Benzothiazol-2-ylcarbonyl)-2-benzyloxyethyl]amide;
N-(4-Morpholinecarbonyl]-L-leucine-[[6-(carbomethoxy)-benzoxazol-2-ylcarbonyl]-3-phenylpropyl]amide;
N-(5-dimethylaminonaphth-1-ylsulfonyl)-L-(4-methyl)leucine (1R-cyano-2-benzyloxyethyl)amide;
N-(4-morpholinecarbonyl)-L-cyclohexylalanine (1S-cyano-3-phenylpropyl)amide;
N-(4-Morpholinecarbonyl)-L-leucine-[1R,S-[(4-(4-benzyloxycarbonylamino)phenyl-thiazol-2-yl)-carbonyl]-3-phenylpropyl]amide;
N-(4-morpholinecarbonyl)-L-leucine (1R-cyano-2-(3-methoxyphenyl)methyloxyethyl)amide;
N-(4-morpholinecarbonyl)-L-(4-methyl)leucine (1R-cyano-2-(benzylsulfanyl)ethyl)amide;
N-(4-morpholinecarbonyl)-L-leucine (1R-cyano-2-(benzylsulfonyl)ethyl)amide;
N-(4-morpholinecarbonyl)-L-leucine (1R-cyano-2-(benzylsulfinyl)ethyl)amide;
N-(4-morpholinecarbonyl)-L-leucine (1R-cyano-2-((4-methoxyphenyl)methylsulfanyl)ethyl)amide;
N-(4-morpholinecarbonyl)-L-leucine (1R-cyano-2-((4-methylphenyl)methylsulfanyl)ethyl)amide;
N-(4-morpholinecarbonyl)-L-leucine (1R-cyano-2-(4-chlorophenyl)methyloxyethyl)amide;
N-(4-morpholinecarbonyl)-L-leucine (1R-cyano-2-(3-chlorophenyl)methyloxyethyl)amide;

N-(5-dimethylaminonaphth-1-ylsulfonyl)-L-leucine (1R-cyano-2-benzyloxyethyl)amide;

N-(4-Morpholinecarbonyl]-L-leucine 1S-((2-phenyloxazol-5-yl)carbonyl)-3-phenylpropylamide;

N-(4-morpholinecarbonyl)-L-(p-phenylcarbonyl) phenylalanine (1S-cyano-3-phenylpropyl)amide;

N-(4-morpholinecarbonyl)-L-leucine (1R-cyano-2-(2-methylphenyl)methyloxyethyl)amide;

N-(4-morpholinecarbonyl)-L-leucine (1R-cyano-2-(3-methylphenyl)methyloxyethyl)amide;

N-(4-morpholinecarbonyl)-L-leucine (1R-cyano-2-(4-methylphenyl)methyloxyethyl)amide;

N-(4-Morpholinecarbonyl]-L-leucine 1RS-((5-phenyloxazol-2-yl)carbonyl)-3-phenylpropylamide;

N-(4-morpholinecarbonyl)-L-cyclohexylalanine (1R-cyano-2-benzyloxyethyl)amide;

N-(4-morpholinecarbonyl)-L-nor-leucine (1S-cyano-3-phenylpropyl)amide;

N-(Benzyloxycarbonyl)-L-(O-t-butyl)serine (1R-cyano-2-benzyloxyethyl)amide;

N-(4-Morpholinecarbonyl]-L-leucine 1S-(oxazol-2-ylcarbonyl)-3-phenylpropylamide;

N-(4-morpholinecarbonyl)-L-(4-methyl)leucine [1-(Benzothiazol-2-ylcarbonyl)-3-phenylpropyl]amide;

N-(5-dimethylaminonaphth-1-ylsulfonyl)-L-cyclohexylalanine (1R-cyano-2-benzyloxyethyl)amide;

N-(4-morpholinecarbonyl)-L-leucine (1R-cyano-2-(3-carbomethoxyphenyl)methyloxyethyl)amide;

N-(4-morpholinecarbonyl)-L-leucine (1R-cyano-2-(4-carbomethoxyphenyl)methyloxyethyl)amide;

N-(4-Morpholinecarbonyl]-L-leucine 1S-(pyrid-2-ylcarbonyl)-3-phenylpropylamide;

N-(4-Morpholinecarbonyl)-L-leucine-[1R,S-[(4-(2-benzyloxyamino)phenyl-thiazol-2-yl)-carbonyl]-3-phenylpropyl]amide;

N-(4-morpholinecarbonyl)-L-(O-t-butyl)serine (1R-cyano-2-benzyloxyethyl)amide;

N-(4-morpholinecarbonyl)-L-leucine (1R-cyano-2-hydroxyethyl)amide;

N-(4-morpholinecarbonyl)-L-leucine (1S-cyano-3-(carbo-t-butoxy)propyl)amide;

N-(cyclohexylcarbonyl)-L-leucine (1R-cyano-2-benzyloxyethyl)amide;

N-(4-morpholinecarbonyl)-L-leucine (1S-cyano-3-(carbo-t-butoxy)ethyl)amide;

N-(4-morpholinecarbonyl)-L-leucine dicyanomethylamide;

N-(4-morpholinecarbonyl)-L-(2-naphthyl)alanine (1S-cyano-3-phenylpropyl)amide;

N-(4-morpholinecarbonyl)-L-(O-Benzyl)glutamate (1S-cyano-3-phenylpropyl)amide;

N-(4-morpholinecarbonyl)-L-homo-tyrosine (1S-cyano-3-phenylpropyl)amide;

N-(4-morpholinecarbonyl)-L-norvaline (1S-cyano-3-phenylpropyl)amide;

N-(4-morpholinecarbonyl)-L-(2-chlorophenyl)alanine (1S-cyano-3-phenylpropyl)amide;

N-Benzoyl-L-leucine (1R-cyano-2-benzyloxyethyl)amide;

N-(4-morpholinecarbonyl)-L-(4,5-dehydro)leucine(1S-cyano-3-phenylpropyl)amide;

N-(4-morpholinecarbonyl)-L-(O-methyl)tyrosine(1S-cyano-3-phenylpropyl)amide;

N-(4-morpholinecarbonyl)-L-iso-leucine (1S-cyano-3-phenylpropyl)amide;

N-(4-morpholinecarbonyl)-L-(4-nitrophenyl)alanine (1S-cyano-3-phenylpropyl)amide;

N-(4-morpholinecarbonyl)-L-(4-fluorophenyl)alanine (1S-cyano-3-phenylpropyl)amide;

N-(4-morpholinecarbonyl)-L-tyrosine (1S-cyano-3-phenylpropyl)amide;

N-(4-morpholinecarbonyl)-L-(1-naphthyl)alanine (1S-cyano-3-phenylpropyl)amide;

N-(4-morpholinecarbonyl)-L-methionine (1S-cyano-3-phenylpropyl)amide;

N-(4-morpholinecarbonyl)-L-phenylalanine (1S-cyano-2-(1-benzyl-4-imidazolyl)ethyl)amide;

N-(4-morpholinecarbonyl)-L-leucine (1S-cyano-2-(1-benzyl-4-imidazolyl)ethyl)amide;

N-(4-morpholinecarbonyl)-L-phenylalanine (1S-cyano-2-(carbobenzyloxy)ethyl)amide;

N-(4-morpholinecarbonyl)-L-leucine(1S-cyano-2-(carbobenzyloxy)ethyl)amide;

N-(4-morpholinecarbonyl)-L-phenylalanine (1S-cyano-1-phenylmethyl)amide;

N-(4-morpholinecarbonyl)-L-leucine (1S-cyano-1-phenylmethyl)amide;

N-(4-morpholinecarbonyl)-L-phenylalanine (1S-cyano-2-(4-benzyloxyphenyl)ethyl)amide;

N-(4-morpholinecarbonyl)-L-leucine (1S-cyano-2-(4-benzyloxyphenyl)ethyl)amide;

N-(4-morpholinecarbonyl)-L-phenylalanine (1-cyanocyclopropyl)amide;

N-(4-morpholinecarbonyl)-L-leucine (1-cyanocyclopropyl)amide;

N-(4-morpholinecarbonyl)-L-phenylalanine (1S-cyano-2-(4-phenylphenyl)ethyl)amide;

N-(4-morpholinecarbonyl)-L-leucine (1S-cyano-2-(4-phenylphenyl)ethyl)amide;

N-(4-morpholinecarbonyl)-L-phenylalanine (1S-cyano-2-(4-benzoylphenyl)ethyl)amide;

N-(4-morpholinecarbonyl)-L-leucine(1S-cyano-2-(4-benzoylphenyl)ethyl)amide;

N-(4-morpholinecarbonyl)-L-phenylalanine (1S-cyano-2-(1-naphthyl)ethyl)amide;

N-(4-morpholinecarbonyl)-L-leucine (1S-cyano-2-(1-naphthyl)ethyl)amide;

N-(4-morpholinecarbonyl)-L-phenylalanine (1S-cyano-2-(2-naphthyl)ethyl)amide;

N-(4-morpholinecarbonyl)-L-leucine (1S-cyano-2-(2-naphthyl)ethyl)amide;

N-(4-morpholinecarbonyl)-L-phenylalanine (1S-cyano-2-(2-chlorophenyl)ethyl)amide;

N-(4-morpholinecarbonyl)-L-leucine (1S-cyano-2-(2-chlorophenyl)ethyl)amide;

N-(4-morpholinecarbonyl)-L-phenylalanine (1S-cyano-2-(4-chlorophenyl)ethyl)amide;

N-(4-morpholinecarbonyl)-L-leucine (1S-cyano-2-(4-chlorophenyl)ethyl)amide;

N-(4-morpholinecarbonyl)-L-phenylalanine (1S-cyano-2-(3,4-dichlorophenyl)ethyl)amide;

N-(4-morpholinecarbonyl)-L-leucine (1S-cyano-2-(3,4-dichlorophenyl)ethyl)amide;

N-(4-morpholinecarbonyl)-L-phenylalanine (1S-cyanobut-3-ynyl)amide;

N-(4-morpholinecarbonyl)-L-leucine(1S-cyanobut-3-ynyl)amide;

N-(4-morpholinecarbonyl)-L-leucine (1S-cyanopropyl)amide;

N-(4-morpholinecarbonyl)-L-phenylalanine;

N-(4-morpholinecarbonyl)-L-leucine (1S-cyano-2-(4-(2,6-dichloromethyloxy)phenyl)ethyl)amide;

N-(4-morpholinecarbonyl)-L-leucine (1S-cyano-2S-methylbutyl)amide;

N-(4-morpholinecarbonyl)-L-phenylalanine (1S-cyanopentyl)amide;

N-(4-morpholinecarbonyl)-L-leucine (1S-cyanopentyl) amide;
N-(4-morpholinecarbonyl)-L-phenylalanine (1S-cyano-2,2-dimethylpropyl)amide;
N-(4-morpholinecarbonyl)-L-leucine (1S-cyano-2,2-dimethylpropyl)amide;
N-(4-morpholinecarbonyl)-L-phenylalanine (1S-cyano-3-methylbutyl)amide;
N-(4-morpholinecarbonyl)-L-leucine (1S-cyano-3-methylbutyl)amide;
N-(4-morpholinecarbonyl)-L-phenylalanine (1S-cyano-2-(4-nitrophenylethyl)amide;
N-(4-morpholinecarbonyl)-L-leucine (1S-cyano-2-(4-nitrophenylethyl)amide;
N-(4-morpholinecarbonyl)-L-phenylalanine (1S-cyanobutyl)amide;
N-(4-morpholinecarbonyl)-L-leucine (1S-cyanobutyl) amide;
N-(4-morpholinecarbonyl)-L-phenylalanine (1R-cyano-2R-benzyloxypropyl)amide;
N-(4-morpholinecarbonyl)-L-phenylalanine (1S-cyanoethyl)amide;
N-(4-morpholinecarbonyl)-L-leucine (1S-cyanoethyl) amide;
N-(4-morpholinecarbonyl)-L-phenylalanine (1S-cyano-3-(carbobenzyloxy)propyl)amide;
N-(4-morpholinecarbonyl)-L-leucine (1S-cyano-3-(carbobenzyloxy)propyl)amide;
N-(4-morpholinecarbonyl)-L-phenylalanine (1S-cyano-2-(3-benzimidazolyl)ethyl)amide;
N-(4-morpholinecarbonyl)-L-leucine (1S-cyano-2-(3-benzimidazolyl)ethyl)amide;
N-(4-morpholinecarbonyl)-L-phenylalanine (1-cyano-1-methylethyl)amide;
N-(4-morpholinecarbonyl)-L-leucine (1-cyano-1-methylethyl)amide;
N-(4-morpholinecarbonyl)-L-phenylalanine (1S-cyano-2-(4-hydroxyphenyl)ethyl)amide;
N-(4-morpholinecarbonyl)-L-leucine (1S-cyano-2-(4-hydroxyphenyl)ethyl)amide;
N-(4-morpholinecarbonyl)-L-phenylalanine (1S,3-dicyanopropyl)amide;
N-(4-morpholinecarbonyl)-L-leucine (1S,3-dicyanopropyl) amide;
N-(4-morpholinecarbonyl)-L-phenylalanine (1S-cyano-2-(4-hydroxy-3-iodophenyl)ethyl)amide;
N-(4-morpholinecarbonyl)-L-leucine (1S-cyano-2-(4-hydroxy-3-iodophenyl)ethyl)amide;
N-(4-morpholinecarbonyl)-L-phenylalanine (1S,2-dicyanoethyl)amide;
N-(4-morpholinecarbonyl)-L-leucine (1S,2-dicyanoethyl) amide;
N-(4-morpholinecarbonyl)-L-phenylalanine (1R-cyano-2-benzyloxyethyl)amide;
N-(4-morpholinecarbonyl)-L-phenylalanine (1S-cyano-2-(2-thienyl)ethyl)amide;
N-(4-morpholinecarbonyl)-L-leucine (1S-cyano-2-(2-thienyl)ethyl)amide;
N-(4-morpholinecarbonyl)-L-phenylalanine (1S-cyano-3-(methylsulfonyl)propyl)amide;
N-(4-morpholinecarbonyl)-L-leucine (1S-cyano-3-(methylsulfonyl)propyl)amide;
N-(4-morpholinecarbonyl)-L-phenylalanine (1S-cyano-2-phenylethyl)amide;
N-(4-morpholinecarbonyl)-L-leucine (1S-cyano-2-phenylethyl)amide;
N-(4-morpholinecarbonyl)-L-phenylalanine (1S-cyano-3-(4-hydroxyphenyl)propyl)amide;
N-(4-morpholinecarbonyl)-L-leucine (1S-cyano-3-(4-hydroxyphenyl)propyl)amide;
N-(4-morpholinecarbonyl)-L-phenylalanine (1S-cyano-2-cyclohexylethyl)amide;
N-(4-morpholinecarbonyl)-L-leucine (1S-cyano-2-cyclohexylethyl)amide;
N-(4-morpholinecarbonyl)-L-phenylalanine (1S-cyano-2-(3-chlorophenyl)ethyl)amide;
and
N-(4-morpholinecarbonyl)-L-leucine (1S-cyano-2-(3-chlorophenyl)ethyl)amide.

Preferred compounds of the invention include:
N-(5-dimethylaminonaphth-1-ylsulfonyl)-L-leucine (1S-cyano-3-phenylpropyl)amide;
N-(4-morpholinecarbonyl)-L-leucine (1R-cyano-3-phenylpropyl)amide;
N-(1-naphthylsulfonyl)-L-leucine (1S-cyano-3-phenylpropyl)amide;
N-(4-morpholinecarbonyl)-L-(4-methyl)leucine (1S-cyano-3-phenylpropyl)amide;
N-(4-morpholinecarbonyl)-L-leucine (1R-cyano-2-benzyloxyethyl)amide;
N-(4-morpholinecarbonyl)-L-(4-methyl)leucine (1R-cyano-2-benzyloxyethyl)amide;
N-((4-dimethylaminophenyl)sulfonyl)-L-leucine (1S-cyano-3-(phenylpropyl))amide;
N-(4-morpholinecarbonyl)-L-leucine (1R-cyano-2R-benzyloxypropyl)amide;
N-(4-morpholinecarbonyl)-L-leucine (1R-cyano-2-(benzylsulfanyl)ethyl)amide;
N-(4-morpholinecarbonyl)-L-leucine (1R-cyano-2-(2-chlorophenyl)methyloxyethyl)amide;
N-(5-dimethylaminonaphth-1-ylsulfonyl)-L-(4-methyl)leucine (1R-cyano-2-benzyloxyethyl)amide;
N-(4-morpholinecarbonyl)-L-leucine (1R-cyano-2-(3-methoxyphenyl)methyloxyethyl)amide;
N-(4-morpholinecarbonyl)-L-(4-methyl)leucine (1R-cyano-2-(benzylsulfanyl)ethyl)amide;
N-(4-morpholinecarbonyl)-L-leucine (1R-cyano-2-(benzylsulfonyl)ethyl)amide;
N-(4-morpholinecarbonyl)-L-leucine (1R-cyano-2-(benzylsulfinyl)ethyl)amide;
N-(4-morpholinecarbonyl)-L-leucine (1R-cyano-2-((4-methoxyphenyl)methylsulfanyl)ethyl)amide;
N-(4-morpholinecarbonyl)-L-leucine (1R-cyano-2-((4-methylphenyl)methylsulfanyl)ethyl)amide;
N-(4-morpholinecarbonyl)-L-leucine (1R-cyano-2-(4-chlorophenyl)methyloxyethyl)amide;
N-(4-morpholinecarbonyl)-L-leucine (1R-cyano-2-(3-chlorophenyl)methyloxyethyl)amide;
N-(5-dimethylaminonaphth-1-ylsulfonyl)-L-leucine (1R-cyano-2-benzyloxyethyl)amide;
N-(4-morpholinecarbonyl)-L-leucine (1R-cyano-2-(2-methylphenyl)methyloxyethyl)amide;
N-(4-morpholinecarbonyl)-L-leucine (1R-cyano-2-(3-methylphenyl)methyloxyethyl)amide;
N-(4-morpholinecarbonyl)-L-leucine (1R-cyano-2-(4-methylphenyl)methyloxyethyl)amide;
N-(5-dimethylaminonaphth-1-ylsulfonyl)-L-cyclohexylalanine (1R-cyano-2-benzyloxyethyl)amide;
N-(4-morpholinecarbonyl)-L-leucine (1R-cyano-2-(3-carbomethoxyphenyl)methyloxyethyl)amide;
N-(4-morpholinecarbonyl)-L-leucine (1R-cyano-2-(4-carbomethoxyphenyl)methyloxyethyl)amide;
N-(4-morpholinecarbonyl)-L-leucine (1R-cyano-2-hydroxyethyl)amide;
N-(4-morpholinecarbonyl)-L-leucine (1S-cyano-3-(carbo-t-butoxy)propyl)amide;

N-(cyclohexylcarbonyl)-L-leucine (1R-cyano-2-benzyloxyethyl)amide;
N-(4-morpholinecarbonyl)-L-leucine (1S-cyano-3-(carbo-t-butoxy)ethyl)amide;
N-(4-morpholylinecarbonyl)-L-leucine (1S-cyano-3-phenylpropyl)amide;
N-(4-morpholinecarbonyl)-L-Homophenylalanine(1S-cyano-3-phenylpropyl)amide;
N-(4-morpholinecarbonyl)-L-leucine (cyanomethyl)amide;
N-(4-Morpholinecarbonyl)-L-leucine [1S-cyano-5-((benzyloxycarbonyl)-amino)-pentyl]amide;
N-(4-Morpholinecarbonyl]-L-leucine-(1S-cyano-5-aminopentyl)amide;
N-(4-morpholinecarbonyl]-L-phenylalanine-(1S-cyano-3-phenylpropyl)amide;
N-(4-morpholinecarbonyl)-L-(p-ethoxy)phenylalanine-(1S-cyano-3-phenylpropyl)amide;
N-(4-Morpholinecarbonyl)-L-leucine-[1S-cyano-4-(benzyloxycarbonylamino)-butyl]amide;
N-(4-Morpholinecarbonyl)-L-leucine-[1R,S(benzthiazol-2-ylcarbonyl)-3-phenylpropyl]amide;
N-(4-Morpholinecarbonyl)-L-leucine-[1R,S(benzoxazol-2-ylcarbonyl)-3-phenylpropyl]amide;
N-(4-Morpholinecarbonyl)-L-leucine-[1-(benzthiazol-2-ylcarbonyl)-5-[(benzyloxycarbonyl)amino]-pentyl]amide;
N-(4-Morpholinecarbonyl]-L-leucine-[[6-(carbomethoxy)-benzoxazol-2-ylcarbonyl]-3-phenylpropyl]amide;
N-(4-morpholinecarbonyl)-L-leucine [[1-[(6-phenylcarbamoyl)benzothiazol-2-ylcarbonyl]-3-phenylpropyl]]amide;
N-(4-morpholinecarbonyl)-L-(p-phenyl)phenylalanine (1S-cyano-3-phenylpropyl)amide;
N-(4-morpholinecarbonyl)-L-phenylglycine (1S-cyano-3-phenylpropyl)amide;
N-(4-morpholinecarbonyl)-L-cyclohexylalanine (1S-cyano-3-phenylpropyl)amide;
N-(4-Morpholinecarbonyl]-L-leucine 1S-((2-phenyloxazol-5-yl)carbonyl)-3-phenylpropylamide;
N-(4-morpholinecarbonyl)-L-(p-phenylcarbonyl)phenylalanine (1S-cyano-3-phenylpropyl)amide;
N-(4-Morpholinecarbonyl]-L-leucine 1RS-((5-phenyloxazol-2-yl)carbonyl)-3-phenylpropylamide;
N-(4-Morpholinecarbonyl]-L-leucine 1S-(oxazol-2-ylcarbonyl)-3-phenylpropylamide;
N-(4-morpholinecarbonyl)-L-cyclohexylalanine (1R-cyano-2-benzyloxyethyl)amide;
N-(4-morpholinecarbonyl)-L-nor-leucine (1S-cyano-3-phenylpropyl)amide;
N-(4-morpholinecarbonyl)-L-(4-methyl)leucine [1-(Benzothiazol-2-ylcarbonyl)-3-phenylpropyl]amide;
N-(4-Morpholinecarbonyl]-L-leucine 1S-(pyrid-2-ylcarbonyl)-3-phenylpropylamide;
N-(4-morpholinecarbonyl)-L-(O-t-butyl)serine (1R-cyano-2-benzyloxyethyl)amide;
N-(4-morpholinecarbonyl)-L-(2-naphthyl)alanine (1S-cyano-3-phenylpropyl)amide;
N-(4-morpholinecarbonyl)-L-(O-Benzyl)glutamate (1S-cyano-3-phenylpropyl)amide;
N-(4-morpholinecarbonyl)-L-homo-tyrosine (1S-cyano-3-phenylpropyl)amide;
N-(4-morpholinecarbonyl)-L-norvaline (1S-cyano-3-phenylpropyl)amide;
N-(4-morpholinecarbonyl)-L-(2-chlorophenyl)alanine (1S-cyano-3-phenylpropyl)amide;
N-Benzoyl-L-leucine (1R-cyano-2-benzyloxyethyl)amide;
N-(4-morpholinecarbonyl)-L-(4,5-dehydro)leucine(1S-cyano-3-phenylpropyl)amide;
N-(4-morpholinecarbonyl)-L-(O-methyl)tyrosine(1S-cyano-3-phenylpropyl)amide;
N-(4-morpholinecarbonyl)-L-iso-leucine (1S-cyano-3-phenylpropyl)amide;
N-(4-morpholinecarbonyl)-L-(4-nitrophenyl)alanine (1S-cyano-3-phenylpropyl)amide;
N-(4-morpholinecarbonyl)-L-(4-fluorophenyl)alanine (1S-cyano-3-phenylpropyl)amide;
N-(4-morpholinecarbonyl)-L-tyrosine (1S-cyano-3-phenylpropyl)amide;
N-(4-morpholinecarbonyl)-L-(1-naphthyl)alanine (1S-cyano-3-phenylpropyl)amide;
N-(4-morpholinecarbonyl)-L-methionine (1S-cyano-3-phenylpropyl)amide;
N-(4-morpholinecarbonyl)-L-phenylalanine (1S-cyano-2-(1-benzyl-4-imidazolyl)ethyl)amide;
N-(4-morpholinecarbonyl)-L-leucine (1S-cyano-2-(1-benzyl-4-imidazolyl)ethyl)amide;
N-(4-morpholinecarbonyl)-L-phenylalanine (1S-cyano-2-(carbobenzyloxy)ethyl)amide;
N-(4-morpholinecarbonyl)-L-leucine(1S-cyano-2-(carbobenzyloxy)ethyl)amide;
N-(4-morpholinecarbonyl)-L-phenylalanine (1S-cyano-1-phenylmethyl)amide;
N-(4-morpholinecarbonyl)-L-leucine (1S-cyano-1-phenylmethyl)amide;
N-(4-morpholinecarbonyl)-L-phenylalanine (1S-cyano-2-(4-benzyloxyphenyl)ethyl)amide;
N-(4-morpholinecarbonyl)-L-leucine (1S-cyano-2-(4-benzyloxyphenyl)ethyl)amide;
N-(4-morpholinecarbonyl)-L-phenylalanine (1-cyanocyclopropyl)amide;
N-(4-morpholinecarbonyl)-L-leucine (1-cyanocyclopropyl)amide;
N-(4-morpholinecarbonyl)-L-phenylalanine (1S-cyano-2-(4-phenylphenyl)ethyl)amide;
N-(4-morpholinecarbonyl)-L-leucine (1S-cyano-2-(4-phenylphenyl)ethyl)amide;
N-(4-morpholinecarbonyl)-L-phenylalanine (1S-cyano-2-(4-benzoylphenyl)ethyl)amide;
N-(4-morpholinecarbonyl)-L-leucine(1S-cyano-2-(4-benzoylphenyl)ethyl)amide;
N-(4-morpholinecarbonyl)-L-phenylalanine (1S-cyano-2-(1-naphthyl)ethyl)amide;
N-(4-morpholinecarbonyl)-L-leucine (1S-cyano-2-(1-naphthyl)ethyl)amide;
N-(4-morpholinecarbonyl)-L-phenylalanine (1S-cyano-2-(2-naphthyl)ethyl)amide;
N-(4-morpholinecarbonyl)-L-leucine (1S-cyano-2-(2-naphthyl)ethyl)amide;
N-(4-morpholinecarbonyl)-L-phenylalanine (1S-cyano-2-(2-chlorophenyl)ethyl)amide;
N-(4-morpholinecarbonyl)-L-leucine (1S-cyano-2-(2-chlorophenyl)ethyl)amide;
N-(4-morpholinecarbonyl)-L-phenylalanine (1S-cyano-2-(4-chlorophenyl)ethyl)amide;
N-(4-morpholinecarbonyl)-L-leucine (1S-cyano-2-(4-chlorophenyl)ethyl)amide;
N-(4-morpholinecarbonyl)-L-phenylalanine (1S-cyano-2-(3,4-dichlorophenyl)ethyl)amide;
N-(4-morpholinecarbonyl)-L-leucine (1S-cyano-2-(3,4-dichlorophenyl)ethyl)amide;
N-(4-morpholinecarbonyl)-L-phenylalanine (1S-cyanobut-3-ynyl)amide;
N-(4-morpholinecarbonyl)-L-leucine(1S-cyanobut-3-ynyl)amide;
N-(4-morpholinecarbonyl)-L-leucine (1S-cyanopropyl)amide;

N-(4-morpholinecarbonyl)-L-phenylalanine (1S-cyano-2-(4-(2,6-dichloromethyloxy)phenyl)ethyl)amide;
N-(4-morpholinecarbonyl)-L-leucine (1S-cyano-2-(4-(2,6-dichloromethyloxy)phenyl)ethyl)amide;
N-(4-morpholinecarbonyl)-L-leucine (1S-cyano-2S-methylbutyl)amide;
N-(4-morpholinecarbonyl)-L-phenylalanine (1S-cyanopentyl)amide;
N-(4-morpholinecarbonyl)-L-leucine (1S-cyanopentyl)amide;
N-(4-morpholinecarbonyl)-L-phenylalanine (1S-cyano-2,2-dimethylpropyl)amide;
N-(4-morpholinecarbonyl)-L-leucine (1S-cyano-2,2-dimethylpropyl)amide;
N-(4-morpholinecarbonyl)-L-phenylalanine (1S-cyano-3-methylbutyl)amide;
N-(4-morpholinecarbonyl)-L-leucine (1S-cyano-3-methylbutyl)amide;
N-(4-morpholinecarbonyl)-L-phenylalanine (1S-cyano-2-(4-nitrophenylethyl)amide;
N-(4-morpholinecarbonyl)-L-leucine (1S-cyano-2-(4-nitrophenylethyl)amide;
N-(4-morpholinecarbonyl)-L-phenylalanine (1S-cyanobutyl)amide;
N-(4-morpholinecarbonyl)-L-leucine (1S-cyanobutyl)amide;
N-(4-morpholinecarbonyl)-L-phenylalanine (1R-cyano-2R-benzyloxypropyl)amide;
N-(4-morpholinecarbonyl)-L-phenylalanine (1S-cyanoethyl)amide;
N-(4-morpholinecarbonyl)-L-leucine (1S-cyanoethyl)amide;
N-(4-morpholinecarbonyl)-L-phenylalanine (1S-cyano-3-(carbobenzyloxy)propyl)amide;
N-(4-morpholinecarbonyl)-L-leucine (1S-cyano-3-(carbobenzyloxy)propyl)amide;
N-(4-morpholinecarbonyl)-L-phenylalanine (1S-cyano-2-(3-benzimidazolyl)ethyl)amide;
N-(4-morpholinecarbonyl)-L-leucine (1S-cyano-2-(3-benzimidazolyl)ethyl)amide;
N-(4-morpholinecarbonyl)-L-phenylalanine (1-cyano-1-methylethyl)amide;
N-(4-morpholinecarbonyl)-L-leucine (1-cyano-1-methylethyl)amide;
N-(4-morpholinecarbonyl)-L-phenylalanine (1S-cyano-2-(4-hydroxyphenyl)ethyl)amide;
N-(4-morpholinecarbonyl)-L-leucine (1S-cyano-2-(4-hydroxyphenyl)ethyl)amide;
N-(4-morpholinecarbonyl)-L-phenylalanine (1S,3-dicyanopropyl)amide;
N-(4-morpholinecarbonyl)-L-leucine (1S,3-dicyanopropyl)amide;
N-(4-morpholinecarbonyl)-L-phenylalanine (1S-cyano-2-(4-hydroxy-3-iodophenyl)ethyl)amide;
N-(4-morpholinecarbonyl)-L-leucine (1S-cyano-2-(4-hydroxy-3-iodophenyl)ethyl)amide;
N-(4-morpholinecarbonyl)-L-phenylalanine (1S,2-dicyanoethyl)amide;
N-(4-morpholinecarbonyl)-L-leucine (1S,2-dicyanoethyl)amide;
N-(4-morpholinecarbonyl)-L-phenylalanine (1R-cyano-2-benzyloxyethyl)amide;
N-(4-morpholinecarbonyl)-L-phenylalanine (1S-cyano-2-(2-thienyl)ethyl)amide;
N-(4-morpholinecarbonyl)-L-leucine (1S-cyano-2-(2-thienyl)ethyl)amide;
N-(4-morpholinecarbonyl)-L-phenylalanine (1S-cyano-3-(methylsulfonyl)propyl)amide;
N-(4-morpholinecarbonyl)-L-leucine (1S-cyano-3-(methylsulfonyl)propyl)amide;
N-(4-morpholinecarbonyl)-L-phenylalanine (1S-cyano-2-phenylethyl)amide;
N-(4-morpholinecarbonyl)-L-leucine (1S-cyano-2-phenylethyl)amide;
N-(4-morpholinecarbonyl)-L-phenylalanine (1S-cyano-3-(4-hydroxyphenyl)propyl)amide;
N-(4-morpholinecarbonyl)-L-leucine (1S-cyano-3-(4-hydroxyphenyl)propyl)amide;
N-(4-morpholinecarbonyl)-L-phenylalanine (1S-cyano-2-cyclohexylethyl)amide;
N-(4-morpholinecarbonyl)-L-leucine (1S-cyano-2-cyclohexylethyl)amide;
N-(4-morpholinecarbonyl)-L-phenylalanine (1S-cyano-2-(3-chlorophenyl)ethyl)amide;
and
N-(4-morpholinecarbonyl)-L-leucine (1S-cyano-2-(3-chlorophenyl)ethyl)amide.

More preferred compounds of the invention include:
N-(4-morpholinecarbonyl)-L-(4-methyl)leucine (1S-cyano-3-phenylpropyl)amide;
N-(4-morpholinecarbonyl)-L-leucine (1R-cyano-2-benzyloxyethyl)amide;
N-(4-morpholinecarbonyl)-L-(4-methyl)leucine (1R-cyano-2-benzyloxyethyl)amide;
N-(4-morpholinecarbonyl)-L-leucine (1R-cyano-2R-benzyloxypropyl)amide;
N-(4-morpholinecarbonyl)-L-leucine (1R-cyano-2-(benzylsulfanyl)ethyl)amide;
N-(4-morpholinecarbonyl)-L-leucine (1R-cyano-2-(2-chlorophenyl)methyloxyethyl)amide;
N-(4-morpholinecarbonyl)-L-leucine (1R-cyano-2-(4-chlorophenyl)methyloxyethyl)amide;
N-(4-morpholinecarbonyl)-L-leucine (1R-cyano-2-(3-methoxyphenyl)methyloxyethyl)amide;
N-(4-morpholinecarbonyl)-L-(4-methyl)leucine (1R-cyano-2-(benzylsulfanyl)ethyl)amide;
N-(4-morpholinecarbonyl)-L-leucine (1R-cyano-2-(benzylsulfonyl)ethyl)amide;
N-(4-morpholinecarbonyl)-L-leucine (1R-cyano-2-(benzylsulfinyl)ethyl)amide;
N-(4-morpholinecarbonyl)-L-leucine (1R-cyano-2-((4-methoxyphenyl)methylsulfanyl)ethyl)amide;
N-(4-morpholinecarbonyl)-L-leucine (1R-cyano-2-(3-chlorophenyl)methyloxyethyl)amide;
N-(5-dimethylaminonaphth-1-ylsulfonyl)-L-leucine (1R-cyano-2-benzyloxyethyl)amide;
N-(4-morpholinecarbonyl)-L-leucine (1R-cyano-2-(2-methylphenyl)methyloxyethyl)amide;
N-(4-morpholinecarbonyl)-L-leucine (1R-cyano-2-(3-methylphenyl)methyloxyethyl)amide;
N-(4-morpholinecarbonyl)-L-leucine (1R-cyano-2-(4-methylphenyl)methyloxyethyl)amide;
N-(4-morpholinecarbonyl)-L-leucine (1R-cyano-2-(3-carbomethoxyphenyl)methyloxyethyl)amide;
N-(4-morpholinecarbonyl)-L-leucine (1R-cyano-2-(4-carbomethoxyphenyl)methyloxyethyl)amide;
N-(4-morpholinecarbonyl)-L-leucine (1S-cyano-3-(carbo-t-butoxy)propyl)amide;
N-(4-morpholylinecarbonyl)-L-leucine (1S-cyano-3-phenylpropyl)amide;
N-(4-Morpholinecarbonyl)-L-leucine-[1S(benzthiazol-2-ylcarbonyl)-3-phenylpropyl]amide;
N-(4-Morpholinecarbonyl)-L-leucine [1S-cyano-5-((benzyloxycarbonyl)-amino)-pentyl]amide;
N-(4-Morpholinecarbonyl)-L-leucine-[1R,S(benzoxazol-2-ylcarbonyl)-3-phenylpropyl]amide;

N-(4-morpholinecarbonyl)-L-leucine [[1-[(6-phenylcarbamoyl)benzothiazol-2-ylcarbonyl]-3-phenylpropyl]]amide;
N-(4-Morpholinecarbonyl]-L-leucine-[[6-(carbomethoxy)-benzoxazol-2-ylcarbonyl]-3-phenylpropyl]amide;
N-(4-morpholinecarbonyl)-L-cyclohexylalanine (1S-cyano-3-phenylpropyl)amide;
N-(4-morpholinecarbonyl)-L-cyclohexylalanine (1R-cyano-2-benzyloxyethyl)amide;
N-(4-morpholinecarbonyl)-L-nor-leucine (1S-cyano-3-phenylpropyl)amide;
N-(4-Morpholinecarbonyl]-L-leucine 1RS-((5-phenyloxazol-2-yl)carbonyl)-3-phenylpropylamide;
N-(4-Morpolinecarbonyl]-L-leucine 1S-(oxazol-2-ylcarbonyl)-3-phenylpropylamide;
N-(4-morpholinecarbonyl)-L-(4-methyl)leucine [1-(Benzothiazol-2-ylcarbonyl)-3-phenylpropyl]amide;
N-(4-morpholinecarbonyl)-L-(2-naphthyl)alanine (1S-cyano-3-phenylpropyl)amide;
N-(4-morpholinecarbonyl)-L-(2-chlorophenyl)alanine (1S-cyano-3-phenylpropyl)amide;
N-Benzoyl-L-leucine (1R-cyano-2-benzyloxyethyl)amide;
N-(4-morpholinecarbonyl)-L-(O-methyl)tyrosine (1S-cyano-3-phenylpropyl)amide;
N-(4-morpholinecarbonyl)-L-leucine(1S-cyano-2-(carbobenzyloxy)ethyl)amide;
N-(4-morpholinecarbonyl)-L-leucine (1S-cyano-1-phenylmethyl)amide;
N-(4-morpholinecarbonyl)-L-leucine (1-cyanocyclopropyl)amide;
N-(4-morpholinecarbonyl)-L-leucine (1S-cyano-2-(2-chlorophenyl)ethyl)amide;
N-(4-morpholinecarbonyl)-L-leucine (1S-cyano-2-(4-(2,6-dichloromethyloxy)phenyl)ethyl)amide;
N-(4-morpholinecarbonyl)-L-leucine (1S-cyano-3-(carbobenzyloxy)propyl)amide;
N-(4-morpholinecarbonyl)-L-leucine (1S,3-dicyanopropyl)amide;
N-(4-morpholinecarbonyl)-L-leucine (1S,2-dicyanoethyl)amide;
N-(4-morpholinecarbonyl)-L-leucine (1S-cyano-3-(methylsulfonyl)propyl)amide;
N-(4-morpholinecarbonyl)-L-leucine (1S-cyano-3-(4-hydroxyphenyl)propyl)amide; and
N-(4-morpholinecarbonyl)-L-leucine (1S-cyano-2-cyclohexylethyl)amide.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formulas (I), (Ia) and formulas (II), (IIa) can exist in more than one tautomeric form. The invention includes all such tautomers.

It shall be understood by one of ordinary skill in the art that all compounds of the invention are those which are chemically stable.

The invention includes pharmaceutically acceptable derivatives of compounds of formulas (I), (Ia) and formulas (II), (IIa). A "pharmaceutically acceptable derivative" refers to any pharmaceutically acceptable salt or ester of a compound of this invention, or any other compound which, upon administration to a patient, is capable of providing (directly or indirectly) a compound of this invention, a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

In addition, the compounds of this invention include prodrugs of compounds of the formulas (I), (Ia) and formulas (II), (IIa). Prodrugs include those compounds that, upon simple chemical transformation, are modified to produce the compounds of the invention. Simple chemical transformations include hydrolysis, oxidation and reduction. Specifically, when a prodrug of this invention is administered to a patient, the prodrug may be transformed into a compound of formulas (I), (Ia) or formulas (II), (IIa), thereby imparting the desired pharmacological effect.

In order that the invention herein described may be more fully understood, the following detailed description is set forth. As used herein, the following abbreviations are used:

BOC or t-BOC is tertiary butoxycarbonyl;
t-Bu is tertiary butyl;
DMF is dimethylformamide;
EtOAc is ethyl acetate;
THF is tetrahydrofuran;
Ar is argon;
TFA is trifluoroacetic acid;
EDC is 1-(3-dimethylaminopropyl)-3-ethylcarbodiimide hydrochloride.
HOBT is 1-hydroxybenzotriazole Also, as used herein, each of the following terms, used alone or in conjunction with other terms, are defined as follows (except where noted to the contrary):

The term "alkyl" refers to a saturated aliphatic radical containing from one to ten carbon atoms or a mono- or polyunsaturated aliphatic hydrocarbon radical containing from two to twelve carbon atoms, containing at least one double or triple bond, respectively. "Alkyl" refers to both branched and unbranched alkyl groups. Preferred alkyl groups are straight chain alkyl groups containing from one to eight carbon atoms and branched alkyl groups containing from three to eight carbon atoms. More preferred alkyl groups are straight chain alkyl groups containing from one to six carbon atoms and branched alkyl groups containing from three to six carbon atoms. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl refers to an alkyl group linked to a carbonyl group (C=O).

The term "cycloalkyl" refers to the cyclic analog of an alkyl group, as defined above. Preferred cycloalkyl groups are saturated cycloalkyl groups containing from three to eight carbon atoms, and more preferably three to six carbon atoms.

The term "aryl" refers to phenyl and naphthyl. "Aroyl" refers to an aryl group linked to a carbonyl group (C=O).

The term "halo" refers to a halogen radical selected from fluoro, chloro, bromo and iodo. Preferred halo groups are fluoro, chloro and bromo.

The term "heteroaryl" refers to a stable 5–8 membered (but preferably, 5 or 6 membered) monocyclic or 8–11 membered bicyclic aromatic heterocycle radical. Each heterocycle consists of carbon atoms and from 1 to 4 heteroatoms selected from the group consisting of nitrogen, oxygen and sulfur. As used herein, "nitrogen" and "sulfur" include any oxidized form of nitrogen and sulfur and the quaternized form of any basic nitrogen. The heterocycle may be attached by any atom of the cycle, which results in the creation of a stable structure. Preferred heteroaryl radicals include, for example, furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl or phenoxazinyl, The term "heterocycle" refers to a stable 5–8 membered (but preferably, 5 or 6 membered) monocyclic or 8–11 membered bicyclic heterocycle radical which may be either saturated or unsaturated, and is non-aromatic. Each heterocycle consists of carbon atoms and from 1 to 4 heteroatoms selected from the group consisting of nitrogen, oxygen and sulfur. As used herein, "nitrogen" and "sulfur" include any oxidized form of nitrogen and sulfur and the quaternized form of any basic nitrogen. The heterocycle may be attached by any atom of the cycle, which results in the creation of a stable structure. Preferred heterocycle radicals include, for example, pyrrolinyl, pyrrolidinyl, pyrazolinyl, pyrazolidinyl, piperidinyl, morpholinyl, thiomorpholinyl, pyranyl, thiopyranyl, piperazinyl and indolinyl.

GENERAL SYNTHETIC METHODS

The invention also provides processes of making the present novel compounds. Compounds of the invention may be prepared by methods described below. Standard peptide coupling, protection and deprotection reactions (see for example M. Bodanszky, The Practice of Peptide Synthesis, Springer-Verlag, 1984) are employed in these syntheses.

Compounds of the invention having formula (II) or (IIa) (nitriles) may be prepared by Method A (Scheme I)

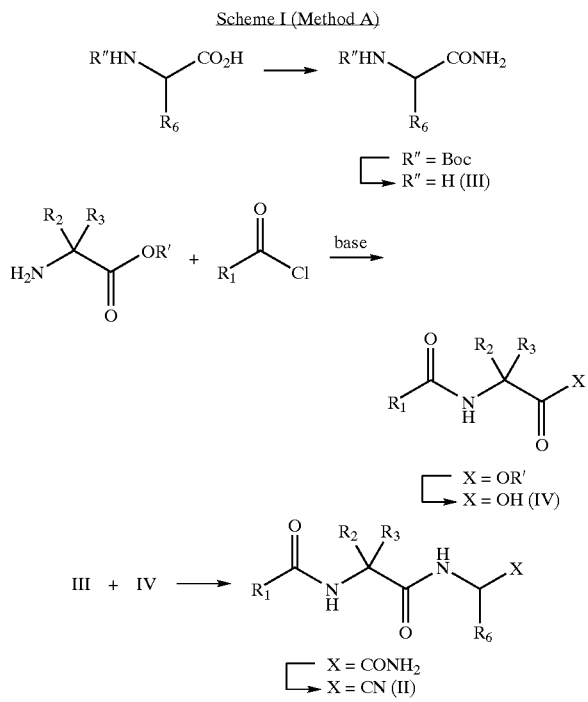

According to Method A a suitably protected amino acid bearing $R_6$ is allowed to react with ammonia under standard coupling conditions. An example of a suitable protecting group is the t-butoxycarbonyl (Boc) group. An example of standard coupling conditions would be combining the starting materials in the presence of a coupling reagent such as 1-(3-dimethylaminopropyl)-3-ethylcarbodiimide (EDC) with 1-hydroxybenzotriazole (HOBT), in a suitable solvent such as DMF or methylene chloride. A base such as N-methylmorpholine may be added. This is followed by deprotection to give amino acid amide III. An amino acid ester bearing $R_2$ and $R_3$ is then reacted with an acid chloride bearing $R_1$ in the presence of a suitable base such as N,N-diisopropylethylamine. Conversion to the carboxylic acid provides IV. Standard peptide coupling of III and IV, followed by dehydration of the amide provides the desired nitrile II or IIa. An example of suitable dehydration conditions is cyanuric chloride in DMF.

In a variation (Method B) illustrated in Scheme II, an amino acid amide bearing $R_6$ is coupled with an amine-protected amino acid bearing $R_2$ and $R_3$. A suitable protecting group and coupling conditions would be as described above. Deprotection is then followed by reaction with an acid chloride bearing $R_1$. Conversion of the amide to the nitrile as above provides II or IIa.

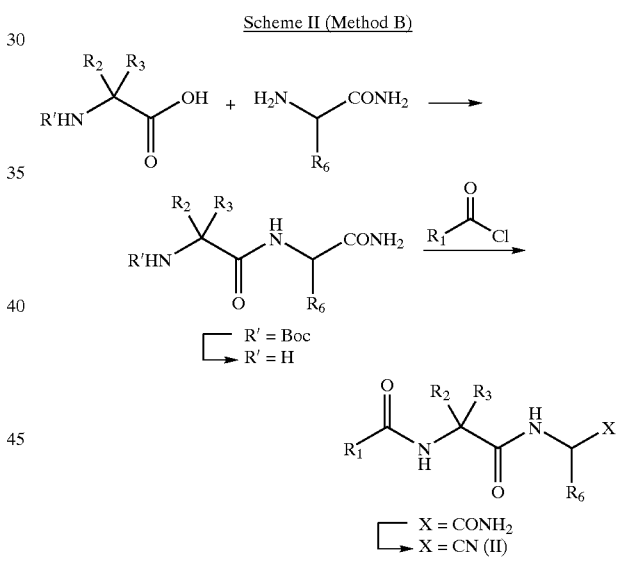

Compounds of the invention having formulas (I) or (Ia) (ketones) may be prepared by Methods C (Scheme III) or D (Scheme IV) as described below.

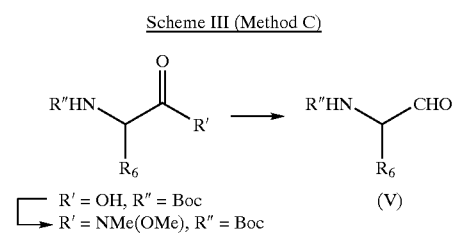

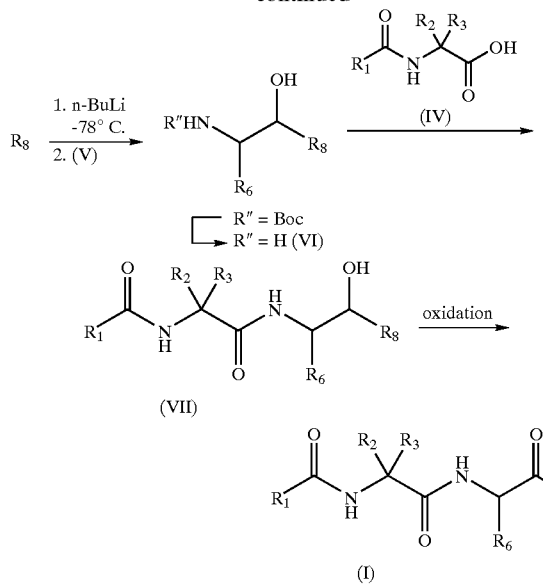

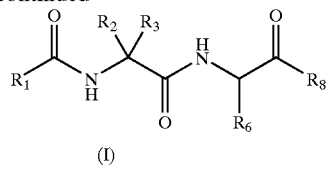

According to Method C, a suitably protected (for example Boc protected) amino acid is coupled with N,O-dimethylhydroxylamine under standard coupling conditions, such as with carbonyldiimidazole (CDI) in a solvent such as DMF, to give the corresponding amide. This is reduced to the aldehyde (V) with a suitable reducing agent such as LiAlH$_4$, in a suitable solvent such as THF.

The aldehyde (V) is reacted with the anion of a heterocycle R$_8$, which is generated by reacting R$_8$ with a strong base such as n-BuLi in a solvent such as THF at a temperature of about −30° C. to −100° C. and preferably at about −78° C. This is followed by removal of the protecting group providing alcohol (VI). This is coupled with (IV), prepared as described in Scheme I, under standard coupling conditions such as EDC and HOBT in DMF in the presence of a base such as N-methylmorpholine to provide (VII). Oxidation of (VII) with, for example, the Dess Martin Reagent (1,1,1,-triacetoxy-1,1-dihydro-1,2-benziodoxol-3(1H)-one) in methylene chloride and t-BuOH, provides the desired ketone of formulas (I) or (Ia).

Scheme IV (Method D)

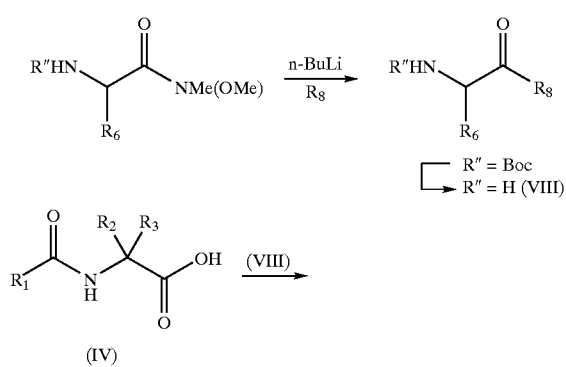

In Method D, a suitably protected amino acid N-methoxy-N-methylamide (prepared as described in Scheme III) is treated with the anion of a heterocycle R$_8$, generated by reacting R$_8$ with a strong base such as n-BuLi in a suitable solvent such as THF at a temperature of about −30° C. to −100° C. and preferably at about −78° C. Deprotection of the resulting ketone provides (VIII). This is coupled with (IV), which is prepared as described in Scheme I, under standard coupling conditions such as EDC and HOBT in DMF in the presence of a base such as N-methylmorpholine to provide the desired ketone of formulas (I) or (Ia).

Compounds of the invention where A is a bond (formulas I, Ia and II, IIa) could be prepared in analogous fashion to the Schemes above by using R$_1$X, where X=Br, Cl, or I, instead of an acyl halide (R$_1$C(O)Cl) in Schemes I and II, or by using R$_1$NHC(R$_2$)(R$_3$)CO$_2$H instead of (IV) in Schemes III and IV.

Intermediates used in Schemes I–IV are either commercially available or easily prepared by methods known to those skilled in the art. A procedure (Method E) that is useful for preparing substituted oxazoles which may be used as R$_8$ in Scheme III and IV (Methods C and D) is illustrated below in Scheme V.

Scheme V (Method E)

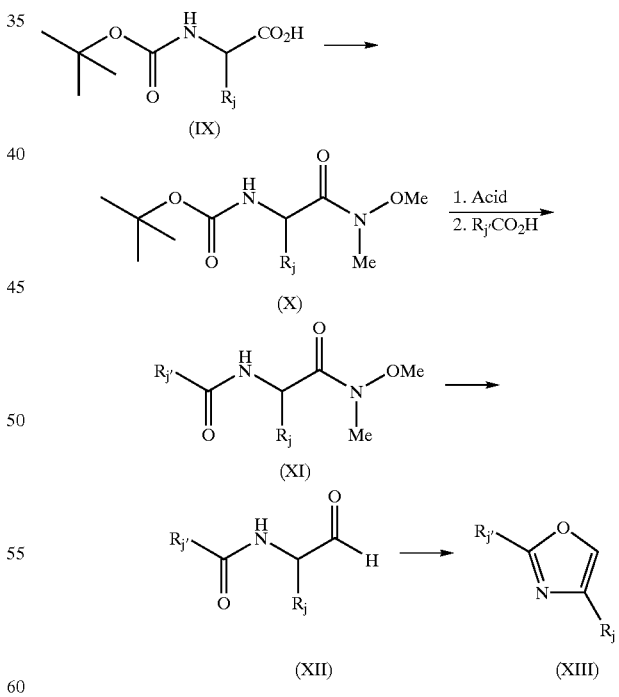

An N-protected amino acid, for example a t-Boc protected amino acid (IX) is coupled with N,O-dimethylhydroxylamine using a suitable coupling agent, such as carbonyldiimidazole (CDI), in a suitable solvent, such as CH$_2$Cl$_2$, THF or DMF, at about 0° C. to provide (X). The N-protecting group is then removed, for example the t-Boc group may be removed by treatment with a suitable acid, such as trifluoroacetic acid, in a suitable solvent, such as $CH_2Cl_2$. The resulting amine is coupled with the desired carboxylic acid using suitable coupling conditions, such as EDC with HOBT in a suitable solvent such as DMF, in the presence of a base such as N-methylmorpholine to provide a diamide (XI). The N-methoxy-methyl amide is then treated with a suitable reducing agent, such as $LiAlH_4$ in a suitable solvent, such as THF, to provide an aldehyde (XII). Cyclodehydration (see for example P. Wipf and S. Lim, J. Amer. Chem. Soc., 1995, 117, 558) of (XII) with triphenylphosphine and hexachloroethane in a suitable solvent, such as acetonitrile in the presence of a suitable base, such as $Et_3N$ provides the desired oxazole (XIII).

Desired disubstituted thiazoles, which may be used as $R_8$ in Scheme III and IV (Method C and D) may be prepared by the Hantzsch method in which a thioamide is condensed with an alpha-halocarbonyl compound. This method is known to those skilled in the art and is well-documented in the chemical literature (for example, J. Metzger and E. J. Vincent, The Chemistry of Heterocyclic Compounds, Vol. 34, 1979; A. R. Katritzky et al., J. Org. Chem., 1995, 60, 5638; R. Flaig and H. Hartmann, Heterocycles, 1997, 45, 875).

METHODS OF THERAPEUTIC USE

The compounds of this invention effectively block degradation of the invariant chain to CLIP by cathepsin S, and thus inhibit antigen presentation and antigen-specific immune responses. Control of antigen specific immune responses is an attractive means for treating autoimmune diseases and other undesirable T-cell mediated immune responses. Thus, there is provided methods of treatment using the compounds of this invention for such conditions. These encompass autoimmune diseases including, but not limited to, rheumatoid arthritis, systemic lupus erythematosus, Crohn's disease, ulcerative colitis, multiple sclerosis, Guillain-Barre syndrome, psoriasis, Grave's disease, myasthenia gravis, scleroderma, glomerulonephritis, atopic dermatitis and insulin-dependent diabetes mellitus. The compounds of the invention can also be used to treat other disorders associated with extracellular proteolysis such as Alzheimer's disease. The compounds of the invention can also be used to treat other disorders associated with inappropriate autoimmune responses, T-cell mediated immune responses, or extracellular proteolysis mediated by cathepsin S, unrelated to those listed above or discussed in the Background of the Invention. Therefore, the invention also provides methods of modulating an autoimmune disease comprising administering to a patient in need of such treatment a pharmaceutically effect amount of a compound according to the invention.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically, or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 15%, but more preferably at least about 20%, of a compound of formulas (I), (Ia), (II) or (IIa) (w/w) or a combination thereof. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 10–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

SYNTHETIC EXAMPLES

Example 1

Morpholine-4-carboxylic acid [1-(S)-(1-(S)-cyano-3-phenylpropylcarbamoyl)-3-methylbutyl] amide

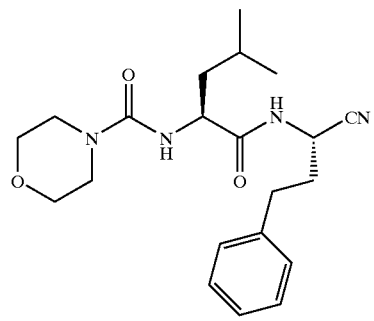

As outlined generally in Scheme I (Method A), N-Boc-L-homophenylalanine (0.50 g, 1.79 mmol) was dissolved in 20 mL of DMF which was cooled with an ice-water bath. 1-Hydroxybenzotriazole (HOBT) (0.29 g, 2.14 mmol) and EDC (0.41 g, 2.00 mmol) were added followed by stirring for 20 min. Ammonium hydroxide was added (0.5 mL) and stirring was continued overnight (16 h). The reaction mixture was diluted with 50 mL of methylene chloride to give a white precipitate. The mixture was filtered and the filtrate was washed with brine (100 mL) followed by saturated bicarbonate (100 mL). The organic layer was dried over $MgSO_4$, filtered and concentrated by rotary evaporation to give the corresponding amide (0.45 g, 90%) that was used without further purification.

Benzyl L-leucine p-toluenesulfonate salt (8.00 g, 20.3 mmol) was dissolved in 20 mL of DMF followed by addition of N,N-diisopropylethylamine (10.61 mL, 60.9 mmol) and stirring under Ar for 15 min. 4-Morpholinecarbonyl chloride (4.55 g, 30.4 mmol) was added and stirring was continued overnight (16 h). The solution was diluted with 500 mL of EtOAc and washed with 3×500 mL of water. The organic layer was dried over $MgSO_4$, filtered and concentrated by rotary evaporation to 8.01 g of the crude product. The product was purified by flash chromatography ($SiO_2$, 40% EtOAc/hexane) resulting in a thick oil. This oil (18 g, 53.8 mmol) was dissolved in ethanol (500 mL). $Pd(OH)_2$ (642 mg) was added followed by cyclohexene (100 mL). The mixture was refluxed for 45 min at which time TLC indicated consumption of the benzyl ester. The reaction was cooled and filtered through diatomaceous earth and evaporated to dryness to give N-(4-morpholinecarbonyl)-L-leucine as a very thick oil (13 g, 99%) that was used without further purification.

N-Boc-L-homophenylalaninamide (from the first paragraph) (114 mg, 0.41 mmol) was dissolved in 10 mL of $CH_2Cl_2$ and 10 mL of trifluoroacetic acid (TFA) was added. Stirring was continued for 30 min at which time the reaction mixture was evaporated to dryness giving the TFA salt of L-homophenylalanine amide. N-(4-morpholinecarbonyl)-L-leucine (100 mg, 0.41 mmol), from above, was dissolved in 10 mL of DMF and cooled by an ice-water bath. HOBT (72 mg, 0.53 mmol) and EDC (102 mg, 0.53 mmol) were added and the mixture was stirred at 0° C. for 15 min. To the cold solution was added the TFA salt of L-homophenylalaninamide as a solution in 5 mL of DMF, followed by addition of N-methylmorpholine (94 μL, 0.86 mmol). The ice bath was removed and the reaction was stirred at ambient temperature overnight (16 h). The reaction was diluted with 50 mL of $CH_2Cl_2$ to give a white precipitate. The mixture was filtered and the solid washed with an additional 50 mL of $CH_2Cl_2$. The filtrates were combined and washed with saturated bicarbonate (100 mL), 1 N HCl (100 mL) and brine (2×100 mL). The organic layer was dried over $MgSO_4$ and concentrated by rotary evaporation to give an oily residue. The residue was chromatographed ($SiO_2$, 5% MeOH in $CH_2Cl_2$) to give the a white solid (130 mg, 78%).

This amide (150 mg, 0.37 mmol) (material from more than one reaction) was dissolved in 2 mL of DMF and cooled to 0° C. with an ice-water bath. To the solution was added cyanuric chloride (46 mg, 0.37 mmol). The ice bath was removed and the reaction stirred to ambient temperature over the next hour. During the course of the reaction a white precipitate formed. The reaction was diluted with 100 mL of EtOAc and washed with 100 mL of water (3×). The organic layer was dried over $MgSO_4$, filtered and concentrated by rotary evaporation to give the crude residue. The residue was purified by chromatography ($SiO_2$, 40% hexane in EtOAc) to give the title compound as a hard white glass (120 mg, 84%). $^1H$ NMR (270 MHz, $CDCl_3$): δ 8.00–7.87 (1H, m), 7.35–7.13 (3H), m), 7.12–7.05 (2H, m), 5.10–5.02 (1H, m), 4.80–4.60 (1H, m), 4.45–4.20 (1H, m), 3.75–3.50 (4H, m), 3.45–3.30 (4H, m), 2.80–2.60 (2H, m), 2.10–1.90 (2H, m), 1.70–1.45 (3H, m), 1.05–0.90 (6H, m).

Example 2

2-(S)-(4-Dimethylaminobenzenesulfonylamino)-4-methylpentanoic acid (1-(S)-cyano-3-phenylpropyl) amide

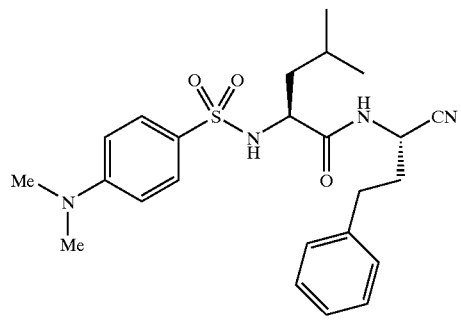

$NH_4OH$ (4 mL) was added to a premixed (15 min) solution of N-(t-butoxycarbonyl)-L-homophenylalanine (4.00 g, 14.3 mmol), EDC (3.24 g, 17.2 mmol), and HOBT (2.32 g, 17.2 mmol) in DMF (20 mL) at room temperature. After 16 h the reaction mixture was diluted with $CH_2Cl_2$ and filtered, washed sequentially with 10% aqueous HCl, satd. $NaHCO_3$, $H_2O$ (×3), brine, dried over $Na_2SO_4$, and concentrated giving N-(t-butoxycarbonyl)-L-homophenylalaninamide (3.10 g, 78%) as a white solid.

TFA (2.5 mL) was added to a solution of N-(t-butoxycarbonyl)-L-homophenylalaninamide (1.00 g, 3.59 mmol) in $CH_2Cl_2$ (10 mL) at room temperature. After stirring for 0.5 h the reaction mixture was concentrated giving a colorless oil. As described generally by Scheme II, Method B, the oil was dissolved in $CH_2Cl_2$ (10 mL) and N,N-diisopropylethylamine (1.90 g, 14.4 mmol) and added to a premixed (15 min) solution of N-(t-butoxycarbonyl)-L-leucine (913 mg, 3.95 mmol), EDC (826 mg, 4.30 mmol), HOBT (581 mg, 4.30 mmol) in $CH_2Cl_2$ (10 mL) at room temperature. After stirring for 16 h the reaction was quenched by the addition of $H_2O$, diluted with EtOAc, washed sequentially with 10% aqueous HCl, satd. $NaHCO_3$, $H_2O$ brine, dried over $Na_2SO_4$, and concentrated giving 1.3 g of a white solid. The crude solid was triturated with 5% EtOAc/Hexane giving N-[N-(t-butoxycarbonyl)-L-leucinyl]-L-homophenylalaninamide (1.1 g, 78%) as a white solid.

TFA (2.5 mL) was added to a solution of N-[N-(t-butoxycarbonyl)-L-leucinyl]-L-homophenylalaninamide (500 mg, 1.28 mmol) in $CH_2Cl_2$ (10 mL) at room temperature. After stirring for 0.5 h the reaction mixture was concentrated giving a colorless oil which was diluted with $CH_2Cl_2$ (2.5 mL). Diisopropylethylamine (588 mg, 4.55 mmol) and p-$Me_2NC_6H_4SO_2Cl$ [prepared by the reaction of p-Me$_2$NC$_6$H$_4$SO$_3^-$Na$^+$ (1.0 g, 4.48 mmol) with thionyl chloride and pyridine (1 mL) at 55° C. for 2 h followed by cooling, diluting with toluene and concentrating to give p-Me$_2$NC$_6$H$_4$SO$_2$Cl.] was added at room temperature. After stirring for 16 h the reaction was quenched by the addition of H$_2$O, diluted with EtOAc, washed sequentially with 10% aqueous HCl, satd. NaHCO$_3$, H$_2$O (×3), brine, dried over Na$_2$SO$_4$, and concentrated giving a yellow solid (408 mg). The crude residue was fractionated by flash chromatography (25–100% EtOAc/Hexane) giving N-[N-((4-dimethylaminophenyl)sulfonyl)-L-leucinyl]-L-homophenylalaninamide (90 mg, 15%) as a white solid. Some title compound (60 mg, 10%) was isolated from this reaction as well.

Cyanuric chloride (33 mg, 0.18 mmol) was added to a solution of N-[N-((4-dimethylaminophenyl)sulfonyl)-L-leucinyl]-L-homophenylalaninamide (80 mg, 0.18 mmol) in DMF (2 mL) at 0° C. After stirring for 2 h, the reaction was quenched by addition of satd. NaHCO$_3$, filtered, diluted with EtOAc, washed sequentially with H$_2$O (×5), brine, dried over Na$_2$SO$_4$, and concentrated giving a yellow foam. The crude residue was fractionated by preparative HPLC (65% AcCN/H$_2$0/0.1% TFA) giving the title compound (47 mg, 57%) as a white solid, m.p. 46–48° C. $^1$H NMR (400 MHz, CDCl$_3$): δ: 7.74 (2H, d, J=9), 7.37–7.34 (2H, m), 7.30–7.26 (2H, m), 7.23–7.21 (3H, m), 6.79 (1H, d, J=8.5), 4.91 (1H, bs), 4.70 (1H, ddd, J=8, 8, 8), 3.68–3.73 (1H, m), 3.06 (3H, s), 2.84–2.76 (2H, m), 2.16–2.09 (2H, m), 1.63–1.56 (2H, m), 1.42–1.37 (1H, m), 0.88 (3H, d, J=6), 0.71 (3H, d, J=6).

Example 3

2-(2-(S)-{4-Methyl-2-(S)-[(morpholine-4-carbonyl)amino]pentamoylamino}-4-phenylbutyryl)benzothiazole-6-carboxylic acid phenylamide

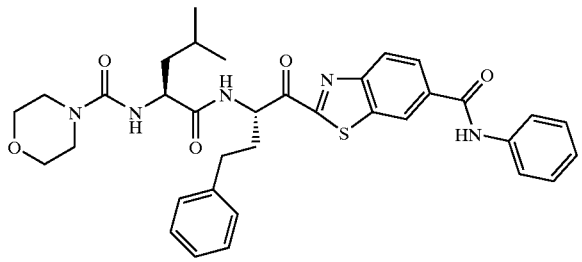

As described generally in Method C, N-(t-Boc)-L-homophenylalanine (10.0 g, 35.8 mmol) was dissolved in 50 mL of DMF. The solution was cooled to 0° C. with an ice-water bath. Carbonyldiimidazole (6.4 g, 39.4 mmol) was added to the reaction solution followed by N-methylmorpholine (3.9 g, 39.4 mmol). The reaction was stirred for 1 h at which time N,O-dimethylhydroxylamine hydrochloride (3.8 g, 39.4 mmol) was added. The ice bath was removed and the reaction was stirred at ambient temperature for 3 h. The reaction solution was poured into 200 mL of 1N HCl and extracted with 200 mL of EtOAc. The organic layer was washed with 2×100 mL of 1N HCl, 100 mL of saturated sodium bicarbonate, 2×100 mL water, and 2×100 mL brine. The organic layer was dried over Na$_2$SO$_4$, decanted and concentrated by rotary evaporation to give the desired amide as a thick oil (11.1 g, 96% crude) which was used without further purification.

The amide (3.7 g, 11.5 mmol), dissolved in 20 mL THF was added dropwise over 20 min to a suspension of LiAlH$_4$ (0.53 g, 13.9 mmol) in 60 mL THF which was cooled to 0° C. in an ice-water bath. The mixture was stirred for 15 min, then quenched with 10 mL of a saturated solution of sodium bicarbonate, diluted with 200 mL water and extracted with 3×100 mL EtOAc. The organic layers were combined and washed with 100 mL 1 N HCl and 2×100 mL brine. The organic layer was dried over Na$_2$SO$_4$, filtered over a pad of diatomaceous earth and concentrated by rotary evaporation. The residue was purified by flash chromatography (SiO$_2$, 5% i-PrOH in CH$_2$Cl$_2$) to give the desired aldehyde as an oily solid (2.4 g, 79%).

To a dry 100 mL flask was added 6-(phenylcarbamoyl)benzothiazole (0.58 g, 2.3 mmol) and THF (12 mL). The reaction mixture was cooled to −78° C. with a dry-ice/acetone bath. n-BuLi (2.5 M in hexanes) (1.8 mL, 4.5 mmol) was added dropwise to the reaction mixture. The reaction was stirred for 20 min to give a suspension. A solution of the above aldehyde (200 mg, 0.75 mmol) in 3 mL of dry THF was added all at once via syringe. The temperature was gradually increased to −40° C. and the reaction was stirred for 3 h at which time TLC showed consumption of the aldehyde. The reaction was quenched at −78° C. by the addition of a saturated solution of NH$_4$Cl and the product was extracted with 50 mL EtOAc. The organic layer was dried over MgSO$_4$, filtered and concentrated to give a residue that was purified by chromatography (SiO$_2$, 2% MeOH in CH$_2$Cl$_2$) to give the desired alcohol as a solid (194 mg, 50%).

N-(4-morpholinecarbonyl)-L-leucine (26.4 mg, 0.11 mmol) (prepared as described in Example 1) was dissolved in 2 mL of DMF. The solution was cooled to 0° C. with an ice-water bath and HOBT (19 mg, 0.14 mmol) and EDC (27 mg, 0.14 mmol) were added and the solution stirred for 20 min. The TFA salt of the N-deprotected alcohol from above (prepared by stirring the above N-Boc protected alcohol in methylene chloride with TFA at room temperature for 30 min and evaporation to dryness) (57 mg, 0.11 mmol of N-Boc precursor) was added to the reaction as a solution in 1 mL of DMF followed by addition of N-methylmorpholine (35 μL, 0.32 mmol). The reaction was stirred for 3 h, diluted with EtOAc and washed with 10 mL 1N HCl and 10 mL saturated bicarbonate and 2×100 mL brine. The organic layer was dried over MgSO$_4$, filtered and concentrated. The residue was purified by chromatography (SiO$_2$, 2% MeOH in CH$_2$Cl$_2$) to give the desired coupled product as a white solid (57 mg, 82%).

To the above product (50.4 mg, 0.08 mmol) was added the Dess-Martin periodinane (133 mg, 0.31 mmol), 10 mL CH$_2$Cl$_2$ and 4 mL t-BuOH. The reaction mixture was allowed to stir overnight at room temperature. It was then was diluted with 20 mL CH$_2$Cl$_2$, washed with 20 mL of saturated solution of Na$_2$S$_2$O$_3$ and 20 mL NaHCO$_3$ solution, the organic layer was washed with brine, dried over MgSO$_4$, filtered and concentrated. The residue was purified by chromatography (SiO$_2$, 2% MeOH in CH$_2$Cl$_2$) to give the title compound as a white solid (30 mg, 60%). H$^1$ NMR (270 MHz, CDCl$_3$): δ 8.77–8.70 (1H, m), 8.57–8.52 (1H, m), 8.28–8.20 (1H, m), 8.15–8.07 (1H, m), 7.78–7.68 (2H, m), 7.45–7.35 (2H, m), 7.29–7.05 (7H, m), 5.75–5.65 (1H, m), 5.00–4.92 (1H, m), 4.54–4.41 (1H, m), 3.74–3.58 (4H, m), 3.40–3.24 (4H, m), 2.78–2.62 (2H, m), 2.51–2.32 (1H, m), 2.21–2.20 (1H, m), 1.90–1.40 (3H, m), 1.00–0.80 (6H, m).

Example 4

Morpholine-4-carboxylic acid {1-(S)-[1-(S)-(benzothiazole-2-carbonyl)-3-phenylpropylcarbamoyl]-3-methylbutyl} amide

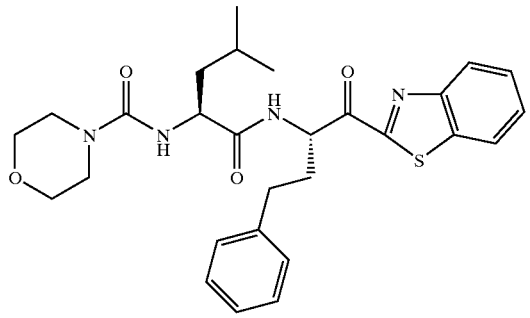

Dry THF (1.5 mL), under Ar, was cooled to −78° C. with a dry-ice/acetone bath. n-BuLi (2.0 M in hexanes) (698 μL, 1.40 mmol) was added to reaction flask followed by dropwise addition of freshly distilled benzothiazole (180 mg, 1.40 mmol) as a solution in 0.5 mL of dry THF. The reaction was stirred for 15 min to give a suspension. A solution of N-(t-butoxycarbonyl)-(N'-methyl-N'-methoxy)-L-homophenylalaninamide (300 mg, 0.930 mmol) (prepared as described in Example 3) in 1 mL of dry THF was added all at once via syringe. The reaction was stirred for 5 min at which time TLC showed consumption of the amide. The reaction was quenched by the addition of water and the product extracted with 50 mL of EtOAc. The organic layer was dried over $MgSO_4$, filtered and concentrated to give a residue that was purified by preparative TLC ($CH_2Cl_2$) to give the desired ketone as a clear colorless oil.

N-(4-morpholinecarbonyl)-L-leucine (82 mg, 0.34 mmol) (prepared as described in Example 1) was dissolved in 2 mL of DMF. The solution was cooled to 0° C. with an ice-water bath and HOBT (60 mg, 0.44 mmol) and EDC (83 mg, 0.44 mmol) were added and the solution stirred for 20 min. The TFA salt of the N-deprotected ketone from above (prepared by stirring the above N-Boc protected alcohol in methylene chloride with TFA at room temperature for 30 min and evaporation to dryness) (133 mg, 0.34 mmol of N-Boc precursor) was added to the reaction as a solution in 1 mL of DMF followed by addition of N-methylmorpholine (77 μL, 0.70 mmol). The reaction was stirred for 3 h, diluted with EtOAc and washed with 100 mL 1N HCl and 100 mL saturated bicarbonate and 2×100 mL brine. The organic layer was dried over $MgSO_4$, filtered and concentrated. The residue was purified by chromatography ($SiO_2$, 50% EtOAc in hexane) to give the title compound as a white solid (40 mg, 23%) that was shown to be a 1 to 1 mixture of two epimers. $^1$H NMR (270 MHz, $CDCl_3$): δ 8.15–8.08 (1H, m), 7.98–7.88 (1H, m), 7.60–7.40 (2H, m), 7.25–7.07 (5H, m), 7.02–6.92 (1H, m), 5.90–5.75 (1H, m), 4.98–4.90 (1H, m), 4.50–4.35 (1H, m), 3.66–3.57 (4H, m), 3.40–3.30 (4H, m), 2.80–2.70 (2H, m), 2.50–2.35 (1H, m), 2.25–2.10 (1H, m), 1.80–1.40 (3H, m), 1.00–0.88 (6H, m).

Example 5

Morpholine-4-carboxylic acid {1-(S)-[1-(S)-(2,4-diphenyloxazole-5-carbonyl)-3-phenylpropylcarbamoyl]-3-methylbutyl} amide

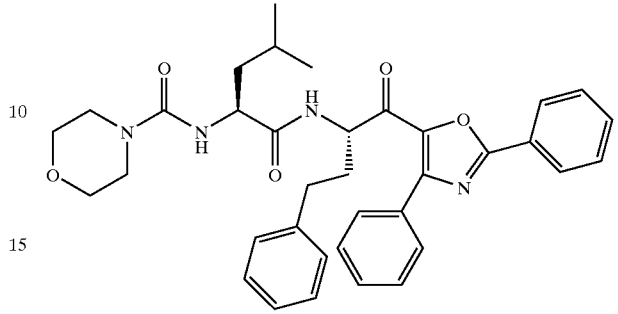

As outlined generally in Scheme IV (Method D), 2,4-diphenyloxazole (361 mg, 1.63 mmol) in 15 mL dry THF was cooled to −78° C. and n-butyllithium (1.16 mL of a 1.4 M solution, 1.63 mmol) was added. After stirring for 1 h at −78° C., a solution of the free base of N-[N-(t-butoxycarbonyl)-L-leucinyl]-L-homophenylalaninamide (prepared as described in Example 3) in 5 mL of dry THF was added dropwise. The temperature of the reaction mixture was allowed to rise to −20° C. and maintained for 2 h after which time the reaction mixture was quenched with 100 mL of $NH_4Cl$ (10% aqueous) and extracted with 3×100 mL EtOAc. The combined extracts were washed with 2×100 mL brine, dried with $Na_2SO_4$, filtered and concentrated. The resulting residue was purified by chromatography (florisil, 15%–20% hexane in EtOAc) yielding 190 mg (72%) of [1-(2,4-diphenyloxazole-5-carbonyl)-3-phenylpropyl] carbamic acid tert-butyl ester.

N-[(4-Morpholinyl)carbonyl]-L-leucine (100 mg, 0.35 mmol) (prepared as described in Example 1) was dissolved in 10 mL DMF and cooled to 0° C. To the solution was added EDC (77 mg, 0.4 mmol) and HOBt (54 mg, 0.4 mmol) and the reaction was stirred for 1 h. In a separate flask, [1-(2,4-diphenyloxazole-5-carbonyl)-3-phenylpropyl] carbamic acid tert-butyl ester (158 mg, 0.31 mmol) was dissolved in 4 mL $CH_2Cl_2$ and 2 mL TFA was added. After stirring for 1 h, the solvents were evaporated, the residue was dissolved in 5 mL DMF and N-methylmorpholine (406 mg, 0.4 mmol) was added. The resulting solution was added to the previously prepared solution of activated leucine derivative at 0° C. The reaction mixture was stirred at room temperature for 3 h, cooled to 0° C., and quenched with 100 mL of a 10% solution of citric acid in water. The resulting mixture was extracted with 3×100 mL EtOAc. The combined organic extracts were washed with 2×100 mL of saturated bicarbonate and 1×100 mL brine. The organic layer was dried over $Na_2SO_4$, filtered and concentrated to a residue that was purified by chromatography (florisil, 30%–50% EtOAc in hexane) to give the title compound as a white solid (90 mg, 84%), m.p. 83–5° C., MS (ES) 609 ($M^+$).

The following compounds were also prepared using the procedure described in Example 5:

Morpholine-4-carboxylic acid {1-(S)-[1(S)-(2,4-diphenyl-oxazole-5-carbonyl)-3-phenyl-propylcarbamoyl]-3,3-dimethylbutyl} amide, m.p. 95–7° C., MS (ES) 623 ($M^+$).

Morpholine-4-carboxylic acid {2-cyclohexyl-1-(S)-[1-(S)-(2,4-diphenyl-oxazole-5-carbonyl)-3-phenyl-propylcarbamoyl]-ethyl} amide, m.p. 93–5° C., MS (ES) 649 ($M^+$).

Morpholine-4-carboxylic acid {1-(S)-[2,4-diphenyl-oxazole-5-yl)-2-oxo-ethylcarbamoyl]-3-methylbutyl} amide, m.p. 155–7° C., MS (ES) 505 (M+).

Morpholine-4-carboxylic acid {2-cyclohexyl-1-(S)-[2-(2,4-diphenyl-oxazol-5-yl)-2-oxo-ethylcarbamoyl]-ethyl}-amide, m.p. 122–3° C., MS (ES) 545 (M+).

Morpholine-4-carboxylic acid {1-(S)-[2-(2,4-diphenyl-oxazol-5-yl)-2-oxo-ethylcarbamoyl]-3,3-dimethylbutyl}-amide, m.p. 97–9° C., MS (ES) 519 (M+).

Morpholine-4-carboxylic acid (1-(S)-{1-(S)-[2-(3-benzyloxy-phenyl)-oxazole-5-carbonyl]-3-phenyl-propylcarbamoyl}-3-methyl-butyl)-amide, m.p. 61–3° C., MS (ES) 639 (M+).

Morpholine-4-carboxylic acid {2-cyclohexyl-1-(S)-[1-(R, S)-(4-isobutyl-2-pyrinin-2-yl-oxazole-5-carbonyl)-3-phenyl-propylcarbamoyl]-ethyl} amide, m.p. 93–5° C., MS (ES) 649 (M+).

Example 6

2-(4-Isobutyloxazol-2-yl)pyridine (Method E)

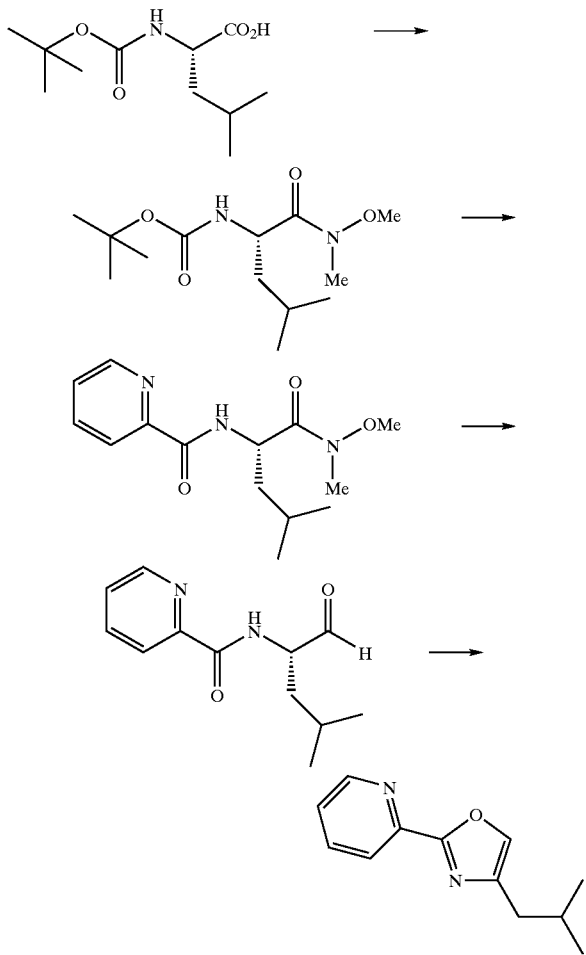

N-(t-Butoxy)-L-leucine (10 g, 43 mmol) was dissolved in 200 mL of CH$_2$Cl$_2$. The solution was cooled to 0° C. with an ice-water bath. Carbonyldiimidazole (7.7 g, 47.5 mmol) was added and the reaction mixture was stirred for 1 h. N,O-dimethylhydroxylamine hydrochloride (4.64 g, 47.8 mmol) was added at 0° C. The ice bath was removed and the reaction was stirred at ambient temperature for 16 h. The reaction solution was poured into 200 mL of an ice-cooled solution of 5% citric acid. The organic layer was separated, washed with 2×100 mL of 1N HCl, 1×100 mL of saturated NaHCO$_3$, and 2×100 mL brine. The organic layer was dried over Na$_2$SO$_4$, filtered, and concentrated by rotary evaporation to give [1-(N-methoxy-N-methylcarbamoyl)-3-methylbutyl]carbamic acid tert-butyl ester as a thick oil (7.39 g, 59% crude) which was used without further purification.

The tert-butyl ester from above (1 g, 3.47 mmol) was dissolved in 10 mL CH$_2$Cl$_2$ and 5 mL trifluoroacetic acid was added. The reaction mixture was stirred for 1 h. Solvents were evaporated and the residue was taken up in 2×10 mL CH$_2$Cl$_2$ and evaporated to an oil. In a separate flask, picolinic acid (470 mg, 3.82 mmol) was dissolved in 10 mL DMF and the resulting solution was cooled to 0° C. EDC (787 mg, 4.1 mmol) and HOBT (554 mg, 4.1 mmol) were added and the reaction mixture was stirred at 0° C. for 1 h. In a separate flask, the free amine prepared above was dissolved in 5 mL DMF and 1.5 mL N-methylmorpholine was added. This solution was added to the reaction mixture at 0° C. The reaction mixture was allowed to stir at ambient temperature for 16 h after which time it was poured into a mixture of ice/5% citric acid (100 mL) and extracted with 4×30 mL EtOAc. The combined EtOAc extracts were washed with 3×100 mL brine, 2×100 mL NaHCO$_3$, 1×100 mL brine, dried with Na$_2$SO$_4$, and evaporated to an oil which was dried under vacuum yielding 990 mg (100%) of pyridine-2-carboxylic acid [1-(N-methoxy-N-methylcarbamoyl)-3-methylbutyl]amide. This was used without further purification.

The amide from above (4.7 g, 14.7 mmol) was dissolved in 50 mL THF and added to a slurry of LiAlH$_4$ (558 mg, 14.7 mmol) in 50 mL THF at −78° C. The reaction mixture was allowed to warm to 0° C. and maintained for 15 min, after which time it was cooled to −78° C. and cannulated into an ice-cooled solution of KHSO$_4$ (8.16 g, 60 mmol) in 200 mL H$_2$O. The resulting mixture was extracted with 5×100 mL EtOAc. The combined extracts were washed with 2×100 mL satd. NaHCO$_3$ and 1×100 mL brine, dried with Na$_2$SO$_4$ and evaporated to an oily residue which was flash chromatographed through SiO$_2$ (25% EtOAc/hexane–35% EtOAc/hexane) yielding 2.8 g (86%) of pyridine-2-carboxylic acid (1-formyl-3-methylbutyl)amide as a colorless oil which solidified on standing.

Hexachloroethane (445 mg, 1.87 mmol) was dissolved in 5 mL CH$_3$CN. A solution of pyridine-2-carboxylic acid (1-formyl-3-methylbutyl)amide (137.5 mg, 0.625 mmol) in 2 mL CH$_3$CN was added followed by triethylamine (375 mg, 3.75 mmol) and triphenylphosphine (491 mg, 1.87 mmol). The resulting mixture was stirred for ½ h, poured into brine, and extracted with 2×25 mL EtOAc. The combined extracts were washed with 1×50 mL brine, dried with Na$_2$SO$_4$ and evaporated to 665 mg of a tan solid which was flash chromatographed through SiO$_2$ (20%–35% hexane/EtOAc) yielding 100 mg (76%) of the title compound as an amber oil, MS (ES) 203 (M+).

ASSESSMENT OF BIOLOGICAL PROPERTIES

Expression and Purification of Recombinant Human Cathepsin S

Cloning of human cathepsin S:

U937 RNA was subjected to reverse transcriptase/polymerase chain reaction with primer A (5'cacaatgaaacggctggtttg 3') and primer B (5'ctagatttctgggtaagaggg 3') designed to specifically amplify the cathepsin S cDNA. The resulting 900 bp DNA fragment was subcloned into pGEM-T (Promega) and sequenced to confirm its identity. This construct was used for all subsequent manipulations. This procedure is typical for cloning of known genes and is established in its field.

Human Pre-Pro-Cat S was removed from pGem-T vector (Promega, 2800 Woods Hollow Rd, Madison, Wis. 53711) by digestion with restriction enzyme SacII, followed by treatment with T4 DNA polymerase to generate a blunt end, and a second restriction enzyme digest with SalI. It was subcloned into pFastBac1 donor plasmid (GibcoBRL, 8717 Grovemont Cr., Gaithersburg, Md. 20884) which had been cut with restriction enzyme BamHI and blunt-ended and then cut with restriction enzyme SalI. The ligation mixture was used to transform DH5a competent cells (GibcoBRL) and plated on LB plates containing 100 ug/ml ampicillin. Colonies were grown in overnight cultures of LB media containing 50 ug/ml Ampicillin, plasmid DNA isolated and correct insert confirmed by restriction enzyme digestion. Recombinant pFastBac donor plasmid was transformed into DH10Bac competent cells (GibcoBRL). Large white colonies were picked from LB plates containing 50 ug/ml kanamycin, 7 ug/ml gentamicin, 10 ug/ml tetracycline, 100 ug/ml Bluo-gal, and 40 ug/ml IPTG. DNA was isolated and used to transfect Sf9 insect cells using CellFECTIN reagent (GibcoBRL). Cells and supernatant were harvested after 72 hours. Viral supernatant was passaged twice and presence of Cat S confirmed by PCR of the supernatant.

Sf9 cells were infected with recombinant baculovirus at a MOI of 5 for 48–72 hrs. Cell pellet was lysed and incubated in buffer at pH 4.5 at 37 for 2 hours to activate Cat S from pro-form to active mature form (Bromme, D & McGrath, M., *Protein Science,* 1996, 5:789–791.) Presence of Cat S was confirmed by SDS-PAGE and Western blot using rabbit anti-human proCat S.

Inhibition of Cathepsin S

Human recombinant cathepsin S expressed in Baculovirus is used at a final concentration of 10 nM in buffer. Buffer is 50 mM Na Acetate, pH 6.5, 2.5 mMEDTA, 2.5 mMTCEP. Enzyme is incubated with either compound or DMSO for 10 min at 37 C. Substrate 7-amino-4-methylcoumarin, CBZ-L-valyl-L-valyl-L-arginineamide (custom synthesis by Molecular Probes) is diluted to 20 uM in water (final concentration of 5 uM), added to assay and incubated for additional 10 minutes at 37 C. Compound activity is measured by diminished fluorescence compared to DMSO control when read at 360 nm excitation and 460 nm emission.

Examples listed above were evaluated for inhibition of cathepsin S in the above assay. All had $IC_{50}$ of 100 micromolar or below.

The following prophetic compounds may be made in accordance with the procedure outlined in Scheme IV (Method D), and the specific example 5:

Morpholine-4-carboxylic acid {1-[2-(4-isobutyl-2-pyridin-2-yl-oxazol-5-yl)-2-oxo-ethylcarbamoyl]-3-methyl-butyl}-amide;

Morpholine-4-carboxylic acid {1-[2-(4-cyclohexylmethyl-2-pyridin-2-yl-oxazol-5-yl)-2-oxo-ethylcarbamoyl]-3-methyl-butyl}-amide;

Morpholine-4-carboxylic acid {1-[2-(4-cyclohexylmethyl-2-pyridin-3-yl-oxazol-5-yl)-2-oxo-ethylcarbamoyl]-3-methyl-butyl}-amide;

Morpholine-4-carboxylic acid {2-cyclohexyl-1-[2-(4-cyclohexylmethyl-2-pyridin-3-yl-oxazol-5-yl)-2-oxo-ethylcarbamoyl]-ethyl}-amide;

Morpholine-4-carboxylic acid {2-cyclohexyl-1-[2-(4-isobutyl-2-pyridin-3-yl-oxazol-5-yl)-2-oxo-ethylcarbamoyl]-ethyl}-amide;

Morpholine-4-carboxylic acid {1-[2-(4-isobutyl-2-pyridin-3-yl-oxazol-5-yl)-2-oxo-ethylcarbamoyl]-3-methyl-butyl}-amide;

Morpholine-4-carboxylic acid {1-[1-(4-isobutyl-2-pyridin-3-yl-oxazole-5-carbonyl)-3-phenyl-propylcarbamoyl]-3-methyl-butyl}-amide;

Morpholine-4-carboxylic acid {1-[1-(4-isobutyl-2-pyridin-3-yl-oxazole-5-carbonyl)-3-phenyl-propylcarbamoyl]-3,3-dimethyl-butyl}-amide;

Morpholine-4-carboxylic acid {1-[1-(4-isobutyl-2-pyridin-4-yl-oxazole-5-carbonyl)-3-phenyl-propylcarbamoyl]-3,3-dimethyl-butyl}-amide;

Morpholine-4-carboxylic acid {2-cyclohexyl-1-[1-(4-isobutyl-2-pyridin-4-yl-oxazole-5-carbonyl)-3-phenyl-propylcarbamoyl]-ethyl}-amide;

Morpholine-4-carboxylic acid {2-cyclohexyl-1-[1-(4-cyclohexylmethyl-2-pyridin-4-yl-oxazole-5-carbonyl)-3-phenyl-propylcarbamoyl]-ethyl}-amide;

Morpholine-4-carboxylic acid (2-cyclohexyl-1-{1-[4-isobutyl-2-(1-methylpiperidin-4-yl)-oxazole-5-carbonyl]-3-phenyl-propylcarbamoyl}-ethyl)-amide;

Morpholine-4-carboxylic acid (1-{1-[4-isobutyl-2-(1-methyl-piperidin-4-yl)-oxazole-5-carbonyl]-3-phenyl-propylcarbamoyl}-3,3-dimethyl-butyl)-amide;

Morpholine-4-carboxylic acid (1-{1-[4-isobutyl-2-(1-pyrimidin-2-yl-piperidin-4-yl)-oxazole-5-carbonyl]-3-phenyl-propylcarbamoyl}-3,3-dimethyl-butyl)-amide;

Morpholine-4-carboxylic acid (1-{2-[4-isobutyl-2-(1-pyrimidin-2-yl-piperidin-4-yl)-oxazol-5-yl]-2-oxo-ethylcarbamoyl}-3,3-dimethyl-butyl)-amide;

Morpholine-4-carboxylic acid (1-{2-[4-cyclohexylmethyl-2-(1-pyrimidin-2-yl-piperidin-4-yl)-oxazol-5-yl]-2-oxo-ethylcarbamoyl}-3-methyl-butyl)-amide;

Morpholine-4-carboxylic acid {1-[2-(4-cyclohexylmethyl-2-piperidin-3-yl-oxazol-5-yl)-2-oxo-ethylcarbamoyl]-3-methyl-butyl}-amide;

Morpholine-4-carboxylic acid {1-[2-(4-isobutyl-2-piperidin-3-yl-oxazol-5-yl)-2-oxo-ethylcarbamoyl]-3-methyl-butyl}-amide;

Morpholine-4-carboxylic acid (1-{2-[4-isobutyl-2-(1-methyl-piperidin-3-yl)-oxazol-5-yl]-2-oxo-ethylcarbamoyl}-3-methyl-butyl)-amide;

Morpholine-4-carboxylic acid (1-{2-[4-isobutyl-2-(1-methyl-piperidin-3-yl)-oxazol-5-yl]-2-oxo-ethylcarbamoyl}-3,3-dimethyl-butyl)-amide;

Morpholine-4-carboxylic acid (1-{2-[4-isobutyl-2-(1-methyl-piperidin-2-yl)-oxazol-5-yl]-2-oxo-ethylcarbamoyl}-3,3-dimethyl-butyl)-amide;

Morpholine-4-carboxylic acid (1-{1-[4-isobutyl-2-(1-methyl-piperidin-2-yl)-oxazole-5-carbonyl]-3-phenyl-propylcarbamoyl}-3-methyl-butyl)-amide;

Morpholine-4-carboxylic acid {1-[4-isobutyl-2-phenyl-oxazole-5-carbonyl)-3-phenyl-propylcarbamoyl]-3-methyl-butyl}-amide;

Morpholine-4-carboxylic acid {1-[1-(4-dimethylaminomethyl-2-phenyl-oxazole-5-carbonyl)-3-phenyl-propylcarbamoyl]-3-methyl-butyl}-amide;

Morpholine-4-carboxylic acid {1-[2-(4-dimethylaminomethyl-2-phenyl-oxazol-5-yl)-2-oxo-ethylcarbamoyl]-3-methyl-butyl}-amide;

Morpholine-4-carboxylic acid {2-cyclohexyl-1-[2-(4-dimethylaminomethyl-2-phenyl-oxazol-5-yl)-2-oxo-ethylcarbamoyl]-ethyl}-amide;

Morpholine-4-carboxylic acid {1-[2-(4-dimethylaminomethyl-2-phenyl-oxazol-5-yl)-2-oxo-ethylcarbamoyl]-3,3-dimethyl-butyl}-amide;

Morpholine-4-carboxylic acid {1-[1-(4-dimethylaminomethyl-2-phenyl-oxazol-5-carbonyl)-3-phenyl-propylcarbamoyl]-3,3-dimethyl-butyl}-amide;

Morpholine-4-carboxylic acid {1-[1-(4-hydroxymethyl-2-phenyl-oxazol-5-carbonyl)-3-phenyl-propylcarbamoyl]-3,3-dimethyl-butyl}-amide;

Morpholine-4-carboxylic acid (3,3-dimethyl-1-{2-[4-(4-methyl-piperazin-1-ylmethyl)-2-phenyl-oxazol-5-yl]-2-oxo-ethylcarbamoyl}-butyl)-amide;
Morpholine-4-carboxylic acid (3,3-dimethyl-1-{2-[4-(4-methyl-piperazin-1-ylmethyl)-2-pyridin-4-yl-oxazol-5-yl]-2-oxo-ethylcarbamoyl}-butyl)-amide;
Morpholine-4-carboxylic acid (3-methyl-1-{1-[4-(4-methyl-piperazin-1-ylmethyl)-2-pyridin-4-yl-oxazole-5-carbonyl]-3-phenyl-propylcarbamoyl}-butyl)-amide;
{1-[4-Isobutyl-5-(2-{4-methyl-2-[(morpholine-4-carbonyl)-amino]-pentoylamino}-acetyl)-oxazol-2-yl]-3-methyl-butyl}carbamic acid benzyl ester;
Morpholine-4-carboxylic acid {2-cyclohexyl-1-[1-(4-isobutyl-2-pyrimidin-4-yl-oxazole-5-carbonyl)-3-phenyl-propylcarbamoyl]ethyl}-amide;
Morpholine-4-carboxylic acid {2-cyclohexyl-1-[3-phenyl-1-(4-phenyl-2-pyridin-4-yl-thiazole-5-carbonyl)-propylcarbamoyl]-ethyl}-amide; and
Morpholine-4-carboxylic acid {2-cyclohexyl-1-[2-oxo-2-(2-pyridin-4-yl-4-p-tolyl-thiazole-5-yl)-ethylcarbamoyl]-ethyl}-amide.

Preferred prophetic compounds have S-stereochemistry at their asymmetric carbons.

What is claimed is:

1. A compound of formula (I):

$$R_1-A-N(H)-C(R_2)(R_3)-C(X)-N(R_4)-C(R_5)(R_6)(R_7) \quad (I)$$

wherein:

A is —C(Y)— or —SO$_2$—
  Y is O, S or NR$_a$ wherein R$_a$ is selected from the group consisting of H, alkyl, aryl, alkoxy, aryloxy, alkylamino and arylamino;
  R$_1$ is piperidinyl;
R$_2$ is H or alkyl;
R$_3$ is H, alkyl, cycloalkyl, aryl, heterocyclyl or heteroaryl, wherein R$_3$ is unsubstituted or substituted by one or more groups of the formula R$_d$;
  R$_d$ is selected from the group consisting of alkyl, cycloalkyl, aryl, heterocyclyl, heteroaryl, alkoxy, aryloxy, arylalkoxy, alkoxycarbonyl, aryloxycarbonyl, alkanoyl, aroyl, alkanoyloxy, aroyloxy, carbamoyl wherein the nitrogen atom is unsubstituted or independently mono or di-substituted by alkyl, aryl, heterocyclyl or heteroaryl, alkanoylamino, aroylamino, alkylthio wherein the sulfur atom is unoxidized or oxidized to a sulfoxide or sulfone, arylthio wherein the sulfur atom is unoxidized or oxidized to a sulfoxide or sulfone, ureido wherein either nitrogen atom is unsubstituted or independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom is unsubstituted or independently mono or di-substituted by alkyl, aryl, heterocyclyl or heteroaryl, halogen, hydroxy, oxo, carboxy, cyano, nitro, amidino and guanidino, R$_d$ is unsubstituted or substituted by one or more R$_e$;
    R$_e$ is selected from the group consisting of alkyl, cycloalkyl, aryl, arylalkyl, alkoxy, aryloxy, arylalkoxy, alkanoyl, aroyl, amino, halogen, hydroxy, oxo, carboxy, cyano, nitro, amidino and guanidino;
R$_4$ is H or alkyl;
R$_5$ is H, alkyl or cycloalkyl;
R$_6$ is H, alkyl, cycloalkyl, aryl, heterocyclyl or heteroaryl, wherein R$_6$ is unsubstituted or substituted by one or more groups of the formula R$_f$;
  R$_f$ is selected from the group consisting of alkyl, cycloalkyl, aryl, heterocyclyl, heteroaryl, alkoxy, aryloxy, alkanoyl, aroyl, arylalkoxy, heteroarylalkoxy, alkoxycarbonyl, aryloxycarbonyl, alkanoyloxy, aroyloxy, carbamoyl wherein the nitrogen atom is unsubstituted or independently mono or di-substituted by alkyl, aryl, heterocyclyl or heteroaryl, alkanoylamino, aroylamino, alkylthio wherein the sulfur atom is unoxidized or oxidized to a sulfoxide or sulfone, arylthio wherein the sulfur atom is unoxidized or oxidized to a sulfoxide or sulfone, arylalkylthio wherein the sulfur atom is unoxidized or oxidized to a sulfoxide or sulfone, ureido wherein either nitrogen atom is unsubstituted or independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom is unsubstituted or independently mono or di-substituted by alkyl, aryl, heterocyclyl or heteroaryl, halogen, hydroxy, oxo, carboxy, cyano, nitro, amidino and guanidino, R$_f$ is unsubstituted or substituted by one or more R$_g$;
    R$_g$ is selected from the group consisting of alkyl, cycloalkyl, aryl unsubstituted or substituted by halogen, C1-5alkyl or C1-5alkoxy, heterocyclyl, heteroaryl, alkoxy, aryloxy, arylalkoxy, alkoxycarbonyl, aryloxycarbonyl, alkanoyloxy, aroyloxy, carbamoyl wherein the nitrogen atom is unsubstituted or independently mono or di-substituted by alkyl, aryl, heterocyclyl or heteroaryl; alkanoylamino, aroylamino, alkylthio wherein the sulfur atom is unoxidized or oxidized to a sulfoxide or sulfone, arylthio wherein the sulfur atom is unoxidized or oxidized to a sulfoxide or sulfone, ureido wherein either nitrogen atom is unsubstituted or independently substituted by alkyl, aryl, heterocyclyl or heteroaryl; alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom is unsubstituted or independently mono or di-substituted by alkyl, aryl, heterocyclyl or heteroaryl; halogen, hydroxy, oxo, carboxy, cyano, nitro, amidino and guanidino;
or R$_5$ together with R$_6$ form a 3 to 6 membered carbocyclic ring, the carbocyclic ring being unsubstituted or substituted with one or more R$_h$;
  R$_h$ is selected from the group consisting of alkyl, aryl, alkoxycarbonyl, aryloxycarbonyl, arylalkoxycarbonyl, carbamoyl wherein the nitrogen atom is unsubstituted or mono or di-substituted by alkyl, cycloalkyl, aryl, arylalkyl, heterocyclyl or heteroaryl; halogen, hydroxy, carboxy and cyano;
R$_7$ is R$_8$-C(Z)—;
  wherein Z is O, S, or NR$_i$ wherein R$_i$ is selected from the group consisting of H, alkyl, aryl, alkoxy, aryloxy and hydroxy;

$R_8$ is a heteroaryl ring selected from the group consisting of furanyl, thienyl, pyrrolyl, oxazolyl, thiazolyl, imidazolyl, pyrazolyl, isoxazolyl, isothiazolyl, pyridyl, pyridazinyl, pyrimidinyl, pyrazinyl, triazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl and phenazinyl, wherein any of the above $R_8$ can be unsubstituted or substituted by one or more $R_j$;

$R_j$ is selected from the group consisting of C1-8alkyl, C3-7cycloclyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl, and phenoxyazinyl; arylC1-8alkyl, C1-8alkoxy, aryloxy, arylC1-8alkoxy, C1-8alkoxycarbonyl, aryloxycarbonyl, C1-8alkanoyloxy, aroyloxy, carbamoyl wherein the nitrogen atom is unsubstituted or independently mono or di-substituted by C1-8alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxyazinyl, C1-8alkanoylamino, aroylamino, C1-8alkylthio wherein the sulfur atom is unoxidized or oxidized to a sulfoxide or sulfone, arylthio wherein the sulfur atom is unoxidized or oxidized to a sulfoxide or sulfone, arylC1-8alkylthio wherein the sulfur atom is unoxidized or oxidized to a sulfoxide or sulfone, ureido wherein either nitrogen atom is unsubstituted or independently substituted by C1-8alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxyazinyl, alkoxycarbonylamino, aryloxycarbonylamino, C1-8alkylcarbamoyloxy, arylcarbamoyloxy,, alkylsulfonylamino, arylsulfonylamino, alkylaminosulfonyl, arylaminosulfonyl, amino wherein the nitrogen atom is unsubstituted or independently mono or di-substituted by C1-8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxyazinyl, halogen, hydroxy, oxo, carboxy, cyano, nitro, amidino and guanidine, $R_j$ is unsubstituted or substituted by one or more $R_k$;

$R_k$ is selected from the group consisting of C1-8alkyl, C3-7 cycloalkyl, aryl, heterocyclyl, selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxyazinyl, C1-8 alkoxy, aryloxy, arylC1-8alkoxy, C1-8alkoxycarbonyl, aryloxycarbonyl, C1-8alkanoyloxy, aroyloxy, carbamoyl wherein the nitrogen atom is unsubstituted or independently mono or di-substituted by C1-8alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxyazinyl, alkanoylamino, aroylamino, C1-8alkylthio wherein the sulfur atom is unoxidized or oxidized to a sulfoxide or sulfone, arylthio wherein the sulfur atom is unoxidized or oxidized to a sulfoxide or sulfone, ureido wherein either nitrogen atom is unsubstituted or independently substituted by C1-8alkyl, aryl, heterocyclyl selected from the group consisting of pyrrolidinyl, piperidinyl, morpholinyl, thiomorpholinyl, piperazinyl and indolinylor heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxyazinyl, C1-8alkoxycarbonylamino, aryloxycarbonylamino, arylC1-8arylalkoxycarbonylamino, arylalkoxycarbonylaminoalkylC1-8alkyl, C1-8 alkylcarbamoyloxy, arylcarbamoyloxy, C1-8alkylsulfonylamino, arylsulfonylamino, C1-8alkylaminosulfonyl, arylaminosulfonyl, amino wherein the nitrogen atom is unsubstituted or independently mono or di-substituted by C1-8alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino; and X is O; or the pharmaceutically acceptable salts, esters, tautomers, individual isomers and mixtures of isomers thereof;

with the proviso that when $R_6$ is alkyl the alkyl must be substituted with $R_f$ wherein $R_f$ is not hydroxy, sulfhydryl or halogen.

2. The compound according to claim 1 wherein:

$R_a$ is selected from the group consisting of H, alkyl and aryl;

$R_3$ is H, C1-8 alkyl, C3-7 cycloalkyl or aryl wherein $R_3$ is unsubstituted or substituted by one or more $R_d$;

$R_d$ is selected from the group consisting of C1-8 alkyl, C3-7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1-8 alkoxy, aryloxy, alkanoyl, aroyl, C1-8 alkoxycarbonyl, aryloxycarbonyl, C1-8 alkanoyloxy, aroyloxy, carbamoyl wherein the nitrogen atom is unsubstituted or independently mono or di-substituted by C1-8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1-8 alkanoylamino, aroylamino, C1-8 alkylthio wherein the sulfur atom is unoxidized or oxidized to a sulfoxide or sulfone, arylthio wherein the sulfur atom is unoxidized or oxidized to a sulfoxide or sulfone, ureido wherein either nitrogen atom is unsubstituted or independently substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, C1-8 alkylcarbamoyloxy, arylcarbamoyloxy, alkylsulfonylamino, arylsulfonylamino, alkylaminosulfonyl, arylaminosulfonyl, amino wherein the nitrogen atom is unsubstituted or independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_d$ is unsubstituted or substituted by one or more $R_e$;

$R_e$ is selected from the group consisting of C1-8 alkyl, C3-6 cycloalkyl, aryl, arylalkyl, C1-8 alkoxy, aryloxy, arylalkoxy, aroyl, amino, halogen, hydroxy, oxo, carboxy, cyano, nitro, amidino and guanidino;

$R_5$ is H or alkyl;

$R_6$ is H, C1-8 alkyl, C3-7 cycloalkyl or aryl wherein $R_6$ is unsubstituted or substituted by one or more $R_f$;

$R_f$ is selected from the group consisting of C1-8 alkyl, C3-7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1-8 alkoxy, aryloxy, arylC1-8alkoxy, heteroarylC1-8alkoxy, C1-8 alkoxycarbonyl, aryloxycarbonyl, C1-8 alkanoyloxy, aroyloxy, carbamoyl wherein the nitrogen atom is unsubstituted or independently mono or di-substituted by C1-8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1-8 alkanoylamino, aroylamino, C1-8 alkylthio wherein the sulfur atom is unoxidized or oxidized to a sulfoxide or sulfone, arylthio wherein the sulfur atom is unoxidized or oxidized to a sulfoxide or sulfone, arylC1-8 alkylthio wherein the sulfur atom is unoxidized or oxidized to a sulfoxide or sulfone, ureido wherein either nitrogen atom is unsubstituted or independently substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, C1-8 alkylcarbamoyloxy, arylcarbamoyloxy, alkylsulfonylamino, arylsulfonylamino, alkylaminosulfonyl, arylaminosulfonyl, amino wherein the nitrogen atom is unsubstituted or independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_f$ is unsubstituted or substituted by one or more $R_g$;

$R_g$ is selected from the group consisting of C1-8 alkyl, C3-7 cycloalkyl, aryl unsubstituted or substituted by halogen, C1-3alkyl or C1-3alkoxy; heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1-8 alkoxy, aryloxy, arylC1-8alkoxy, C1-8 alkoxycarbonyl, aryloxycarbonyl, C1-8 alkanoyloxy, aroyloxy, carbamoyl wherein the nitrogen atom is unsubstituted or independently mono or di-substituted by C1-8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1-8 alkanoylamino, aroylamino, C1-8 alkylthio wherein the sulfur atom is unoxidized or oxidized to a sulfoxide or sulfone, arylthio wherein the sulfur atom is unoxidized or oxidized to a sulfoxide or sulfone, ureido wherein either nitrogen atom is unsubstituted or independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, C1-8 alkylcarbamoyloxy, arylcarbamoyloxy, alkylsulfonylamino, arylsulfonylamino, alkylaminosulfonyl and arylaminosulfonyl, amino wherein the nitrogen atom is unsubstituted or independently mono or di-substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino;

$R_h$ is selected from the group consisting of C1-8 alkyl, aryl, C1-8 alkoxycarbonyl, aryloxycarbonyl, arylC1-8alkoxycarbonyl, carbamoyl wherein the nitrogen atom is unsubstituted or mono or di-substituted by C1-8 alkyl, C3-7 cycloalkyl, aryl, arylC1-8alkyl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, carboxy and cyano.

3. The compound according to claim 2 wherein:

Y is O or S;

$R_2$ is H or C1-3 alkyl;

$R_3$ is H, C1-5 alkyl, C3-7 cycloalkyl or aryl, wherein $R_3$ is unsubstituted or substituted by one or more $R_d$;

$R_d$ is selected from the group consisting of C1-5 alkyl, C3-7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1-5 alkoxy, aryloxy, C1-5alkanoyl, aroyl, C1-5 alkoxycarbonyl, aryloxycarbonyl, C1-5 alkanoyloxy, aroyloxy, carbamoyl wherein the nitrogen atom is unsubstituted or independently mono or di-substituted by C1-5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1-5 alkanoylamino, aroylamino, C1-5 alkylthio wherein the sulfur atom is unoxidized or oxidized to a sulfoxide or sulfone, arylthio wherein the sulfur atom is unoxidized or oxidized to a sulfoxide or sulfone, ureido wherein either nitrogen atom is unsubstituted or independently substituted by C1-5 alkyl, aryl, heterocyclyl selected from the group consisting of pyrrolidinyl, piperidinyl, morpholinyl, thiomorpholinyl, piperazinyl and indolinyl or heteroaryl selected the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1-5 alkoxycarbonylamino, aryloxycarbonylamino, C1-5 alkylcarbamoyloxy, arylcarbamoyloxy, C1-5 alkylsulfonylamino, arylsulfonylamino, C1-5 alkylaminosulfonyl, arylaminosulfonyl, amino wherein the nitrogen atom is unsubstituted or independently mono or di-substituted by C1-5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, halogen, hydroxy, oxo, carboxy, cyano, nitro, amidino and guanidino, $R_d$ is unsubstituted or substituted by one or more $R_e$;

$R_e$ is selected from the group consisting of C1-5 alkyl, C3-6 cycloalkyl, aryl, arylalkyl, C1-5 alkoxy, aryloxy, arylC1-5alkoxy, aroyl, amino, halogen, hydroxy, oxo, carboxy, cyano, nitro, amidino and guanidino;

$R_4$ is H or C1-3 alkyl;

$R_5$ is H or C1-8 alkyl;

$R_6$ is H, C1-5 alkyl, C3-7 cycloalkyl or aryl wherein $R_6$ is unsubstituted or substituted by one or more $R_f$;

$R_f$ is selected from the group consisting of C1-5 alkyl, C3-7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1-5 alkoxy, aryloxy, arylC1-5alkoxy, heteroarylC1-5alkoxy, C1-5 alkoxycarbonyl, aryloxycarbonyl, C1-5 alkanoyloxy, aroyloxy, carbamoyl wherein the nitrogen atom is unsubstituted or independently mono or di-substituted by C1-5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1-5 alkanoylamino, aroylamino, C1-5 alkylthio wherein the sulfur atom is unoxidized or oxidized to a sulfoxide or sulfone, arylthio wherein the sulfur atom is unoxidized or oxidized to a sulfoxide or sulfone, arylC1-5 alkylthio wherein the sulfur atom is unoxidized or oxidized to a sulfoxide or sulfone, ureido wherein either nitrogen atom is unsubstituted or independently substituted by C1-5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1-5 alkoxycarbonylamino, aryloxycarbonylamino, C1-5 alkylcarbamoyloxy, arylcarbamoyloxy, C1-5 alkylsulfonylamino, arylsulfonylamino, C1-5 alkylaminosulfonyl, arylaminosulfonyl, amino wherein the nitrogen atom is unsubstituted or independently mono or di-substituted by C1-5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, halogen, hydroxy, oxo, carboxy, cyano, nitro, amidino and guanidino, $R_f$ is unsubstituted or substituted by one or more $R_g$;

$R_g$ is selected from the group consisting of C1-5 alkyl, C3-7 cycloalkyl, aryl unsubstituted or substituted by halogen, methyl or methoxy; heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1-5 alkoxy, aryloxy, arylC1-5alkoxy, C1-5 alkoxycarbonyl, aryloxycarbonyl, C1-5 alkanoyloxy, aroyloxy, carbamoyl wherein the nitrogen atom is unsubstituted or independently mono or di-substituted by C1-5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1-5 alkanoylamino, aroylamino, C1-5 alkylthio wherein the sulfur atom is unoxidized or oxidized to a sulfoxide or sulfone, arylthio wherein the sulfur atom is unoxidized or oxidized to a sulfoxide or sulfone, ureido wherein either nitrogen atom is unsubstituted or independently substituted by C1-5 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1-5 alkoxycarbonylamino, aryloxycarbonylamino, C1-5 alkylcarbamoyloxy, arylcarbamoyloxy, C1-5 alkylsulfonylamino, arylsulfonylamino, C1-5 alkylaminosulfonyl, arylaminosulfonyl, amino wherein the nitrogen atom is unsubstituted or independently mono or di-substituted by C1-5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, halogen, hydroxy, oxo, carboxy, cyano, nitro, amidino and guanidino;

$R_h$ is selected from the group consisting of C1-5 alkyl, aryl, C1-5 alkoxycarbonyl, aryloxycarbonyl, arylC1-5alkoxycarbonyl, carbamoyl wherein the nitrogen atom is unsubstituted or mono or di-substituted by C1-5 alkyl, C3-7 cycloalkyl, aryl, arylC1-5alkyl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, halogen, hydroxy, carboxy and cyano;

$R_1$ is alkoxy, aryloxy or hydroxy.

4. The compound according to claim 3 wherein:

Y is O;

$R_2$ is H or methyl;

$R_3$ is H, C1-5 alkyl, C3-7 cycloalkyl or phenyl, wherein $R_3$ is unsubstituted or substituted by one or more $R_d$;

$R_d$ is selected from the group consisting of C1-3 alkyl, C3-6 cycloalkyl, phenyl, naphthyl, heterocyclyl selected from the group consisting of piperidinyl, morpholinyl and piperazinyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1-5 alkoxy, aryloxy, aroyl, C1-5 alkoxycarbonyl, aryloxycarbonyl, C1-5 alkanoyloxy, aroyloxy, carbamoyl wherein the nitrogen atom is unsubstituted or independently mono or di-substituted by C1-5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1-5 alkanoylamino, aroylamino, C1-5 alkylthio wherein the sulfur atom is unoxidized or oxidized to a sulfoxide or sulfone, arylthio wherein the sulfur atom is unoxidized or oxidized to a sulfoxide or sulfone, ureido wherein either nitrogen atom is unsubstituted or independently substituted by C1-5 alkyl, phenyl, naphthyl, heterocyclyl selected from the group consisting of piperidinyl, morpholinyl and piperazinyl or heteroaryl selected the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1-5 alkoxycarbonylamino, aryloxycarbonylamino, C1-5 alkylcarbamoyloxy, arylcarbamoyloxy, C1-5 alkylsulfonylamino, arylsulfonylamino, C1-5 alkylaminosulfonyl, arylaminosulfonyl, amino wherein the nitrogen atom is unsubstituted or independently mono or di-substituted by C1-5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, halogen, hydroxy, oxo, carboxy and cyano, $R_d$ is unsubstituted or substituted by one or more $R_e$;

$R_e$ is selected from the group consisting of C1-5 alkyl, C3-6 cycloalkyl, aryl, arylC1-5alkyl, C1-5 alkoxy, aryloxy, arylC1-3alkoxy, aroyl, amino, halogen, hydroxy, oxo, carboxy and cyano;

$R_4$ is H or methyl;

$R_5$ is H or C1-5 alkyl;

$R_6$ is H, C1-5 alkyl, C3-7 cycloalkyl, phenyl or naphthyl wherein $R_6$ is unsubstituted or substituted by one or more $R_f$;

$R_f$ is selected from the group consisting of C1-5 alkyl, C3-7 cycloalkyl, phenyl, naphthyl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1-5 alkoxy, aryloxy, arylC1-5alkoxy, pyridylC1-5alkoxy, thienylC1-5alkoxy, furanylC1-5alkoxy, C1-5 alkoxycarbonyl, aryloxycarbonyl, C1-5 alkanoyloxy, aroyloxy, carbamoyl wherein the nitrogen atom is unsubstituted or independently mono or di-substituted by C1-5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1-5 alkanoylamino, aroylamino, C1-5 alkylthio wherein the sulfur atom is unoxidized or oxidized to a sulfoxide or sulfone, arylthio wherein the sulfur atom is unoxidized or oxidized to a sulfoxide or sulfone, arylC1-5 alkylthio wherein the sulfur atom is unoxidized or oxidized to a sulfoxide or sulfone, ureido wherein either nitrogen atom is unsubstituted or independently substituted by C1-5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1-5 alkoxycarbonylamino, aryloxycarbonylamino, C1-5 alkylcarbamoyloxy, arylcarbamoyloxy, C1-5 alkylsulfonylamino, arylsulfonylamino, C1-5 alkylaminosulfonyl, arylaminosulfonyl, amino wherein the nitrogen atom is unsubstituted or independently mono or di-substituted by C1-5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, halogen, hydroxy, oxo, carboxy and cyano, Rf is unsubstituted or substituted by one or more $R_g$;

$R_g$ is selected from the group consisting of C1-5 alkyl, C3-7 cycloalkyl, phenyl unsubstituted or substituted by halogen, methyl or methoxy; naphthyl unsubstituted or substituted by halogen, methyl or methoxy; heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1-5 alkoxy, aryloxy, arylC1-5alkoxy, C1-5 alkoxycarbonyl, aryloxycarbonyl, C1-5 alkanoyloxy, aroyloxy, carbamoyl wherein the nitrogen atom is unsubstituted or independently mono or di-substituted by C1-5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1-5 alkanoylamino, aroylamino, C1-5 alkylthio wherein the sulfur atom is unoxidized or oxidized to a sulfoxide or sulfone, arylthio wherein the sulfur atom is unoxidized or oxidized to a sulfoxide or sulfone, ureido wherein either nitrogen atom is unsubstituted or independently substituted by C1-5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1-5 alkoxycarbonylamino, aryloxycarbonylamino, C1-5 alkylcarbamoyloxy, arylcarbamoyloxy, C1-5 alkylsulfonylamino, arylsulfonylamino, C1-5 alkylaminosulfonyl, arylaminosulfonyl, amino wherein the nitrogen atom is unsubstituted or independently mono or di-substituted by C1-5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, halogen, hydroxy, oxo, carboxy and cyano;

$R_h$ is selected from the group consisting of C1-5 alkyl, phenyl, naphthyl, C1-5 alkoxycarbonyl, aryloxycarbonyl, arylC1-3alkoxycarbonyl, carbamoyl wherein the nitrogen atom is unsubstituted or mono or di-substituted by C1-5 alkyl, C3-6 cycloalkyl, phenyl, naphthyl, arylC1-3alkyl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, halogen, hydroxy, carboxy and cyano;

Z is O or S;

$R_j$ is selected from the group consisting of C1-5alkyl, C3-6cycloalkyl, phenyl, naphthyl, heterocyclyl selected from the group consisting of piperidinyl, morpholinyl and piperazinyl; heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl and isoquinolinyl, arylC1-5alkyl, C1-5alkoxy, aryloxy, arylC1-5alkoxy, C1-5alkoxycarbonyl, aryloxycarbonyl, C1-5alkanoyloxy, aroyloxy, carbamoyl wherein the nitrogen atom is unsubstituted or independently mono or di-substituted by C1-5alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl and isoquinolinyl, C1-5alkanoylamino, aroylamino, C1-5alkylthio wherein the sulfur atom is unoxidized or oxidized to a sulfoxide or sulfone, arylthio wherein the sulfur atom is unoxidized or oxidized to a sulfoxide or sulfone, arylC1-5alkylthio wherein the sulfur atom is unoxidized or oxidized to a sulfoxide or sulfone, ureido wherein either nitrogen atom is unsubstituted or independently substituted by C1-5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl and isoquinolinyl, C1-5alkoxycarbonylamino, aryloxycarbonylamino, C1-5 alkylcarbamoyloxy, arylcarbamoyloxy, C1-5alkylsulfonylamino, arylsulfonylamino, C1-5alkylaminosulfonyl, arylaminosulfonyl, amino wherein the nitrogen atom is unsubstituted or independently mono or di-substituted by C1-5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, purinyl, quinolinyl and isoquinolinyl, halogen, hydroxy, oxo, carboxy, cyano, nitro, amidino and guanidino, $R_j$ is unsubstituted or substituted by one or more $R_k$;

$R_k$ is selected from the group consisting of C1-3 alkyl, C3-6 cycloalkyl, phenyl, naphthyl, heterocyclyl selected from the group consisting of piperidinyl, morpholinyl and piperazinyl; heteroaryl selected from the group consisting of furanyl, thienyl, pyrrolyl, tetrazolyl and pyridinyl, C1-3 alkoxy, aryloxy, arylC1-3alkoxy, C1-3alkoxycarbonyl, aryloxycarbonyl, C1-3alkanoyloxy, aroyloxy, carbamoyl wherein the nitrogen atom is unsubstituted or independently mono or di-substituted by C1-3 alkyl, aryl, heterocyclyl selected from the group consisting of morpholinyl and piperazinyl or heteroaryl selected from the group consisting of furanyl, thienyl, pyrrolyl, oxazolyl, thiazolyl, imidazolyl, tetrazolyl, and pyridinyl, C1-3alkanoylamino, aroylamino, C1-3alkylthio wherein the sulfur atom is unoxidized or oxidized to a sulfoxide or sulfone, arylthio wherein the sulfur atom is unoxidized or oxidized to a sulfoxide or sulfone, ureido wherein either nitrogen atom is unsubstituted or independently substituted by C1-3alkyl, phenyl, naphthyl or heteroaryl selected from the group consisting of furanyl, thienyl, pyrrolyl, oxazolyl, thiazolyl, imidazolyl, tetrazolyl and pyridinyl, C1-3alkoxycarbonylamino, aryloxycarbonylamino, arylC1-3alkoxycarbonylamino, benzyloxycarbonylaminoC1-5 alkyl, C1-3 alkylcarbamoyloxy, arylcarbamoyloxy, C1-3alkylsulfonylamino, arylsulfonylamino, C1-3alkylaminosulfonyl, arylaminosulfonyl, amino wherein the nitrogen atom is unsubstituted or independently mono or di-substituted by C1-3alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, tetrazolylpyridinyl, indolyl, benzofuranyl, benzothienyl, benzimidazoyl, benzthiazolyl, benzoxazolyl, quinolinyl and isoquinolinyl, halogen, hydroxy, oxo, carboxy, cyano and nitro.

5. The compound according to claim 4 wherein:
$R_2$ is H;
$R_3$ is C1-5 alkyl, C3-6 cycloalkyl or phenyl, wherein $R_3$ is unsubstituted or substituted by one or more $R_d$;

$R_d$ is selected from the group consisting of C1-3 alkyl, C3-6 cycloalkyl, phenyl, naphthyl, heterocyclyl selected from the group consisting of piperidinyl, morpholinyl and piperazinyl; heteroaryl selected from the group consisting of furanyl, thienyl, thiazolyl, imidazolyl, pyridinyl, indolyl, quinolinyl and isoquinolinyl, C1-5 alkoxy, phenoxy, aroyl, C1-5 alkoxycarbonyl, aryloxycarbonyl, C1-5 alkanoyloxy, aroyloxy, carbamoyl wherein the nitrogen atom is unsubstituted or independently mono or di-substituted by C1-5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, C1-5 alkanoylamino, aroylamino, C1-3 alkylthio wherein the sulfur atom is unoxidized or oxidized to a sulfoxide or sulfone, phenylthio wherein the sulfur atom is unoxidized or oxidized to a sulfoxide or sulfone, ureido wherein either nitrogen atom is unsubstituted or independently substituted by C1-3 alkyl, phenyl or heteroaryl selected the group consisting of furanyl, thienyl, pyrrolyl, oxazolyl, thiazolyl, imidazolyl, pyridinyl and indolyl, C1-5 alkoxycarbonylamino, C1-5 alkylcarbamoyloxy, arylcarbamoyloxy, C1-5 alkylsulfonylamino, arylsulfonylamino, amino wherein the nitrogen atom is unsubstituted or independently mono or di-substituted by C1-3 alkyl, phenyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, halogen, hydroxy, oxo, carboxy and cyano, $R_d$ is unsubstituted or substituted by one or more $R_e$;

$R_e$ is selected from the group consisting of C1-5 alkyl, C5-6 cycloalkyl, phenyl, naphthyl, arylC1-3alkyl, C1-5 alkoxy, phenoxy, arylC1-3alkoxy, aroyl, amino, halogen, hydroxy, oxo, carboxy and cyano;

wherein the configuration at the stereocenter defined by $R_2$ and $R_3$ and the carbon they are attached to is L enantiomer;
$R_4$ is H;
$R_5$ is H or C1-3 alkyl;
$R_6$ is H, C1-5 alkyl, C3-6 cycloalkyl or phenyl, wherein $R_6$ is unsubstituted or substituted by one or more $R_f$;

$R_f$ is selected from the group consisting of C1-3 alkyl, C3-6 cycloalkyl, phenyl, naphthyl, heterocyclyl selected from the group consisting of pyrrolidinyl, piperidinyl, morpholinyl and piperazinyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1-5 alkoxy, aryloxy, arylC1-3alkoxy, pyridylC1-5alkoxy, thienylC1-5alkoxy, furanylC1-5alkoxy, C1-5 alkoxycarbonyl, aryloxycarbonyl, C1-5 alkanoyloxy, aroyloxy, carbamoyl wherein the nitrogen atom is unsubstituted or independently mono or di-substituted by C1-5 alkyl, phenyl or heteroaryl selected from the group consisting of furanyl, thienyl, pyrrolyl, oxazolyl, thiazolyl, imidazolyl, pyridinyl and indolyl, C1-5 alkanoylamino, aroylamino, C1-3 alkylthio wherein the sulfur atom is unoxidized or oxidized to a sulfoxide or sulfone, arylthio wherein the sulfur atom is unoxidized or oxidized to a sulfoxide or sulfone, arylC1-3 alkylthio wherein the sulfur atom is unoxidized or oxidized to a sulfoxide or sulfone, ureido wherein either nitrogen atom is unsubstituted or independently substituted by C1-5 alkyl or phenyl; C1-5 alkoxycarbonylamino, C1-5 alkylsulfonylamino, arylsulfonylamino, amino wherein the nitrogen atom is unsubstituted or independently mono or di-substituted by C1-5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, halogen, hydroxy, oxo, carboxy and cyano, $R_f$ is unsubstituted or substituted by one or more $R_g$;

$R_g$ is selected from the group consisting of C1-3 alkyl, C5-6 cycloalkyl, phenyl unsubstituted or substituted by halogen, methyl or methoxy; heterocyclyl selected from the group consisting of pyrrolidinyl, piperidinyl, morpholinyl and piperazinyl; heteroaryl selected from the group consisting of furanyl, thienyl, pyrrolyl, oxazolyl, thiazolyl, imidazolyl, pyridinyl, pyrimidinyl, pyrazinyl and indolyl, C1-5 alkoxy, aryloxy, arylC1-3alkoxy, C1-5 alkoxycarbonyl, aryloxycarbonyl, C1-5 alkanoyloxy, aroyloxy, carbamoyl wherein the nitrogen atom is unsubstituted or independently mono or di-substituted by C1-5 alkyl or aryl; C1-5 alkanoylamino, aroylamino, C1-5 alkylthio wherein the sulfur atom is unoxidized or oxidized to a sulfoxide or sulfone, arylthio wherein the sulfur atom is unoxidized or oxidized to a sulfoxide or sulfone, ureido wherein either nitrogen atom is unsubstituted or independently substituted by C1-5 alkyl or aryl; C1-5 alkoxycarbonylamino, aryloxycarbonylamino, C1-5 alkylcarbamoyloxy, arylcarbamoyloxy, C1-5 alkylsulfonylamino, arylsulfonylamino, C1-5 alkylaminosulfonyl, arylaminosulfonyl, amino wherein the nitrogen atom is unsubstituted or independently mono or di-substituted by C1-5 alkyl or aryl; halogen, hydroxy, oxo, carboxy and cyano;

$R_h$ is selected from the group consisting of C1-5 alkyl, phenyl, C1-5 alkoxycarbonyl, aryloxycarbonyl, arylC1-3alkoxycarbonyl, carbamoyl wherein the nitrogen atom is unsubstituted or mono or di-substituted by C1-5 alkyl, C3-6 cycloalkyl, phenyl or naphthyl, arylC1-3alkyl, halogen, hydroxy, carboxy and cyano;

Z is O;

$R_g$ is a heteroaryl ring selected from the group consisting of oxazolyl, thiazolyl, imidazolyl, pyrazolyl, isoxazolyl, isothiazolyl, pyridyl, pyridazinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, wherein any of the above $R_g$ can be unsubstituted or substituted by one or more $R_j$;

$R_j$ is selected from the group consisting of C1-3 alkyl, C5-6 cycloalkyl, phenyl, naphthyl, morpholinyl, piperazinyl, furanyl, thienyl, pyrrolyl, tetrazolyl, pyridinyl, indolyl, benzofuranyl, benzothienyl, benzimidazolyl, benzthiazolyl, benzoxazolyl, arylC1-3alkyl, C1-3alkoxy, aryloxy, arylC1-3alkoxy, C1-3alkoxycarbonyl, aryloxycarbonyl, C1-3alkanoyloxy, aroyloxy, carbamoyl wherein the nitrogen atom is unsubstituted or independently mono or di-substituted by C1-3alkyl, phenyl, naphthyl, piperidinyl, furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl or isoquinolinyl; C1-3alkanoylamino, aroylamino, C1-3alkylthio wherein the sulfur atom is unoxidized or oxidized to a sulfoxide or sulfone, arylthio wherein the sulfur atom is unoxidized or oxidized to a sulfoxide or sulfone, arylC1-3alkylthio wherein the sulfur atom is unoxidized or oxidized to a sulfoxide or sulfone, ureido wherein either nitrogen atom is unsubstituted or independently substituted by C1-3 alkyl, phenyl, naphthyl, piperidinyl, morpholinyl, thiazolyl, imidazolyl, tetrazolyl, pyridinyl, indolyl, benzofuranyl, benzothienyl, benzimidazolyl, benzthiazolyl, benzoxazolyl, quinolinyl or isoquinolinyl; C1-3 alkoxycarbonylamino, aryloxycarbonylamino, C1-3 alkylcarbamoyloxy, arylcarbamoyloxy, C1-3 alkylsulfonylamino, arylsulfonylamino, C1-3 alkylaminosulfonyl, arylaminosulfonyl, amino wherein the nitrogen atom is unsubstituted or independently mono or di-substituted by C1-3 alkyl, phenyl, naphthyl, piperidinyl, furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl or isoquinolinyl; halogen, hydroxy, oxo, carboxy, cyano and nitro, $R_j$ is unsubstituted or substituted by one or more $R_k$;

$R_k$ is selected from the group consisting of methyl, C5-6 cycloalkyl, phenyl, morpholinyl, furanyl, thienyl, pyrrolyl, tetrazolyl, pyridinyl, methoxy, phenoxy, benzyloxy, methoxycarbonyl, acetyloxy, benzoyloxy, carbamoyl wherein the nitrogen atom is unsubstituted or independently mono or di-substituted by C1-3 alkyl, phenyl, furanyl, thienyl, pyrrolyl, oxazolyl, thiazolyl, imidazolyl or pyridinyl; acetylamino, benzoylamino, methylthio wherein the sulfur atom is unoxidized or oxidized to a sulfoxide or sulfone, ureido wherein either nitrogen atom is unsubstituted or independently substituted by methyl, phenyl, furanyl, thienyl, pyrrolyl, oxazolyl, thiazolyl, imidazolyl or pyridinyl; arylC1-3alkoxycarbonylamino, benzyloxycarbonylaminoC1-5alkyl, amino wherein the nitrogen atom is unsubstituted or independently mono or di-substituted by C1-3alkyl, phenyl, naphthyl, furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl or isoquinolinyl, halogen, hydroxy, oxo, carboxy, cyano and nitro.

6. The compound according to claim 5 wherein:

$R_3$ is C1-5 alkyl, C5-6 cycloalkyl or phenyl wherein $R_3$ is unsubstituted or substituted by one or more $R_d$;

$R_d$ is selected from the group consisting of C1-3 alkyl, C3-6 cycloalkyl, phenyl, naphthyl, 4-piperidinyl, 4-morpholinyl, piperazinyl, furanyl, thienyl, thiazolyl, imidazolyl, pyridinyl, indolyl, C1-5 alkoxy, phenoxy, aroyl, C1-5 alkoxycarbonyl, aryloxycarbonyl, C1-5 alkanoyloxy, aroyloxy, carbamoyl wherein the nitrogen atom is unsubstituted or independently mono or di-substituted by C1-5 alkyl or phenyl; C1-5 alkanoylamino, C1-3 alkylthio wherein the sulfur atom is unoxidized or oxidized to a sulfoxide or sulfone, ureido wherein either nitrogen atom is unsubstituted or independently substituted by C1-3 alkyl or phenyl; C1-5 alkoxycarbonylamino, C1-5 alkylsulfonylamino, arylsulfonylamino, amino wherein the nitrogen atom is unsubstituted or independently mono or di-substituted by C1-3 alkyl or phenyl; halogen, hydroxy, oxo, carboxy and cyano, $R_d$ is unsubstituted or substituted by one or more $R_e$;

$R_e$ is selected from the group consisting of C1-5 alkyl, C5-6 cycloalkyl, phenyl, benzyl, C1-5 alkoxy, phenoxy, benzyloxy, aroyl, halogen, hydroxy, oxo, carboxy and cyano;

$R_6$ is H, C1-5 alkyl or phenyl wherein $R_6$ is unsubstituted or substituted by one or more $R_f$;

$R_f$ is selected from the group consisting of C1-3 alkyl, C3-6 cycloalkyl, phenyl, naphthyl, furanyl, thienyl, thiazolyl, imidazolyl, pyridinyl, indolyl, C1-3 alkoxy, benzyloxy, pyridyl, C1-3alkoxy, thienylC1-3alkoxy, furanylC1-3alkoxy, C1-3 alkoxycarbonyl, phenoxyoxycarbonyl, C1-5 alkanoyloxy, aroyloxy, carbamoyl wherein the nitrogen atom is unsubstituted or independently mono or di-substituted by C1-3 alkyl or phenyl; C1-5 alkanoylamino, aroylamino, methylthio wherein the sulfur atom is unoxidized or oxidized to a sulfoxide or sulfone, benzylthio wherein the sulfur atom is unoxidized or oxidized to a sulfoxide or sulfone, ureido wherein either nitrogen atom is unsubstituted or independently substituted by C1-5 alkyl or phenyl; C1-3 alkoxycarbonylamino, amino wherein the nitrogen atom is unsubstituted or independently mono or di-substituted by C1-5 alkyl or phenyl; halogen, hydroxy, oxo, carboxy and cyano, $R_f$ is unsubstituted or substituted by one or more $R_g$;

$R_g$ is selected from the group consisting of C1-3 alkyl, phenyl unsubstituted or substituted by halogen, methyl or methoxy; heterocyclyl selected from the group consisting of piperidinyl, morpholinyl and piperazinyl; heteroaryl selected from the group consisting of furanyl, thienyl, pyrrolyl and pyridinyl, C1-3 alkoxy, aryloxy, benzyloxy, C1-5 alkoxycarbonyl, C1-5 alkanoyloxy, aroyloxy, carbamoyl wherein the nitrogen atom is unsubstituted or independently mono or di-substituted by C1-5 alkyl or phenyl; C1-5 alkanoylamino, aroylamino, C1-5 alkylthio wherein the sulfur atom is unoxidized or oxidized to a sulfoxide or sulfone, ureido wherein either nitrogen atom is unsubstituted or independently substituted by C1-5 alkyl or phenyl; C1-5 alkoxycarbonylamino, C1-5 alkylcarbamoyloxy, arylcarbamoyloxy, C1-3 alkylsulfonylamino, arylsulfonylamino, C1-3 alkylaminosulfonyl, arylaminosulfonyl, amino wherein the nitrogen atom is unsubstituted or independently mono or di-substituted by C1-3 alkyl or phenyl; halogen, hydroxy, oxo, carboxy and cyano;

$R_h$ is selected from the group consisting of C1-3 alkyl, phenyl, C1-3 alkoxycarbonyl, phenoxyoxycarbonyl, benzyloxy, carbamoyl wherein the nitrogen atom is unsubstituted or mono or di-substituted with C1-5 alkyl, phenyl, benzyl, halogen, hydroxy, carboxy and cyano;

$R_8$ is a heteroaryl ring selected from the group consisting of oxazolyl, thiazolyl, imidazolyl, pyridyl, indolyl, benzofuranyl, benzothienyl, benzimidazolyl, benzthiazolyl, benzoxazolyl, quinolinyl and isoquinolinyl, wherein any of the above $R_8$ can be unsubstituted or substituted by one or more $R_j$;

$R_j$ is selected from the group consisting of C1-3 alkyl, C5-6 cycloalkyl, phenyl, naphthyl, morpholinyl, piperazinyl, furanyl, thienyl, pyrrolyl, tetrazolyl, pyridinyl, benzyl, C1-3alkoxy, phenoxy, benzyloxy, C1-3alkoxycarbonyl, acetyloxy, benzoyloxy, carbamoyl wherein the nitrogen atom is unsubstituted or independently mono or di-substituted by methyl, phenyl, furanyl, thienyl, pyrrolyl, oxazolyl, thiazolyl, imidazolyl or pyridinyl; acetylamino, benzoylamino, methylthio wherein the sulfur atom is unoxidized or oxidized to a sulfoxide or sulfone, benzylthio wherein the sulfur atom is unoxidized or oxidized to a sulfoxide or sulfone, ureido wherein either nitrogen atom is unsubstituted or independently substituted by methyl, phenyl, thiazolyl, imidazolyl or pyridinyl; C1-3 alkoxycarbonylamino, C1-3 alkylcarbamoyloxy, arylcarbamoyloxy, C1-3alkylsulfonylamino, arylsulfonylamino, amino wherein the nitrogen atom is unsubstituted or independently mono or di-substituted by methyl, phenyl, furanyl, thienyl, pyrrolyl, oxazolyl, thiazolyl, imidazolyl or pyridinyl; halogen, hydroxy, carboxy, cyano and nitro, $R_j$ is unsubstituted or substituted by one or more $R_k$;

$R_k$ is selected from the group consisting of methyl, C5-6 cycloalkyl, phenyl, furanyl, thienyl, pyrrolyl, pyridinyl, methoxy, phenoxy, benzyloxy, methoxycarbonyl, acetyloxy, benzoyloxy, carbamoyl wherein the nitrogen atom is unsubstituted or independently mono or di-substituted by methyl, phenyl, furanyl or thienyl; acetylamino, benzoylamino, methylthio wherein the sulfur atom is unoxidized or oxidized to a sulfoxide or sulfone, ureido wherein either nitrogen atom is unsubstituted or independently substituted by methyl, phenyl, furanyl, thienyl, pyrrolyl, oxazolyl and thiazolyl, benzyloxycarbonylamino, benzyloxycarbonyl-aminoC1-5alkyl, amino wherein the nitrogen atom is unsubstituted or independently mono or di-substituted by C1-3alkyl, phenyl, furanyl, thienyl, pyrrolyl, oxazolyl, thiazolyl, imidazolyl and pyridinyl, halogen, hydroxy, carboxy, cyano and nitro.

7. The compound according to claim 6 wherein:

$R_d$ is selected from the group consisting of C1-3 alkyl, C3-6 cycloalkyl, phenyl, naphthyl, 4-piperidinyl, furanyl, thienyl, thiazolyl, imidazolyl, pyridinyl, indolyl, C1-3alkoxy, C1-5alkoxycarbonyl, C1-5alkanoyloxy, benzoyloxy, carbamoyl wherein the nitrogen atom is unsubstituted or independently mono or di-substituted by C1-3alkyl or phenyl; C1-5alkanoylamino, C1-3 alkylthio wherein the sulfur atom is unoxidized or oxidized to a sulfoxide or sulfone, C1-3alkoxycarbonylamino, C1-3alkylsulfonylamino, amino wherein the nitrogen atom is unsubstituted or independently mono or di-substituted by C1-3 alkyl or phenyl, halogen, hydroxy, oxo, carboxy and cyano, $R_d$ is unsubstituted or substituted by one or more $R_e$;

$R_e$ is selected from the group consisting of C1-3 alkyl, phenyl, benzyl, C1-3 alkoxy, phenoxy, benzyloxy, benzoyl, halogen, hydroxy, oxo, carboxy and cyano;

$R_5$ is H or methyl;

$R_6$ is C1-5 alkyl or phenyl, wherein $R_6$ is unsubstituted or substituted by one or more groups of the formula $R_f$, $R_f$ is selected from the group consisting of methyl, C3-6 cycloalkyl, phenyl, naphthyl, furanyl, thienyl, thiazolyl, imidazolyl, pyridinyl, indolyl, C1-3 alkoxy, benzyloxy, C1-5 alkanoylamino, aroylamino, methylthio wherein the sulfur atom is unoxidized or oxidized to a sulfoxide or sulfone, benzylthio wherein the sulfur atom is unoxidized or oxidized to a sulfoxide or sulfone, C1-3 alkoxycarbonylamino, amino wherein the nitrogen atom is unsubstituted or independently mono or di-substituted by C1-5 alkyl or phenyl; halogen, hydroxy, oxo, carboxy and cyano, $R_f$ is unsubstituted or substituted by one or more $R_g$;

$R_g$ is selected from the group consisting of C1-3 alkyl, phenyl unsubstituted or substituted by halogen or methyl; C1-3 alkoxy, aryloxy, benzyloxy, C1-3 alkoxycarbonyl, carbamoyl wherein the nitrogen atom is unsubstituted or independently mono or di-substituted by C1-3 alkyl or phenyl; C1-5 alkanoylamino, aroylamino, amino wherein the nitrogen atom is unsubstituted or independently mono or di-substituted by C1-3 alkyl or phenyl; halogen, hydroxy, oxo, carboxy and cyano;

$R_h$ is selected from the group consisting of C1-3 alkyl, phenyl, C1-3 alkoxycarbonyl, benzyloxy and carboxy;

$R_8$ is a heteroaryl ring selected from the group consisting of oxazolyl, thiazolyl, imidazolyl, pyridyl, benzimidazolyl, benzthiazolyl and benzoxazolyl, wherein any of the above $R_8$ can be unsubstituted or substituted by one or more $R_j$;

$R_j$ is selected from the group consisting of methyl, cyclohexyl, phenyl, furanyl, thienyl, benzyl, methoxy, phenoxy, benzyloxy, methoxycarbonyl, acetyloxy, benzoyloxy, carbamoyl wherein the nitrogen atom is unsubstituted or independently mono or di-substituted by methyl, phenyl, furanyl or thienyl; acetylamino, benzoylamino, ureido wherein either nitrogen atom is unsubstituted or independently substituted by methyl or phenyl; methoxycarbonylamino, C1-3 alkylsulfonylamino, arylsulfonylamino, amino wherein the nitrogen atom is unsubstituted or independently mono or di-substituted by methyl, phenyl, furanyl or thienyl; halogen, hydroxy, carboxy and cyano, $R_j$ is unsubstituted or substituted by one or more $R_k$;

$R_k$ is selected from the group consisting of methyl, phenyl, furanyl, thienyl, methoxy, phenoxy, benzyloxy, methoxycarbonyl, acetyloxy, benzoyloxy, carbamoyl wherein the nitrogen atom is unsubstituted or independently mono or di-substituted by methyl or phenyl; acetylamino, benzoylamino, ureido wherein either nitrogen atom is unsubstituted or independently substituted by methyl or phenyl; benzyloxycarbonylamino, benzyloxycarbonylaminoC1-3alkyl, amino wherein the nitrogen atom is unsubstituted or independently mono or di-substituted by C1-3alkyl, phenyl, furanyl or thienyl; halogen, hydroxy, carboxy, cyano and nitro.

8. The compound according to claim 7 wherein:

A is —C(O)— or —SO$_2$—;

$R_3$ is C1–5 alkyl or C5–6 cycloalkyl, wherein $R_3$ is unsubstituted or substituted by one or more $R_d$;

$R_d$ is selected from the group consisting of methyl, C3–6 cycloalkyl, phenyl, thienyl, imidazolyl, pyridinyl, indolyl, C1–4 alkoxy, C1–5 alkanoylamino, methylthio, wherein the sulfur atom is unoxidized or oxidized to a sulfoxide or sulfone, halogen, hydroxy, oxo, carboxy and cyano, $R_d$ is unsubstituted or substituted by one or more $R_e$;

$R_e$ is selected from the group consisting of methyl, phenyl, benzyl, methoxy, phenoxy, benzyloxy, benzoyl, halogen and hydroxy;

$R_f$ is selected from the group consisting of C3–6 cycloalkyl, phenyl, naphthyl, thienyl, imidazolyl, pyridinyl, indolyl, methoxy, benzyloxy, C1–3 alkanoylamino, methylthio wherein the sulfur atom is unoxidized or oxidized to a sulfoxide or sulfone, benzylthio wherein the sulfur atom is unoxidized or oxidized to a sulfoxide or sulfone, methoxycarbonylamino, amino wherein the nitrogen atom is unsubstituted or independently mono or di-substituted by C1–3 alkyl; halogen, hydroxy, carboxy and cyano, $R_f$ is unsubstituted or substituted by one or more $R_g$;

$R_g$ is selected from the group consisting of methyl, phenyl unsubstituted or substituted by halogen or methyl; methoxy, phenoxy, benzyloxy, methoxycarbonyl, amino wherein the nitrogen atom is unsubstituted or independently mono or di-substituted by C1–3 alkyl or phenyl; halogen, hydroxy and carboxy;

$R_g$ is a heteroaryl ring selected from the group consisting of oxazolyl, thiazolyl, imidazolyl, pyridyl, benzthiazolyl and benzoxazolyl, wherein any of the above $R_8$ can be unsubstituted or substituted by one or more $R_j$;

$R_j$ is selected from the group consisting of methyl, phenyl, furanyl, thienyl, benzyl, methoxy, methoxycarbonyl, acetyloxy, benzoyloxy, carbamoyl wherein the nitrogen atom is unsubstituted or independently mono or di-substituted by methyl or phenyl; acetylamino, benzoylamino, ureido wherein either nitrogen atom is unsubstituted or independently substituted by methyl or phenyl; methoxycarbonylamino, amino wherein the nitrogen atom is unsubstituted or independently mono or di-substituted by methyl or phenyl; halogen, hydroxy, carboxy and cyano, $R_j$ is unsubstituted or substituted by one or more $R_k$;

$R_k$ is selected from the group consisting of methyl, phenyl, methoxy, phenoxy, benzyloxy, methoxycarbonyl, carbamoyl wherein the nitrogen atom is unsubstituted or independently mono or di-substituted by methyl or phenyl; ureido wherein either nitrogen atom is unsubstituted or independently substituted by methyl or phenyl; benzyloxycarbonylamino, benzyloxycarbonylaminoC1–5alkyl, amino wherein the nitrogen atom is unsubstituted or independently mono or di-substituted by C1–3alkyl, phenyl, furanyl or thienyl; halogen, hydroxy, carboxy, cyano and nitro.

9. The compound according to claim 8 wherein:

$R_d$ is selected from the group consisting of methyl, C3–6 cycloalkyl, phenyl, C1–4 alkoxy, C1–3 alkanoylamino, methylthio wherein the sulfur atom is unoxidized or oxidized to a sulfoxide or sulfone, halogen, hydroxy, oxo, carboxy and cyano, $R_d$ is unsubstituted or substituted by one or more $R_e$;

$R_e$ is selected from the group consisting of methyl, phenyl, methoxy, halogen and hydroxy;

$R_5$ is H;

$R_f$ is selected from the group consisting of C5–6 cycloalkyl, phenyl, naphthyl, thienyl, indolyl, methoxy, methylthio wherein the sulfur atom is unoxidized or oxidized to a sulfoxide or sulfone, methoxycarbonylamino, halogen, hydroxy, carboxy and cyano, $R_f$ is unsubstituted or substituted by one or more $R_g$;

$R_g$ is selected from the group consisting of methyl, phenyl unsubstituted or substituted by halogen; methoxy, phenoxy, benzyloxy, methoxycarbonyl, halogen, hydroxy and carboxy;

$R_8$ is a heteroaryl ring selected from the group consisting of oxazolyl, pyridyl, benzthiazolyl and benzoxazolyl, wherein any of the above $R_8$ can be unsubstituted or substituted by one or more $R_j$;

$R_j$ is selected from the group consisting of methyl, phenyl, benzyl, methoxy, methoxycarbonyl, acetyloxy, benzoyloxy, carbamoyl wherein the nitrogen atom is unsubstituted or independently mono or di-substituted by methyl or phenyl; methoxycarbonylamino, halogen, hydroxy and carboxy, $R_j$ is unsubstituted or substituted by one or more $R_k$;

$R_k$ is selected from the group consisting of methyl, phenyl, methoxy, methoxycarbonyl, carbamoyl wherein the nitrogen atom is unsubstituted or independently mono or di-substituted by methyl or phenyl; benzyloxycarbonylamino, amino wherein the nitrogen atom is unsubstituted or independently mono or di-substituted by methyl or phenyl; halogen, hydroxy and carboxy.

10. The compound according to claim 9 wherein:

$R_3$ is C1–5 alkyl wherein $R_3$ is unsubstituted or substituted by one or more $R_d$;

$R_d$ is selected from the group consisting of C3–6 cycloalkyl and phenyl, $R_d$ is unsubstituted or substituted by one or more $R_e$;
  $R_e$ is selected from the group consisting of methyl and halogen;
$R_6$ is C1–5 alkyl unsubstituted or substituted by one or more $R_f$;
  $R_f$ is selected from the group consisting of C5–6 cycloalkyl, phenyl, methylthio wherein the sulfur atom is unoxidized or oxidized to a sulfoxide or sulfone, and halogen, $R_f$ is unsubstituted or substituted by one or more $R_g$;
  $R_g$ is selected from the group consisting of methyl, methoxy, methoxycarbonyl, halogen and hydroxy;
$R_j$ is selected from the group consisting of phenyl, methoxycarbonyl, carbamoyl wherein the nitrogen atom is unsubstituted or independently mono or disubstituted by methyl or phenyl; methoxycarbonylamino and halogen, $R_j$ is unsubstituted or substituted by one or more $R_k$;
  $R_k$ is selected from the group consisting of phenyl, methoxycarbonyl, carbamoyl, benzyloxycarbonylamino and halogen.

11. A compound of formula (Ia):

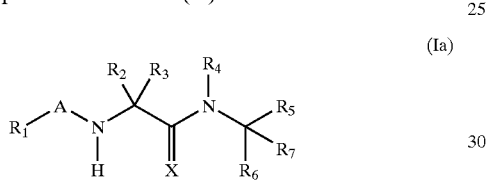

wherein:
A is —C(Y)— or —SO$_2$—
  Y is O, S or NR$_4$ wherein R$_4$ is selected from the group consisting of H, alkyl, aryl, alkoxy, aryloxy, alkylamino and arylamino;
$R_1$ is piperidinyl;
$R_2$ is H or alkyl;
$R_3$ is H, alkyl, cycloalkyl, aryl, heterocyclyl or heteroaryl, wherein $R_3$ is unsubstituted or substituted by one or more groups of the formula $R_d$;
  $R_d$ is selected from the group consisting of alkyl, cycloalkyl, aryl, heterocyclyl, heteroaryl, alkoxy, aryloxy, arylakoxy, alkoxycarbonyl, aryloxycarbonyl, alkanoyl, aroyl, alkanoyloxy, aroyloxy, carbamoyl wherein the nitrogen atom is unsubstituted or independently mono or di-substituted by alkyl, aryl, heterocyclyl or heteroaryl, alkanoylamino, aroylmaino, alkylthio wherein the sulfur atom is unoxidized or oxidized to a sulfoxide or sulfone, arylthio wherein the sulfur atom is unoxidized or oxidized to a sulfoxide or sulfone, ureido wherein either nitrogen atom is unsubstituted or independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom is unsubstituted or independently mono or di-substituted by alkyl, aryl, heterocyclyl or heteroaryl, halogen, hydroxy, oxo, carboxy, cyano, nitro, amidino and guanidino, $R_d$ is unsubstituted or substituted by one or more $R_e$;
  $R_e$ is selected from the group consisting of alkyl, cycloalkyl, aryl, arylalkyl, alkoxy, aryloxy, arylalkoxy, alkanoyl, aroyl, amino, halogen, hydroxy, oxo, carboxy, cyano, nitro, amidino and guanidino;
$R_4$ is H or alkyl;
$R_5$ is H, alkyl or cycloalkyl;
$R_6$ is H, alkyl, cycloalkyl, aryl, heterocyclyl or heteroaryl, wherein $R_6$ is unsubstituted or substituted by one or more groups of the formula $R_f$;
  $R_f$ is selected from the group consisting of alkyl, cycloalkyl, aryl, heterocyclyl, heteroaryl, alkoxy, aryloxy, alkanoyl, aroyl, arylakoxy, heteroarylalkoxy, alkoxycarbonyl, aryloxycarbonyl, alkanoyloxy, aroyloxy, carbamoyl wherein the nitrogen atom is unsubstituted or independently mono or di-substituted by alkyl, aryl, heterocyclyl or heteroaryl, alkanoylamino, aroylamino, alkylthio wherein the sulfur atom is unoxidized or oxidized to a sulfoxide or sulfone, arylthio wherein the sulfur atom is unoxidized or oxidized to a sulfoxide or sulfone, arylaklylthio wherein the sulfur atom is unoxidized or oxidized to a sulfoxide or sulfone, ureido wherein either nitrogen atom is unsubstituted or independently substituted by alkyl, aryl, heterocyclyl or heteroaryl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom is unsubstituted or independently mono or di-substituted by alkyl, aryl heterocyclyl or heteroaryl, halogen, hydroxy, oxo, carboxy, cyano, nitro, amidino and guanidino, $R_f$ is unsubstituted or substituted by one or more $R_g$;
  $R_g$ is selected from the group consisting of alkyl, cycloalkyl, aryl unsubstituted or substituted by halogen, C1–5alkyl or C1–5alkoxy, heterocyclyl, heteroaryl, alkoxy, aryloxy, arylalkoxy, alkoxycarbonyl, aryloxycarbonyl, alkanoyloxy, aroyloxy, carbamoyl wherein the nitrogen atom is unsubstituted or independently mono or di-substituted by alkyl, aryl, heterocyclyl or heteroaryl; alkanoylamino, aroylamino, alkylthio wherein the sulfur atom is unoxidized or oxidized to a sulfoxide or sulfone, arylthio wherein the sulfur atom is unoxidized or oxidized to a sulfoxide or sulfone, ureido wherein either nitrogen atom is unsubstituted or independently substituted by alkyl, aryl, heterocyclyl or heteroaryl; alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom is unsubstituted or independently mono or di-substituted by alkyl, aryl, heterocyclyl or heteroaryl; halogen, hydroxy, oxo, carboxy, cyano, nitro, amidino and guanidino;
or $R_5$ together with $R_6$ form a 3 to 6 membered carbocyclic ring, the carbocyclic ring being unsubstituted or substituted with one or more $R_h$;
  $R_h$ is selected from the group consisting of alkyl, aryl, alkoxycarbonyl, aryloxycarbonyl, arylalkoxycarbonyl, carbamoyl wherein the nitrogen atom is unsubstituted or mono or di-substituted by alkyl, cycloalkyl, aryl, arylalkyl, heterocyclyl or heteroaryl; halogen, hydroxy, carboxy and cyano;
$R_7$ is $R_8$—C(Z)—;
  wherein Z is O, S, or NR$_i$ wherein R$_i$ is selected from the group consisting of H, alkyl, aryl, alkoxy, aryloxy and hydroxy;

$R_8$ is a heteroaryl ring selected from the group consisting of furanyl, thienyl, pyrrolyl, oxazolyl, thiazolyl, imidazolyl, pyrazolyl, isoxazolyl, isothiazolyl, pyridyl, pyridazinyl, pyrimidinyl, pyrazinyl, triazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl and phenazinyl, wherein any of the above $R_8$ can be unsubstituted or substituted by one or more $R_j$;

$R_j$ is selected from the group consisting of C1–8alkyl, C3–7cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxazolinyl, carbazolyl, phenothiazinyl and phenoxazinyl; arylC1–8alkyl, C1–8alkoxy, aryloxy, arylC1–8alkoxy, C1–8alkoxycarbonyl, aryloxycarbonyl, C1–8alkanoyloxy, aroyloxy, carbamoyl wherein the nitrogen atom is unsubstituted or independently mono or di-substituted by C1–8alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8alkanoylamino, aroylamino, C1–8alkylthio wherein the sulfur atom is unoxidized or oxidized to a sulfoxide or sulfone, arylthio wherein the sulfur atom is unoxidized or oxidized to a sulfoxide or sulfone, arylC1–8alkylthio wherein the sulfur atom is unoxidized or oxidized to a sulfoxide or sulfone, ureido wherein either nitrogen atom is unsubstituted or independently substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, C1–8 alkylcarbamoyloxy, arylcarbamoyloxy, alkylsulfonylamino, arylsulfonylamino, alkylaminosulfonyl, arylaminosulfonyl, amino wherein the nitrogen atom is unsubstituted or independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidine $R_j$ is unsubstituted or substituted by one or more $R_k$;

$R_k$ is selected from the group consisting of C1–8 alkyl, C3–7 cycloalkyl, aryl, heterocyclyl selected from the group consisting of pyrrolidinyl, piperidinyl, morpholinyl, thiomorpholinyl, piperazinyl and indolinyl, heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxazolinyl, carbazolyl, phenothiazinyl and phenoxazinyl, C1–8 alkoxy, aryloxy, arylC1–8alkoxy, C1–8alkoxycarbonyl, aryloxycarbonyl, C1–8alkanoyloxy, aroyloxy, carbamoyl wherein the nitrogen atom is unsubstituted or independently mono or di-substituted by C1–8alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkanoylamino, aroylamino, C1–8alkylthio wherein the sulfur atom is unoxidized or oxidized to a sulfoxide or sulfone, arylthio wherein the sulfur atom is unoxidized or oxidized to a sulfoxide or sulfone, ureido wherein either nitrogen atom is unsubstituted or independently substituted by C1–8alkyl, aryl, heterocyclyl selected from the group consisting of pyrrolidinyl, piperidinyl, morpholinyl, thiomorpholinyl, piperazinyl and indolinylor heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8alkoxycarbonylamino, aryloxycarbonylamino, arylC1–8alkoxycarbonylamino, arylalkoxycarbonylaminoC1–8alkyl, C1–8alkylcarbamoyloxy, arylcarbamoyloxy, C1–8alkylsulfonylamino, arylsulfonylamino, C1–8alkylaminosulfonyl, arylaminosulfonyl, amino wherein the nitrogen atom is unsubstituted or independently mono or di-substituted by C1–8alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidine; and X is O;

or the pharmaceutically acceptable salts, esters, tautomers, individual isomers and mixtures of isomers thereof;

with the following provisos;

when $R_6$ is alkyl the alkyl must be substituted with $R_f$ wherein $R_f$ is not hydroxy, sulfhydryl or halogen.

12. The compound according to claim 11 wherein:

$R_a$ is selected from the group consisting of H, alkyl and aryl;

$R_3$ is H, C1–8 alkyl, C3–7 cycloalkyl or aryl wherein $R_3$ is unsubstituted or substituted by one or more $R_d$;

$R_d$ is selected from the group consisting of C1–8 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkoxy, aryloxy, alkanoyl, aroyl, C1–8 alkoxycarbonyl, aryloxycarbonyl, C1–8 alkanoyloxy, aroyloxy, carbamoyl wherein the nitrogen atom is unsubstituted or independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom is unoxidized or oxidized to a sulfoxide or sulfone, arylthio wherein the sulfur atom is unoxidized or oxidized to a sulfoxide or sulfone, ureido wherein either nitrogen atom is unsubstituted or independently substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, C1–8 alkylcarbamoyloxy, arylcarbamoyloxy, alkylsulfonylamino, arylsulfonylamino, alkylaminosulfonyl, arylaminosulfonyl, amino wherein the nitrogen atom is unsubstituted or independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_d$ is unsubstituted or substituted by one or more $R_e$;

$R_e$ is selected from the group consisting of C1–8 alkyl, C3–6 cycloalkyl, aryl, arylalkyl, C1–8 alkoxy, aryloxy, arylalkoxy, aroyl, amino, halogen, hydroxy, oxo, carboxy, cyano, nitro, amidino and guanidino;

$R_5$ is H or alkyl;

$R_6$ is H, C1–8 alkyl, C3–7 cycloalkyl or aryl wherein $R_6$ is unsubstituted or substituted by one or more $R_f$;

$R_f$ is selected from the group consisting of C1–8 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkoxy, aryloxy, arylC1–8alkoxy, heteroarylC1–8alkoxy, C1–8 alkoxycarbonyl, aryloxycarbonyl, C1–8 alkanoyloxy, aroyloxy, carbamoyl wherein the nitrogen atom is unsubstituted or independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom is unoxidized or oxidized to a sulfoxide or sulfone, arylthio wherein the sulfur atom is unoxidized or oxidized to a sulfoxide or sulfone, arylC1–8 alkylthio wherein the sulfur atom is unoxidized or oxidized to a sulfoxide or sulfone, ureido wherein either nitrogen atom is unsubstituted or independently substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, C1–8 alkylcarbamoyloxy, arylcarbamoyloxy, alkylsulfonylamino, arylsulfonylamino, alkylaminosulfonyl arylaminosulfonyl, amino wherein the nitrogen atom is unsubstituted or independently mono or di-substituted by alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, triazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino, $R_f$ is unsubstituted or substituted by one or more $R_g$;

$R_g$ is selected from the group consisting of C1–8 alkyl, C3–7 cycloalkyl, aryl unsubstituted or substituted by halogen, C1–3alkyl or C1–3alkoxy; heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkoxy, aryloxy, arylC1–8alkoxy, C1–8 alkoxycarbonyl, aryloxycarbonyl, C1–8 alkanoyloxy, aroyloxy, carbamoyl wherein the nitrogen atom is unsubstituted or independently mono or di-substituted by C1–8 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, C1–8 alkanoylamino, aroylamino, C1–8 alkylthio wherein the sulfur atom is unoxidized or oxidized to a sulfoxide or sulfone, alkylthio wherein the sulfur atom is unoxidized or oxidized to a sulfoxide or sulfone, ureido wherein either nitrogen atom is unsubstituted or independently substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, alkoxycarbonylamino, aryloxycarbonylamino, C1–8 alkylcarbamoyloxy, arylcarbamoyloxy, alkylsulfonylamino, arylsulfonylamino, alkylaminosulfonyl and arylaminosulfonyl, amino wherein the nitrogen atom is unsubstituted or independently mono or di-substituted by alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, oxo, carboxy, cyano, nitro, amidino and guanidino;

$R_h$ is selected from the group consisting of C1–8 alkyl, aryl, C1–8 alkoxycarbonyl, aryloxycarbonyl, arylC1–8alkoxycarbonyl, carbamoyl wherein the nitrogen atom is unsubstituted or mono or di-substituted by C1–8 alkyl, C3–7 cycloalkyl, aryl, arylC1–8alkyl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, isoxazolyl, isothiazolyl, oxadiazolyl, triazolyl, tetrazolyl, thiadiazolyl, pyridinyl, pyridazinyl, pyrimidinyl, pyrazinyl, indolyl, isoindolyl, benzofuranyl, benzothienyl, benzimidazolyl, benzthiazolyl, benzoxazolyl, purinyl, quinolinyl, isoquinolinyl, quinazolinyl, quinoxalinyl, carbazolyl, phenothiazinyl and phenoxazinyl, halogen, hydroxy, carboxy and cyano.

13. The compound according to claim 12 wherein:
Y is O or S;
$R_2$ is H or C1–3 alkyl;
$R_3$ is H, C1–5 alkyl, C3–7 cycloalkyl or aryl, wherein $R_3$ is unsubstituted or substituted by one or more $R_d$;
$R_d$ is selected from the group consisting of C1–5 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxy, aryloxy, C1–5alkanoyl, aroyl, C1–5 alkoxycarbonyl, aryloxycarbonyl, C1–5 alkanoyloxy, aroyloxy, carbamoyl wherein the nitrogen atom is unsubstituted or independently mono or di-substituted by C1–5 alkyl, aryl, heterocyclyl selected from the group consisting of pyrrolidinyl, piperidinyl, morpholinyl, thiomorpholinyl, piperazinyl and indolinylor heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkanoylamino, aroylamino, C1–5 alkylthio wherein the sulfur atom is unoxidized or oxidized to a sulfoxide or sulfone, arylthio wherein the sulfur atom is unoxidized or oxidized to a sulfoxide or sulfone, ureido wherein either nitrogen atom is unsubstituted or independently substituted by C1–5 alkyl, aryl, heterocyclyl selected from the group consisting of pyrrolidinyl, piperidinyl, morpholinyl, thiomorpholinyl, piperazinyl and indolinyl or heteroaryl selected the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom is unsubstituted or independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, halogen, hydroxy, oxo, carboxy, cyano, nitro, amidino and guanidino, $R_4$ is unsubstituted or substituted by one or more $R_e$;

$R_e$ is selected from the group consisting of C1–5 alkyl, C3–6 cycloalkyl, aryl, arylalkyl, C1–5 alkoxy, aryloxy, arylC1–5alkoxy, aroyl, amino, halogen, hydroxy, oxo, carboxy, cyano, nitro, amidino and guanidino;

$R_4$ is H or C1–3 alkyl;

$R_5$ is H or C1–8 alkyl;

$R_6$ is H, C1–5 alkyl, C3–7 cycloalkyl or aryl wherein $R_6$ is unsubstituted or substituted by one or more $R_f$;

$R_f$ is selected from the group consisting of C1–5 alkyl, C3–7 cycloalkyl, aryl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxy, aryloxy, arylC1–5alkoxy, heteroarylC1–5alkoxy, C1–5 alkoxycarbonyl, aryloxycarbonyl, C1–5 alkanoyloxy, aroyloxy, carbamoyl wherein the nitrogen atom is unsubstituted or independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkanoylamino, aroylamino, C1–5 alkylthio wherein the sulfur atom is unoxidized or oxidized to a sulfoxide or sulfone, arylthio wherein the sulfur atom is unoxidized or oxidized to a sulfoxide or sulfone, arylC1–5 alkylthio wherein the sulfur atom is unoxidized or oxidized to a sulfoxide or sulfone, ureido wherein either nitrogen atom is unsubstituted or independently substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom is unsubstituted or independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, halogen, hydroxy, oxo, carboxy, cyano, nitro, amidino and guanidino, $R_f$ is unsubstituted or substituted by one or more $R_g$;

$R_g$ is selected from the group consisting of C1–5 alkyl, C3–7 cycloalkyl, aryl unsubstituted or substituted by halogen, methyl or methoxy; heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxy, aryloxy, arylC1–5alkoxy, C1–5 alkoxycarbonyl, aryloxycarbonyl, C1–5 alkanoyloxy, aroyloxy, carbamoyl wherein the nitrogen atom is unsubstituted or independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkanoylamino, aroylamino, C1–5 alkylthio wherein the sulfur atom is unoxidized or oxidized to a sulfoxide or sulfone, arylthio wherein the sulfur atom is unoxidized or oxidized to a sulfoxide or sulfone, ureido wherein either nitrogen atom is unsubstituted or independently substituted by C1–5 alkyl, aryl, heterocyclyl selected from the group consisting of pyrrolidinyl, piperidinyl, morpholinyl, thiomorpholinyl, piperazinyl and indolinyl, or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom is unsubstituted or independently mono or di-substituted by C1–5 alkyl, aryl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, halogen, hydroxy, oxo, carboxy, cyano, nitro, amidino and guanidino;

$R_h$ is selected from the group consisting of C1–5 alkyl, aryl, C1–5 alkoxycarbonyl, aryloxycarbonyl, arylC1–5alkoxycarbonyl, carbamoyl wherein the nitrogen atom is unsubstituted or mono or di-substituted with a group selected from C1–5 alkyl, C3–7 cycloalkyl, aryl, arylC1–5alkyl, heterocyclyl selected from the group consisting of pyrrolidinyl, piperidinyl, morpholinyl, thiomorpholinyl, piperazinyl and indolinyl or heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, halogen, hydroxy, carboxy and cyano;

$R_i$ is alkoxy, aryloxy or hydroxy.

14. The compound according to claim 13 wherein:

Y is O;

$R_2$ is H or methyl;

$R_3$ is H, C1–5 alkyl, C3–7 cycloalkyl or phenyl, wherein $R_3$ is unsubstituted or substituted by one or more $R_d$;

$R_d$ is selected from the group consisting of C1–3 alkyl, C3–6 cycloalkyl, phenyl, naphthyl, heterocyclyl selected from the group consisting of piperidinyl, morpholinyl and piperazinyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1–5 alkoxy, aryloxy, aroyl, C1–5 alkoxycarbonyl, aryloxycarbonyl, C1–5 alkanoyloxy, aroyloxy, carbamoyl wherein the nitrogen atom is unsubstituted or independently mono or di-substituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1–5 alkanoylamino, aroylamino, C1–5 alkylthio wherein the sulfur atom is unoxidized or oxidized to a sulfoxide or sulfone, arylthio wherein the sulfur atom is unoxidized or oxidized to a sulfoxide or sulfone, ureido wherein either nitrogen atom is unsubstituted or independently substituted by C1–5 alkyl, phenyl, naphthyl, heterocyclyl selected from the group consisting of piperidinyl, morpholinyl and piperazinyl or heteroaryl selected the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom is unsubstituted or independently mono or di-substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, halogen, hydroxy, oxo, carboxy and cyano, $R_d$ is unsubstituted or substituted by one or more $R_e$;

$R_e$ is selected from the group consisting of C1–5 alkyl, C3–6 cycloalkyl, aryl, arylC1–5alkyl, C1–5 alkoxy, aryloxy, arylC1–3 alkoxy, aroyl, amino, halogen, hydroxy, oxo, carboxy and cyano;

$R_4$ is H or methyl;

$R_5$ is H or C1–5 alkyl;

$R_6$ is H, C1–5 alkyl, C3–7 cycloalkyl, phenyl or naphthyl wherein $R_6$ is unsubstituted or substituted by one or more $R_f$;

$R_f$ is selected from the group consisting of C1–5 alkyl, C3–7 cycloalkyl, phenyl, naphthyl, heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxy, aryloxy, arylC1–5alkoxy, pyridylC1–5alkoxy, thienylC1–5alkoxy, furanylC1–5alkoxy, C1–5 alkoxycarbonyl, aryloxycarbonyl, C1–5 alkanoyloxy, aroyloxy, carbamoyl wherein the nitrogen atom is unsubstituted or independently mono or di-substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1–5 alkanoylamino, aroylamino, C1–5 alkylthio wherein the sulfur atom is unoxidized or oxidized to a sulfoxide or sulfone, arylthio wherein the sulfur atom is unoxidized or oxidized to a sulfoxide or sulfone, arylC1–5 alkylthio wherein the sulfur atom is unoxidized or oxidized to a sulfoxide or sulfone, ureido wherein either nitrogen atom is unsubstituted or independently substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom is unsubstituted or independently mono or di-substituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, halogen, hydroxy, oxo, carboxy and cyano, Rf is unsubstituted or substituted by one or more $R_g$;

$R_g$ is selected from the group consisting of C1–5 alkyl, C3–7 cycloalkyl, phenyl unsubstituted or substituted by halogen, methyl or methoxy; naphthyl unsubstituted or substituted by halogen, methyl or methoxy; heterocyclyl selected from the group consisting of pyrrolidinyl, piperidinyl, morpholinyl, thiomorpholinyl, piperazinyl and indolinyl; heteroaryl selected from the group consisting of furanyl, thienyl, pyrrolyl, oxazolyl, thiazolyl, imidazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, C1–5 alkoxy, aryloxy, arylC1–5alkoxy, C1–5 alkoxycarbonyl, aryloxycarbonyl, C1–5 alkanoyloxy, aroyloxy, carbamoyl wherein the nitrogen atom is unsubstituted or independently mono or di-substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1–5 alkanoylamino, aroylamino, C1–5 alkylthio wherein the sulfur atom is unoxidized or oxidized to a sulfoxide or sulfone, arylthio wherein the sulfur atom is unoxidized or oxidized to a sulfoxide or sulfone, ureido wherein either nitrogen atom is unsubstituted or independently substituted by C1–5 alkyl, aryl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom is unsubstituted or independently mono or di-substituted by C1–5 alkyl, aryl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, halogen, hydroxy, oxo, carboxy and cyano;

$R_h$ is selected from the group consisting of C1–5 alkyl, phenyl, naphthyl, C1–5 alkoxycarbonyl, aryloxycarbonyl, arylC1–3alkoxycarbonyl, carbamoyl wherein the nitrogen atom is unsubstituted or mono or di-substituted by C1–5 alkyl, C3–6 cycloalkyl, phenyl, naphthyl, arylC1–3alkyl, heterocyclyl selected from the group consisting of pyrrolidinyl, piperidinyl, morpholinyl and piperazinyl or heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, halogen, hydroxy, carboxy and cyano;

Z is O or S;

$R_j$ is selected from the group consisting of C1–5alkyl, C3–6cycloalkyl, phenyl, naphthyl, heterocyclyl selected from the group consisting of pyrrolidinyl, piperidinyl, morpholinyl and piperazinyl; heteroaryl selected from the group consisting of furanyl, thienyl, pyrrolyl, oxazolyl, thiazolyl, imidazolyl, pyridinyl, pyridazinyl, pyrimidinyl, pyrazinyl, indolyl, benzofuranyl, benzothienyl, benzimidazolyl, benzthiazolyl, benzoxazolyl, quinolinyl and isoquinolinyl, arylC1–5alkyl, C1–5alkoxy, aryloxy, arylC1–5alkoxy, C1–5alkoxycarbonyl, aryloxycarbonyl, C1–5alkanoyloxy, aroyloxy, carbamoyl wherein the nitrogen atom is unsubstituted or independently mono or di-substituted by C1–5alkyl, aryl, heterocyclyl selected from the group consisting of piperidinyl, morpholinyl and piperazinyl, heteroaryl selected from furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl and isoquinolinyl, C1–5alkanoylamino, aroylamino, C1–5alkylthio wherein the sulfur atom is unoxidized or oxidized to a sulfoxide or sulfone, arylthio wherein the sulfur atom is unoxidized or oxidized to a sulfoxide or sulfone, arylC1–5alkylthio wherein the sulfur atom is unoxidized or oxidized to a sulfoxide or sulfone, ureido wherein either nitrogen atom is unsubstituted or independently substituted by C1–5 alkyl, aryl, heterocyclyl selected from the group consisting of piperidinyl, morpholinyl and piperazinyl; heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl and isoquinolinyl, C1–5alkoxycarbonylamino, aryloxycarbonylamino, C1–5 alkylcarbamoyloxy, arylcarbamoyloxy, C1–5alkylsulfonylamino, arylsulfonylamino, C1–5alkylaminosulfonyl, arylaminosulfonyl, amino wherein the nitrogen atom is unsubstituted or independently mono or di-substituted by C1–5 alkyl, aryl, heterocyclyl selected from the group consisting of piperidinyl, morpholinyl and piperazinyl; heteroaryl selected from the group consisting of furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, purinyl, quinolinyl and isoquinolinyl, halogen, hydroxy, oxo, carboxy, cyano, nitro, amidino and guanidino, wherein $R_j$ is unsubstituted or substituted by one or more $R_k$;

$R_k$ is selected from the group consisting of C1–3 cycloalkyl, phenyl, naphthyl, heterocyclyl selected from the group consisting of pyrrolidinyl, piperidinyl, morpholinyl and piperazinyl; heteroaryl selected from the group consisting of furanyl, thienyl, pyrrolyl, tetrazolyl, pyridinyl, pyridazinyl, pyrimidinyl and pyrazinyl, C1–3 alkoxy, aryloxy, arylC1–3alkoxy, C1–3 alkoxycarbonyl, aryloxycarbonyl, C1–3alkanoyloxy, aroyloxy, carbamoyl wherein the nitrogen atom is unsubstituted or independently mono or di-substituted by C1–3 alkyl, aryl, heterocyclyl selected from the group consisting of morpholinyl and piperazinyl; heteroaryl selected from the group consisting of furanyl, thienyl, pyrrolyl, oxazolyl, thiazolyl, imidazolyl, tetrazolyl and pyridinyl, C1–3alkanoylamino, aroylamino, C1–3alkylthio wherein the sulfur atom is unoxidized or oxidized to a sulfoxide or sulfone, arylthio wherein the sulfur atom is unoxidized or oxidized to a sulfoxide or sulfone, which wherein either nitrogen atom is unsubstituted or independently substituted by C1–3alkyl, phenyl, naphthyl, heteroaryl selected from the group of furanyl, thienyl, pyrrolyl, oxazolyl, thiazolyl, imidazolyl, tetrazolyl and pyridinyl, C1–3alkoxycarbonylamino, aryloxycarbonylamino, arylC1–3alkoxycarbonylamino, benzyloxycarbonylaminoC1–5alkyl, C1–3 alkylcarbamoyloxy, arylcarbamoyloxy, C1–3alkylsulfonylamino, arylsulfonylamino, C1–3alkylaminosulfonyl, arylaminosulfonyl, amino wherein the nitrogen atom is unsubstituted or independently mono or di-substituted by C1–3alkyl, aryl, heterocyclyl selected from the group consisting of pyrrolidinyl, piperidinyl, morpholinyl and piperazinyl; heteroaryl selected from the group consisting of furanyl, thienyl, pyrrolyl, oxazolyl, thiazolyl, imidazolyl, tetrazolyl, pyridinyl, pyridazinyl, pyrimidinyl, pyrazinyl, indolyl, benzofuranyl, benzothienyl, benzimidazolyl, benzthiazolyl, benzoxazolyl, quinolinyl and isoquinolinyl, halogen, hydroxy, oxo, carboxy, cyano and nitro.

15. The compound according to claim 14 wherein:

$R_2$ is H;

$R_3$ is C1–5 alkyl, C3–6 cycloalkyl or phenyl, wherein $R_3$ is unsubstituted or substituted by one or more $R_d$;

$R_d$ is selected from the group consisting of C1–3 alkyl, C3–6 cycloalkyl, phenyl, naphthyl, heterocyclyl selected from the group consisting of piperidinyl, morpholinyl and piperazinyl; heteroaryl selected from the group consisting of furanyl, thienyl, thiazolyl, imidazolyl, pyridinyl, indolyl, quinolinyl and isoquinolinyl, C1–5 alkoxy, phenoxy, aroyl, C1–5 alkoxycarbonyl, aryloxycarbonyl, C1–5 alkanoyloxy, aroyloxy, carbamoyl wherein the nitrogen atom is unsubstituted or independently mono or di-substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, C1–5 alkanoylamino, aroylamino, C1–3 alkylthio wherein the sulfur atom is unoxidized or oxidized to a sulfoxide or sulfone, phenylthio wherein the sulfur atom is unoxidized or oxidized to a sulfoxide or sulfone, ureido wherein either nitrogen atom is unsubstituted or independently substituted by C1–3 alkyl, phenyl or heteroaryl selected the group consisting of furanyl, thienyl, pyrrolyl, oxazolyl, thiazolyl, imidazolyl, pyridinyl and indolyl, C1–5 alkoxycarbonylamino, C1–5 alkylcarbamoyloxy, arylcarbamoyloxy, C1–5 alkylsulfonylamino, arylsulfonylamino, amino wherein the nitrogen atom is unsubstituted or independently mono or di-substituted by C1–3 alkyl, phenyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, halogen, hydroxy, oxo, carboxy and cyano, $R_d$ is unsubstituted or substituted by one or more $R_e$;

$R_e$ is selected from the group consisting of C1–5 alkyl, C5–6 cycloalkyl, phenyl, naphthyl, arylC1–3alkyl, C1–5 alkoxy, phenoxy, arylC1–3alkoxy, aroyl, amino, halogen, hydroxy, oxo, carboxy and cyano;

wherein the configuration at the stereocenter defined by $R_2$ and $R_3$ and the carbon they are attached to is the L enantiomer;

$R_4$ is H;

$R_5$ is H or C1–3 alkyl;

$R_6$ is H, C1.4 alkyl, C3–6 cycloalkyl or phenyl, wherein $R_6$ is unsubstituted or substituted by one or more $R_f$;

$R_f$ is selected from the group consisting of C1–3 alkyl, C3–6 cycloalkyl, phenyl, naphthyl, heterocyclyl selected from the group consisting of pyrrolidinyl, piperidinyl, morpholinyl and piperazinyl; heteroaryl selected from the group consisting of furanyl, thienyl, pyrrolyl, oxazolyl, thiazolyl, imidazolyl, pyridinyl, indolyl, benzofuranyl, benzothienyl, benzimidazolyl, benzthiazolyl, benzoxazolyl, quinolinyl and isoquinolinyl, C1–5 alkoxy, aryloxy, arylC1–3alkoxy, pyridylC1–5alkoxy, thienylC1–5alkoxy, furanylC1–5alkoxy, C1–5 alkoxycarbonyl, aryloxycarbonyl, C1–5 alkanoyloxy, aroyloxy, carbamoyl wherein the nitrogen atom is unsubstituted or independently mono or di-substituted by C1–5 alkyl, phenylor heteroaryl selected from the group consisting of furanyl, thienyl, pyrrolyl, oxazolyl, thiazolyl, imidazolyl, pyridinyl and indolyl, C1–5 alkanoylamino, aroylamino, C1–3 alkylthio wherein the sulfur atom is unoxidized or oxidized to a sulfoxide or sulfone, arylthio wherein the sulfur atom is unoxidized or oxidized to a sulfoxide or sulfone, arylC1–3alkylthio wherein the sulfur atom is unoxidized or oxidized to a sulfoxide or sulfone, ureido wherein either nitrogen atom is unsubstituted or independently substituted by C1–5 alkyl or phenyl; C1–5 alkoxycarbonylamino, C1–5 alkylsulfonylamino, arylsulfonylamino, amino wherein the nitrogen atom is unsubstituted or independently mono or di-substituted by C1–5 alkyl, phenyl, naphthyl, heterocyclyl selected from the group consisting of piperidinyl, morpholinyl and piperazinyl or heteroaryl selected from the group consisting of furanyl, thienyl, pyrrolyl, oxazolyl, thiazolyl, imidazolyl, pyridinyl and indolyl, halogen, hydroxy, oxo, carboxy and cyano, $R_f$ is unsubstituted or substituted by one or more $R_g$;

$R_g$ is selected from the group consisting of C1–3 alkyl, C5–6 cycloalkyl, phenyl unsubstituted or substituted by halogen, methyl or methoxy; heterocyclyl selected from the group consisting of pyrrolidinyl, piperidinyl, morpholinyl and piperazinyl; heteroaryl selected from the group consisting of furanyl, thienyl, pyrrolyl, oxazolyl, thiazolyl, imidazolyl, pyridinyl, pyrimidinyl, pyrazinyl and indolyl, C1–5 alkoxy, aryloxy, arylC1–3alkoxy, C1–5 alkoxycarbonyl, aryloxycarbonyl, C1–5 alkanoyloxy, aroyloxy, carbamoyl wherein the nitrogen atom is unsubstituted or independently mono or di-substituted by C1–5 alkyl or aryl; C1–5 alkanoylamino, aroylamino, C1–5 alkylthio wherein the sulfur atom is unoxidized or oxidized to a sulfoxide or sulfone, arylthio wherein the sulfur atom is unoxidized or oxidized to a sulfoxide or sulfone, ureido wherein either nitrogen atom is unsubstituted or independently substituted by C1–5 alkyl or aryl; C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom is unsubstituted or independently mono or di-substituted by C1–5 alkyl or aryl; halogen, hydroxy, oxo, carboxy and cyano;

$R_h$ is selected from the group consisting of C1–5 alkyl, phenyl, C1–5 alkoxycarbonyl, aryloxycarbonyl, arylC1–3alkoxycarbonyl, carbamoyl wherein the nitrogen atom is unsubstituted or mono or di-substituted with C1–5 alkyl, C3–6 cycloalkyl, phenyl, naphthyl or arylC1–3alkyl, halogen, hydroxy, carboxy and cyano;

Z is O;

$R_g$ is heteroaryl ring selected from the group consisting of oxazolyl, thiazolyl, imidazolyl, pyrazolyl, isoxazolyl, isothiazolyl, pyridyl, pyridazinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl and quinoxalinyl, wherein any of the above $R_g$ can be unsubstituted or substituted by one or more $R_j$;

$R_j$ is selected from the group consisting of C1–5 alkyl, C5–6 alkyl, C5–6 cycloalkyl, phenyl, naphthyl, pyrrolidinyl, piperidinyl, morpholinyl, piperazinyl, furanyl, thienyl, pyrrolyl, tetrazolyl, pyridinyl, pyridazinyl, pyrimidinyl, pyrazinyl, indolyl, benzofuranyl, benzothienyl, benzimidazolyl, benzthiazolyl, benzoxazolyl, arylC1–3alkyl, C1–3alkoxy, aryloxy, arylC1–3alkoxy, C1–3alkoxycarbonyl, aryloxycarbonyl, C1–3alkanoyloxy, aroyloxy, carbamoyl wherein the nitrogen atom is unsubstituted or independently mono or di-substituted by C1–3alkyl, phenyl, naphthyl, piperidinyl, furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl and isoquinolinyl; C1–3alkanoylamino, aroylamino, C1–3alkylthio wherein the sulfur atom is unoxidized or oxidized to a sulfoxide or sulfone, arylthio wherein the sulfur atom is unoxidized or oxidised to a sulfoxide or sulfone, arylC1–3alkylthio wherein the sulfur atom is unoxidized or oxidised to a sulfoxide or sulfone, ureido wherein either nitrogen atom is unsubstituted or independently substituted by C1–3 alkyl, phenyl, naphthyl, piperidinyl, morpholinyl, thiazolyl, imidazolyl, tetrazolyl, pyridinyl, indolyl, benzofuranyl, benzothienyl, benzimidazolyl, benzthiazolyl, benzoxazolyl, quinolinyl and isoquinolinyl; C1–3 alkoxycarbonylamino, aryloxycarbonylamino, C1–3 alkylcarbamoyloxy, arylcarbamoyloxy, C1–3alkylsulfonylamino, arylsulfonylamino, C1–3alkylaminosulfonyl, arylaminosulfonyl, amino wherein the nitrogen atom is unsubstituted or independently mono or di-substituted by C1–3 alkyl, phenyl, naphthyl, piperidinyl, furanyl, thienyl, pyrrolyl, oxazolyl, thiazolyl, imidazolyl, tetrazolyl, pyridinyl, indolyl, benzofuranyl, benzothienyl, benzimidazolyl, benzthiazolyl, benzoxazolyl, quinolinyl and isoquinolinyl; halogen, hydroxy, oxo, carboxy, cyano and nitro, $R_j$ is unsubstituted or substituted by one or more $R_k$;

$R_k$ is selected from the group consisting of methyl, C5–6 cycloalkyl, phenyl, pyrrolidinyl, piperidinyl, morpholinyl, piperazinyl, furanyl, thienyl, pyrrolyl, tetrazolyl, pyridinyl, pyrimidinyl, C1–3 alkoxy, phenoxy, benzyloxy, methoxycarbonyl, acetyloxy, benzoyloxy carbamoyl wherein the nitrogen atom is unsubstituted or independently mono or di-substituted by C1–3 alkyl, phenyl, furanyl, thienyl, pyrrolyl, oxazolyl, thiazolyl, imidazolyl or pyridinyl; acetylamino, benzoylamino, methylthio wherein the sulfur atom is unoxidized or oxidised to a sulfoxide or sulfone, ureido wherein either nitrogen atom is unsubstituted or independently substituted by methyl, phenyl, furanyl, thienyl, pyrrolyl, oxazolyl, thiazolyl, imidazolyl or pyridinyl; arylC1–3alkoxycarbonylamino, benzyloxycarbonylaminoC1–5alkyl, methylcarbamoyloxy, amino wherein the nitrogen atom is unsubstituted or independently mono or di-substituted by C1–3alkyl, phenyl, naphthyl, pyrrolidinyl, piperidinyl, furanyl, thienyl, pyrrolyl, oxazolyl, thiazolyl, imidazolyl, pyridinyl, pyrimidinyl, indolyl, benzofuranyl, benzothienyl, benzimidazolyl, benzthiazolyl, benzoxazolyl, quinolinyl or isoquinolinyl, halogen, hydroxy, oxo, carboxy, cyano and nitro.

16. The compound according to claim 15 wherein:

$R_3$ is C1–5 alkyl, C5–6 cycloalkyl or phenyl wherein $R_3$ is unsubstituted or substituted by one or more $R_d$;

$R_d$ is selected from the group consisting of C1–3 alkyl, C3–6 cycloalkyl, phenyl, naphthyl, 4-piperidinyl, 4-morpholinyl, piperazinyl, furanyl, thienyl, thiazolyl, imidazolyl, pyridinyl, indolyl, C1–5 alkoxy, phenoxy, aroyl, C1–5 alkoxycarbonyl, aryloxycarbonyl, C1–5 alkanoyloxy, aroyloxy, carbamoyl wherein the nitrogen atom is unsubstituted or independently mono or di-substituted by C1–5 alkyl or phenyl; C1–5 alkanoylamino, C1–3 alkylthio wherein the sulfur atom is unoxidized or oxidized to a sulfoxide or sulfone, ureido wherein either nitrogen atom is unsubstituted or independently substituted by C1–3 alkyl or phenyl; C1–5 alkoxycarbonylamino, C1–5 alkylsulfonylamino, arylsulfonylamino, amino wherein the nitrogen atom is unsubstituted or independently mono or di-substituted by C1–3 alkyl or phenyl; halogen, hydroxy, oxo, carboxy and cyano, $R_d$ is unsubstituted or substituted by one or more $R_e$;

$R_e$ is selected from the group consisting of C1–5 alkyl, C5–6 cycloalkyl, phenyl, benzyl, C1–5 alkoxy, phenoxy, benzyloxy, aroyl, halogen, hydroxy, oxo, carboxy and cyano;

$R_6$ is H, C1–5 alkyl or phenyl wherein $R_6$ is unsubstituted or substituted by one or more $R_f$;

$R_f$ is selected from the group consisting of C1–3 alkyl, C3–6 cycloalkyl, phenyl, naphthyl, furanyl, thienyl, thiazolyl, imidazolyl, pyridinyl, indolyl, C1–3 alkoxy, benzyloxy, pyridyl, C1–3alkoxy, thienylC1–3alkoxy, furanylC1–3alkoxy, C1–3 alkoxycarbonyl, phenoxyoxycarbonyl, C1–5 alkanoyloxy, aroyloxy, carbamoyl wherein the nitrogen atom is unsubstituted or independently mono or di-substituted by C1–3 alkyl or phenyl; C1–5 alkanoylamino, aroylamino, methylthio wherein the sulfur atom is unoxidized or oxidized to a sulfoxide or sulfone, benzylthio wherein the sulfur atom is unoxidized or oxidized to a sulfoxide or sulfone, ureido wherein either nitrogen atom is unsubstituted or independently substituted by C1–5 alkyl or phenyl; C1–3 alkoxycarbonylamino, amino wherein the nitrogen atom is unsubstituted or independently mono or di-substituted by C1–5 alkyl or phenyl; halogen, hydroxy, oxo, carboxy and cyano, $R_f$ is unsubstituted or substituted by one or more $R_g$;

$R_g$ is selected from the group consisting of C1–3 alkyl, phenyl unsubstituted or substituted by halogen, methyl or methoxy; heterocyclyl selected from the group consisting of piperidinyl, morpholinyl and piperazinyl; heteroaryl selected from the group consisting of furanyl, thienyl, pyrrolyl and pyridinyl, C1–3 alkoxy, aryloxy, benzyloxy, C1–5 alkoxycarbonyl, C1–5 alkanoyloxy, aroyloxy, carbamoyl wherein the nitrogen atom is unsubstituted or independently mono or di-substituted by C1–5 alkyl or phenyl; C1–5 alkanoylamino, aroylamino, C1–5 alkylthio wherein the sulfur atom is unoxidized or oxidized to a sulfoxide or sulfone, ureido wherein either nitrogen atom is unsubstituted or independently substituted by C1–5 alkyl or phenyl; C1–5 alkoxycarbonylamino, C1–5 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom is unsubstituted or independently mono or di-substituted by C1–3 alkyl or phenyl; halogen, hydroxy, oxo, carboxy and cyano;

$R_h$ is selected from the group consisting of C1–3 alkyl, phenyl, C1–3 alkoxycarbonyl, phenoxyoxycarbonyl, benzyloxy, carbamoyl wherein the nitrogen atom is unsubstituted or mono or di-substituted with C1–5 alkyl, phenyl or benzyl, halogen, hydroxy, carboxy and cyano;

$R_g$ is a heteroaryl ring selected from the group consisting of oxazolyl, thiazolyl, imidazolyl, pyridyl, indolyl, benzofuranyl, benzothienyl, benzimidazolyl, benzthiazolyl, benzoxazolyl, quinolinyl and isoquinolinyl, wherein any of the above $R_g$ can be unsubstituted or substituted by one or more $R_j$;

$R_j$ is selected from the group consisting of C1–5 alkyl, C5–6 cycloalkyl, phenyl, naphthyl, pyrrolidinyl, piperidinyl, morpholinyl, piperazinyl, furanyl, thienyl, pyrrolyl, tetrazolyl, pyridinyl, pyrimidinyl, benzyl, C1–3alkoxy, phenoxy, benzyloxy, C1–3alkoxycarbonyl, acetyloxy, benzoyloxy, carbamoyl wherein the nitrogen atom is unsubstituted or independently mono or di-substituted by methyl, phenyl, furanyl, thienyl, pyrrolyl, oxazolyl, thiazolyl, imidazolyl or pyridinyl; acetylamino, benzoylamino, methylthio wherein the sulfur atom is unoxidized or oxidised to a sulfoxide or sulfone, benzylthio wherein the sulfur atom is unoxidized or oxidised to a sulfoxide or sulfone, ureido wherein either nitrogen atom is unsubstituted or independently substituted by methyl, phenyl, thiazolyl, imidazolyl or pyridinyl; C1–3 alkoxycarbonylamino, C1–3 alkylcarbamoyloxy, arylcarbamoyloxy, C1–3alkylsulfonylamino, arylsulfonylamino, amino wherein the nitrogen atom is unsubstituted or independently mono or di-substituted by methyl, phenyl, furanyl, thienyl, pyrrolyl, oxazolyl, thiazolyl, imidazolyl or pyridinyl; halogen, hydroxy, carboxy, cyano and nitro, $R_j$ is unsubstituted or substituted by one or more $R_k$;

$R_k$ is selected from the group consisting of methyl, C5–6 cycloalkyl, phenyl, pyrrolidinyl, piperidinyl, morpholinyl, piperazinyl, furanyl, thienyl, pyrrolyl, pyridinyl, C1–3 alkoxy, phenoxy, benzyloxy, methoxycarbonyl, acetyloxy, benzoyloxy, carbamoyl wherein the nitrogen atom is unsubstituted or independently mono or di-substituted by methyl, phenyl, furanyl, thienyl; acetylamino, benzoylamino, methylthio wherein the sulfur atom is unoxidized or oxidised to a sulfoxide or sulfone, ureido wherein either nitrogen atom is unsubstituted or independently substituted by methyl, phenyl, furanyl, thienyl, pyrrolyl, oxazolyl and thiazolyl, benzyloxycarbonylamino, benzyloxycarbonylaminoC1–5alkyl, amino wherein the nitrogen atom is unsubstituted or independently mono or di-substituted by C1–3alkyl, phenyl, furanyl, thienyl, pyrrolyl, oxazolyl, thiazolyl, imidazolyl and pyridinyl, halogen, hydroxy, carboxy, cyano and nitro.

17. The compound according to claim 16 wherein:

$R_d$ is selected from the group consisting of C1–3 alkyl, C3–6 cycloalkyl, phenyl, naphthyl, 4-piperidinyl, furanyl, thienyl, thiazolyl, imidazolyl, pyridinyl, indolyl, C1–3alkoxy, C1–5alkoxycarbonyl, C1–5alkanoyloxy, benzoyloxy, carbamoyl wherein the nitrogen atom is unsubstituted or independently mono or di-substituted by C1–3alkyl or phenyl; C1–5alkanoylamino, C1–3 alkylthio wherein the sulfur atom is unoxidized or oxidized to a sulfoxide or sulfone, C1–3alkoxycarbonylamino, C1–3alkylsulfonylamino, amino wherein the nitrogen atom is unsubstituted or independently mono or di-substituted by C1–3 alkyl or phenyl, halogen, hydroxy, oxo, carboxy and cyano, $R_d$ is unsubstituted or substituted by one or more $R_e$;

$R_e$ is selected from the group consisting of C1–3 alkyl, phenyl, benzyl, C1–3 alkoxy, phenoxy, benzyloxy, benzoyl, halogen, hydroxy, oxo, carboxy and cyano;

$R_5$ is H or methyl;

$R_6$ is C1–5 alkyl or phenyl, wherein $R_6$ is unsubstituted or substituted by one or more groups of the formula $R_f$, $R_f$ is selected from the group consisting of methyl, C3–6 cycloalkyl, phenyl, naphthyl, furanyl, thienyl, thiazolyl, imidazolyl, pyridinyl, indolyl, C1–3 alkoxy, benzyloxy, C1–5 alkanoylamino, aroylamino, methylthio wherein the sulfur atom is unoxidized or oxidized to a sulfoxide or sulfone, benzylthio wherein the sulfur atom is unoxidized or oxidized to a sulfoxide or sulfone, C1–3 alkoxycarbonylamino, amino wherein the nitrogen atom is unsubstituted or independently mono or di-substituted by C1–5 alkyl or phenyl; halogen, hydroxy, oxo, carboxy and cyano, $R_f$ is unsubstituted or substituted by one or more $R_g$;

$R_g$ is selected from the group consisting of C1–3 alkyl, phenyl unsubstituted or substituted by halogen methyl; C1–3 alkoxy, aryloxy, benzyloxy, C1–3 alkoxycarbonyl, carbamoyl wherein the nitrogen atom is unsubstituted or independently mono or di-substituted by C1–3 alkyl or phenyl; C1–5 alkanoylamino, arylamino, amino wherein the nitrogen atom is unsubstituted or independently mono or di-substituted by C1–3 alkyl or phenyl; halogen, hydroxy, oxo, carboxy and cyano;

$R_h$ is selected from the group consisting of C1–3 alkyl, phenyl, C1–3 alkoxycarbonyl, benzyloxy and carboxy;

$R_g$ is a heteroaryl ring selected from the group consisting of oxazolyl, thiazolyl, imidazolyl, pyridyl, benzimidazolyl, benzthiazolyl and benzoxazolyl, wherein any of the above $R_g$ can be unsubstituted or substituted by one or more $R_j$;

$R_j$ is selected from the group consisting of C1–5 alkyl, cyclohexyl, phenyl, piperidinyl, furanyl, thienyl, pyridinyl, benzyl, methoxy, phenoxy, benzyloxy, methoxycarbonyl, acetyloxy, benzoyloxy, carbamoyl wherein the nitrogen atom is unsubstituted or independently mono or di-substituted by methyl, phenyl, furanyl or thienyl; acetylamino, benzoylamino, ureido wherein either nitrogen atom is unsubstituted or independently substituted by methyl or phenyl; methoxycarbonylamino, C1–3 alkylsulfonylamino, arylsulfonylamino, amino wherein the nitrogen atom is unsubstituted or independently mono or di-substituted by methyl, phenyl, furanyl or thienyl; halogen, hydroxy, carboxy and cyano, $R_j$ is unsubstituted or substituted by one or more $R_k$;

$R_k$ is selected from the group consisting of methyl, C5–6 cycloalkyl, phenyl, piperidinyl, piperazinyl, furanyl, thienyl, C1–3 alkoxy, phenoxy, benzyloxy, methoxycarbonyl, acetyloxy, benzoyloxy, carbamoyl wherein the nitrogen atom is unsubstituted or independently mono or di-substituted by methyl or phenyl; acetylamino, benzoylamino, ureido wherein either nitrogen atom is unsubstituted or independently substituted by methyl or phenyl; benzyloxycarbonylamino, benzyloxycarbonylamino C1–5alkyl, amino wherein the nitrogen atom is unsubstituted or independently mono or di-substituted by C1–3 alkyl, phenyl, furanyl or thienyl; halogen, hydroxy, carboxy, cyano and nitro.

18. The compound according to claim 17 wherein:

A is —C(O)— or —SO$_2$—;

$R_3$ is C1–5 alkyl or C5–6 cycloalkyl, wherein $R_3$ is unsubstituted or substituted by one or more $R_d$;

$R_d$ is selected from the group consisting of methyl, C3–6 cycloalkyl, phenyl, thienyl, imidazolyl, pyridinyl, indolyl, C1–4alkoxy, C1–5 alkanoylamino, methylthio wherein the sulfur atom is unoxidized or oxidized to a sulfoxide or sulfone, halogen, hydroxy, oxo, carboxy and cyano, $R_d$ is unsubstituted or substituted by one or more $R_e$;

$R_e$ is selected from the group consisting of methyl, phenyl, benzyl, methoxy, phenoxy, benzyloxy, benzoyl, halogen and hydroxy;

$R_f$ is selected from the group consisting of C3–6 cycloalkyl, phenyl, naphthyl, thienyl, imidazolyl, pyridinyl, indolyl, methoxy, benzyloxy, C1–3 alkanoylamino, methylthio wherein the sulfur atom is unoxidized or oxidized to a sulfoxide or sulfone, benzylthio wherein the sulfur atom is unoxidized or oxidized to a sulfoxide or sulfone, methoxycarbonylamino, amino wherein the nitrogen atom is unsubstituted or independently mono or di-substituted by C1–3 alkyl; halogen, hydroxy, carboxy and cyano, $R_f$ is unsubstituted or substituted by one or more $R_g$;

$R_g$ is selected from the group consisting of methyl, phenyl unsubstituted or substituted by halogen or methyl; methoxy, phenoxy, benzyloxy, methoxycarbonyl, amino wherein the nitrogen atom is unsubstituted or independently mono or di-substituted by C1–3 alkyl or phenyl; halogen, hydroxy and carboxy;

$R_d$ is a heteroaryl ring selected from the group consisting of oxazolyl, thiazolyl, imidazolyl, pyridyl, benzthiazolyl and benzoxazolyl, wherein any of the above $R_g$ can be unsubstituted or substituted by one or more $R_j$;

$R_j$ is selected from the group consisting of C1–5 alkyl, phenyl, furanyl, thienyl, piperidinyl, pyridinyl, benzyl, methoxy, methoxycarbonyl, acetyloxy, benzoyloxy carbamoyl wherein the nitrogen atom is unsubstituted or independently mono or di-substituted by methyl or phenyl; acetylamino, benzoylamino, ureido wherein either nitrogen atom is unsubstituted or independently substituted by methyl or phenyl; methoxycarbonylamino, amino wherein the nitrogen atom is unsubstituted or independently mono or di-substituted by methyl or phenyl; halogen, hydroxy, carboxy and cyano, $R_j$ is unsubstituted or substituted by one or more $R_k$; and $R_k$ is selected from the group consisting of methyl, C5–6 cycloalkyl, phenyl, piperidinyl, methoxy, phenoxy, benzyloxy, methoxycarbonyl, carbamoyl wherein the nitrogen atom is unsubstituted or independently mono or di-substituted by methyl or phenyl; ureido wherein either nitrogen atom is unsubstituted or independently substituted by methyl or phenyl; benzyloxycarbonylamino, benzyloxycarbonylaminoC1–5alkyl, amino wherein the nitrogen atom is unsubstituted or independently mono or di-substituted by C1–3alkyl, phenyl, furanyl or thienyl; halogen, hydroxy, carboxy, cyano and nitro.

19. The compound according to claim 18 wherein:

$R_d$ is selected from the group consisting of methyl, C3–6 cycloalkyl, phenyl, C1–4 alkoxy, C1–3 alkanoylamino, methylthio wherein the sulfur atom is unoxidized or oxidized to a sulfoxide or sulfone, halogen, hydroxy, oxo, carboxy and cyano, $R_d$ is unsubstituted or substituted by one or more $R_e$;

$R_e$ is selected from the group consisting of methyl, phenyl, methoxy, halogen and hydroxy;

$R_5$ is H;

$R_f$ is selected from the group consisting of C5–6 cycloalkyl, phenyl, naphthyl, thienyl, indolyl, methoxy, methylthio wherein the sulfur atom is unoxidized or oxidized to a sulfoxide or sulfone, methoxycarbonylamino, halogen, hydroxy, carboxy and cyano, $R_f$ is unsubstituted or substituted by one or more $R_g$;

$R_g$ is selected from the group consisting of methyl, phenyl unsubstituted or substituted by halogen; methoxy, phenoxy, benzyloxy, methoxycarbonyl, halogen, hydroxy and carboxy;

$R_g$ is a heteroaryl ring selected from the group consisting of oxazolyl, pyridyl, benzthiazolyl and benzoxazolyl, wherein any of the above $R_g$ can be unsubstituted or substituted by one or more $R_j$;

$R_j$ is selected from the group consisting of C1–5 alkyl, phenyl, piperidinyl, pyridinyl, benzyl, methoxy, methoxycarbonyl, acetyloxy, benzoyloxy, carbamoyl wherein the nitrogen atom is unsubstituted or independently mono or di-substituted by methyl or phenyl; methoxycarbonylamino, halogen, hydroxy and carboxy, $R_j$ is unsubstituted or substituted by one or more $R_k$;

$R_k$ is selected from the group consisting of methyl, C5–6 cycloalkyl, phenyl, piperidinyl, methoxy, methoxycarbonyl, carbamoyl wherein the nitrogen atom is unsubstituted or independently mono or di-substituted by methyl or phenyl; benzyloxycarbonylamino, amino wherein the nitrogen atom is unsubstituted or independently mono or di-substituted by methyl or phenyl; halogen, hydroxy and carboxy.

20. The compound according to claim 9 wherein:

$R_3$ is C1–5 alkyl wherein $R_3$ is unsubstituted or substituted by one or more $R_d$;

$R_d$ is selected from the group consisting of C3–6 cycloalkyl and phenyl, $R_d$ is unsubstituted or substituted by one or more $R_e$;

$R_e$ is selected from the group consisting of methyl and halogen;

$R_6$ is C1–5 alkyl unsubstituted or substituted by one or more $R_f$;

$R_f$ is selected from the group consisting of C5–6 cycloalkyl, phenyl, methylthio wherein the sulfur atom is unoxidized or oxidized to a sulfoxide or sulfone and halogen, $R_f$ is unsubstituted or substituted by one or more $R_g$;

$R_g$ is selected from the group consisting of methyl, methoxy, methoxycarbonyl, halogen and hydroxy;

$R_j$ is selected from the group consisting of C1–5 alkyl, phenyl, pyridinyl, piperidinyl, methoxycarbonyl, carbamoyl wherein the nitrogen atom is unsubstituted or independently mono or disubstituted by methyl or phenyl; methoxycarbonylamino and halogen, $R_j$ is unsubstituted or substituted by one or more $R_k$;

$R_k$ is selected from the group consisting of methyl, C5–6 cycloalkyl, phenyl, methoxycarbonyl, carbamoyl, benzyloxycarbonylamino and halogen.

21. A method of making a compound of the formula (I)

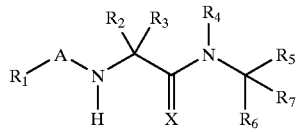

(I)

wherein A is —C(O)—, X is O, $R_7$ is $R_8$—C(O)— and $R_1$, $R_2$, $R_3$, $R_4$, $R_5$, $R_6$ and $R_8$ are as defined in claim 1; comprising a) coupling a protected amino acid with N,O-dimethylhydroxylamine under coupling conditions in a suitable solvent to give the corresponding amide below:

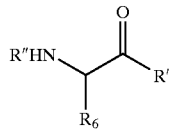

wherein R" is an amino protecting group, and R' is NMe(OMe);

b) reducing the compound produced in a step a) with a reducing agent in a suitable solvent to form a compound of the formula (V):

(V)

d) reacting a heterocycle $R_8$ according to claim 1, with n-BuLi to form a corresponding heterocyclic anion in a suitable solvent at a temperature about −30 to −100° C.; reacting the heterocycle $R_8$ anion with a compound of formula V;

e) removing the protecting group R" from the compound produced in step d) and subsequently coupling with a compound of the formula (IV) under coupling conditions to produce a compound of the formula (VII):

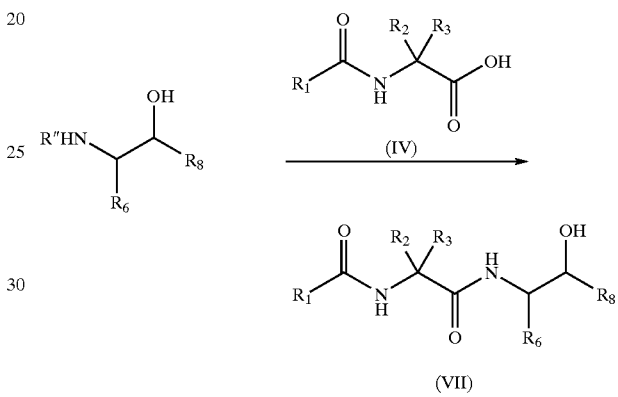

and f) oxidizing compound VII from step e) to produce a compound of the formula (I).

22. A pharmaceutical composition comprising a pharmaceutically effective amount of a compound according to claims 1 or 11 and one or more pharmaceutically acceptable carriers or adjuvants.

23. A method of treating a disease is selected from the group consisting of: rheumatoid arthritis, systemic lupus erythematosus, Crohn's disease, ulcerative colitis, multiple sclerosis, Guillain-Barry syndrome, psoriasis, Grave's disease, myasthenia gravis, scleroderma, glomerulonephritis, atopic dermatitis and insulin-dependent diabetes mellitus said method comprising administering to a patient in need of such treatment a pharmaceutically effect amount of a compound according to claims 1 or 11.

24. A method of treating Alzheimer's disease comprising administering to a patient in need of such treatment a pharmaceutically effective amount of a compound according to claims 1 or 11.

25. A method of treating atherosclerosis comprising administering to a patient in need of such treatment a pharmaceutically effective amount of a compound according to claims 1 or 11.

* * * * *